United States Patent
Iwase et al.

(10) Patent No.: US 12,100,154 B2
(45) Date of Patent: Sep. 24, 2024

(54) MEDICAL IMAGE PROCESSING APPARATUS, MEDICAL IMAGE PROCESSING METHOD, COMPUTER-READABLE MEDIUM, AND LEARNED MODEL

(71) Applicant: CANON KABUSHIKI KAISHA, Tokyo (JP)

(72) Inventors: Yoshihiko Iwase, Kanagawa (JP); Hideaki Mizobe, Kanagawa (JP); Ritsuya Tomita, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 566 days.

(21) Appl. No.: 17/168,776

(22) Filed: Feb. 5, 2021

(65) Prior Publication Data
US 2021/0158525 A1 May 27, 2021

Related U.S. Application Data

(63) Continuation of application No. PCT/JP2019/031883, filed on Aug. 13, 2019.

(30) Foreign Application Priority Data

Aug. 14, 2018 (JP) .................. 2018-152632
Dec. 10, 2018 (JP) .................. 2018-230612
Aug. 9, 2019 (JP) .................. 2019-147739

(51) Int. Cl.
*G06T 7/00* (2017.01)
*A61B 3/00* (2006.01)
(Continued)

(52) U.S. Cl.
CPC .......... *G06T 7/0014* (2013.01); *A61B 3/0025* (2013.01); *A61B 3/102* (2013.01);
(Continued)

(58) Field of Classification Search
CPC ......... G06T 7/0014; G06T 5/002; G06T 7/11; G06T 7/97; G06T 2207/10101;
(Continued)

(56) References Cited

U.S. PATENT DOCUMENTS 8,870,377 B2   10/2014   Iwase et al.
9,053,536 B2   6/2015    Imamura et al.
(Continued)

FOREIGN PATENT DOCUMENTS

CN    107292887 A    10/2017
EP    3530176 A1    8/2019
(Continued)

OTHER PUBLICATIONS

Examination Report issued by the Intellectual Property Office of UK on Feb. 18, 2022 in corresponding GB Patent Application No. 2103260.2.
(Continued)

*Primary Examiner* — Wesley J Tucker
(74) *Attorney, Agent, or Firm* — Carter, DeLuca & Farrell LLP

(57) ABSTRACT

A medical image processing apparatus including an obtaining unit configured to obtain a tomographic image of an eye to be examined, and a first processing unit configured to perform first detection processing for detecting at least one layer of a plurality of layers in the obtained tomographic image, by using the obtained tomographic image as an input data of a learned model, wherein the learned model has been obtained by using training data including data indicating at least one layer of a plurality of layers in a tomographic image of an eye to be examined.

22 Claims, 42 Drawing Sheets

(51) Int. Cl.
*A61B 3/10* (2006.01)
*G06T 5/70* (2024.01)
*G06T 7/11* (2017.01)

(52) U.S. Cl.
CPC .................. *G06T 5/70* (2024.01); *G06T 7/11* (2017.01); *G06T 7/97* (2017.01); *G06T 2207/10101* (2013.01); *G06T 2207/20081* (2013.01); *G06T 2207/20084* (2013.01); *G06T 2207/30041* (2013.01)

(58) Field of Classification Search
CPC . G06T 2207/20081; G06T 2207/20084; G06T 2207/30041; G06T 7/0012; G06T 7/10; A61B 3/0025; A61B 3/102; A61B 3/10; G16H 30/40; G16H 50/20
See application file for complete search history.

(56) References Cited

U.S. PATENT DOCUMENTS

| | | | |
|---|---|---|---|
| 9,149,183 B2 | 10/2015 | Iwase et al. | |
| 9,265,418 B2 | 2/2016 | Iwase | |
| 9,436,994 B2 | 9/2016 | Furukawa et al. | |
| 9,824,273 B2 | 11/2017 | Iwase et al. | |
| 10,482,326 B2 | 11/2019 | Iwase et al. | |
| 10,529,045 B2 | 1/2020 | Iwase et al. | |
| 10,552,672 B2 | 2/2020 | Iwase et al. | |
| 10,872,237 B2 | 12/2020 | Iwase et al. | |
| 10,878,574 B2 * | 12/2020 | Mao | G06T 7/136 |
| 2012/0287401 A1 * | 11/2012 | Bizios | A61B 3/0025 351/246 |
| 2013/0136326 A1 | 5/2013 | Iwase et al. | |
| 2013/0194546 A1 * | 8/2013 | Iwase | G06T 7/0012 351/246 |
| 2013/0195340 A1 | 8/2013 | Iwase et al. | |
| 2013/0286354 A1 * | 10/2013 | Stetson | G06T 7/0012 351/246 |
| 2014/0085606 A1 * | 3/2014 | Miyasa | A61B 3/1005 351/206 |
| 2017/0065170 A1 * | 3/2017 | Yamashita | A61B 3/102 |
| 2018/0199807 A1 | 7/2018 | Ohta et al. | |
| 2020/0342595 A1 * | 10/2020 | Jia | G06T 7/0012 |
| 2021/0104313 A1 | 4/2021 | Mizobe et al. | |
| 2021/0224997 A1 * | 7/2021 | Kushida | G06T 5/001 |
| 2022/0036552 A1 * | 2/2022 | He | G06T 7/11 |
| 2022/0400942 A1 * | 12/2022 | Leung | A61B 3/0025 |
| 2023/0137102 A1 * | 5/2023 | Kim | G06T 7/12 382/131 |

FOREIGN PATENT DOCUMENTS

| | | | |
|---|---|---|---|
| JP | 2008073099 A | 4/2008 | |
| JP | 2011-013334 A | 1/2011 | |
| JP | 2011520503 A | 7/2011 | |
| JP | 2012019958 A | 2/2012 | |
| JP | 2014-516646 A | 7/2014 | |
| JP | 2017047111 A | 3/2017 | |
| JP | 2018030013 A | 3/2018 | |
| JP | 2018114068 A | 7/2018 | |
| KR | 2013-0108456 A | 10/2013 | |
| KR | 101857624 B1 | 5/2018 | |
| WO | 2012149175 A1 | 11/2012 | |

OTHER PUBLICATIONS

Examination Report issued by the UK Patent Office on Oct. 12, 2022 in corresponding GB Patent Application No. 2103260.2.
Feng, L. et al., "Automatic segmentation of nine retinal layer boundaries in OCT images of non-exudative AMD patients using deep learning and graph search" Biomedical Optics Express (May 2017) pp. 2732-2744, vol. 8.
Combined Search and Examination Report issued by the UK Patent Office on Feb. 17, 2023 in corresponding GB Patent Application No. 2217205.0.
Decision of Refusal issued by the Japan Patent Office on Nov. 22, 2022 in corresponding JP Patent Application No. 2022-074057, with English translation.
Notice of Reasons for Refusal issued by the JP Patent Office on Aug. 3, 2021 in corresponding JP Patent Application No. 2019-147739, with English translation.
Office Action issued by the Korean Patent Office on Nov. 21, 2022 in corresponding KR Patent Application No. 10-2021-7006768, with English translation.
Notice of Reasons for Refusal issued by the Japan Patent Office on Jul. 28, 2022 in corresponding JP Patent Application No. 2022-074057, with English translation.
Decision of Refusal issued by the Japan Patent Office on Feb. 1, 2022 in corresponding JP Patent Application No. 2019-147739, with English translation.
Examination Report issued by the Intellectual Property Office of India on Jan. 25, 2022 in corresponding IN Patent Application No. 202147009252, with English translation.
International Search Report issued in International Application No. PCT/JP2019/031883 dated Nov. 5, 2019, pp. 1, English Translation.
International Preliminary Report on Patentability issued by the International Bureau on behalf of the Japan Patent Office acting as International Searching Authority on Feb. 16, 2021 in corresponding International Application No. PCT/JP2019/031883, with English translation.
Office Action issued by the The National Intellectual Property Administration of the People's Republic of China on Jan. 9, 2024 in corresponding CN Patent Application No. 201980053915.X, with English translation.
Notice of Reasons for Refusal issued by the Japanese Patent Office on Apr. 16, 2024 in corresponding JP Patent Application No. 2023-024953, with English translation.
Chinese Office Action issued by the China National Intellectual Property Administration on Jul. 17, 2024 in corresponding CN Patent Application No. 201980053915.X, with English translation.
Jun, X. et al., "Correlation between optic nerve head parameters and retinal nerve fiber layer in glaucoma" Journal of Computer-Aided Design & Computer Graphics (Jun. 2017) pp. 977-983, vol. 29, No. 6, with English Abstract.

* cited by examiner

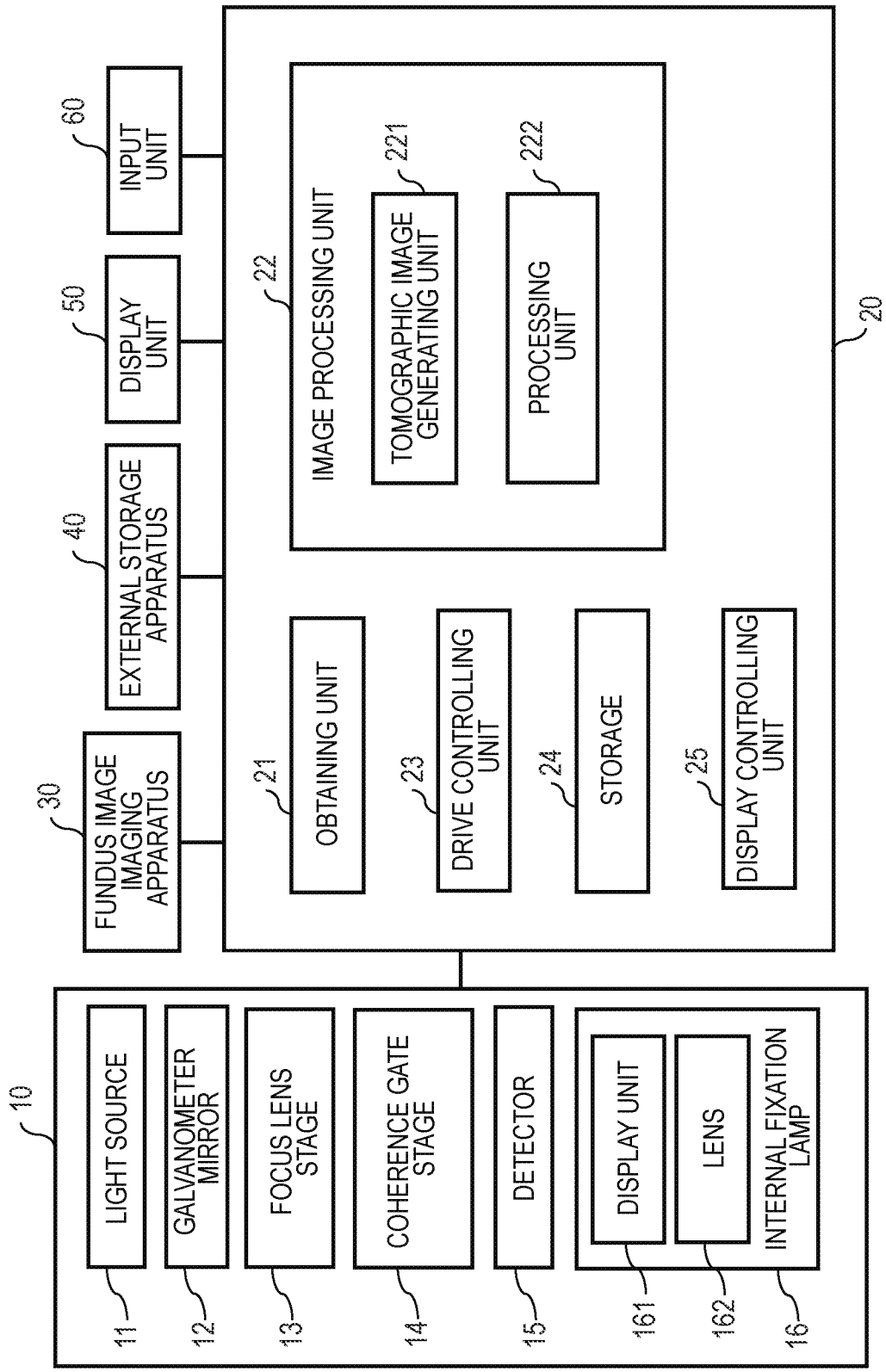

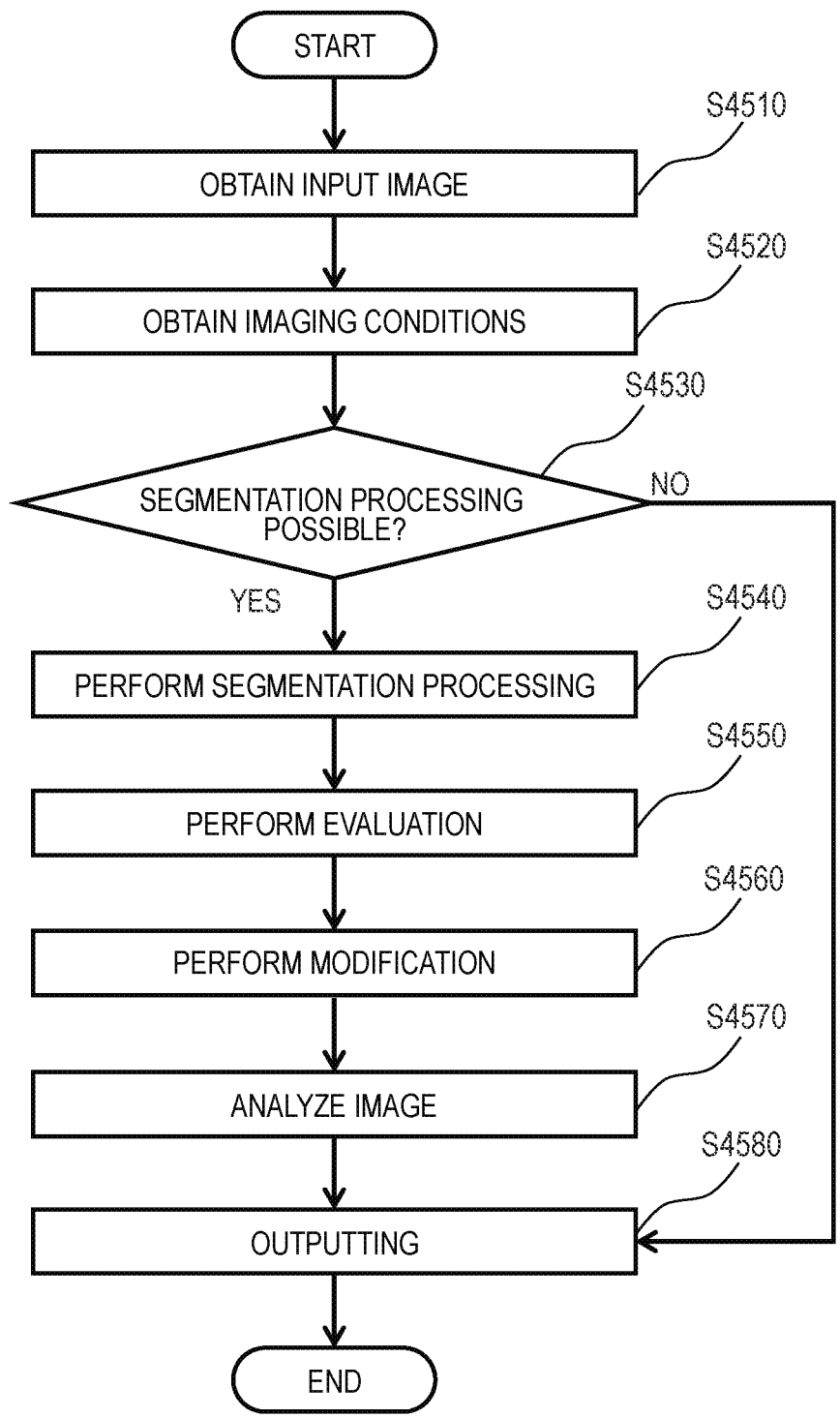

MEDICAL IMAGE PROCESSING APPARATUS, MEDICAL IMAGE PROCESSING METHOD, COMPUTER-READABLE MEDIUM, AND LEARNED MODEL

CROSS-REFERENCE TO RELATED APPLICATIONS

This application is a Continuation of International Patent Application No. PCT/JP2019/031883, filed Aug. 13, 2019, which claims the benefit of Japanese Patent Application No. 2018-152632, filed Aug. 14, 2018, Japanese Patent Application No. 2018-230612, filed Dec. 10, 2018, and Japanese Patent Application No. 2019 147739, filed Aug. 9, 2019, all of which are hereby incorporated by reference herein in their entirety.

BACKGROUND OF THE INVENTION

Field of the Invention

The present invention relates to a medical image processing apparatus, a medical image processing method, a computer-readable medium, and a learned model.

Description of the Related Art

Tomographic image imaging apparatuses for eyes, such as an apparatus (OCT apparatus) using the Optical Coherence Tomography (OCT), can three-dimensionally observe the state inside the retina layers. The tomographic image imaging apparatuses have attracted attention in recent years, since the tomographic image imaging apparatuses are useful in more accurately making diagnoses.

As the forms of the OCT, there is, for example, the TD-OCT (Time domain OCT) in which a broadband light source and a Michelson interferometer are combined. This is configured to measure interference light with back-scattered light of a signal arm by scanning the delay of a reference arm, and to obtain the information on depth decomposition. However, fast image obtaining is difficult in such a TD-OCT.

Therefore, as the method for obtaining an image faster, the SD-OCT (Spectral domain OCT) with the technique of using a broadband light source, and obtaining an interferogram by a spectroscope is known. Additionally, the SS-OCT (Swept Source OCT) with the technique of using a fast wavelength swept light source as a light source, and measuring spectrum interference by a single channel photodetector is known.

In the case where a tomographic image imaged by the OCT is obtained, when the thickness of a nerve fiber layer can be measured, the progress of diseases, such as glaucoma, and the recovery status after treatment can be quantitatively diagnosed. The technology of using a computer to detect the boundaries of each of the layers of a retina from a tomographic image, and to measure the thickness of each of the layers in order to quantitatively measure the thicknesses of these layers is disclosed in Japanese Patent Application Laid-Open No. 2008-73099.

However, conventional technologies had the following problems. Since there are disappearance of a layer, bleeding, and occurrence of vitiligo and new blood vessels, etc., in a diseased eye, the shape of a retina becomes irregular. Therefore, in conventional image processing methods of determining results of image characteristics extraction by utilizing the regularity of the shape of the retina, and performing the boundary detection of the retina layers, there was a limit that erroneous detection, etc., occurs at the time of automatically performing the boundary detection of the retina layer.

Therefore, one of the objects of the present invention is to provide a medical image processing apparatus, a medical image processing method, a computer-readable medium having stored thereon a program, and a learned model, that can perform boundary detection of the retina layers regardless of diseases, sites, etc.

SUMMARY OF THE INVENTION

A medical image processing apparatus according to one embodiment of the present invention includes an obtaining unit configured to obtain a tomographic image of an eye to be examined, and a first processing unit configured to perform first detection processing for detecting at least one layer of a plurality of layers in the obtained tomographic image, by using the obtained tomographic image as an input data of a learned model, wherein the learned model has been obtained by using training data including data indicating at least one layer of a plurality of layers in a tomographic image of an eye to be examined.

Additionally, a medical image processing method according to another embodiment of the present invention includes obtaining a tomographic image of an eye to be examined, and performing first detection processing for detecting at least one layer of a plurality of layers in the obtained tomographic image, by using the obtained tomographic image as an input data of a learned model, wherein the learned model has been obtained by using training data including data indicating at least one layer of a plurality of layers in a tomographic image of an eye to be examined.

Further features of the present invention will become apparent from the following description of exemplary embodiments with reference to the attached drawings.

BRIEF DESCRIPTION OF THE DRAWINGS

FIG. 1 illustrates an example of the schematic configuration of an image processing system according to Example 1.

FIG. 31 is a diagram illustrating an example of a user interface included in an imaging apparatus according to Example 8.

FIG. 42 is a diagram illustrating an example of a user interface included in an imaging apparatus according to Example 15.

FIG. 45 is a flowchart illustrating an example of the processing flow of the image processing apparatus according to Example 19.

DESCRIPTION OF THE EMBODIMENTS

Figure 2A:
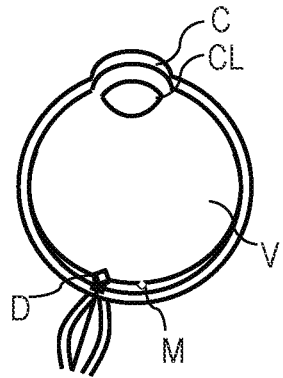
FIG. 2A is a diagram for describing an eye.

Exemplary embodiments of the present invention will now be described in detail in accordance with the accompanying drawings.

However, the dimensions, materials, shapes, relative positions of components and the like described in the following examples are arbitrary, and can be changed according to the configuration of an apparatus to which the present invention is applied or according to various conditions. Additionally, the same reference numerals are used across the drawings to denote identical or functionally similar elements in the drawings.

Example 1

Hereinafter, referring to FIG. 1 to FIG. 7, an image processing system including an image processing apparatus that uses a tomographic image of an eye according to Example 1 of the present invention will be described. In the present example, all targeted retina layers are detected by using a learned model relating to a machine learning model. Note that, hereinafter, a machine learning model refers to a learning model with machine learning algorithms such as deep learning. Additionally, a learned model is a model that has been trained (learned) on a machine learning model with an arbitrary machine learning algorithm by using appropriate training data in advance. However, it does not mean that the learned model does not perform learning any more, and the learned model shall also be able to perform incremental learning. Note that, hereinafter, training data refers to training data, and includes a pair of input data and ground truth. Additionally, correct answer data refers to the ground truth of training data.

FIG. 1 illustrates an example of the schematic configuration of an image processing system 1 including an image processing apparatus 20 (medical image processing apparatus) according to the present example. As illustrated in FIG. 1, the image processing system 1 is provided with an OCT apparatus 10, which is an example of a tomographic image imaging apparatus, the image processing apparatus 20, a fundus image imaging apparatus 30, an external storage apparatus 40, a display unit 50, and an input unit 60.

The OCT apparatus 10 is an example of a tomographic image imaging apparatus, which is an apparatus for imaging a tomographic image of an eye to be examined. An arbitrary kind of OCT apparatus can be used as the OCT apparatus, and for example, an SD-OCT or an SS-OCT can be used.

The image processing apparatus 20 is connected to the OCT apparatus 10, the fundus image imaging apparatus 30, the external storage apparatus 40, the display unit 50, and the input unit 60 via interfaces, and can control them. The image processing apparatus 20 can generate various images, such as a tomographic image and an En-Face image (front image) of an eye to be examined, based on various signals obtained from the OCT apparatus 10, the fundus image imaging apparatus 30, and the external storage apparatus 40. Additionally, the image processing apparatus 20 can perform image processing on these images. Note that the image processing apparatus 20 may include a general-purpose computer, or may include a dedicated computer of the image processing system 1.

The fundus image imaging apparatus 30 is an apparatus for imaging a fundus image of an eye to be examined, and for example, a fundus camera, or an SLO (Scanning Laser Ophthalmoscope) can be used as the apparatus. Note that the apparatus configuration of the OCT apparatus 10 and the fundus image imaging apparatus 30 may be integrated or separated.

The external storage apparatus 40 associates and maintains the information relating to an eye to be examined (a patient's name, age, sex, and the like) with each of various imaged image data, a photographing parameter, an image analysis parameter, and a parameter set by an operator. The external storage apparatus 40 may include an arbitrary storage apparatus, and may include a storage medium such as an optical disk or a memory.

The display unit 50 includes an arbitrary display, and can display information and various images related to an eye to be examined, according to control by the image processing apparatus 20.

The input unit 60 is, for example, a mouse, a keyboard, or a touch operation screen, and the operator can input an instruction for the image processing apparatus 20, the OCT apparatus 10, and the fundus image imaging apparatus 30 to the image processing apparatus 20 via the input unit 60. Note that, when the input unit 60 is a touch operation screen, the input unit 60 can be configured integrally with the display unit 50.

Note that, although these components are illustrated as separate bodies in FIG. 1, some or all of these components may be configured as an integral body.

Next, the OCT apparatus 10 will be described. The OCT apparatus 10 is provided with a light source 11, a galvanometer mirror 12, a focus lens stage 13, a coherence gate stage 14, a detector 15, and an internal fixation lamp 16. Note that, since the OCT apparatus 10 is a known apparatus, a detailed description will be omitted, and here, the imaging of a tomographic image performed by an instruction from the image processing apparatus 20 will be described.

When an instruction for imaging is communicated from the image processing apparatus 20, the light source 11 emits light. The light from the light source 11 is divided into measurement light and reference light by using a divider, which is not illustrated. The OCT apparatus 10 can generate an interference signal including the tomographic information of a subject (eye to be examined) by irradiating the subject with the measurement light, and detecting the return light from the subject, and the interference light with the reference light.

The galvanometer mirror 12 is used for scanning the measurement light in the fundus of the eye to be examined, and the imaging range of the fundus by the OCT imaging can be specified by the scanning range of the measurement light by the galvanometer mirror 12. The image processing apparatus 20 can specify the imaging range and the number of scanning lines in a plane direction (the scanning speed in the plane direction) of the fundus by controlling the driving range and speed of the galvanometer mirror 12. In FIG. 1, the galvanometer mirror 12 is illustrated as one unit in order to simplify the description, but practically, the galvanometer mirror 12 includes two mirrors, i.e., a mirror for X scanning and a mirror for Y scanning, and can scan a desired range in the fundus with the measurement light. Note that the configuration of the scanning unit for scanning the measurement light is not limited to the galvanometer mirror, and can use other arbitrary deflection mirrors. Additionally, a deflection mirror capable of scanning the measurement light in a two-dimensional direction with one mirror, such as a MEMS mirror, may be used as the scanning unit.

The focus lens stage 13 is provided with a focus lens, which is not illustrated. By moving the focus lens stage 13, the focus lens can be moved along the optical axis of the measurement light. Therefore, the measurement light can be focused to the retina layers of the fundus by the focus lens via the anterior ocular segment of the eye to be examined. The measurement light irradiated onto the fundus is reflected and scattered by each retina layer, and returns on an optical path as the return light.

The coherence gate stage 14 is used to adjust the length of the optical path of the reference light or the measurement light, in order to correspond to differences in the ocular axial lengths of eyes to be examined, etc. In the present example, the coherence gate stage 14 includes a stage provided with a mirror, and can make the optical path length of the reference light correspond to the optical path length of the measurement light by moving in the optical axis direction in the optical path of the reference light. Here, a coherence gate represents the position at which the optical distances of the measurement light and the reference light are equal in the OCT. The coherence gate stage 14 can be controlled by the image processing apparatus 20. By controlling the position of the coherence gate by the coherence gate stage 14, the image processing apparatus 20 can control the imaging range in the depth direction of the eye to be examined, and can control the imaging on the retina layers side, or the imaging on the side of a portion deeper than the retina layers, etc.

The detector 15 detects the return light of the measurement light from the eye to be examined and the interference light with the reference light that occur in an interference unit, which is not illustrated, and generates an interference signal. The image processing apparatus 20 can obtain the interference signal from the detector 15, and can generate a tomographic image of the eye to be examined by performing the Fourier transform, etc., on the interference signal.

The internal fixation lamp 16 is provided with a display unit 161 and a lens 162. In the present example, a plurality of light emitting diodes (LD) arranged in a matrix are used as an example of the display unit 161. The lighting position of the light emitting diodes is changed according to a site to be imaged by control of the image processing apparatus 20. The light from the display unit 161 is led to the eye to be examined via the lens 162. The light emitted from the display unit 161 has, for example, a wavelength of 520 nm, and is displayed in a desired pattern by control by the image processing apparatus 20.

Note that the OCT apparatus 10 may be provided with a drive controlling unit for the OCT apparatus 10 that controls driving of each component based on control by the image processing apparatus 20.

Next, referring to FIG. 2A to FIG. 2C, the structure and image of an eye that are obtained by the image processing system 1 will be described. FIG. 2A is a schematic diagram of an eyeball. FIG. 2A represents a cornea C, a crystalline lens CL, a vitreous body V, a macular area M (the center portion of a macula represents a central fovea), and an optic nerve head D. In the present example, a case of mainly imaging the posterior pole of the retina including the vitreous body V, the macular area M, and the optic nerve head D will be described. Note that, although not described below, the OCT apparatus 10 can also image the anterior ocular segment, such as the cornea and the crystalline lens.

Figure 2B:
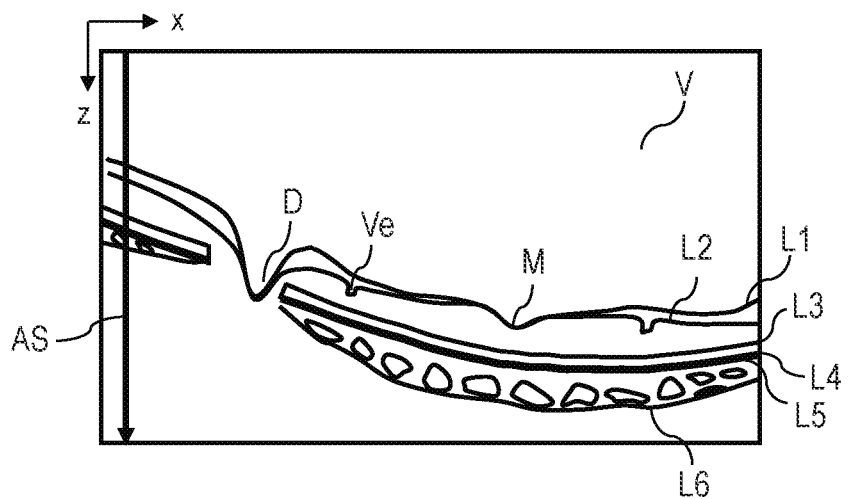
FIG. 2B is a diagram for describing a tomographic image.

FIG. 2B illustrates an example of a tomographic image obtained by imaging the retina by using the OCT apparatus 10. In FIG. 2B, AS indicates an image unit obtained by single A scan. Here, the A scan refers to obtaining the tomographic information in the depth direction at one point of the eye to be examined by the above-described series of operations of the OCT apparatus 10. Additionally, performing the A scan in an arbitrary transverse direction (main scanning direction) a plurality of times to obtain two-dimensional tomographic information in the transverse direction and the depth direction of the eye to be examined is called the B scan. One B scan image can be constituted by collecting a plurality of A scan images obtained by the A scan. Hereinafter, this B scan image is called a tomographic image.

FIG. 2B represents a blood vessel Ve, the vitreous body V, the macular area M, and the optic nerve head D. Additionally, a boundary line L represents the boundary between an inner limiting membrane (ILM) and a nerve fiber layer (NFL), a boundary line L2 represents the boundary between the nerve fiber layer and a ganglion cell layer (GCL), and a boundary line L3 represents a photoreceptor inner segment-outer segment junction (ISOS). Further, a boundary line L4 represents a retinal pigment epithelium (RPE), a boundary line L5 represents a Bruch's membrane (BM), and a boundary line L6 represents a choroid coat. In the tomographic image, it is assumed that a horizontal axis (the main scanning direction of the OCT) is an x axis, and a vertical axis (the depth direction) is a z axis.

Figure 2C:
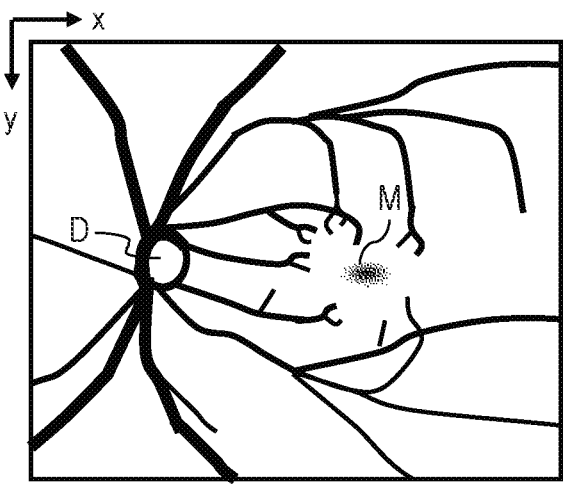
FIG. 2C is a diagram for describing a fundus image.

FIG. 2C illustrates an example of the fundus image obtained by imaging the fundus of the eye to be examined by using the fundus image imaging apparatus 30. FIG. 2C represents the macular area M and the optic nerve head D. and the vessels of the retina are represented by thick curved lines. In a fundus image, it is assumed that a horizontal axis (the main scanning direction of the OCT) is an x axis, and a vertical axis (the sub-scanning direction of the OCT) is a y axis.

Next, the image processing apparatus 20 will be described. The image processing apparatus 20 is provided with an obtaining unit 21, an image processing unit 22, a drive controlling unit 23, a storage 24, and a display controlling unit 25.

The obtaining unit 21 can obtain the data of the interference signal of the eye to be examined from the OCT apparatus 10. Note that the data of the interference signal obtained by the obtaining unit 21 may be an analog signal or a digital signal. When the obtaining unit 21 obtains an analog signal, the analog signal can be converted into a digital signal by the image processing apparatus 20. Additionally, the obtaining unit 21 can obtain various images generated by the image processing unit 22, such as tomographic data, tomographic images, and En-Face images. Here, the tomographic data is data including the information related to the tomography of the subject, and refers to those including the data based on the interference signal by the OCT, and the data subjected to the fast Fourier transform (FFT: Fast Fourier Transform) or arbitrary signal processing.

Further, the obtaining unit 21 obtains imaging conditions for a tomographic image to be subjected to image processing (for example, information related to the date and time of imaging, an imaged site name, an imaged region, an imaging angle of view, an imaging system, the resolution and gradation of an image, the pixel size of the image, an image filter, and the data format of the image). Note that the imaging conditions are not limited to the exemplified imaging conditions. Additionally, the imaging conditions do not need to include all the exemplified imaging conditions, and may include some of them.

Additionally, the obtaining unit 21 can obtain data including the fundus information obtained by the fundus image imaging apparatus 30. Further, the obtaining unit 21 can obtain information for identifying the eye to be examined, such as a subject identification number, from the input unit 60, etc. The obtaining unit 21 can make the storage 24 store various data and images obtained.

The image processing unit 22 can generate a tomographic image, an En-Face image, and the like from the data obtained by the obtaining unit 21 and the data stored in the storage 24, and can perform image processing on the generated or obtained image. Therefore, the image processing unit 22 can function as an example of a generating unit that generates an En-Face image and a motion contrast front image described later. The image processing unit 22 is provided with a tomographic image generating unit 221 and a processing unit 222 (s first processing unit).

The tomographic image generating unit 221 can generate tomographic data by performing processing such as the Fourier transform on the interference signal obtained by the obtaining unit 21, and can generate a tomographic image based on the tomographic data. Note that a known arbitrary method may be employed as the generation method of the tomographic image, and a detailed description will be omitted.

The processing unit 222 can include a learned model related to a machine learning model with machine learning algorithms, such as deep learning. A specific machine learning model will be described later. The processing unit 222 performs detection processing for detecting the retina layers of the eye to be examined in a tomographic image by using the learned model, and detects each retina layer.

The drive controlling unit 23 can control driving of each component of the OCT apparatus 10 and the fundus image imaging apparatus 30 that are connected to the image processing apparatus 20. The storage 24 can store various images, data, and the like such as the tomographic data obtained by the obtaining unit 21, the tomographic image generated and processed by the image processing unit 22. Additionally, the storage 24 can also store a program and the like for achieving the function of each component of the image processing apparatus 20 when executed by a processor.

The display controlling unit 25 can control the display in the display unit 50, of various kinds of information obtained by the obtaining unit 21, the tomographic image generated and processed by the image processing unit 22, information input by the operator, and the like.

Each component of the image processing apparatus 20 other than the storage 24 may be configured by a software module executed by a processor, such as a CPU (Central Processing Unit) or an MPU (Micro Processing Unit). Note that the processor may be, for example, a GPU (Graphical Processing Unit) or an FPGA (Field-Programmable Gate Array). Additionally, the each component may be configured by a circuit or the like that achieves a specific function, such as an ASIC. The storage 24 may be configured by, for example, an arbitrary storage medium, such as an optical disk and a memory.

Figure 3:
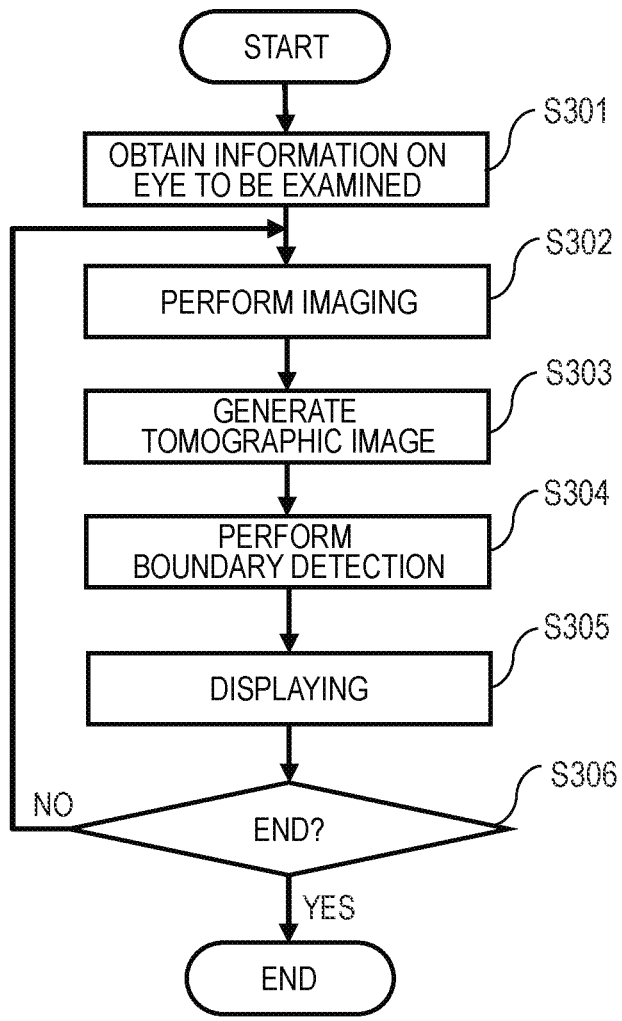
FIG. 3 is a flowchart of a series of processing according to Example 1.

Next, referring to FIG. 3, a series of processing according to the present example will be described. FIG. 3 is a flowchart of the series of processing according to the present example. When the series of processing according to the present example is started, the processing proceeds to step S301.

In step S301, the obtaining unit 21 obtains the subject identification number, which is an example of the information for identifying the eye to be examined, from the outside of the image processing apparatus 20, such as the input unit 60. The obtaining unit 21 obtains the information related to the eye to be examined maintained by the external storage apparatus 40 based on the subject identification number, and stores the information in the storage 24.

In step S302, the drive controlling unit 23 performs imaging by controlling the OCT apparatus 10 to scan the eye to be examined, and the obtaining unit 21 obtains an interference signal including the tomographic information of the eye to be examined from the OCT apparatus 10. The scanning of the eye to be examined is performed by controlling the OCT apparatus 10 by the drive controlling unit 23 according to a scan start instruction by the operator, and operating the light source 11, the galvanometer mirror 12, etc.

The galvanometer mirror 12 includes an X scanner for the horizontal direction, and a Y scanner for the vertical direction. Therefore, the drive controlling unit 23 can scan measurement light in the respective directions of the horizontal direction (X) and the vertical direction (Y) in an apparatus coordinate system by changing each of the orientations of these scanners. Note that the drive controlling unit 23 can scan the measurement light in the combined direction of the horizontal direction and the vertical direction by simultaneously changing the orientations of these scanners. Therefore, the drive controlling unit 23 can scan the measurement light in an arbitrary direction on a fundus plane.

The drive controlling unit 23 adjusts various imaging parameters when performing imaging. Specifically, the drive controlling unit 23 sets at least the position of a pattern displayed by the internal fixation lamp 16, the scanning range and scan pattern by the galvanometer mirror 12, the coherence gate position, and the focus.

The drive controlling unit 23 controls the light emitting diodes of the display unit 161 to control the position of the pattern displayed by the internal fixation lamp 16, so as to perform imaging of the center of the macular area and the optic nerve head of the eye to be examined. Additionally, the drive controlling unit 23 sets a scan pattern, such as raster scan, radial scan, and cross scan, for imaging a three-dimensional volume as the scan pattern of the galvanometer mirror 12. Note that, whichever scan pattern is selected, imaging is repeatedly performed on one line a plurality of times (the number of time of repetition is two or more). In the present example, a case will be described where the scan pattern is the cross scan, and imaging is repeatedly performed on the same location 150 times. After the adjustment of these imaging parameters end, according to an imaging start instruction by the operator, the drive controlling unit 23 controls the OCT apparatus 10 to perform imaging of the eye to be examined. Note that the number of time of repetition according to the present example is an example, and may be set to an arbitrary number of times according to a desired configuration.

Although a detailed description is omitted in the present disclosure, the OCT apparatus 10 can perform tracking of the eye to be examined for imaging the same location for addition average. Accordingly, the OCT apparatus 10 can perform scanning of the eye to be examined by reducing the influence of involuntary eye movement.

In step S303, the tomographic image generating unit 221 performs generation of a tomographic image based on the interference signal obtained by the obtaining unit 21. The tomographic image generating unit 221 can generate a tomographic image by performing general reconstruction processing on each interference signal.

First, the tomographic image generating unit 221 performs fixed pattern noise removal from the interference signal. The fixed pattern noise removal is performed by extracting fixed pattern noise by averaging the plurality of obtained signals of the A scan, and subtracting this from the input interference signal. Then, the tomographic image generating unit 221 performs desired window function processing in order to optimize the depth resolution and the dynamic range, which will be in a trade-off relationship when the interference signal is Fourier transformed in a finite interval. The tomographic image generating unit 221 generates tomographic data by performing fast Fourier transform (FFT) processing on the interference signal subjected to the window function processing.

The tomographic image generating unit 221 derives each pixel value of the tomographic image based on the generated tomographic data, and generates the tomographic image. Note that the generation method of the tomographic image is not limited to this, and may be performed by a known arbitrary method.

Figure 4A:
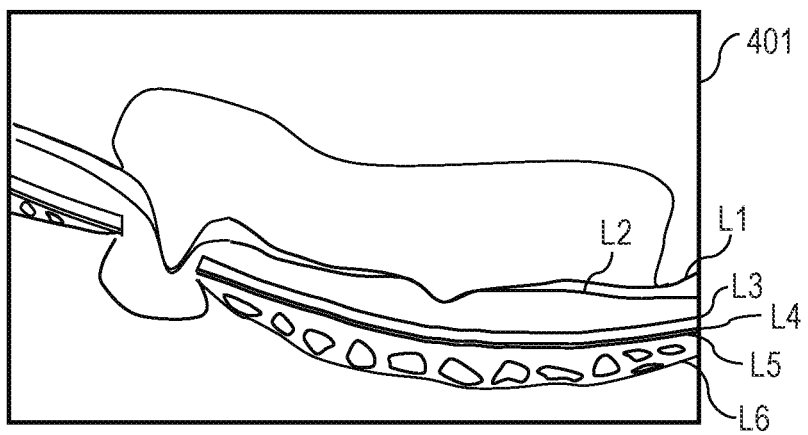
FIG. 4A is a diagram for describing an example of a learning image.
Figure 4B:
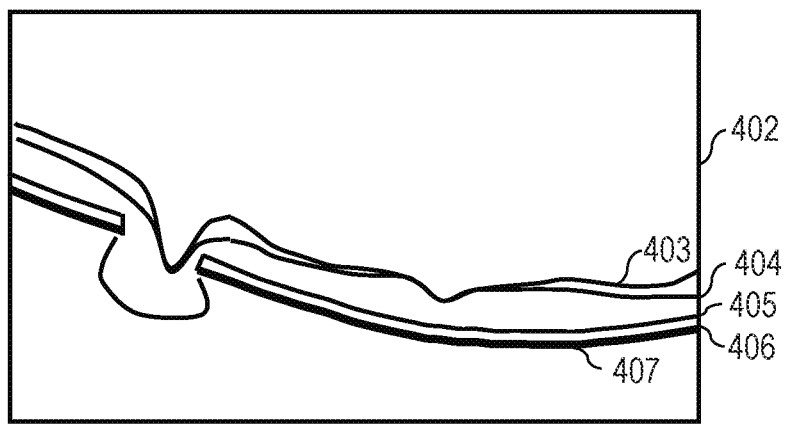
FIG. 4B is a diagram for describing an example of a learning image.

In step S304, the processing unit 222 of the image processing unit 22 performs detection processing of retina layers. Referring to FIG. 4A and FIG. 4B, the processing of the processing unit 222 will be described.

The processing unit 222 detects the boundaries of the retina layers in the plurality of obtained tomographic images by using the OCT apparatus 10. The processing unit 222 detects each retina layer by using a learned model related to a machine learning model for which machine learning has been performed in advance.

Here, referring to FIG. 4A to FIG. 6, a machine learning algorithm according to the present example will be described. The training data for the machine learning model according to the present example includes pairs of one or more input data and ground truth. Specifically, a tomographic image 401 obtained by the OCT is listed as input data, and a boundary image 402 in which the boundaries of the retina layers are specified for the tomographic image is listed as ground truth. In the present example, the image in which a boundary 403 between the ILM and the NFL, a boundary 404 between the NFL and the GCL, an ISOS 405, a RPE 406, and a BM 407 are illustrated is used as the boundary image 402. Note that, although not illustrated, an image in which the boundary between the outside netted layer (OPL) and the outer nuclear layer (ONL), the boundary between the inner plexiform layer (IPL) and the inner nuclear layer (INL), the boundary between the INL and the OPL, the boundary between the GCL and the IPL, etc., are illustrated as the other boundaries may be used.

Note that the boundary image 402 used as the ground truth may be an image in which the boundaries are illustrated in a tomographic image by a doctor, etc., or may be an image in which the boundaries are detected by rule-based boundary detection processing. However, when machine learning is performed by using a boundary image in which the boundary detection is not appropriately performed as the ground truth of training data, an image obtained by using the learned model learned by using the training data may also be a boundary image in which the boundary detection is not appropriately performed. Therefore, the possibility that an inappropriate boundary image is generated by using the learned model can be reduced by removing a pair including such a boundary image from the training data. Here, rule-based processing refers to processing utilizing a known regularity, and the rule-based boundary detection refers to the boundary detection processing utilizing a known regularity, such as the regularity of the shape of a retina.

Additionally, although an example of one certain XZ cross-section in an XY surface of the retina is illustrated in FIG. 4A and FIG. 4B, the cross-section is not limited to this. Although not illustrated, the tomographic images and boundary images for a plurality of arbitrary XZ cross-sections in the XY surface can be learned in advance, so as to be able to correspond to cross-sections imaged by various different scan patterns, such as raster scan and radial scan. For example, when using the data of tomographic images, etc., in which the retina is three-dimensionally imaged by raster scan, the volume data in which alignment among a plurality of adjacent tomographic images is performed can be used for training data. In this case, paired images of an arbitrary angle can be generated from one volume data (three-dimensional tomographic image) and one three-dimensional boundary data (three-dimensional boundary image) corresponding to this. Additionally, the machine learning model may perform learning by using images actually imaged in various scan patterns as training data.

Next, images at the time of learning will be described. Images constituting the pairs of the tomographic image 401 and the boundary image 402, which constitute the training data for the machine learning model, are created with square region images having a constant image size to which positional relationship corresponds. The creation of the images will be described with reference to FIG. 5A to FIG. 5C.

Figure 5A:
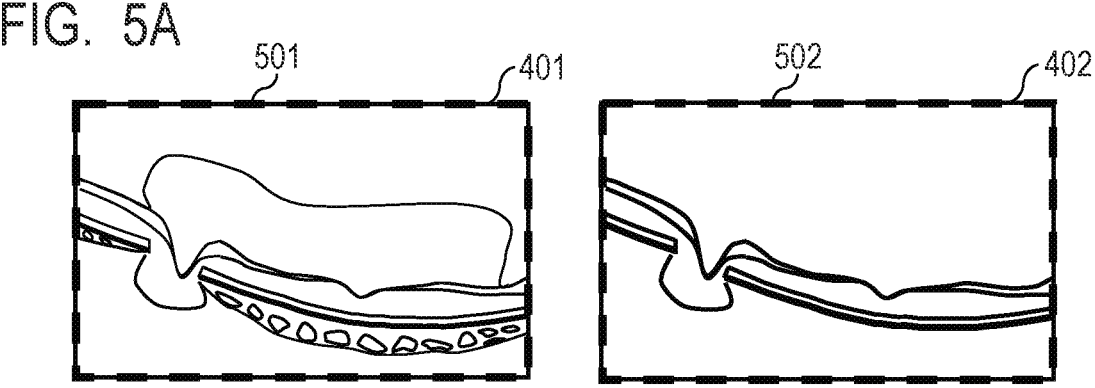
FIG. 5A is a diagram for describing an example of the size of a learning image.

First, a case will be described where one of the pairs constituting the training data is the tomographic image 401 and the boundary image 402. In this case, as illustrated in FIG. 5A, a pair is constituted by using a square region image 501, which is the entire tomographic image 401, as input data, and a square region image 502, which is the entire boundary image 402, as ground truth. Note that, although the pair of the input data and the ground truth is constituted by the respective entire images in the example illustrated in FIG. 5A, the pair is not limited to this.

Figure 5B:
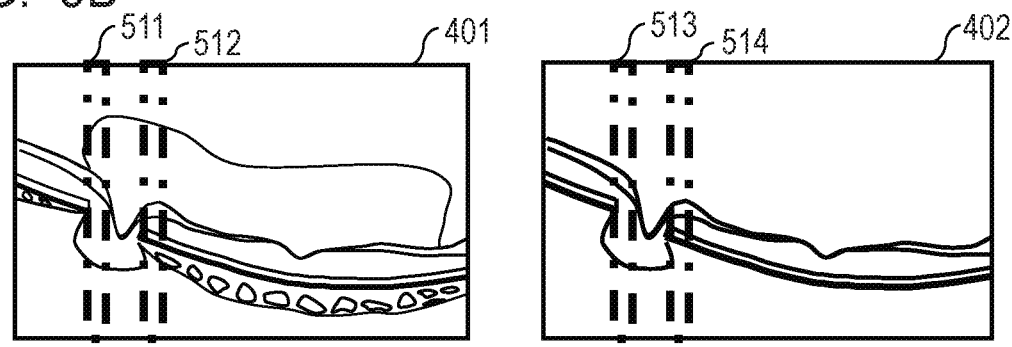
FIG. 5B is a diagram for describing an example of the size of a learning image.

For example, as illustrated in FIG. 5B, the pair may be constituted by using a square region image 511 of the tomographic image 401 as the input data, and a square region image 513, which is a corresponding imaged region in the boundary image 402, as the ground truth. The square regions of the square region images 511 and 513 are based on an A scan unit. The A scan unit may be one A scan unit, or several A scan units.

Note that, although FIG. 5B is based on the A scan unit, the portions outside a square region may be provided up and down for an image without setting the entire depth direction to the region. In other words, the size in the horizontal direction of the square region may be set to several A scans, and the size in the depth direction of the square region may be set smaller than the size in the depth direction of the image.

Figure 5C:
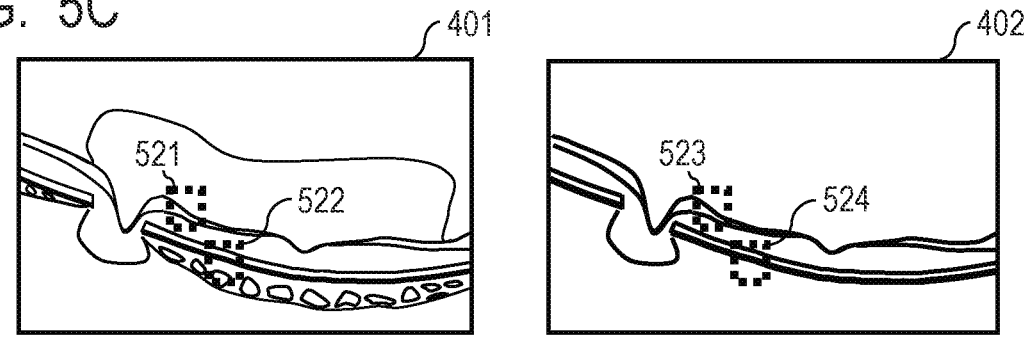
FIG. 5C is a diagram for describing an example of the size of a learning image.

Additionally, as illustrated in FIG. 5C, the pair may be constituted by using a square region image 521 of the tomographic image 401 as the input data, and a square region image 523, which is a corresponding imaged region in the boundary image 402, as the ground truth.

Note that, at the time of learning, the square region size at the time of learning can be made constant by normalizing the scanning range (imaging angle of view) and the scanning density (number of A scans) to align the image size. Additionally, each of the square region images illustrated in FIG. 5A to FIG. 5C is an example of the square region size at the time of learning separately.

The number of square regions can be set to one in the example illustrated in FIG. 5A, and can be set to multiple in the examples illustrated in FIG. 5B and FIG. 5C. For example, in the example illustrated in FIG. 5B, the pair may also be constituted by using a square region image 512 of the tomographic images 401 as the input data, and a square region image 514, which is a corresponding imaged region in the boundary image 402, as the ground truth. Additionally, for example, in the example illustrated in FIG. 5C, the pair may also be constituted by using a square region image 522 of the tomographic images 401 as the input data, and a square region image 524, which is a corresponding imaged region in the boundary image 402, as the ground truth. In this manner, pairs of mutually different square region images can be created from a pair of a single tomographic image and a single boundary image. Note that the pairs constituting the training data can be enriched by creating a large number of pairs of square region images while changing the positions of the regions to different coordinates in the original tomographic image and boundary image.

Although the square regions are discretely illustrated in the examples illustrated in FIG. 5B and FIG. 5C, practically, the original tomographic image and boundary image can be divided into successive square region images having a constant image size without a gap. Additionally, the original tomographic image and boundary image may be divided into mutually corresponding square region images at random positions. In this manner, a lot of pair data can be generated from the tomographic image 401 and the boundary image 402 constituting the original pair, by selecting images of smaller regions as the square regions (or strip regions) for the pair of the input data and the ground truth. Therefore, the time taken for training the machine learning model can be reduced. On the other hand, there is a tendency that the time for image segmentation processing to be performed becomes long in the learned model of the completed machine learning model. Here, the image segmentation processing refers to the processing of identifying and distinguishing regions and boundaries in an image.

Figure 6:
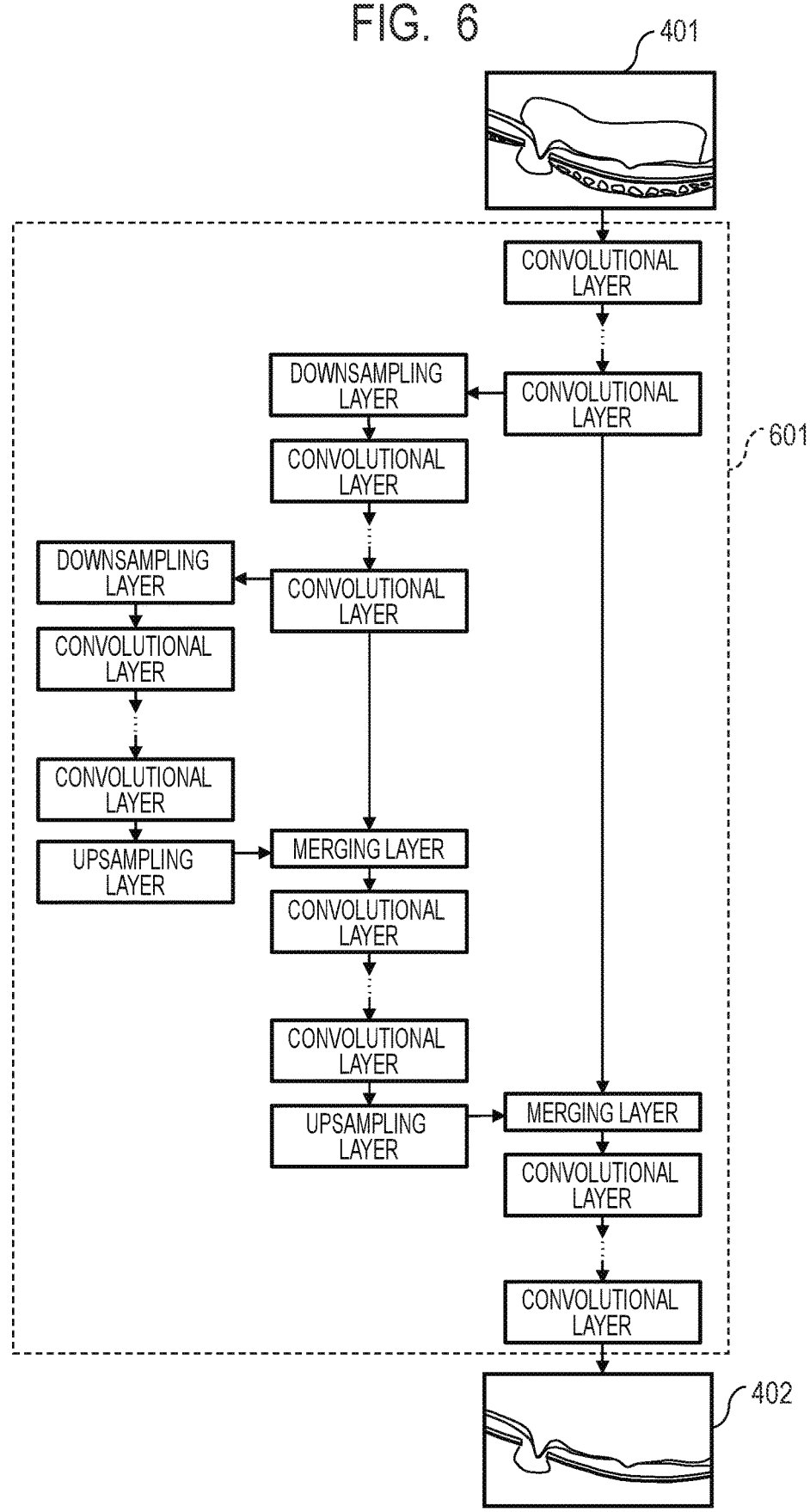
FIG. 6 is a diagram for describing an example of a machine learning model according to Example 1.

Next, a convolutional neural network (CNN) that performs the image segmentation processing on an input tomographic image will be described with reference to FIG. 6, as an example of the machine learning model according to the present example. FIG. 6 illustrates an example of a configuration 601 of the machine learning model in the processing unit 222. Note that, for example, an FCN (Fully Convolutional Network) or a SegNet can also be used as the machine learning model according to the present example. Additionally, a machine learning model that performs object recognition per region according to a desired configuration may be used. For example, a RCNN (Region CNN), a fastRCNN, or a fasterRCNN can be used as the machine learning model that performs object recognition. Further, a YOLO (You Look Only Once) or an SSD (Single Shot MultiBox Detector) can also be used as the machine learning model that performs object recognition per region.

The machine learning model illustrated in FIG. 6 includes a plurality of layers that are responsible for the processing of processing and outputting input values. Note that, as the kinds of the layers included in the configuration 601 of the machine learning model, there are a convolutional (Convolution) layer, a downsampling (Downsampling) layer, an upsampling (Upsampling) layer, and a merging (Merger) layer.

The convolutional layer is a layer that performs the convolutional processing on input values according to parameters, such as the kernel size of a set filter, the number of filters, the value of a stride, and the value of dilation. Note that the number of dimensions of the kernel size of a filter may also be changed according to the number of dimensions of an input image.

The downsampling layer is a layer that performs the processing of making the number of output values less than the number of input values by thinning or combining the input values. Specifically, for example, there is Max Pooling processing as such processing.

The upsampling layer is a layer that performs the processing of making the number of output values more than the number of input values by duplicating the input values or adding a value interpolated from the input values. Specifically, for example, there is linearity interpolation processing as such processing.

The merging layer is a layer to which values, such as the output values of a certain layer and the pixel values constituting an image, are input from a plurality of sources, and that combines them by concatenating or adding them.

Note that the image segmentation processing with a certain accuracy is enabled by, for example, setting the kernel size of a filter to 3 pixels in width, and 3 pixels in height, and setting the number of filters to 64 as the parameters that are set to the convolutional layers included in the configuration 601 illustrated in FIG. 6. However, caution is required, since when the setting of the parameters to the layers and nodes constituting a neural network is different, the degree of tendency trained from the training data that can be reproduced in the output data may be different. In other words, in many cases, since appropriate parameters are different depending on the mode at the time of implementation, the parameters can be changed to preferable values according to the needs.

Additionally, the CNN may obtain better characteristics not only by changing the parameters as described above, but also by changing the configuration of the CNN. The better characteristics are, for example, a high accuracy of the image segmentation processing, a short time for the image segmentation processing, and a short time taken for training of a machine learning model.

Note that the configuration 601 of the CNN used in the present example is a U-net type machine learning model that includes the function of an encoder including a plurality of hierarchies including a plurality of downsampling layers, and the function of a decoder including a plurality of hierarchies including a plurality of upsampling layers. The U-net type machine Teaming model is configured (for example, by using a skip connection) such that the geometry information (space information) that is made ambiguous in the plurality of hierarchies configured as the encoder can be used in a hierarchy of the same dimension (mutually corresponding hierarchy) in the plurality of hierarchies configured as the decoder.

Although not illustrated, as an example of change of the configuration of the CNN, for example, a batch normalization (Batch Normalization) layer, and an activation layer using a normalized linear function (Rectifier Linear Unit) may be incorporated after the convolutional layer.

When data is input to the learned model of such a machine learning model, data according to the design of the machine learning model is output. For example, output data with a high possibility of corresponding to input data is output according to the tendency trained by using the training data.

In the learned model of the processing unit 222 according to the present example, when the tomographic image 401 is input, the boundary image 402 is output according to the tendency trained by using the training data. The processing unit 222 can detect the retina layers and their boundaries in the tomographic image 401 based on the boundary image 402.

Note that, as illustrated in FIG. 5B and FIG. 5C, when the region of an image is divided and learned, the processing unit 222 obtains the square region image, which is a boundary image corresponding to each square region, by using the learned model. Therefore, the processing unit 222 can detect the retina layers in each square region. In this case, the processing unit 222 can generate the boundary image 402 corresponding to the input tomographic image 401 by arranging each of the square region images that are the boundary images obtained by using the learned model in a positional relationship similar to each of the square region images, and combining each of the square region images. Also in this case, the processing unit 222 can detect the retina layers and their boundaries in the tomographic image 401 based on the generated boundary image 402.

In step S304, when the processing unit 222 performs the detection processing of the retina layers, the processing proceeds to step S305. In step S305, the display controlling unit 25 displays the boundaries and the tomographic image that are detected by the processing unit 222 on the display unit 50. Here, FIG. 7 illustrates an example of the screen displayed on the display unit 50.

Figure 7:
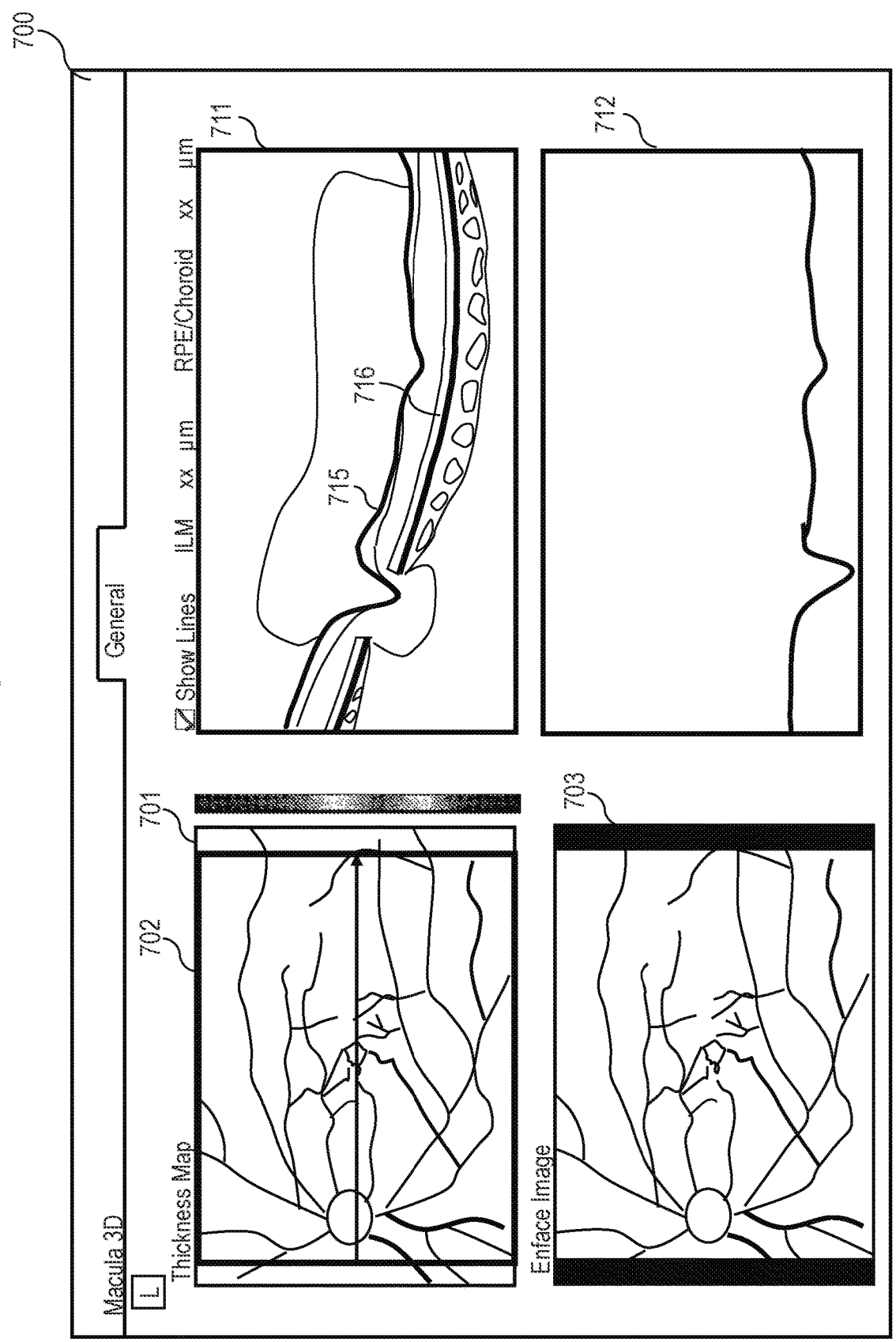
FIG. 7 illustrates an example of a display screen.

A display screen 700 is illustrated in FIG. 7, and an SLO image 701, a thickness map 702 displayed superimposed on the SLO image 701, an En-Face image 703, a tomographic image 711, and a thickness graph 712 of the retina are illustrated in the display screen 700. Boundaries 715 and 716 of the retina are displayed superimposed on the tomographic image 711.

Note that, in the present example, the range of the retina is from the boundary L1 between the inner limiting membrane and the nerve fiber layer to the retinal pigment epithelium L4, and the boundaries 715, 716 correspond to the boundary L1 and the retinal pigment epithelium L4, respectively. The range of the retina is not limited to this, and may be, for example, the range from the boundary L1 between the inner limiting membrane and the nerve fiber layer to the choroid coat L6, and in this case, the boundaries 715, 716 can correspond to the boundary L1 and the choroid coat L6, respectively.

The thickness graph 712 of the retina is a graph that illustrates the thickness of the retina derived from the boundaries 715, 716. Additionally, the thickness map 702 represents the thickness of the retina derived from the boundaries 715, 716 in a color map. Note that, in FIG. 7, although the color information corresponding to the thickness map 702 is not illustrated for description, practically, the thickness map 702 can display the thickness of the retina corresponding to each coordinate in the SLO image 701 according to a corresponding color map.

The En-Face image 703 is a front image generated by projecting the data in the range between the boundaries 715, 716 in the XY direction. The front image is generated by projecting or integrating the data corresponding to the depth range of at least a part of the volume data (three-dimensional tomographic image) obtained by using an optical interference on a two-dimensional plane, the depth range being defined based on two reference surfaces. The En-Face image 703 according to the present example is the front image generated by projecting the data corresponding to the depth range (depth range between the boundaries 715, 716) determined based on the detected retina layers of the volume data on the two-dimensional plane. Note that, as the technique of projecting the data corresponding to the depth range defined based on the two reference surfaces on the two-dimensional plane, for example, the technique can be used that uses representative values of the data in the depth range as pixel values on the two-dimensional plane. Here, the representative values can include values, such as the average value, the median value, or the maximum value of the pixel values, in the range of the depth direction in the region surrounded by the two reference surfaces.

Additionally, the depth range of the En-Face image 703 displayed on the display screen 700 is not limited to the depth range between the boundaries 715, 716. The depth range of the En-Face image 703 may be, for example, a range including a predetermined number of pixels in the deeper direction or the shallower direction, based on one of the two layer boundaries 715, 716 related to the detected retina layers. Additionally, the depth range of the En-Face image 703 may be, for example, an (offset) range that is changed from the range between the two layer boundaries 715, 716 related to the detected retina layers, according to an instruction by the operator.

Note that the front image displayed on the display screen 700 is not limited to the En-Face image based on intensity values (intensity En-Face image). The front image displayed on the display screen 700 may be, for example, a motion contrast front image generated by projecting or integrating the data corresponding to the above-described depth range for the motion contrast data between a plurality of volume data on a two-dimensional plane. Here, the motion contrast data are data indicating the change among a plurality of volume data obtained by controlling such that the measurement light is scanned a plurality of times in the same region (same position) of the eye to be examined. At this time, the volume data is constituted by a plurality of tomographic images obtained at different positions. Then, motion contrast data can be obtained as volume data by obtaining the data indicating the change among the plurality of tomographic images obtained at substantially the same positions in each of the different positions. Note that the motion contrast front image is also called the OCTA front image (OCTA En-Face image) related to the OCT angiography (OCTA) that measures the movement of blood flow, and the motion contrast data is also called the OCTA data. The motion contrast data can be derived as, for example, a decorrelation value between two tomographic images or the interference signals corresponding to these, a variance value, or the value obtained by dividing the maximum value by the minimum value (the maximum value/the minimum value), and may be derived by a known arbitrary method. At this time, the two tomographic images can be obtained by, for example, controlling such that the measurement light is scanned a plurality of times in the same region (same position) of the eye to be examined.

Additionally, three-dimensional OCTA data (OCT volume data) used at the time of generating the OCTA front image may be generated by using at least a part of the interference signals common with the volume data including tomographic images for detecting the retina layers. In this case, the volume data (three-dimensional tomographic image) and the three-dimensional OCTA data can correspond to each other. Therefore, for example, the motion contrast front image corresponding to the depth range determined based on the detected retina layers can be generated, by using the three-dimensional motion contrast data corresponding to the volume data.

Here, the display of the thickness map 702, the En-Face image 703, the thickness graph 712, and the boundaries 715, 716 is an example of what can be generated by the image processing apparatus 20 based on the boundaries and retina layers detected by the processing unit 222. Note that the generation method for generating these may employ a known arbitrary method.

Note that, in addition to these, the display screen 700 of the display unit 50 may be provided with a patient tab, an imaging tab, a report tab, a setting tab, etc. In this case, the content displayed on the display screen 700 of FIG. 7 will be displayed on the report tab. Additionally, a patient information display portion, an examination sorting tab, an examination list, etc., can also be displayed on the display screen 700. The thumbnails of a fundus image, a tomographic image, and an OCTA image may be displayed in the examination list.

Next, in step S306, the obtaining unit 21 obtains, from the outside, an instruction of whether or not to end a series of processing related to the imaging of tomographic images by the image processing system 1. This instruction can be input by the operator by using the input unit 60. When the obtaining unit 21 obtains the instruction to end the processing, the image processing system 1 ends the series of processing according to the present example. On the other hand, when the obtaining unit 21 obtains the instruction of not to end the processing, the processing is returned to step S302 and the imaging is continued.

As described above, the image processing apparatus 20 according to the present example includes the obtaining unit 21, and the processing unit 222 (the first processing unit). The obtaining unit 21 obtains a tomographic image of the eye to be examined. The processing unit 222 performs first detection processing for detecting at least one retina layer among a plurality of retina layers of the eye to be examined in the tomographic image by using the learned model.

When performing the image segmentation processing by using the learned model, the boundary detection can be appropriately performed according to the learned tendency also for, for example, the change in the layer structure due to the pathological change in a disease eye. Therefore, in the image processing apparatus 20 according to the present example, by performing the image segmentation processing by using the learned model, the boundary detection can be performed irrespective of diseases, sites, etc., and the accuracy of the boundary detection can be improved.

Additionally, the image processing apparatus 20 further includes the image processing unit 22 that generates a front image corresponding to the depth range of at least a part of a three-dimensional tomographic image of the eye to be examined, the depth range being determined based on the detected at least one retina layer. The image processing unit 22 can generate a motion contrast front image corresponding to the determined depth range by using the three-dimensional motion contrast data corresponding to the three-dimensional tomographic image.

Note that, although the configuration that performs the image segmentation processing by using one learned model has been described in the present example, the image segmentation processing may be performed by using a plurality of learned models.

Since the learned model generates output data according to the tendency of learning that uses the training data as described above, the reproducibility of the tendency of learning with respect to the output data can be improved by performing learning by using training data with a similar tendency for characteristics. Therefore, for example, a more accurate boundary image can be generated by performing the image segmentation processing for a tomographic image of a corresponding imaged site by using a plurality of learned models for which learning has been performed for each imaged site. In this case, the image processing system can detect the retina layers more accurately. In addition, in this case, since the learning models can also be additionally increased, upgrading the version so as to gradually improve the performance can also be expected.

Further, the processing unit 222 may generate the final output of the processing unit 222 by using a plurality of learning models for which learning has been performed for each region, such as a region near the vitreous body, a retina region, and a region near sclera in a tomographic image, and combining the outputs of the respective learning models. In this case, since a more accurate boundary image can be generated for each region, the retina layers can be detected more accurately.

Additionally, in the present example, although the machine learning model that performs the image segmentation processing has been described as the machine learning model, for example, a machine learning model that estimates the imaged site of a tomographic image can also be used.

Generally, the configuration of a machine learning model is not limited to the configuration that outputs an image corresponding to an image that is the input data. For example, a machine learning model may be configured such that, with respect to the input data, the kinds of output data trained by using training data may be output, or the probability may be output as a numerical value for each of the kinds. Therefore, the format and combination of the input data and ground truth of the pairs constituting the training data can be made suitable for a utilization form, such as one is an image and the other is a numerical value, one includes a plurality of images and the other is a character string, or both are images.

As an example of the training data for the machine learning model that estimates an imaged site, specifically, the training data including pairs of a tomographic image obtained by OCT and an imaged site label corresponding to the tomographic image can be listed. Here, the imaged site label is the unique numerical value or character string representing a site. When a tomographic image obtained by using the OCT is input to the learned model that has been trained by using such training data, the imaged site label of a site currently being imaged is output in an image, or depending on a design, the probability for each imaged site label is output.

The processing unit 222 may perform the image segmentation processing by further using the learned model that estimates such an imaged site to estimate the imaged site of a tomographic image, and using the learned model according to the estimated imaged site or the imaged site with the highest probability. With such a configuration, even when the obtaining unit 21 cannot obtain the imaging condition for the imaged site of a tomographic image, the retina layers can be detected more accurately by estimating the imaged site from the tomographic image, and performing the image segmentation processing corresponding to the imaged site.

Example 2

In Example 1, the image segmentation processing that detects all the target retina layers from a tomographic image is performed by using the learned model. In contrast, in Example 2, the boundary detection according to rule-based image characteristics is performed based on the detection result of the retina region by the learned model.

Conventionally, although the detection of the opening end of the Bruch's membrane is usually performed when performing the detection of the Cup (optic disc cupping) and the Disc (optic nerve head) by using an OCT image in the optic nerve head, in the case of peripapillary chorioretinal atrophy, its detection has been sometimes difficult.

Additionally, in the conventional rule-based image segmentation processing, the robustness to the individual differences and the pathological change in an eye to be examined was low, and the retina region could be initially and erroneously detected. In this case, the subsequent inner retinal layer boundary detection could not be appropriately performed.

In contrast, the accuracy of the boundary detection can be improved by performing the image segmentation processing by using a machine learning model. However, when performing the recognition of an imaged site and the boundary detection of the retina layers by using a machine learning model with machine learning algorithms such as deep learning, since it is the medical image field, it is generally very difficult to collect the number of cases of normal images and lesion images with correct answers. Further, it also takes time to create correct answer data for learning.

Therefore, in the present example, the retina region is detected by using a learned model, and the boundary detection by the image characteristic is used together for the detected retina region. Accordingly, since the erroneous detection of the retina region is suppressed, the detection accuracy of the inner retinal layer boundaries is improved, and in the process of machine learning, only the correct answer data for the retina layers or else may be created at the time of learning, learning can be efficiently performed.

Hereinafter, referring to FIG. 8 to FIG. 13D, an image processing system 8 according to the present example will be described. Hereinafter, the differences from the image processing according to Example 1 will be mainly described for the image processing by the image processing system according to the present example. Note that the configuration and processing of the image processing system according to the present example that are similar to the configuration and processing of the image processing system 1 according to Example 1 will be illustrated by using the same reference numerals, and a description will be omitted.

Figure 8:
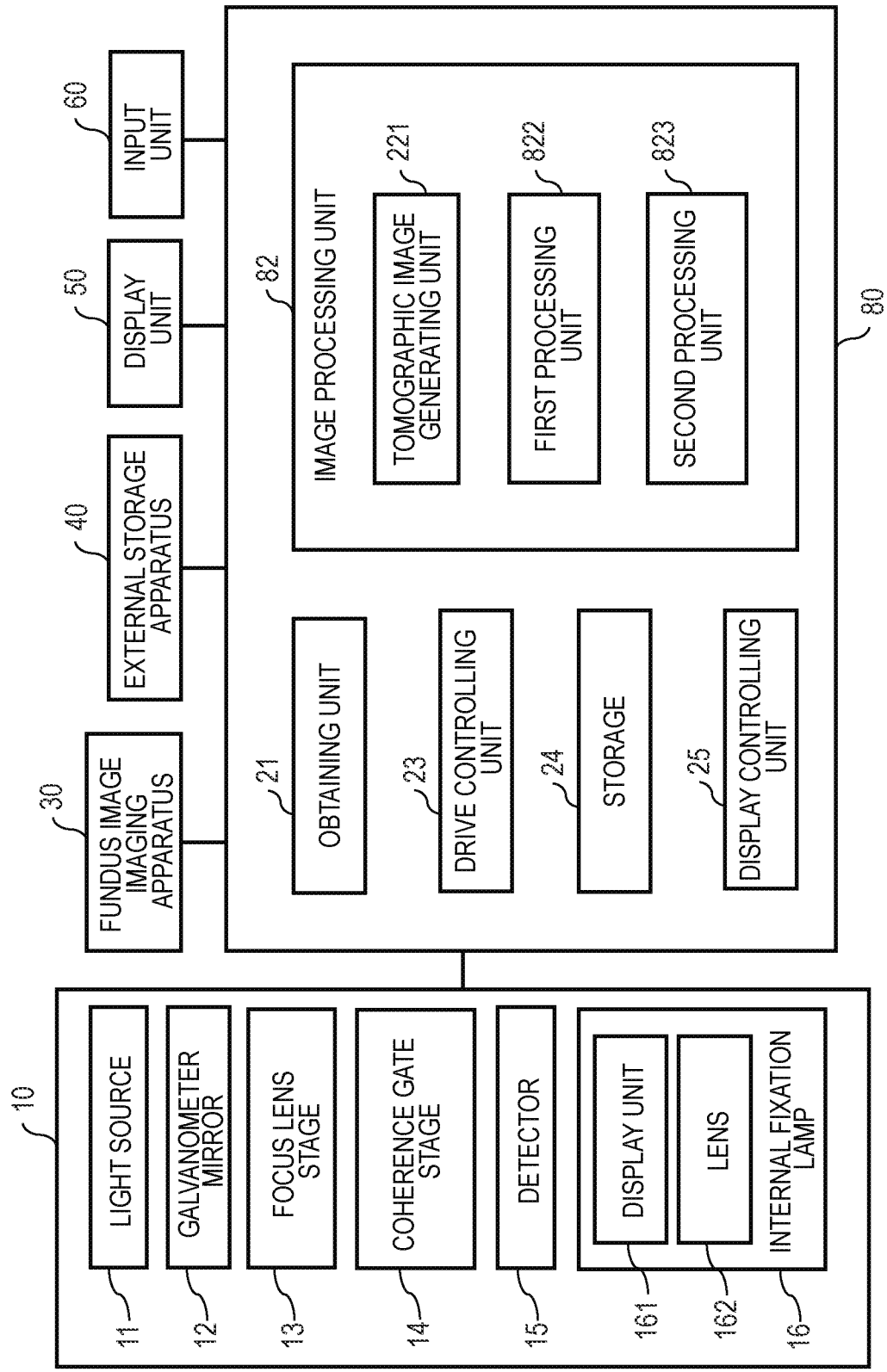
FIG. 8 illustrates an example of the schematic configuration of an image processing system according to Example 2.

FIG. 8 illustrates an example of the schematic configuration of the image processing system 8 according to the present example. In the image processing system 8, in an image processing unit 82 of an image processing apparatus 80, a first processing unit 822 and a second processing unit 823 are provided instead of the processing unit 222.

The first processing unit 822 includes a learned model for a machine learning model with machine learning algorithms, such as deep learning, and detects the retina region in a tomographic image by using the learned model. The second processing unit 823 performs the boundary detection of the retina layers by determining the result of image characteristic extraction in a rule-based manner for the retina region detected by the first processing unit 822.

Figure 9A:
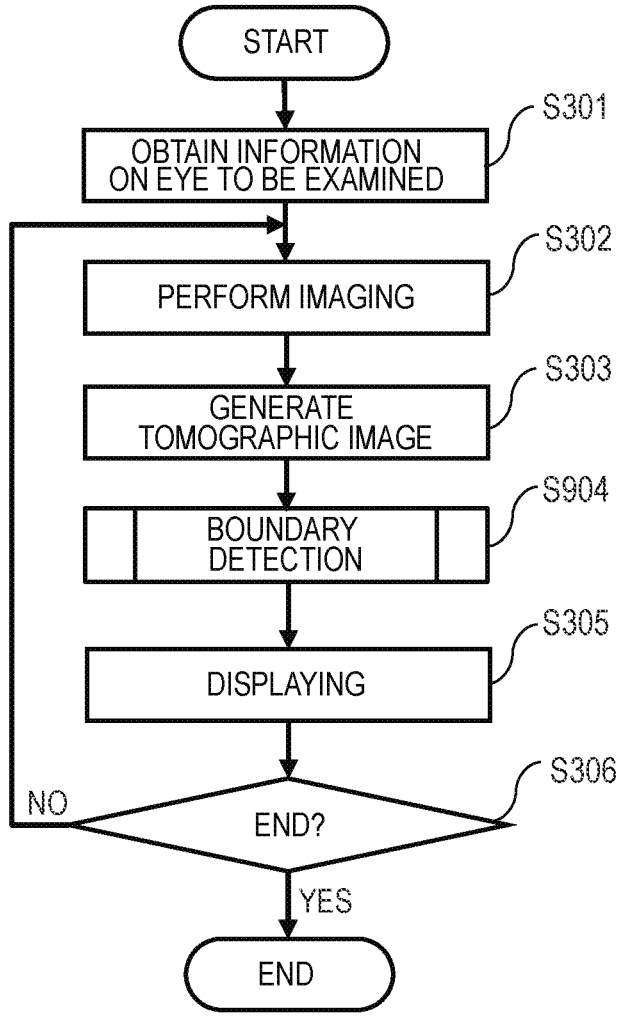
FIG. 9A is a flowchart of a series of processing according to Example 2.
Figure 9B:
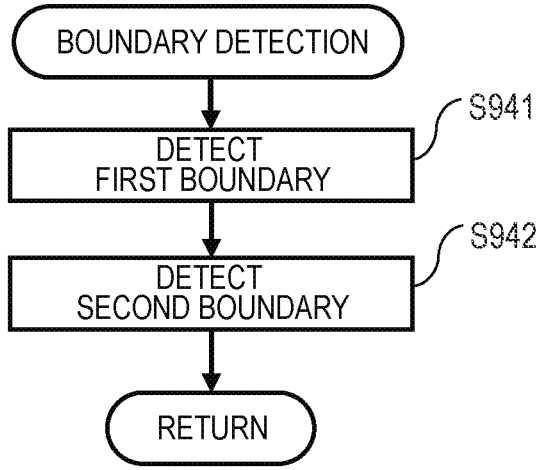
FIG. 9B is a flowchart of boundary detection processing according to Example 2.

Next, referring to FIG. 9A and FIG. 9B, a series of processing according to the present example will be described. FIG. 9A is a flowchart of the series of processing according to the present example, and FIG. 9B is a flowchart of boundary detection processing in the present example. Note that, since the processing other than the boundary detection processing are similar to the processing in Example 1, a description will be omitted. When a tomographic image is generated in step S303, the processing proceeds to step S904.

When the boundary detection processing in step S904 is started, the processing proceeds to step S941. In step S941, the first processing unit 822 detects the retina region in the tomographic image by using the learned model as a first boundary detection processing.

Here, referring to FIG. 10A to FIG. 12, the machine learning model according to the present example will be described. The training data for the machine learning model according to the present example includes pairs of one or more input data and ground truth. As an example of the training data, training data, etc., can be listed that includes pairs of a tomographic image 1001 obtained by the imaging by the OCT illustrated in FIG. 10A, and a label image 1002 that is illustrated in FIG. 10B and in which labels are given to arbitrary layers in the tomographic image 1001.

Here, the label image is an image (image obtained by annotation) in which labeling is performed for each pixel, and in the present example, the label image is an image in which a label is given to each pixel, the label being related to an image appearing (being imaged) in the pixel. In the label image 1002, a label 1003 on the shallower side (vitreous body side) than the retina, a label 1004 for the inner retinal layer, and a label 1005 on the deeper side (choroid coat side) than the retina are given as examples of labels. The first processing unit 822 in the present example detects the inner retinal layer based on such a label image. Note that the range of the retina (the range of the inner retinal layer) is from the boundary L1 between the inner limiting membrane and the nerve fiber layer to the retinal pigment epithelium L4 in the present example, but is not limited to this. For example, the range of the retina may be defined as the range from the boundary LI between the inner limiting membrane and the nerve fiber layer to the photoreceptor inner segment-outer segment junction L3, the range from the boundary L between the inner limiting membrane and the nerve fiber layer to the Bruch's membrane L5, or the range of from the boundary L1 between the inner limiting membrane and the nerve fiber layer to the choroid coat L6.

Figure 10A:
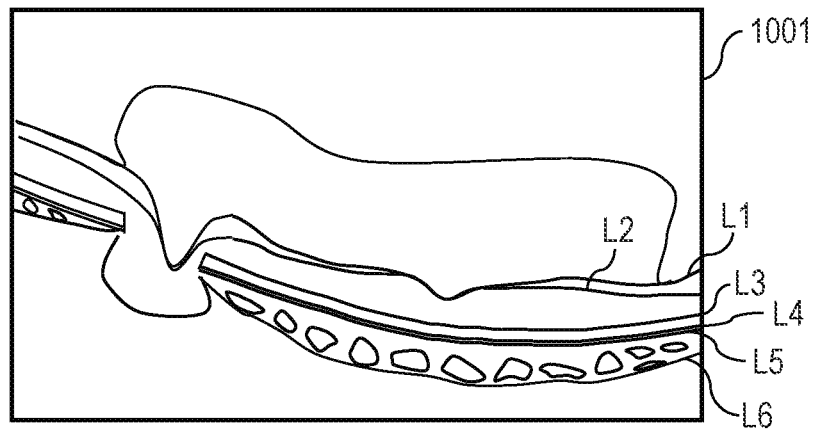
FIG. 10A is a diagram for describing detection of a retina region.
Figure 10B:
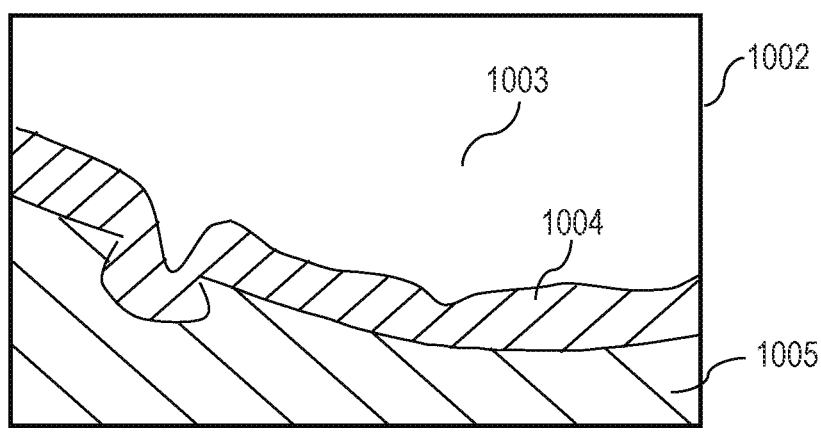
FIG. 10B is a diagram for describing detection of a retina region.

Further, although an example of one XZ cross-section in the XY surface of the retina is illustrated in FIG. 10A and FIG. 10B, the cross-section is not limited to this. Although not illustrated, a plurality of arbitrary XZ cross-sections in the XY surface may be learned in advance, and the learned model can be made to deal with cross-sections imaged by different various scanning patterns, such as raster scan and radial scan. For example, when using the data of tomographic images, etc., in which the retina is three-dimensionally imaged by raster scan, the volume data in which alignment among a plurality of adjacent tomographic images is performed can be used for training data. In this case, paired images of an arbitrary angle can be generated from one volume data and one three-dimensional label data (three-dimensional label image) corresponding to this. Additionally, the machine learning model may perform learning by using images actually imaged in various scan patterns as training images.

Next, images at the time of learning will be described. Images constituting the pairs of the tomographic image 1001 and the label image 1002, which constitute the training data for the machine learning model, are created with square region images having a constant image size to which positional relationship corresponds. The creation of the images will be described with reference to FIG. 11A to FIG. 11C.

Figure 11A:
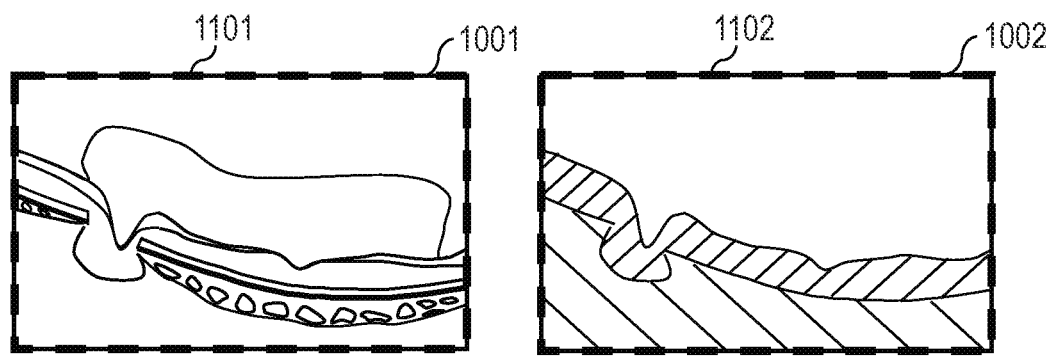
FIG. 11A is a diagram for describing an example of the size of a learning image.

First, a case will be described where one of the pairs constituting the training data is the tomographic image 1001 and the label image 1002. In this case, as illustrated in FIG. 11A, a pair is constituted by using a square region image 1101, which is the entire tomographic image 1001, as input data, and a square region image 1102, which is the entire label image 1002, as ground truth. Note that, although the pair of the input data and the ground truth is constituted by the respective entire images in the example illustrated in FIG. 11A, the pair is not limited to this.

Figure 11B:
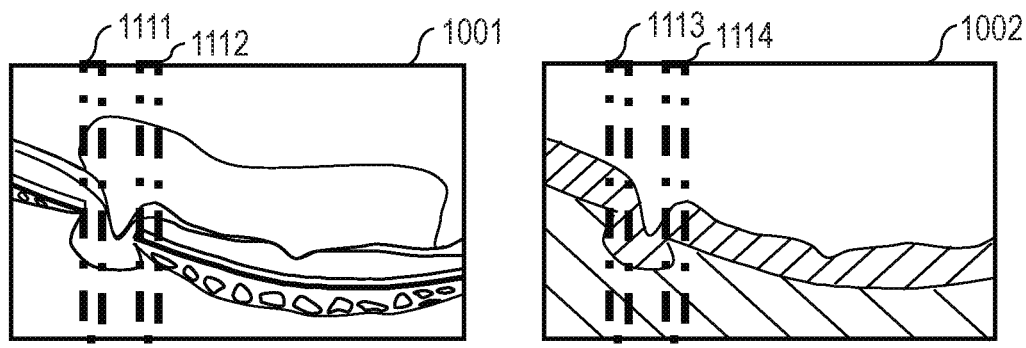
FIG. 11B is a diagram for describing an example of the size of a learning image.

For example, as illustrated in FIG. 11B, the pair may be constituted by using a square region image 1111 of the tomographic image 1001 as the input data, and a square region image 1113, which is a corresponding imaged region in the label image 1002, as the ground truth. The square region images 1111, 1113 are based on the A scan unit. The A scan unit may be one A scan unit, or several A scan units.

Note that, although FIG. 11B is based on the A scan unit, the portions outside a square region may be provided up and down for an image without setting the entire depth direction to the region. In other words, the size in the horizontal direction of the square region may be set to several A scans, and the size in the depth direction of the square region may be set smaller than the size in the depth direction of the image.

Figure 11C:
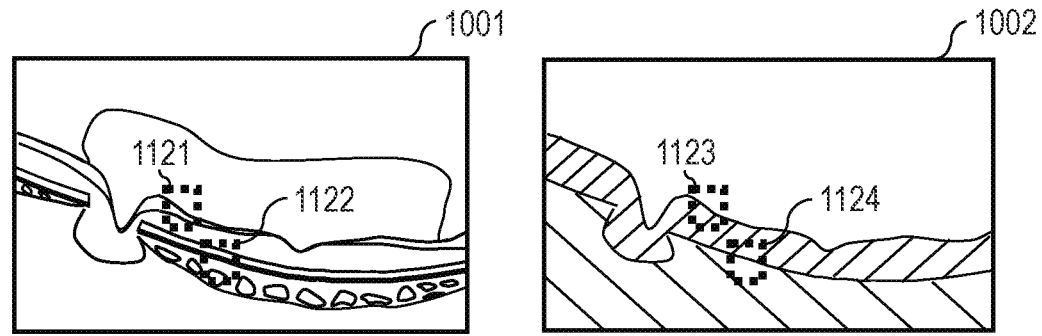
FIG. 11C is a diagram for describing an example of the size of a learning image.

Additionally, as illustrated in FIG. 11C, the pair may be constituted by using a square region image 1121 of the tomographic image 1001 as the input data, and a square region image 1123, which is a corresponding imaged region in the label image 1002, as the ground truth. In this case, it is assumed that the size of the square region is the size including a plurality of labels in one square region.

Note that, at the time of learning, the square region size at the time of learning can be made constant by normalizing the scanning range (imaging angle of view) and the scanning density (number of A scans) to align the image size. Additionally, each of the square region images illustrated in FIG. 11A to FIG. 11C is an example of the square region size at the time of learning separately.

The number of square regions can be set to one in the example illustrated in FIG. 11A, and can be set to multiple in the examples illustrated in FIG. 11B and FIG. 11C. For example, in the example illustrated in FIG. 11B, the pair may also be constituted by using a square region image 1112 of the tomographic images 1001 as the input data, and a square region image 1114, which is a corresponding imaged region in the label image 1002, as the ground truth. Additionally, for example, in the example illustrated in FIG. 11C, the pair may also be constituted by using a square region image 1122 of the tomographic images 1001 as the input data, and a square region image 1124, which is a corresponding imaged region in the label image 1002, as the ground truth. In this manner, pairs of mutually different square region images can be created from a pair of a single tomographic image and a single label image. Note that the pairs constituting the training data can be enriched by creating a large number of pairs of square region images while changing the positions of the regions to different coordinates in the original tomographic image and label image.

Although the square regions are discretely illustrated in the examples illustrated in FIG. 11B and FIG. 11C, practically, the original tomographic image and label image can be divided into successive square region images having a constant image size without a gap. Additionally, the original tomographic image and label image may be divided into mutually corresponding square region images at random positions. In this manner, a lot of pair data can be generated from the tomographic image 1001 and the label image 1002 constituting the original pair, by selecting images of smaller regions as the square regions (or strip regions) for the pair of the input data and the ground truth. Therefore, the time taken for training the machine learning model can be reduced. On the other hand, there is a tendency that the time for image segmentation processing to be performed becomes long in the learned model of the completed machine learning model.

Figure 12:
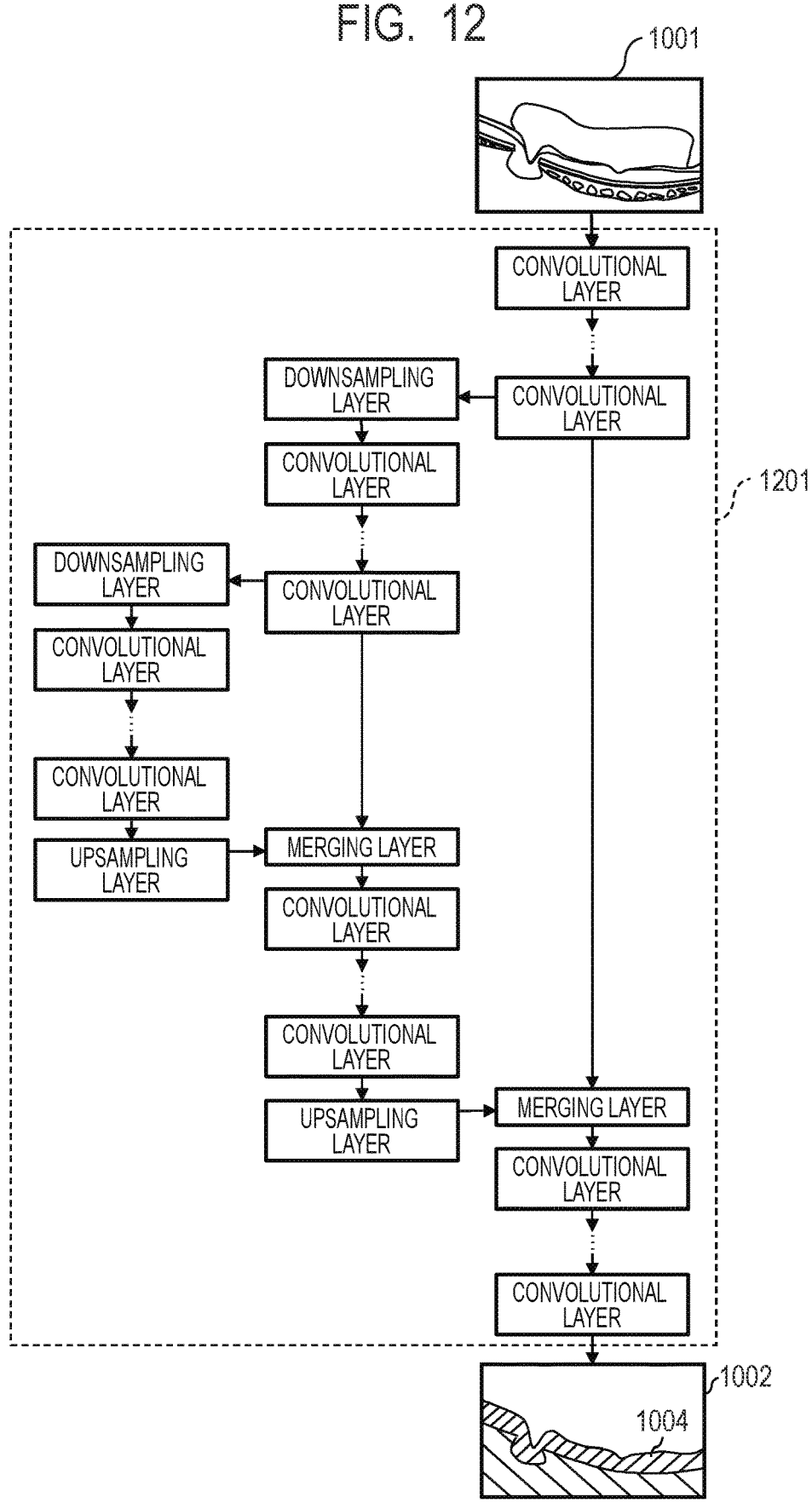
FIG. 12 is a diagram for describing an example of a machine learning model according to Example 2.

Next, a configuration of a convolutional neural network (CNN) that performs the image segmentation processing on an input tomographic image will be described with reference to FIG. 12, as an example of the machine learning model according to the present example. FIG. 12 illustrates an example of a configuration 1201 of the machine learning model in the first processing unit 822. Note that, for example, an FCN or a SegNet can also be used as the machine learning model according to the present example, similar to Example 1. Additionally, the machine learning model that performs object recognition per region as described in Example 1 according to a desired configuration may be used.

Similar to the example of the machine learning model according to Example 1 illustrated in FIG. 6, the machine learning model illustrated in FIG. 12 includes a plurality of layers that are responsible for the processing of processing and outputting input values. As the kinds of the layers included in the configuration 1201 of the machine learning model, there are a convolutional layer, a downsampling layer, an upsampling layer, and a merging layer. Note that, since the configurations of these layers, and modifications of the configuration of the CNN are similar to those in the machine learning model according to Example 1, a detailed description will be omitted. Note that, similar to the configuration 601 of the CNN described in Example 1, the configuration 1201 of the CNN used in the present example is a U-net type machine learning model.

In the learned model of the first processing unit 822 according to the present example, when the tomographic image 1001 is input, the label image 1002 is output according to the tendency trained by using the training data. The first processing unit 822 can detect the retina region in the tomographic image 1001 based on the label image 1002.

Note that, as illustrated in FIG. 11B and FIG. 11C, when the region of an image is divided and learned, the first processing unit 822 obtains the square region image, which is a label image corresponding to each square region, by using the learned model. Therefore, the first processing unit 822 can detect the retina layers in each square region. In this case, the first processing unit 822 arranges each of the square region images that are label images obtained by using the learned model in a positional relationship similar to each of the square region images, and combines each of the square region images. Accordingly, the first processing unit 822 can generate the label image 1002 corresponding to the input tomographic image 1001. Also in this case, the first processing unit 822 can detect the retina region in the tomographic image 1001 based on the generated label image 1002.

In step S941, when the retina region is detected by the first processing unit 822, the processing proceeds to step S942. In step S942, the second processing unit 823 detects, as second detection processing, the remaining boundaries in the inner retinal layer by rule-based image segmentation processing based on the retina region detected by the first processing unit 822 in the tomographic image 1001 illustrated in FIG. 10A.

Figure 13A:
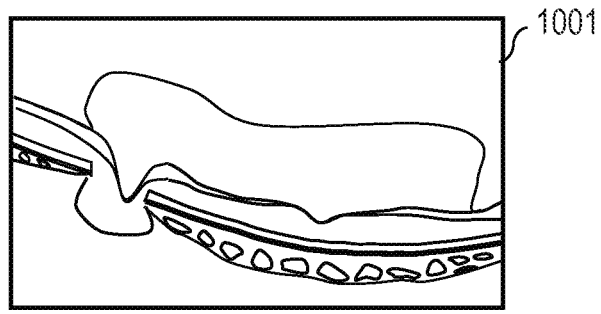
FIG. 13A is a diagram for describing retina layer detection according to Example 2.
Figure 13B:
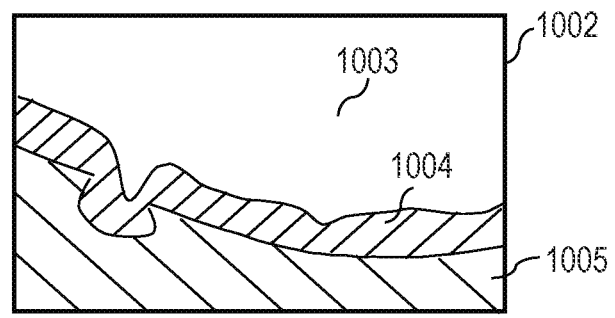
FIG. 13B is a diagram for describing the retina layer detection according to Example 2.

With referring to FIG. 13A to FIG. 13D, second boundary detection processing by the second processing unit 823 will be described. FIG. 13A illustrates the tomographic image 1001, which is an example of the tomographic image used as an input. FIG. 13B is the label image 1002 output by the first processing unit 822, and is the image to which the label 1004 of the retina region, and the labels 1003, 1005 corresponding to the others are given. The second processing unit 823 according to the present example uses the range of the retina region indicated by the label 1004 in the label image 1002 as the target region for layer detection.

Figure 13C:
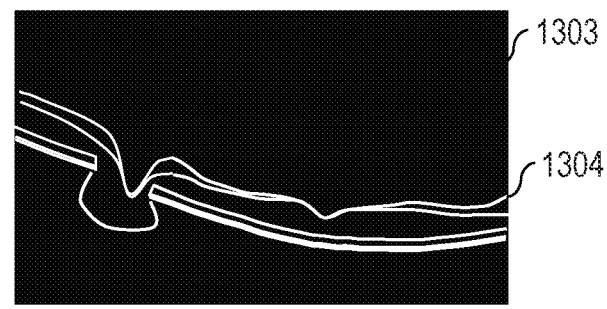
FIG. 13C is a diagram for describing the retina layer detection according to Example 2.
Figure 13D:
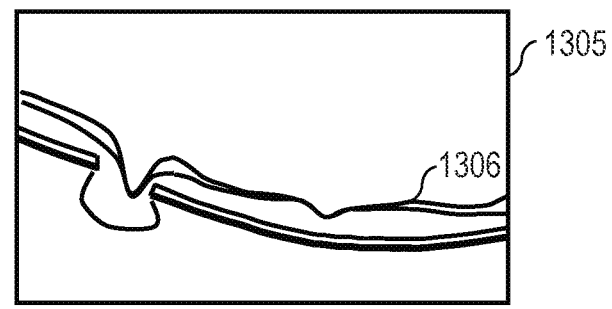
FIG. 13D is a diagram for describing the retina layer detection according to Example 2.

The second processing unit 823 can detect target boundaries by detecting outlines in the retina region indicated by the label 1004 in the label image 1002. FIG. 13C illustrates an edge enhancement processing image 1303 on which the second processing unit 823 has performed processing. The processing by the second processing unit 823 will be described below. Note that, as illustrated in FIG. 13C and FIG. 13D, since the retina layers are interrupted, the boundary detection by the second processing unit 823 is not performed for the optic nerve head.

The second processing unit 823 performs noise removal and edge enhancement processing on the region corresponding to the label 1004 in the tomographic image 1001 to be processed. The second processing unit 823 applies, for example, a median filter or a Gaussian filter as the noise removal processing. Additionally, the second processing unit 823 applies a Sobel filter or a Hessian filter as the edge enhancement processing.

Here, the edge enhancement processing for a two-dimensional tomographic image using a two-dimensional Hessian filter will be described. The Hessian filter can emphasize the secondary local structure of two-dimensional shading distribution based on the relationship between two eigenvalues ($\lambda_1$, $\lambda_2$) of a Hesse matrix. Therefore, in the present example, a two-dimensional line structure is emphasized by using the relationship between the eigenvalues and eigenvectors ($e_1$, $e_2$) of a Hesse matrix. Since the line structure in a two-dimensional tomographic image for the eye to be examined corresponds to the structure of the retina layers, the structure of the retina layers can be emphasized by applying the Hessian filter.

Note that, in order to detect the retina layers having different thicknesses, the resolution of smoothing by a Gaussian function performed at the time of calculating a Hesse matrix may be changed. Additionally, when applying a two-dimensional Hessian filter, the two-dimensional Hessian filter can be applied after transforming data so as to adjust the XZ physical size of an image. In the case of a general OCT, the physical sizes in the XY direction and the Z direction are different. Therefore, a filter is applied by adjusting the physical size of the retina layers for each pixel. Note that, since the physical sizes in the XY direction and the Z direction can be grasped from the design/configuration of the OCT apparatus 10, the data of a tomographic image can be transformed based on the physical sizes. Additionally, when the physical sizes are not normalized, it can also be approximately corresponded by changing the resolution of smoothing by a Gaussian function.

In the above, although the processing with the two-dimensional tomographic image has been described, the object to which a Hessian filter is applied is not limited to this. When the data structure at the time of imaging a tomographic image is a three-dimensional tomographic image by raster scan, a three-dimensional Hessian filter can also be applied. In this case, after the image processing unit 82 performs alignment processing in the XZ direction between adjacent tomographic images, the second processing unit 823 can emphasize the secondary local structure of three-dimensional shading distribution based on the relationship between three eigenvalues ($\lambda_1$, $\lambda_2$, $\lambda_3$) of a Hesse matrix. Therefore, edges can also be three-dimensionally emphasized by emphasizing a three-dimensional layer structure by using the relationship between the eigenvalues and eigenvectors ($e_1$, $e_2$, $e_3$) of a Hesse matrix.

In the edge enhancement processing image 1303, the portion in which edges are emphasized appears as a white line 1304. Note that regions in the tomographic image 1001 that do not correspond to the label 1004 can be treated as regions in which edges are not detected. Additionally, although the configuration of performing the edge enhancement processing by using the Hessian filter has been described here, the processing method of the edge enhancement processing is not limited to this, and may be performed by an existing arbitrary method.

FIG. 13D illustrates a boundary image 1305 illustrating the boundaries of the retina layers detected by the second processing unit 823 by using the label image 1002 and the edge enhancement processing image 1303. In the boundary image 1305, a black line 1306 indicates an example of the boundaries. The processing of detecting the boundaries of the retina layers from the label image 1002 and the edge enhancement processing image 1303 by the second processing unit 823 will be described below.

The second processing unit 823 detects the edge emphasized boundaries from the edge enhancement processing image 1303. In the present example, since the first processing unit 822 has already detected the boundary between the ILM and the NFL, and the RPE, the second processing unit 823 subsequently detects the ISOS, and the boundary between the NFL and the GCL. Note that, although not illustrated, the boundary between the outer plexiform layer (OPL) and the outer nuclear layer (ONL), the boundary between the inner plexiform layer (IPL) and the inner nuclear layer (INL), the boundary between the INL and the OPL, the boundary between the GCL and the IPL, etc., may be detected as the other boundaries.

As the detection method of boundaries, a plurality of locations with strong edge strength are detected as boundary candidates in each A scan, and dots (locations with strong edge strength) are connected as a line based on the continuity of boundary candidates in adjacent A scans. Additionally, when dots are connected as a line, the second processing unit 823 can remove outliers by evaluating the smoothness of the line. More specifically, for example, the positions in the Z direction of connected dots are compared, and when the difference between the positions in the Z direction is greater than a predetermined threshold value, a newly connected dot can be determined as an outlier, and can be excluded from the connecting processing. Additionally, when an outlier is removed, a boundary candidate in the A scan adjacent to the A scan position of the excluded point may be connected as a line. Note that the removal method of outliers is not limited to this, and may be performed by an existing arbitrary method.

The second processing unit 823 determines a corresponding boundary for each line formed by connecting dots, based on the vertical distance in the Z direction of the boundaries of the retina layers and the positional relationship. Note that, when there is no boundary detected as a result of removing the outliers in each A scan, a boundary may be derived by interpolation from peripheral boundaries. Additionally, a boundary candidate may be searched in the horizontal direction (X or Y direction) from the peripheral boundaries by relying on edges, and a boundary may be determined again based on the boundary candidate searched from the peripheral boundaries.

Then, the second processing unit 823 performs processing of correcting the shapes of boundaries to be smooth on the detected boundaries. For example, the shapes of boundaries may be smoothed by using image characteristics and shape characteristics with a dynamic contour model, such as the Snakes and the Level Set method. Additionally, considering that the coordinate values of the boundary shapes are time series data with signals, the shapes may be smoothed by smoothing processing, such as a Savitzky-Golay filter, simple moving average, weighted moving average, and exponential moving average.

With such processing, the second processing unit 823 can detect the retina layers in the retina region detected by the first processing unit 822. Note that the detection processing of the retina layers by the second processing unit 823 described above is an example, and the retina layers can also be detected by using existing arbitrary segmentation processing. When the second processing unit 823 detects the retina layers, the processing proceeds to step S305. Since the subsequent processing are similar to those of Example 1, a description will be omitted.

As described above, the image processing apparatus 80 according to the present example includes the obtaining unit 21, the first processing unit 822, and the second processing unit 823. The obtaining unit 21 obtains a tomographic image of the eye to be examined. The first processing unit 822 performs the first detection processing for detecting at least one retina layer among a plurality of retina layers of the eye to be examined in a tomographic image by using the learned model. The second processing unit 823 performs the second detection processing for detecting at least one retina layer among the plurality of retina layers in the tomographic image without using the learned model.

Specifically, the second processing unit 823 detects, by the second detection processing, at least one retina layer other than the at least one retina layer detected by the first detection processing. Especially, in the present example, the first detection processing is processing that detects layers from the boundary between the inner limiting membrane and the nerve fiber layer of the eye to be examined to one of the photoreceptor inner segment-outer segment junction, the retinal pigment epithelium, and the Bruch's membrane. Additionally, the second detection processing is processing that is performed after the first detection processing, and that detects at least one retina layer included in the layers detected by the first detection processing, that is, at least one retina layer between the detected layers.

In the image processing apparatus 80 according to the present example, the boundary detection can be performed regardless of diseases, sites, etc. Additionally, the accuracy of the boundary detection can be improved by using the boundary detection by the image characteristics together for the region output by the machine learning model. Further, in the process of machine learning, since only the correct answer data for the retina layers or else may be created at the time of learning, learning can also be efficiently performed.

Additionally, when the boundaries detected by the machine learning model are increased, the possibility that erroneous detection occurs in output label images and boundary images may be increased. On the other hand, in the detection of the retina region using the machine learning model according to the present example, since there are few boundaries to be detected, the erroneous detection in output label images and boundary images can be suppressed.

Note that, also in the present example, similar to Example 1, the first processing unit 822 may be configured to perform the detection of the retina region by using a plurality of machine learning models. In this case, the accuracy of the detection of the retina region can be improved. Additionally, since the learning models can also be additionally increased, upgrading the version so as to gradually improve the performance can also be expected.

Modification of Example 2

In above-described Example 2, the example has been illustrated that performs the detection of the retina region by the first processing unit 822 by using the learned model as a preliminary stage, prior to the detection of the boundaries of the retina by the second processing unit 823 based on a rule base. However, the order of the processing by the first processing unit 822 and the processing by the second processing unit 823 is not limited to this. For example, when the detection of the retina region by the first processing unit 822 is very time-consuming, the detection processing of the retina region can be performed first by the second processing unit 823 by a rule base.

In such a case, the second processing unit 823 first detects the boundary between the ILM and the NFL, and the RPE or the ISOS by using a method similar to the method by the second processing unit 823 illustrated in Example 2. This is because these boundaries are at locations with high intensity values, and are boundaries located in a shallow layer portion and a deep layer portion of the retina. When detecting the boundary between the ILM and the NFL, and the RPE or the ISOS, since the characteristics are easier to come out than the other boundaries, these boundaries may be detected based on an image with much blur on which noise processing has been performed several times. In this case, since only the general characteristic can be detected, the erroneous detection of the other boundaries can be prevented. Additionally, the retina region may be limited by performing binarization processing with a dynamic threshold on a tomographic image, and the boundary between the ILM and the NFL, and the RPE or the ISOS may be detected from it. Note that the second processing unit 823 may detect the boundary between the ILM and the NFL, and the BM.

However, when detecting the retina region, which is a first detection target, by such a rule base, as described above, the robustness to the individual differences and the pathological change in the eye to be examined is low, and the retina region could be initially and erroneously detected. In this case, the subsequent detection of the inner retinal layer boundary may not be appropriately performed.

As the countermeasure, in the present modification, the image processing unit 82 compares parameters for checking erroneous detection of the retina region, such as the discontinuity of the retina region boundary, and the distribution of boundary coordinates in a local curvature or local area, with predetermined threshold values. When these parameters exceed the predetermined threshold values, the image processing unit 82 determines that the detection of the retina region by the second processing unit 823 is erroneous detection. Then, the first processing unit 822 is configured to perform the detection of the retina region, when the detection of the retina region by the second processing unit 823 is determined to be erroneous detection by the image processing unit 82.

According to the present modification, even when the detection of the retina region by the first processing unit 822 is very time-consuming, the robustness to the individual differences and the pathological change in the eye to be examined can be ensured, while reducing the substantial processing wait time for an examiner (operator) who performs a large number of examinations.

Additionally, in the present modification, although the configuration has been described that performs the processing by the second processing unit 823 before the processing by the first processing unit 822, these pieces of processing may be started at the same time. In this case, when the detection of the retina region by the second processing unit 823 is determined to be erroneous detection by the image processing unit 82, the second processing unit 823 performs the boundary detection of the inner retinal layer, after waiting for the detection of the retina region by the first processing unit 822. Note that, when the detection of the retina region by the second processing unit 823 is appropriately performed, the processing by the first processing unit 822 can be interrupted, or the processing result by the first processing unit 822 can be discarded.

Additionally, when the first processing unit 822 and the second processing unit 823 detect the retina region (the same retina layers), the display controlling unit 25 may cause the display unit 50 to display the processing results of the detection processing by the first processing unit 822 and the second processing unit 823. In this case, according to an instruction by the operator for the processing result displayed on the display unit 50, the second processing unit 823 may perform the boundary detection of the inner retinal layer on either of the processing results of the detection processing by the first processing unit 822 and second processing unit 823. In this case, the detection processing of the retina region by the second processing unit 823 may be defined as the second detection processing, and the subsequent detection processing of the boundary of the inner retinal layer by the second processing unit 823 may be defined as third detection processing.

Example 3

In Example 2, the example has been illustrated that detects the retina region by using the learned model, and detects the boundary of the inner retinal layer for the detected retina region. On the other hand, in the present example, as the region detected by using the learned model, not only the retina region, but characteristic regions for an imaged site of an image, which is input data, is detected.

Hereinafter, the differences from the image processing according to Example 2 will be mainly described for the image processing by the image processing system according to the present example. Note that, since the configuration and the processing procedure of the image processing system according to the present example are similar to the configuration and the processing procedure of the image processing system 8 according to Example 2, the configuration and the processing procedure of the image processing system according to the present example will be illustrated by using the same reference numerals, and a description will be omitted.

Referring to FIG. 14A to FIG. 14D, the region detected by the first processing unit 822 according to the present example by using a learned model will be described. FIG. 14A to FIG. 14D illustrate examples of images imaged for each site of the eye to be examined, and label images of processing results processed by the first processing unit 822.

Figure 14A:
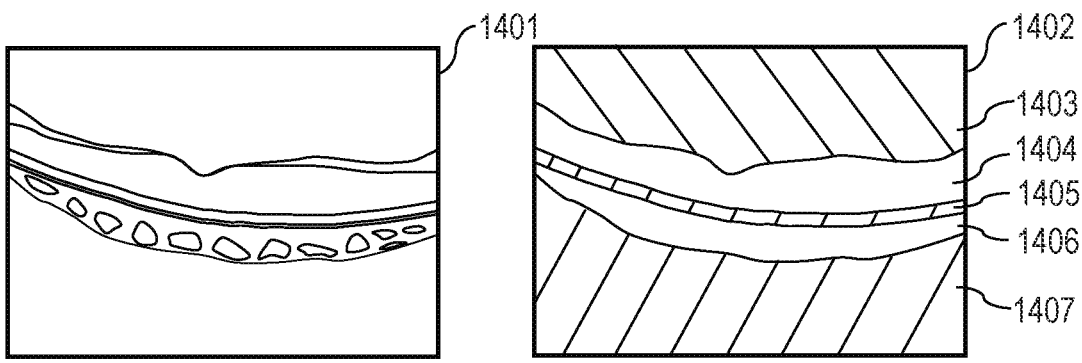
FIG. 14A is a diagram for describing examples of input and output images in a learned model.

FIG. 14A illustrates a tomographic image 1401 in the case where the macular area is imaged, and a label image 1402 in the macular area obtained by using the learned model. A vitreous body label 1403, a label 1404 for the range from the ILM to the ISOS, a label 1405 for the range from the ISOS to the RPE, a choroid coat label 1406, and a sclera label 1407 are illustrated in the label image 1402.

As for the macular area, in order to recognize, for example, the thickness of the entire retina due to bleeding, neovascularization, etc., the defect in photoreceptor related to eyesight, or the thinning of the choroid coat due to pathological myopia, a label is set for each region where a form change easily appears, and is learned by a machine learning model in advance. As for training data, it is assumed that a tomographic image of the macular area is input data, and a label image to which, for example, a vitreous body label, a label for the range from the ILM to the ISOS, a label for the range from the ISOS to the RPE, a choroid coat label, and a sclera label are given is ground truth. Accordingly, the first processing unit 822 can obtain the label image in which the label for each region where the above-described form change easily appears is illustrated, by inputting the tomographic image of the macular area to the learned model, and can detect regions in the units of these labels.

Figure 14B:
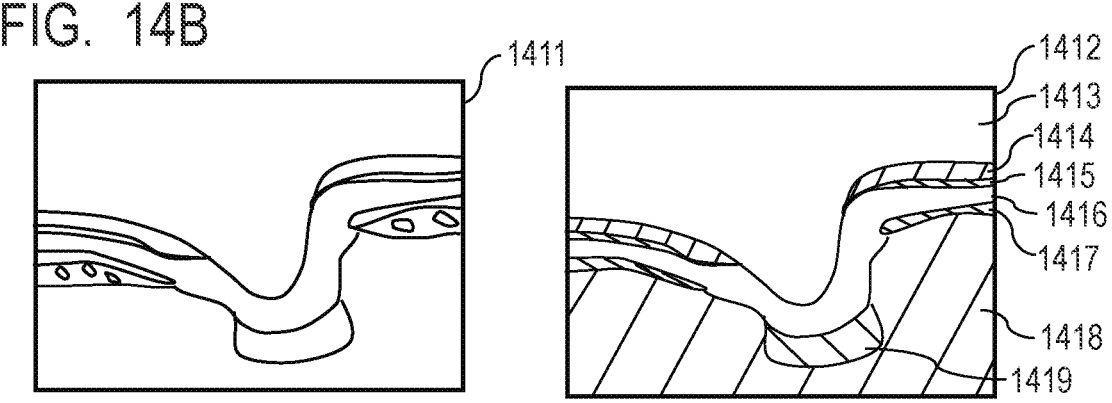
FIG. 14B is a diagram for describing examples of input and output images in the learned model.

FIG. 14B illustrates a tomographic image 1411 in the case where the optic nerve head is imaged, and a label image 1412 in the optic nerve head obtained by using the learned model. A vitreous body label 1413, a label 1414 for the range from the ILM to the boundary between the NFL and the GCL, and a label 1415 for the range from the boundary between the NFL and the GCL to the boundary between the GCL and the IPL are illustrated in the label image 1412. Further, a label 1416 for the range from the boundary between the GCL and the IPL to the NOS, and a label 1417 for the range from the ISOS to the RPE are illustrated in the label image 1412. In addition, a label 1418 for the range deeper than the RPE, and a label 1419 for the range of a lamina cribrosa are illustrated in the label image 1412. As for training data in this case, it is assumed that a tomographic image of the optic nerve head is input data, and a label image to which, for example, a vitreous body label, a label for the range from the ILM to the boundary between the NFL and the GCL, a label for the range from the boundary between the NFL and the GCL to the boundary between the GCL and the IPL, a label for the range from the boundary between the GCL and the IPL to the ISOS, a label for the range from the ISOS to the RPE, a label for the range deeper than the RPE, and a label for the range of the lamina cribrosa are given is ground truth.

Figure 14C:
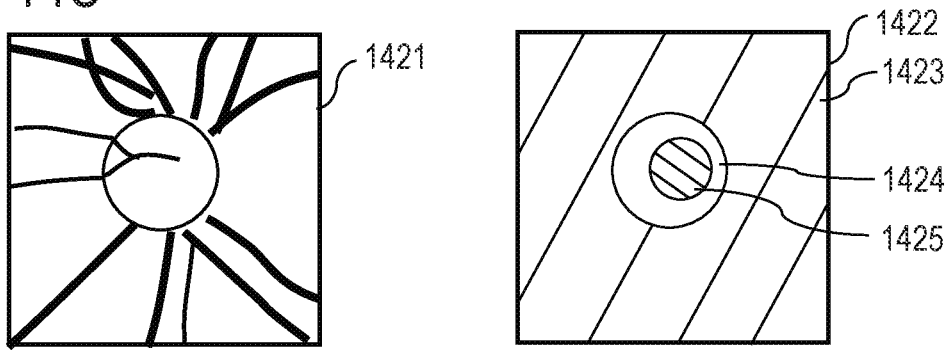
FIG. 14C is a diagram for describing examples of input and output images in the learned model.

A front image 1421 of FIG. 14C is an image seen from the front direction in the XY surface, and is an image imaged by using the fundus image imaging apparatus 30 at the time of optic nerve head imaging. Additionally, a label image 1422 of FIG. 14C is a label image obtained by using the learned model for the front image 1421 of the optic nerve head. A label 1423 for the periphery of the optic nerve head, a Disc label 1424, and a Cup label 1425 are illustrated in the label image 1422.

In the optic nerve head, due to glaucoma, the disappearance of a ganglion cell, and the form change in an end of the RPE (RPE-tip) or an end of the Bruch's membrane opening (BMO), the lamina cribrosa, and Cup and Disc, etc., easily appear. Therefore, a label is set for each of these regions and is learned by the machine learning model in advance. As for training data, it is assumed that a front image of the optic nerve head is input data, and a label image to which, for example, the label for the periphery of the optic nerve head, the Disc label, and the Cup label are given is ground truth. Accordingly, the first processing unit 822 can obtain the label image in which the label for each region where the above-described form change easily appears is illustrated, by inputting the image of the optic nerve head to the learned model, and can detect regions in the units of these labels.

Figure 14D:
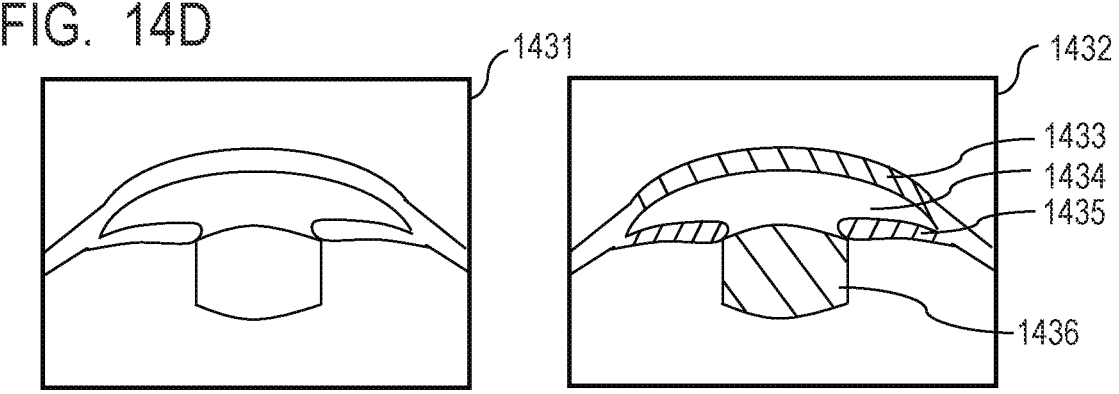
FIG. 14D is a diagram for describing examples of input and output images in the learned model.

FIG. 14D illustrates a tomographic image 1431 in the case where the anterior ocular segment is imaged, and a label image 1432 in the anterior ocular segment imaging obtained by using the learned model. A cornea label 1433, an anterior chamber label 1434, an iris label 1435, and a crystalline lens label 1436 are illustrated in the label image 1432. As for the tomographic image 1431 of the anterior ocular segment, different from a posterior ocular segment image, the main regions as previously described are learned by the machine learning model in advance. As for training data, it is assumed that a tomographic image of the anterior ocular segment is input data, and a label image to which, for example, a cornea label, an anterior chamber label, an iris label, and a crystalline lens label are given is ground truth. Accordingly, the first processing unit 822 can obtain the label image in which the label for each region where the above-described form change easily appears is illustrated, by inputting the image of the anterior ocular segment to the learned model, and can detect regions in the units of these labels.

The second processing unit 823 according to the present example detects the remaining boundaries based on the regions detected by the first processing unit 822 in the tomographic images 1401, 1411, 1431 illustrated in FIG. 14A, FIG. 14B, and FIG. 14D. Additionally, the second processing unit 823 may perform the measurement of the thicknesses of the detected boundaries, layer regions sandwiched by the detected boundaries, or the regions detected by the first processing unit 822.

Additionally, the second processing unit 823 can perform measurement for each of the regions classified by the labels on the front image of FIG. 14C, and can calculate a height, a width, an area, and a Cup/Disc ratio of each of the regions. Note that an existing arbitrary method may be used for these measurement and calculation of the ratio.

In this manner, the second processing unit 823 according to the present example can perform the image processing algorithm corresponding to the region detected by the first processing unit 822, and can change a rule at the time of applying an image processing algorithm for each region. The rule here includes, for example, the kinds of boundary to be detected. For example, similar to Example 1, the second processing unit 823 may perform additional boundary detection in the range from the ILM to the ISOS illustrated with the label 1404 for the tomographic image 1401 of the macular area illustrated in FIG. 14A. Note that the boundary detection method may be similar to the boundary detection method in Example 1. Additionally, the second processing unit 823 may apply an image processing algorithm and a rule, so as to detect the boundary between the ILM and the NFL, the boundary between the OPL and the ONL, the boundary between the IPL and the INL, the boundary between the INL and the OPL, and the boundary between the GCL and the IPL for the tomographic image 1401 of the macular area. In this manner, in the second processing unit 823, an arbitrary image processing algorithm and a rule may be set for each region according to a desired configuration.

As described above, in the image processing apparatus 80 according to the present example, the first processing unit 822 detects the predetermined boundaries for each imaged site for the input image. Therefore, in the present example, since the regions detected by using the learned model are not limited to the retina region, but are characteristic regions related to an imaged site, variations such as diseases can be addressed. Note that, when the input image is a tomographic image of the retina, the first processing unit 822 can detect the predetermined boundaries for the each imaged site as the first detection processing that detects at least one of the retina layers. Additionally, when the input image is an image other than the tomographic image of the retina, the first processing unit 822 can detect the predetermined boundaries for the each imaged site as the processing different from the first detection processing. Note that, similar to Example 1, the respective outputs of a plurality of learning models for which learning has been performed for each region of a tomographic image may be combined to generate the final output of the first processing unit 822.

Additionally, in the image processing apparatus 80 according to the present example, the predetermined shape characteristics, such as the height (thickness), the width, the area, and the Cup/Disc ratio of each region related to the eye to be examined, can be measured based on the result of the first detection processing or the second detection processing.

Example 4

In Example 3, the example has been illustrated in which the region detected by using the learned model is not limited to the retina region, but the characteristic regions in an imaged site are detected. On the other hand, in Example 4, the selection of the performance of the processing using the learned model, and further, the narrowing down of a region detected by using the learned model are performed according to the imaging conditions under which an image has been imaged.

Hereinafter, referring to FIG. 15 to FIG. 16B, the differences from the image processing according to Example 2 will be mainly described for the image processing by an image processing system 150 according to the present example. Note that the configuration and the processing of the image processing system according to the present example that are similar to the configuration and the processing of the image processing system 8 according to Example 2 will be illustrated by using the same reference numerals, and a description will be omitted.

Figure 15:
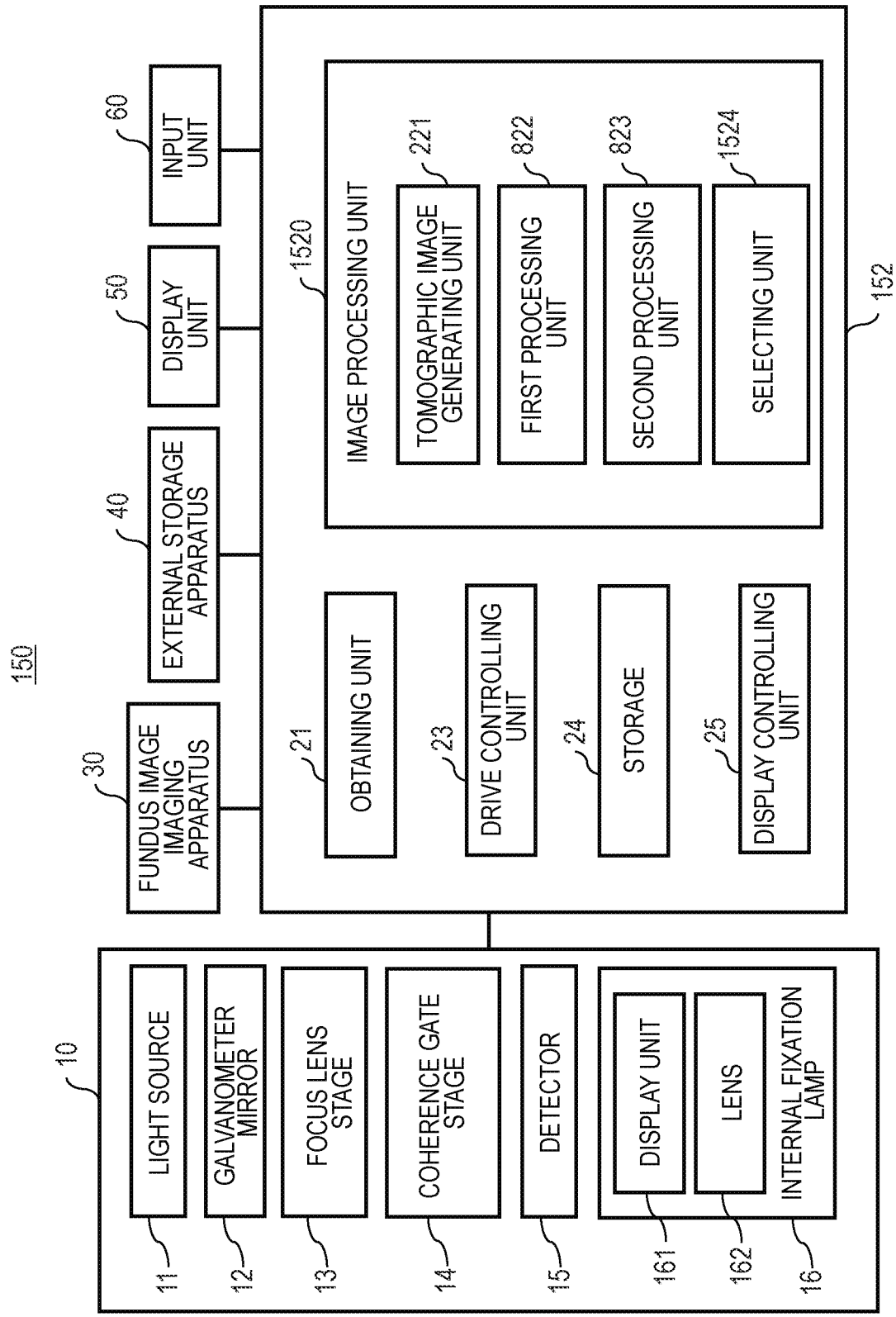
FIG. 15 is an example of the schematic configuration of an image processing system according to Example 4.

FIG. 15 illustrates an example of the schematic configuration of the image processing system 150 according to the present example. The image processing system 150 according to the present example is provided with a selecting unit 1524, in addition to the tomographic image generating unit 221, the first processing unit 822, and the second processing unit 823, in an image processing unit 1520 of an image processing apparatus 152.

The selecting unit 1524 selects image processing performed on a tomographic image, based on the imaging conditions obtained by the obtaining unit 21 and the learned contents (training data) related to the learned model of the first processing unit 822. Specifically, based on the imaging conditions and the learning of the learned model, whether to detect the retina layers only by the first processing unit 822, to detect the retina region by the first processing unit 822 and to detect the retina layers by the second processing unit 823, or to detect the retina layers only by the second processing unit 823 is selected. Additionally, when the first processing unit 822 includes a plurality of learned models, the selecting unit 1524 can select a learned model used for the detection processing by the first processing unit 822, based on the imaging conditions and the learned content related to the learned models of the first processing unit 822.

Figure 16A:
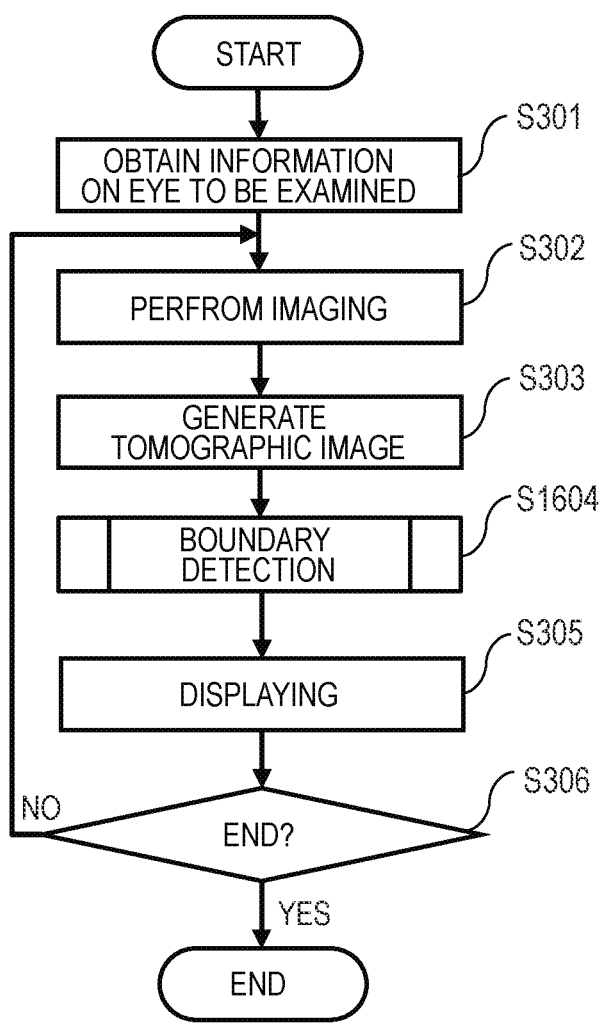
FIG. 16A is a flowchart of a series of processing according to Example 4.
Figure 16B:
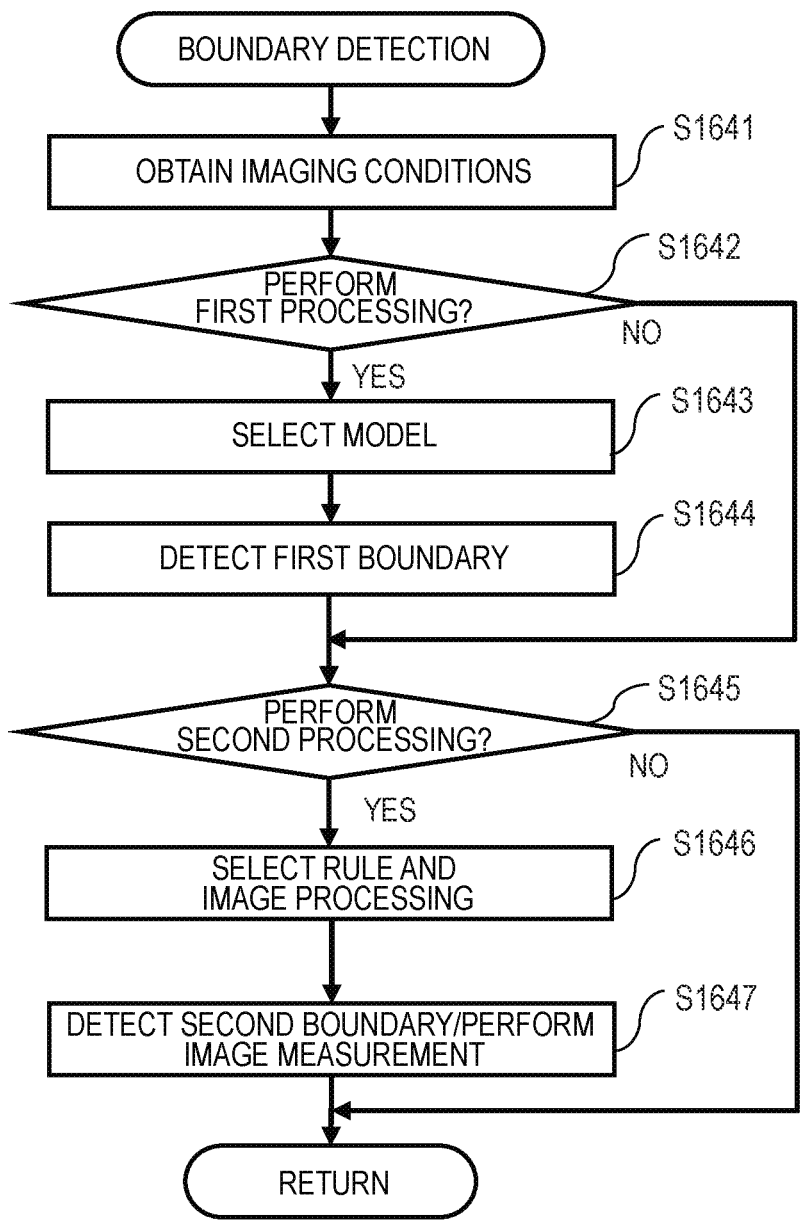
FIG. 16B is a flowchart of a series of processing according to Example 4.

Next, referring to FIG. 16A and FIG. 16B, a series of processing according to the present example will be described. FIG. 16A is a flowchart of the series of processing according to the present example, and FIG. 16B is a flowchart of the boundary detection processing according to the present example. Note that, since the processing other than the boundary detection processing are similar to the processing in Example 2, a description will be omitted. When a tomographic image is generated in step S303, the processing proceeds to step S1604. When the processing proceeds to step S1604, the boundary detection processing is started, and the processing proceeds to step S1641.

In step S1641, the obtaining unit 21 obtains the imaging conditions for the generated tomographic image, and the image processing unit 1520 obtains information required to perform the selection of the processing by the first processing unit 822 and second processing unit 823 from the obtained imaging conditions. For example, these conditions can include the imaged site, the imaging system, the imaged region, the imaging angle of view, and the resolution of an image.

In step S1642, the selecting unit 1524 selects whether or not to perform the processing by the first processing unit 822 based on the imaging conditions obtained in step S1641. Here, as an example, the case is considered where only two, a model for optic nerve heads and a model for macular area, for which learning has been performed by using the training data for each imaged site for each of the optic nerve head and the macular area are prepared for the learned model of the first processing unit 822. Additionally, in this case, the first processing unit 822 will be described as not being able to correspond to a wide angle image (an image for the range in which both the optic nerve head and the macular area are imaged).

In the example, when the selecting unit 1524 determines that an input image is an image of the optic nerve head or the macular area imaged alone, based on, for example, the imaged site name and the information on the imaging angle of view of the imaging conditions, the selecting unit 1524 selects to perform the processing by the first processing unit 822. Accordingly, the processing proceeds to step S1643. On the other hand, when the selecting unit 1524 determines that the input image is an image obtained by imaging other than the optic nerve head and the macular area, or a wide angle image including both the optic nerve head and the macular area, the selecting unit 1524 selects not to perform the processing by the first processing unit 822. Accordingly, the processing proceeds to step S1645.

In step S1643, the selecting unit 1524 selects an appropriate learned model utilized by the first processing unit 822, based on the imaging conditions obtained in step S1641. In the above-described example, when the selecting unit 1524 determines that the input image is an image obtained by imaging the optic nerve head based on, for example, the imaged site name and the information on the imaging angle of view, the selecting unit 1524 selects the model for optic nerve heads. Similarly, when the selecting unit 1524 determines that the input image is an image obtained by imaging the macular area, the selecting unit 1524 selects the model for macular areas.

Note that, here, although the example has been illustrated in which the learned model has learned only the image obtained by imaging the optic nerve head and the macular area, the learned content of the learned model is not limited to this. For example, a learned model that has learned about the other sites, or a learned model for which learning has been performed by using a wide angle image including the optic nerve head and the macular area may be used.

Additionally, when the learned models according to imaging systems, not the imaged sites, are separately prepared, the selection of processing and the selection of a learned model may be performed according to the imaging system. As examples of the imaging system, there are imaging systems of SD-OCT and SS-OCT, and due to the difference between the two imaging systems, the image quality, the imaging range, the invasion depth in the depth direction, etc., are different. Therefore, the selection of appropriate processing and the selection of a learned model may be performed for images of these different imaging systems. Note that, when learning has been performed together regardless of the imaging systems at the time of teaming, the processing may not be changed according to the imaging system. Additionally, when there is only one learned model, since the selection of a learning model in step S1643 is not necessary, this processing can be skipped.

In step S1644, the first processing unit 822 performs the first boundary detection processing by using the learned model selected in step S1643. Note that the processing described in Examples 1 to 3 can be used for this processing. For example, when the model for macular areas has learned about the image segmentation processing of each retina layer in the macular area, similar to Example 1, the first processing unit 822 can detect all the boundaries to be detected as the first detection processing. Additionally, for example, when the model for optic nerve heads has learned about the processing that detects the retina region in the optic nerve head, similar to Example 2, the first processing unit 822 can detect the retina region as the first detection processing. Similarly, when the model for macular areas has learned the processing that detects a characteristic region of the macular area as in Example 3, the first processing unit 822 can detect a characteristic region as the first detection processing as in Example 3. Note that, since the specific detection method is similar to the detection method in Examples 1 to 3, a description will be omitted.

In step S1645, the selecting unit 1524 selects whether or not to perform the processing by the second processing unit 823 based on the imaging conditions obtained in step S1641. When the selecting unit 1524 selects to perform the processing by the second processing unit 823, the processing proceeds to step S1646. On the other hand, when the selecting unit 1524 selects not to perform the processing by the second processing unit 823, the processing in step S1604 ends, and the processing proceeds to step S305.

Here, an example of the selection processing by the selecting unit 1524 in step S1645 will be described. The case where the processing by the second processing unit 823 is performed is, for example, as described in Examples 2 and 3, the case where the second processing unit 823 detects boundaries based on the region detected by the first processing unit 822.

Additionally, in addition to this, the processing by the second processing unit 823 is also performed when an image that is not learned by the first processing unit 822 is input. In this case, in step S1642, since skipping the processing by the first processing unit 822 is selected, the boundary detection is performed by the rule-based image segmentation processing by the second processing unit 823 without using the learned model.

On the other hand, the case where the processing by the second processing unit 823 is not performed is, for example, the case where the first processing unit 822 can detect all the target boundaries by using the learned model. In this case, since the processing is completed only by the first processing unit 822, the processing by the second processing unit 823 can be skipped.

However, even when the first processing unit 822 can detect all the target boundaries by using the learned model, when the measurement of the layer thickness, etc., is performed by the second processing unit 823 based on the detected boundaries, performing the processing by the second processing unit 823 may be selected. On the other hand, the measurement of the layer thickness, etc., based on the detected boundaries may not be limited to being performed by the second processing unit 823, and may be performed in the image processing unit 1520. Therefore, even when the measurement of the layer thickness, etc., is performed, performing of the processing by the second processing unit 823 may not be selected.

In step S1646, the selecting unit 1524 performs selection of the image processing required in order to perform the processing by the second processing unit 823 and a rule at the time of applying the image processing, based on the imaging conditions obtained in step S1641. For example, when input images are tomographic images as illustrated in FIG. 14A, FIG. 14B, and FIG. 14D, the selecting unit 1524 selects the processing and the rule for detecting the remaining boundaries based on the region detected by the first processing unit 822.

Specifically, for example, when an input image is the tomographic image 1401 obtained by imaging the macular area illustrated in FIG. 14A, the selecting unit 1524 selects the image processing and the rule that can correctly perform the layer recognition of the macular area. Additionally, for example, in the case of the tomographic image 1411 obtained by imaging the optic nerve head illustrated in FIG. 14B, the selecting unit 1524 selects the image processing and the rule in consideration of exception processing of the optic nerve head in consideration of the influence of the Bruch's membrane opening end (BMO), the lamina cribrosa, the Cup, the Disc, etc. Further, for example, in the case of the tomographic image 1431 in the case where the anterior ocular segment illustrated in FIG. 14D is imaged, the selecting unit 1524 selects the image processing and the rule that can perform further layer recognition of the cornea portion.

Further, in step S1647, when performing the measurement of the thickness of the detected boundary or the layer region sandwiched by the boundaries, in addition to the detection of the layer boundary or alone, the selecting unit 1524 can also select the image processing required for such an image measurement function.

In step S1647, the second processing unit 823 performs the detection of boundaries and/or the measurement of the detected boundaries and region. Note that, similar to what has been described in Examples 2 and 3, a description will be omitted for the processing of detecting the boundaries in the region based on the region detected by the first processing unit 822 and the processing of measuring of the boundaries, etc.

Here, an example of the processing will be described that is performed by the second processing unit 823 when an image that is not learned by the learned model of the first processing unit 822 is input. In this case, since there is no candidate of the retina region detected from the input image, as described in the modification of Example 2, the second processing unit 823 first detects the boundary between the ILM and the NFL, and the RPE or the ISOS.

After detecting the boundary between the ILM and the NFL, and the RPE or the ISOS, the second processing unit 823 detects the remaining boundaries based on the region between these boundaries. Since the detection processing is similar to the detection processing in Examples 2 and 3, a description will be omitted. When the second processing unit 823 performs these pieces of processing, the processing proceeds to step S305. Note that, similar to the modification of Example 2, the second processing unit 823 may first detect the boundary between the ILM and the NFL, and the BM. Additionally, since the subsequent processing is similar to the processing in Examples 1 to 3, a description will be omitted.

As described above, in the image processing apparatus 152 according to the present example, the obtaining unit 21 obtains the imaging conditions related to tomographic images of the eye to be examined. The image processing apparatus 152 further includes the selecting unit 1524 that selects processing based on the imaging conditions. The selecting unit 1524 selects at least one of the first detection processing and the second detection processing based on the imaging conditions.

Therefore, in the image processing apparatus 152 according to the present example, based on the imaging conditions, whether or not the boundary detection by the learned model performed by the first processing unit 822 is possible, and whether or not performing the processing of the boundary detection by the image characteristics performed by the second processing unit 823 is necessary are determined. Accordingly, even when the boundary detection by the learned model corresponds only to a specific image, the processing can be appropriately performed according to an input image. Therefore, even when the learning model does not correspond to various image patterns, the boundary detection processing can be positively performed. Accordingly, the accuracy of the boundary detection can be improved by using at least one of the machine learning models in various mature phases created by machine learning, together with the image processing method that determines the result of the image characteristics extraction in a rule-based manner to perform the boundary detection of the retina layers.

Additionally, the first processing unit 822 includes a plurality of learned models for which machine learning has been performed by using different training data. Further, the first processing unit 822 performs the first detection processing by using the learned model for which machine learning has been performed by using the training data corresponding to the imaging conditions among the plurality of learned models.

According to the present example, the retina layers can be detected by using an appropriate learning model based on the imaging conditions, and more appropriate processing can be performed according to an input image. Additionally, since the learning models can also be additionally increased, upgrading the version so as to gradually improve the performance can also be expected. Further, according to the selecting unit 1524, the selection of the image processing and the rule that are used in the second processing unit 823 can be performed based on the imaging conditions, and more appropriate processing can be performed according to an input image.

Note that, in the present example, in step S1642 and step S1645, although the selection of the processing by the first processing unit 822 and second processing unit 823 is performed separately, the procedure of selection of the processing is not limited to this. For example, the selecting unit 1524 may be configured to select, in one step, the processing only by the first processing unit 822, the processing only by the second processing unit 823, or the processing by the first processing unit 822 and the second processing unit 823.

Modification of Example 4

In Example 4, it has been illustrated that appropriate processing is enabled in various cases, such as when the first processing unit 822 and the second processing unit 823 share the boundary detection, etc., on both sides, or when the boundary detection, etc., is completed only by either of them. In contrast, the first processing unit 822 and the second processing unit 823 may perform in parallel the same processing, for example, the processing of detecting the same boundary.

As such an example, for example, a case is considered where the first processing unit 822 can detect all the target boundaries by using the learned model, and the second processing unit 823 can detect all the target boundaries including the retina region, which is the first detection target. In this case, the first processing unit 822 and the second processing unit 823 output the results of separately detecting the respective boundaries.

Since these detection results are results of the processing by the learned models and the image processing by the rule base, respectively, there may be a difference in both results. Therefore, in the present modification, the display controlling unit 25 can display both the results side by side, can switch and display both the results, and can display both the results in an overlapping manner on the display unit 50. Additionally, whether both the results match or not can be determined in the image processing unit 1520, and the display controlling unit 25 can display the mismatched portion on the display unit 50 in an emphasized manner. In this case, the reliability of the layer detection can be indicated to the operator. Further, the display controlling unit 25 may cause the display unit 50 to display the mismatched portion, and may allow to select a more satisfying result according to an instruction by the operator.

Example 5

In Examples 2 to 4, the example has been illustrated that detects the retina region by using the learned model, and detects the boundaries of the inner retinal layer on the rule base for the detected retina region. In contrast, in Example 5, correction is performed on the region detected by using the learned model, based on medical characteristics.

Hereinafter, referring to FIG. 17 to FIG. 19D, the differences from the image processing according to Example 2 will be mainly described for the image processing by an image processing system 170 according to the present example. Note that the configuration and the processing of the image processing system according to the present example that are similar to the configuration and the processing of the image processing system 8 according to Example 2 will be illustrated by using the same reference numerals, and a description will be omitted.

Figure 17:
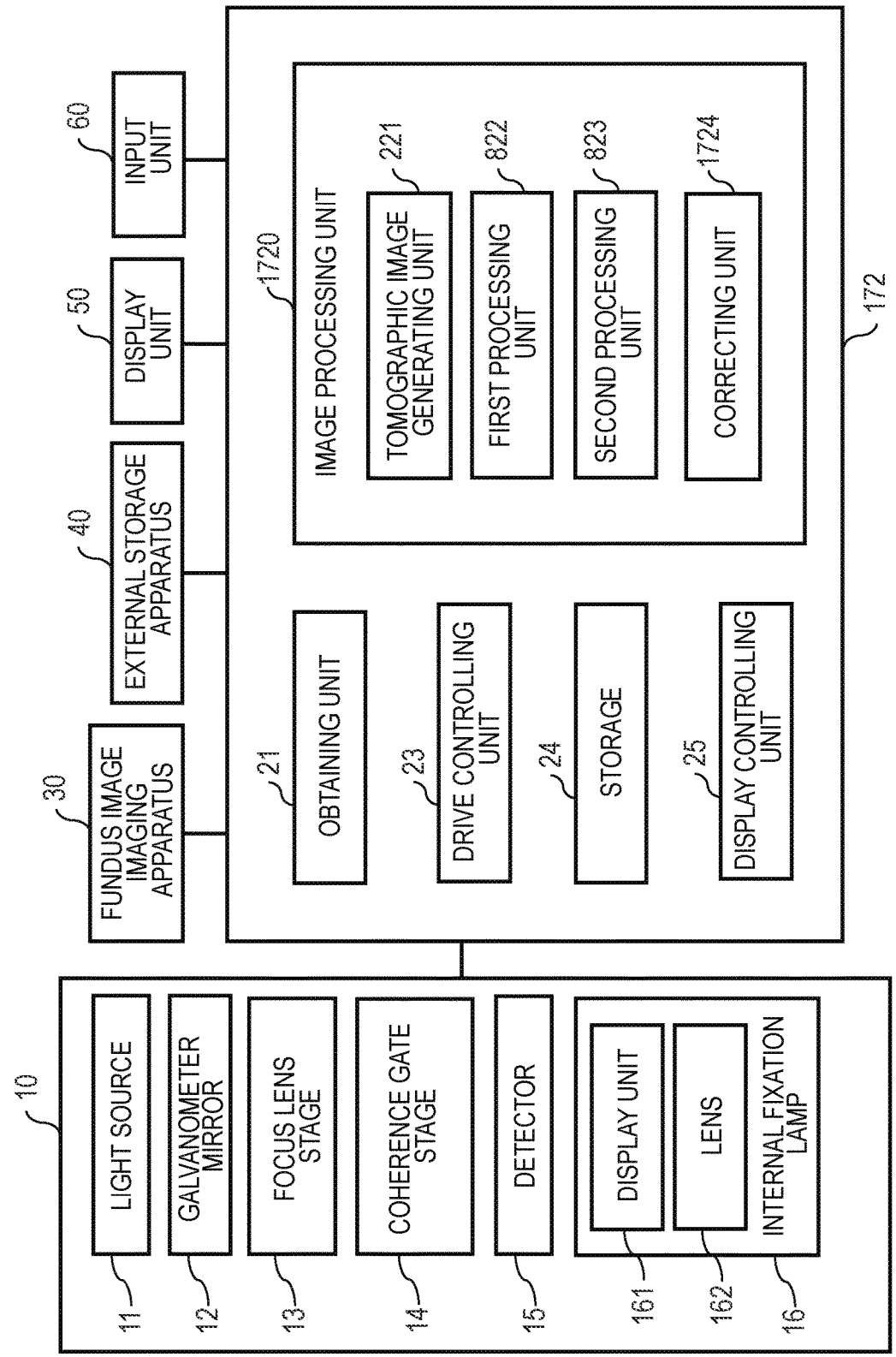
FIG. 17 illustrates an example of the schematic configuration of an image processing system according to Example 5.

FIG. 17 indicates an example of the schematic configuration of the image processing system 170 according to the present example. An image processing unit 1720 of an image processing apparatus 172 in the image processing system 170 according to the present example is provided with a correcting unit 1724, in addition to the tomographic image generating unit 221, the first processing unit 822, and the second processing unit 823.

The correcting unit 1724 corrects a labeled area based on the medical characteristics of an eye for a label image obtained by using the learned model by the first processing unit 822. Accordingly, the image processing unit 1720 can detect a retina region and a characteristic region more appropriately.

Figure 18A:
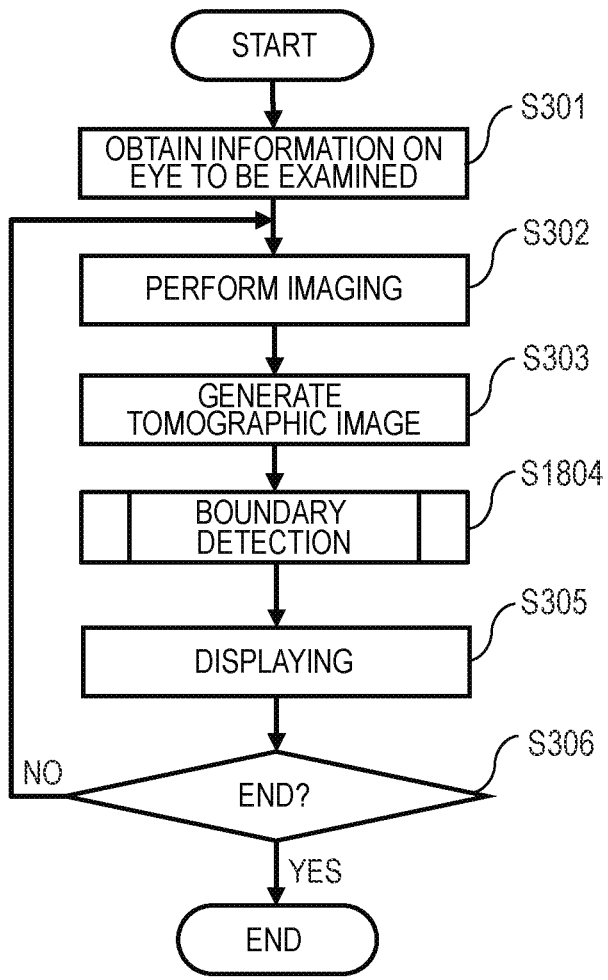
FIG. 18A is a flowchart of a series of processing according to Example 5.
Figure 18B:
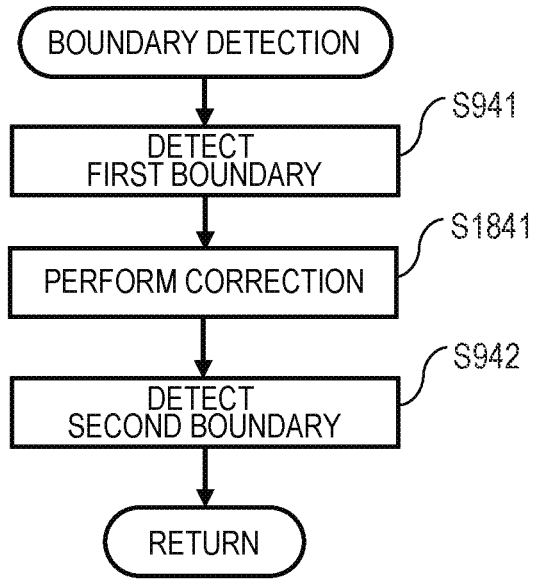
FIG. 18B is a flowchart of boundary detection processing according to Example 5.

Next, referring to FIG. 18A and FIG. 18B, a series of processing according to the present example will be described. FIG. 18A is a flowchart of the series of processing according to the present example, and FIG. 18B is a flowchart of the boundary detection according to the present example. Note that, since the processing other than the boundary detection processing are similar to the processing in Example 2, a description will be omitted. When a tomographic image is generated in step S303, the processing proceeds to step S1804. When the processing proceeds to step S1804, and the processing by the first processing unit 822 is performed in step S941, the processing proceeds to step S1841.

In step S1841, the correcting unit 1724 corrects the retina region detected by the first processing unit 822 in step S941. More specifically, the labeled region is corrected based on the medical characteristics of an eye for the label image obtained by using the learned model by the first processing unit 822.

Figure 19A:
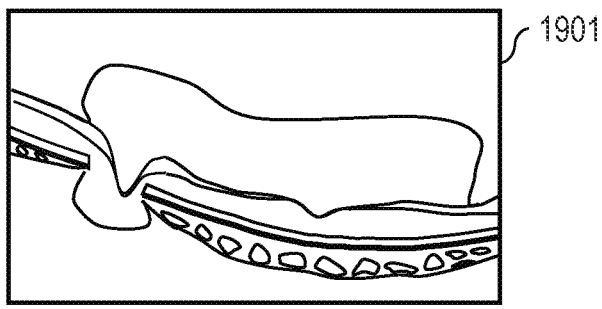
FIG. 19A is a diagram for describing compensation processing of a retina region.
Figure 19B:
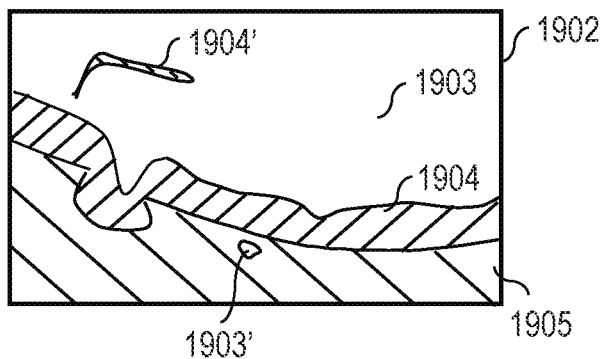
FIG. 19B is a diagram for describing the compensation processing of the retina region.

Here, referring to FIG. 19A to FIG. 19D, the correction processing by the correcting unit 1724 according to the present example will be described. FIG. 19A illustrates an example of a tomographic image 1901 used as the input to the first processing unit 822. FIG. 19B illustrates an example of a label image 1902 obtained by using the learned model by the first processing unit 822 with the tomographic image 1901 as the input. In the label image 1902, a label 1904 for the inner retinal layer, a label 1903 on the shallower side (vitreous body side) than the retina, and a label 1905 on the deeper side (choroid coat side) than the retina are illustrated.

Note that the labeling is based on the setting of labels at the time of learning of the learned model. Therefore, the kinds of labels are not limited to this, and a plurality of labels may be set in the retina layers as illustrated in Example 3. Also in such a case, the correcting processing according to the present example can be applied.

In the present example, the first processing unit 822 performs the image segmentation processing on a pixel-by-pixel basis by using the learned model. Therefore, as indicated by labels 1903', 1904' of FIG. 19B, erroneous detection may be partially performed. The correcting unit 1724 corrects these erroneous detections based on the medical characteristics of an eye.

The first processing unit 822 performs the labeling processing for each detected label, and the pixels with the same label in adjacent pixels are integrated as one region. The kinds of labels given in the present example are three kinds, the label 1904 for the inner retinal layer, the label 1903 on the shallower side (vitreous body side) than the retina, and the label 1905 on the deeper side (choroid coat side) than the retina. Additionally, since the image obtained by imaging the tomographic image of the retina is the target, the order in which these labels appear is in the order of the label 1903, the label 1904, and the label 1905 from the top for the image. Note that, in the case of the EDI (Enhanced Depth Imaging) mode that images the choroid coat side in an emphasized manner, since the retina is imaged inverted, the order in which the labels appear is in the order of the label 1905, the label 1904, and the label 1903 from the top of the image.

As described above, since the image input to the first processing unit 822 is the tomographic image of the retina, the positional relationship between the labels can be estimated based on the medical characteristics from the conditions at the time of imaging and the imaged site. Therefore, the correcting unit 1724 specifies the detection result for each labeled region, and corrects the region considered to be erroneous detection to the region estimated based on the medical characteristics.

Figure 19C:
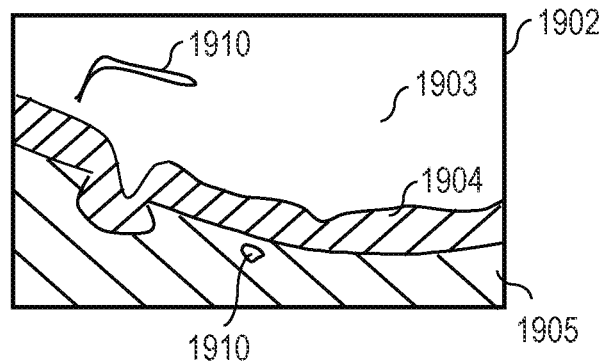
FIG. 19C is a diagram for describing the compensation processing of the retina region.

Specifically, the correcting unit 1724 specifies a labeled region starting from the labeled regions with larger areas, and determines that the labeled region with an area less than a threshold value, and the labeled region with a spatial distance from the already specified region to be erroneous detections. Then, the correcting unit 1724 resets the label information determined to be erroneous detection. The example in this case is illustrated in FIG. 19C. Regions 1910 illustrated in FIG. 19C indicate the regions whose label information has been reset by the correcting unit 1724 for the regions indicated by the label 1903' and label 1904', which are the regions considered to be erroneous detections.

The correcting unit 1724 assigns the label information estimated from surrounding label information to the region 1910 whose label information has been reset. In the example illustrated in FIG. 19C, the label 1903 is assigned to the region 1910 surrounded by the label 1903, and the label 1905 is assigned to the region 1910 surrounded by the label 1905.

Figure 19D:
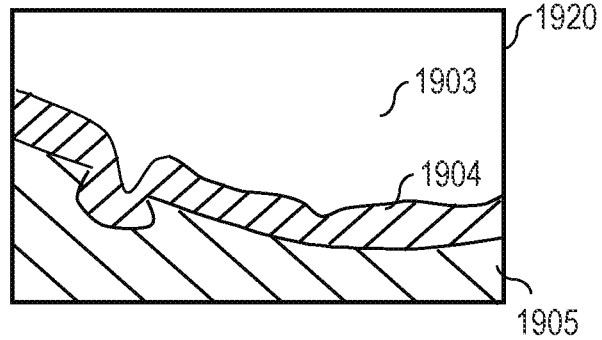
FIG. 19D is a diagram for describing the compensation processing of the retina region.

With these pieces of processing by the correcting unit 1724, a final label image 1920 is output as illustrated in FIG. 19D. Accordingly, the image processing unit 1720 can detect the retina region more appropriately.

When the correction processing by the correcting unit 1724 is performed, the processing proceeds to step S942. In step S942, the second processing unit 823 performs the second boundary detection processing based on the corrected retina region, as in Example 2. Since the subsequent processing are similar to that of Example 2, a description will be omitted.

As described above, the image processing apparatus 172 according to the present example further includes the correcting unit 1724 that corrects the structure of the retina layers detected by the first processing unit 822, based on the medical characteristics in the retina layers.

Therefore, in the image processing apparatus 172 according to the present example, for the region detected by using the learned model, the correction of the region can be performed by using the medical characteristics. Therefore, erroneous detections can be reduced even when an image is detected on a pixel-by-pixel basis.

Note that, in the present example, although the correction processing by the correcting unit 1724 is added to the processing according to Example 2, the correction processing may be added to the processing according to Example 3 and Example 4.

Example 6

In Examples 1 to 5, the boundaries of the inner retinal layer and the retina region are detected for the imaged tomographic image by using the learned model. In contrast, in the present example, a high quality image in which the image quality of a tomographic image has been improved by using another learned model is generated, and the boundary detection and the region detection using the learned model according to Example 1 or 2, etc., is performed on the high quality image. Note that the improvement of the image quality in the present example includes the reduction of noise, the conversion of an imaging target to the color and gradation that are easy to observe, the improvement in the resolution or spatial resolution, and the enlargement of the image size with suppressed deterioration of the resolution.

Hereinafter, the differences from the image processing according to Example 2 will be mainly described for the image processing by the image processing system according to the present example. Note that, since the configuration and the processing procedure of the image processing system according to the present example are similar to the configuration and the processing procedure of the image processing system 8 according to Example 2, the configuration and the processing procedure of the image processing system according to the present example will be illustrated by using the same reference numerals, and a description will be omitted.

In the present example, the first processing unit 822 performs the processing that improves the image quality of an input image by using a learned model related to an image quality improving model, which is a machine learning model different from the machine learning model for detecting the retina region. The image quality improving model is a learned model that outputs an image in which the image quality of the input image has been improved by training the machine learning model with arbitrary machine learning algorithms in advance by using appropriate training data.

Figure 20:
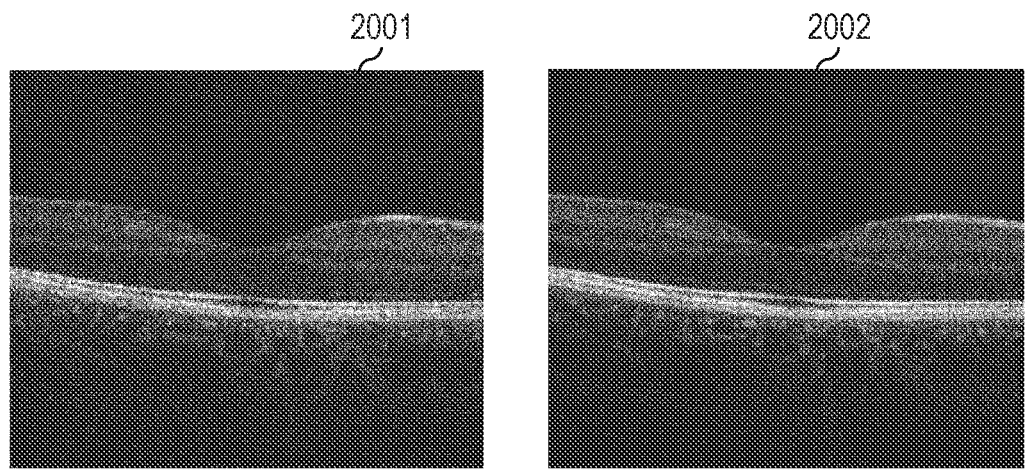
FIG. 20 is a diagram for describing examples of a learning image according to Example 6.

Here, an example of the training data of an image quality improving model according to the present example is illustrated in FIG. 20. In FIG. 20, a tomographic image 2001 illustrates an example of the tomographic image obtained by imaging of the OCT, and a tomographic image 2002 illustrates a tomographic image obtained by performing the image quality improving processing on the tomographic image 2001. The tomographic image 2001 illustrates an example of input data, the tomographic image 2002 illustrates an example of ground truth, and the training data includes pairs including these images.

Note that, as the image quality improving processing, performing the alignment on tomographic images obtained by imaging spatially the same position a plurality of times, and performing additive averaging processing on those aligned tomographic images can be listed. Note that the image quality improving processing is not limited to additive averaging processing, and may be, for example, processing using a smoothing filter, maximum a posteriori estimation processing (MAP estimation processing), or gray scale conversion processing. Additionally, an image on which the image quality improving processing has been performed may be, for example, an image on which filtering processing such as noise removal and edge emphasis has been performed, or an image whose contrast has been adjusted so as to make a low intensity image a high intensity image may be used. Further, since the ground truth of the training data for the image quality improving model may be a high quality image, the ground truth of the training data for the image quality improving model may be a tomographic image imaged by using an OCT apparatus with higher performance than the OCT apparatus at the time of imaging of a tomographic image, which is the input data, or a tomographic image imaged with high load settings.

The first processing unit 822 inputs the tomographic image obtained by imaging of the OCT to the image quality improving model trained by using such training data, and obtains an image-quality-improved tomographic image. Note that the first processing unit 822 can obtain an image-quality-improved volume tomographic image by inputting, to the image quality improving model, a tomographic image with a volume obtained by three-dimensionally scanning the retina by raster scan.

The first processing unit 822 detects a retina region or a characteristic region by using the learned model by using the high quality image obtained by using the image quality improving model as the input, as in Examples 2 to 5.

Additionally, the second processing unit 823 can detect the retina layers based on the high quality image obtained by the first processing unit 822 and the detected retina region or characteristic region.

As described above, in the image processing apparatus 80 according to the present example, the first processing unit 822 performs the first detection processing for the image-quality-improved tomographic image by using the learned model.

Accordingly, the image processing apparatus 80 according to the present example can improve the image quality of an input image by using the learned model of the machine learning model, and can perform detection of the retina layers on the image whose image quality has been improved. Therefore, the detection of the retina layers can be performed by using an image on which image quality improvement such as noise reduction has been performed, and erroneous detection can be reduced.

Additionally, in the present example, although the processing that performs the image quality improvement of the tomographic image, which is the input image, is added to the processing according to Example 2, the image quality improvement processing may be added to the processing according to Example 1 and Examples 3 to 5.

Additionally, in the present example, the image quality improving model that performs image quality improvement is the machine learning model different from the machine learning model that performs the detection processing. However, the machine learning model that performs the detection processing may be made to learn the image quality improving processing, and the machine learning model may be configured to perform both the image quality improvement and the detection processing.

Note that, in the present example, the first processing unit 822 generates the high quality image obtained by improving the image quality of the tomographic image by using the learned model (image quality improving model) related to the image quality improving processing. However, the component that generates a high quality image by using the image quality improving model is not limited to the first processing unit 822. For example, a third processing unit (image quality improving unit) different from the first processing unit 822 may be provided, and the third processing unit may generate a high quality image by using the image quality improving model. Therefore, the first processing unit 822 or the third processing unit can function as an example of the generating unit that generates, from a tomographic image, an image-quality-improved tomographic image compared with the tomographic image, by using the learned model for image quality improvement. Note that the third processing unit and the image quality improving model may include a software module executed by a processor, such as a CPU, an MPU, a GPU, and an FPGA, or may include a circuit that achieves specific functions, such as an ASIC.

Example 7

Next, referring to FIG. 21A to FIG. 23, the image processing apparatus 80 according to Example 7 will be described. In Example 6, the first processing unit 822 performs the first detection processing on the image-quality-improved tomographic image by using the image quality improving model, and detects the retina region or the characteristic region. In this regard, the first processing unit 822 may perform the image quality improving processing on other images by using the image quality improving model, and the display controlling unit 25 may cause the display unit 50 to display various image-quality-improved images. For example, the first processing unit 822 may perform the image quality improving processing on an intensity En-Face image, an OCTA front image, etc., generated based on the information on the retina layers (for example, a boundary image) detected by the first detection processing and the second detection processing. Additionally, the display controlling unit 25 can cause the display unit 50 to display at least one of a tomographic image on which the image quality improving processing has been performed by the first processing unit 822, an intensity En-Face image, and an OCTA front image. Note that an image whose image quality is improved and that is displayed may be an SLO image, a fundus image obtained by a fundus camera, etc., a fluorescence fundus image, etc. Here, an SLO image is a front image of the fundus obtained by an SLO (Scanning Laser Ophthalmoscope) optical system, which is not illustrated.

Here, as for the training data for the image quality improving model for performing the image quality improving processing on various images, similar to the training data for the image quality improving model according to Example 6, for various images, images before the image quality improving processing are used as input data, and images after the image quality improving processing are used as ground truth. Note that, the image quality improving processing related to training data may be, similar to Example 6, for example, additive averaging processing, processing using a smoothing filter, maximum a posteriori estimation processing (MAP estimation processing), or gray scale conversion processing. Additionally, an image after the image quality improving processing may be, for example, an image on which filtering processing such as noise removal and edge emphasis has been performed, or an image whose contrast has been adjusted so as to make a low intensity image a high intensity image may be used. Further, since the ground truth of the training data for the image quality improving model may be a high quality image, the ground truth of the training data for the image quality improving model may be an image imaged by using an OCT apparatus with higher performance than the OCT apparatus at the time of imaging of an image, which is the input data, or an image imaged with high load settings.

Figure 21A:
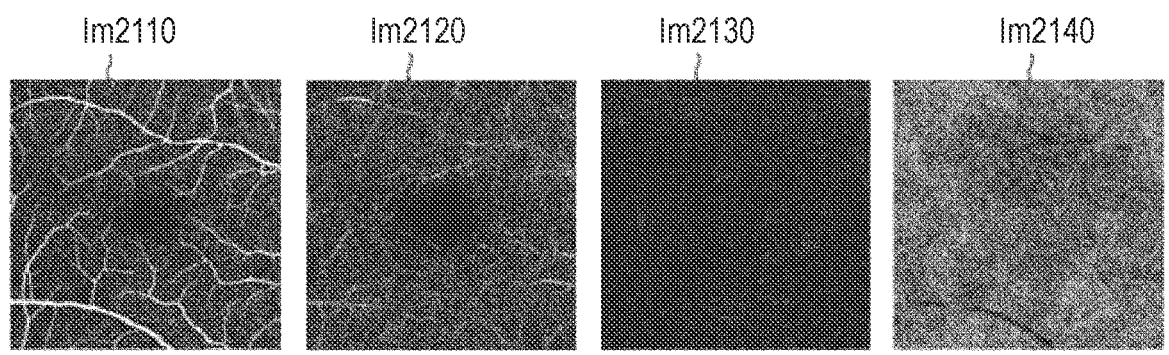
FIG. 21A illustrates an example of a plurality of OCTA En-Face images.

Additionally, the image quality improving model may be prepared for each kind of image on which the image quality improving processing is performed. For example, an image quality improving model for tomographic images, an image quality improving model for intensity En-Face images, and an image quality improving model for OCTA front images may be prepared. Further, the image quality improving model for intensity En-Face images and the image quality improving model for OCTA front images may be learned models that have comprehensively learned images in different depth ranges for the depth ranges (generation ranges) related to generation of images. As for images in different depth ranges, for example, as illustrated in FIG. 21A, images for a surface layer (Im2110), a deep layer (Im2120), an outer layer (Im2130), and a choroidal vascular network (Im1940) may be included. Additionally, a plurality of image quality improving models that have learned images for respective different depth ranges may be prepared for the image quality improving model for intensity En-Face images and the image quality improving model for OCTA front images.

Figure 21B:
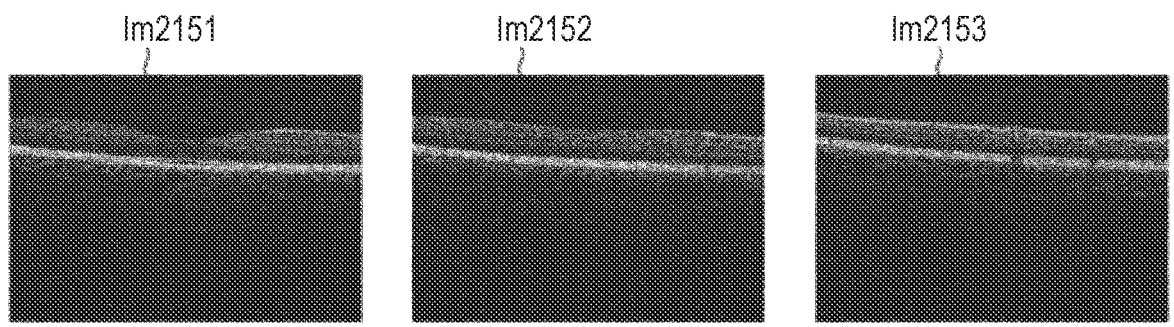
FIG. 21B illustrates an example of a plurality of intensity tomographic images.

Additionally, when preparing the image quality improving model for tomographic images, the image quality improving model for tomographic images may be the learned model that have comprehensively learned tomographic images obtained at different position in a sub-scanning (Y) direction. Tomographic images Im2151 to Im2153 illustrated in FIG. 21B are examples of the tomographic images obtained at different positions in the sub-scanning direction. However, in the case of images obtained by imaging locations of different imaged sites (for example, the center of the macular area, the center of the optic nerve head), learning may be performed separately for each site, or learning may be collectively performed without caring about imaged sites. Note that, as tomographic images whose image quality is to be improved, an intensity tomographic image, and a tomographic image of motion contrast data may be included. However, since the image characteristic amount is greatly different between the intensity tomographic image and the tomographic image of motion contrast data, learning may be separately performed for respective image quality improving models.

Hereinafter, the differences from the image processing according to Example 6 will be mainly described for the image processing by the image processing system according to the present example. Note that, since the configuration and the processing procedure of the image processing system according to the present example are similar to the configuration and the processing procedure of the image processing system 8 according to Example 6, the configuration and the processing procedure of the image processing system according to the present example will be illustrated by using the same reference numerals, and a description will be omitted.

In the present example, an example will be described in which the display controlling unit 25 performs displaying, on the display unit 50, an image on which the first processing unit 822 has performed the image quality improving processing. Note that, in the present example, although a description will be given by using FIG. 22A and FIG. 22B, a display screen is not limited to this. The image quality improving processing (processing for improving image quality) can be similarly applied also to a display screen that arranges and displays a plurality of images side by side obtained at different dates and times, such as in follow-up observation. Additionally, the image quality improving processing can be similarly applied also to a display screen for the examiner to confirm whether or not imaging is successful immediately after the imaging, such as an imaging confirmation screen. The display controlling unit 25 can cause the display unit 50 to display a plurality of high quality images generated by the first processing unit 822 and a low quality image for which image quality improvement has not been performed. Additionally, the display controlling unit 25 can cause the display unit 50 to display each of a low quality image and a high quality image that are selected according to an instruction by the examiner, for the plurality of high quality images and the low quality image for which image quality improvement has not been performed that are displayed on the display unit 50. In addition, the image processing apparatus 80 can also output, to the outside, the low quality image and the high quality image that are selected according to the instruction by the examiner.

Hereinafter, referring to FIG. 22A and FIG. 22B, an example of a display screen 2200 of an interface according to the present example is illustrated. The display screen 2200 illustrates the entire screen, and a patient tab 2201, an imaging tab 2202, a report tab 2203, and a setting tab 2204 are illustrated in the display screen 2200. Additionally, the oblique lines in the report tab 2203 represent the active state of a report screen. In the present example, an example of displaying the report screen will be described.

Figure 22A:
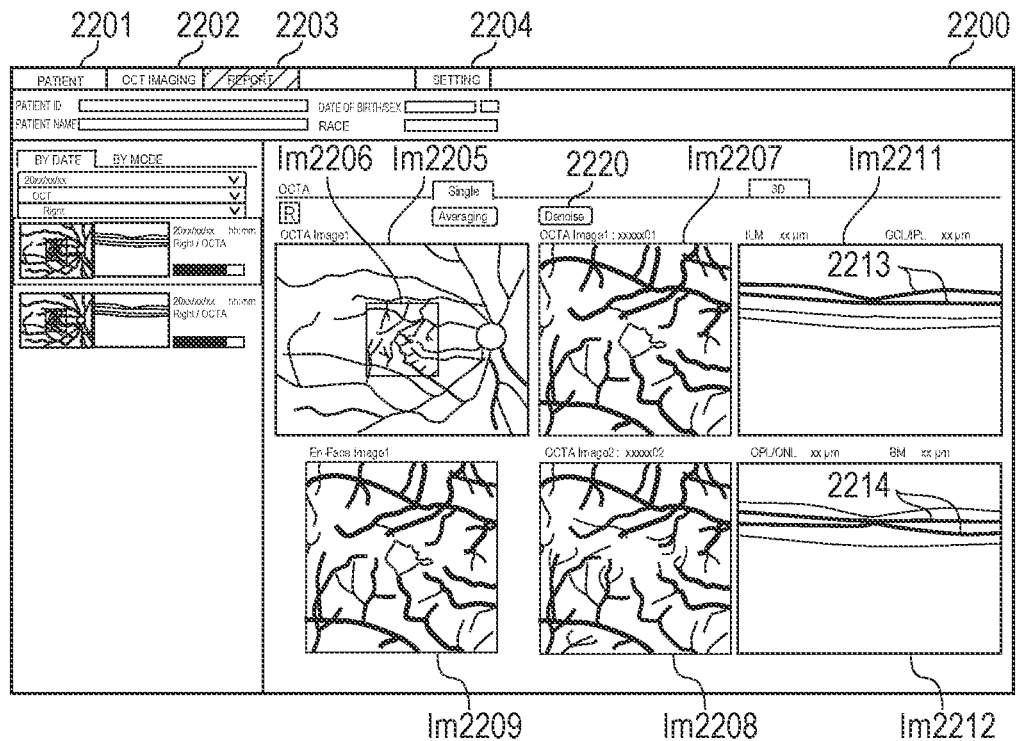
FIG. 22A illustrates an example of a user interface according to Example 7.

An SLO image Im2205, OCTA front images Im2207, 2208, an intensity En-Face image Im2209, tomographic images Im2211, 2212, and a button 2220 are illustrated in the report screen illustrated in FIG. 22A. Additionally, an OCTA front image Im2206 corresponding to the OCTA front image Im2207 is displayed superimposed in the SLO image Im2205. Further, boundary lines 2213, 2214 of the depth ranges of the OCTA front images Im2207, Im2208 are displayed superimposed in the tomographic images Im2211, 2212, respectively. The button 2220 is a button for specifying the execution of the image quality improving processing. The button 2220 may be a button for instructing the display of a high quality image, as described later.

In the present example, the execution of the image quality improving processing is performed by specifying the button 2220, or whether or not to perform execution is determined based on information saved (stored) in a database. First, an example will be described in which the display of a high quality image and the display of a low quality image are switched by specifying the button 2220 according to an instruction from the examiner. Note that, hereinafter, a target image of the image quality improving processing will be described as an OCTA front image.

Note that the depth ranges of the OCTA front images Im2207, Im2208 may be defined by using the information on the retina layers detected by the first detection processing and the second detection processing. The depth range may be, for example, a range between two layer boundaries related to the detected retina layers, or may be a range including a predetermined number of pixels in the deeper direction or the shallower direction based on one of the two layer boundaries related to the detected retina layers. Additionally, the depth range may be, for example, a range changed (offset) from the range between the two layer boundaries related to the detected retina layers, according to an instruction by the operator.

When the examiner specifies the report tab 2203 to make a transition to the report screen, the display controlling unit 25 displays the low image quality OCTA front images Im2207, Im2208. Then, when the examiner specifies the button 2220, the first processing unit 822 performs the image quality improving processing on the OCTA front images Im2207, Im2208 displayed on a screen. After the image quality improving processing is completed, the display controlling unit 25 displays a high quality image generated by the first processing unit 822 on the report screen. Note that, since the OCTA front image Im2206 is the OCTA front image Im2207 displayed superimposed on the SLO image Im2205, the display controlling unit 25 can also display the image obtained by performing the image quality improving processing on the OCTA front Im2206. Additionally, the display controlling unit 25 can change the display of the button 2220 to the active state, so that it can be seen from the display that the image quality improving processing has been performed.

Here, the execution of the processing in the first processing unit 822 does not need to be limited to the timing when the button 2220 is specified by the examiner. Since the kinds of the OCTA front images Im2207, Im2208 displayed at the time of opening the report screen are known in advance, the first processing unit 822 may perform the execution of the image quality improving processing at the time when the displayed screen is transitioned to the report screen. Then, the display controlling unit 25 may display a high quality image on the report screen at the timing when the button 2220 is pressed. Further, the kinds of images on which the image quality improving processing is performed in response to an instruction from the examiner, or when transitioning to the report screen do not need to be two kinds. The processing may be performed on images highly likely to be displayed, for example, a plurality of OCTA front images, such as the surface layer (Im2110), the deep layer (Im2120), the outer layer (Im2130), and the choroidal vascular network (Im2140) as illustrated in FIG. 21A. In this case, the images on which the image quality improving processing has been performed may be temporarily stored in a memory, or may be stored in a database.

Next, a case will be described in which the image quality improving processing is performed based on the information saved (stored) in the database. In a case where a state in which the execution of the image quality improving processing is performed is saved in the database, when transitioned to the report screen, the display controlling unit 25 causes, by default, the display unit 50 to display a high quality image obtained by performing the image quality improving processing by the first processing unit 822. Then, the system can be configured for the examiner to see that a high quality image obtained by performing the image quality improving processing is displayed, by causing, by default, the button 2220 to be displayed in the active state by the display controlling unit 25. When the examiner wants to display a low quality image before the image quality improving processing, by specifying the button 2220 to cancel the active state, the display controlling unit 25 can cause the display unit 50 to display the low quality image. On this occasion, when the examiner wants to return the displayed image to the high quality image, by specifying the button 2220 to be in the active state, the display controlling unit 25 causes the display unit 50 to display the high quality image again.

Whether or not the image quality improving processing has been performed may be specified in the database for each hierarchy, such as common to the entire data saved in the database, and for each imaged data (each examination). For example, when a state of performing the image quality improving processing on the entire database is saved, a state in which the examiner does not perform the image quality improving processing can be saved for individual imaged data (individual examination). In this case, the individual imaged data for which the state of not performing the image quality improving processing is saved can be displayed in the state in which the image quality improving processing is not performed the next time the individual imaged data is displayed. According to such a configuration, when whether or not to perform the image quality improving processing is not specified in the units of imaged data (in the units of examination), the processing can be performed based on the information specified for the entire database. Additionally, when specified in the units of imaged data (in the units of examination), the processing can be individually performed based on the information.

Note that a user interface (for example, a saving button), which is not illustrated, may be used to save the performing state of the image quality improving processing for each imaged data (each examination). Additionally, the state of performing the image quality improving processing may be saved based on the display state (for example, the state of the button 2220), when transitioning to other imaged data (other examination) or other patient data (for example, changing to a display screen other than the report screen according to an instruction from the examiner).

Although the example of displaying the OCTA front images Im2207, Im2208 as the OCTA front images has been illustrated in the present example, the OCTA front images to be displayed can be changed according to the specification by the examiner. Therefore, the changing of an image to be displayed in a case where the performing of the image quality improving processing is specified (the button 2220 is in the active state) will be described.

The changing of an image to be displayed can be performed by using a user interface (for example, a combo box), which is not illustrated. For example, when the examiner changes the kind of an image to the choroidal vascular network from the surface layer, the first processing unit 822 performs the image quality improving processing on a choroidal vascular network image, and the display controlling unit 25 displays a high quality image generated by the first processing unit 822 on the report screen. In other words, according to an instruction from the examiner, the display controlling unit 25 may change the display of a high quality image of a first depth range to the display of a high quality image of a second depth range that is at least partially different from the first depth range. At this time, the display controlling unit 25 may change the display of the high quality image of the first depth range to the display of the high quality image of the second depth range, when the first depth range is changed to the second depth range according to the instruction from the examiner. Note that, as for images highly likely to be displayed at the time of transition to the report screen as described above, when a high quality image is already generated, the display controlling unit 25 may display the generated high quality image.

Additionally, the changing method of the kinds of images is not limited to the method described above, and an OCTA front image for which a different depth range is set by changing the layer or offset value used as a reference can be generated, and a high quality image obtained by performing the image quality improving processing on the generated OCTA front image can also be displayed. In that case, when the layer or offset value used as the reference is changed, the first processing unit 822 performs the image quality improving processing on an arbitrary OCTA front image, and the display controlling unit 25 displays a high quality image on the report screen. Note that the changing of the layer and offset value used as the reference can be performed by using a user interface (for example, a combo box and a text box), which is not illustrated. Additionally, the depth range (generation range) of the OCTA front image can also be changed by dragging either of the boundary lines 2213, 2214 that are displayed superimposed on the tomographic images Im2211, Im2212, respectively (moving the layer boundary).

When changing the boundary line by dragging, execution commands of the image quality improving processing are consecutively performed. Therefore, the first processing unit 822 may always perform the processing of the execution commands, or may perform the processing after the layer boundary is changed by dragging. Alternatively, while execution of the image quality improving processing is consecutively ordered, at the time point % Olen the next command comes, the pervious command may be canceled, and the latest command may be executed.

Note that the image quality improving processing may take a relatively long time. Therefore, no matter when the command is executed at any of the above described timings, it may take a relatively long time until a high quality image is displayed. Thus, until a high quality image is displayed since the depth range for generating an OCTA front image is set according to an instruction from the examiner, a low image quality OCTA front image (low quality image) corresponding to the set depth range may be displayed. In other words, the system may be configured such that, when the above-described depth range is set, the low image quality OCTA front image (low quality image) corresponding to the set depth range is displayed, and when the image quality improving processing ends, the display of the low image quality OCTA front image is changed to the display of the high quality image. Additionally, until the high quality image is displayed since the above-described depth range is set, the information indicating that the image quality improving processing is being performed may be displayed. Note that these pieces of processing are not limited to the configuration applied in a case where the state in which the performing of the image quality improving processing is already specified (the button 2220 is in the active state) is assumed. For example, when the performing of the image quality improving processing is instructed according to an instruction from the examiner, these pieces of processing can also be applied until the high quality image is displayed.

In the present example, although the example has been illustrated that displays the OCTA front images Im2207, 2108 related to different layers as the OCTA front images, and that displays low quality and high quality images in a switching manner, the images displayed are not limited to these. For example, a low image quality OCTA front image and a high image quality OCTA front image may be displayed side by side as the OCTA front image Im2207 and the OCTA front image Im2208, respectively. When displaying images in a switching manner, since the images are switched at the same location, comparison of portions with change can be easily performed, and when displaying the images side by side, since the images can be displayed at the same time, the entire images can be easily compared.

Next, using FIG. 22A and FIG. 22B, the execution of the image quality improving processing in screen transition will be described. FIG. 22B is a screen example of displaying the OCTA front image Im2207 in FIG. 22A in an enlarged manner. Similar to FIG. 22A, the button 2220 is also displayed in FIG. 22B. As for the screen transition from FIG. 22A to FIG. 22B, for example, transition is made by double-clicking the OCTA front image Im2207, and transition from FIG. 22B to FIG. 22A is made with a close button 2230. Note that, regarding the screen transition, the screen transition is not limited to the method illustrated here, and a user interface, which is not illustrated, may be used.

When the execution of the image quality improving processing is specified in the screen transition (the button 2220 is active), the state is also maintained at the time of the screen transition. In other words, when transition is made to the screen of FIG. 22B in the state in which the high quality image is displayed on the screen of FIG. 22A, the high quality image is also displayed in the screen of FIG. 22B. Then, the button 2220 is turned into the active state. The same also applies to a case where transition is made from FIG. 22B to FIG. 22A. The display can be switched to a low quality image by specifying the button 2220 in FIG. 22B.

As for the screen transition, the screen transition is not limited to the screens illustrated here, and as long as transition is made to a screen displaying the same imaged data, such as a display screen for follow-up observation or a display screen for panorama, the transition can be performed while maintaining the display state of the high quality image. In other words, in the display screen after transition, an image corresponding to the state of the button 2220 in the display screen before the transition can be displayed. For example, when the button 2220 in the display screen before transition is in the active state, a high quality image is displayed in the display screen after the transition. Additionally, for example, when the active state of the button 2220 in the display screen before transition is canceled, a low quality image is displayed in the display screen after the transition. Note that, when the button 2220 in the display screen for follow-up observation turns into the active state, a plurality of images that are obtained at different dates and times (different examination dates), and arranged and displayed side by side on the display screen for follow-up observation may be switched to high quality images. In other words, it may be configured such that, when the button 2220 in the display screen for follow-up observation turns into the active state, it may be collectively reflected to the plurality of images obtained at different dates and times.

Figure 23:
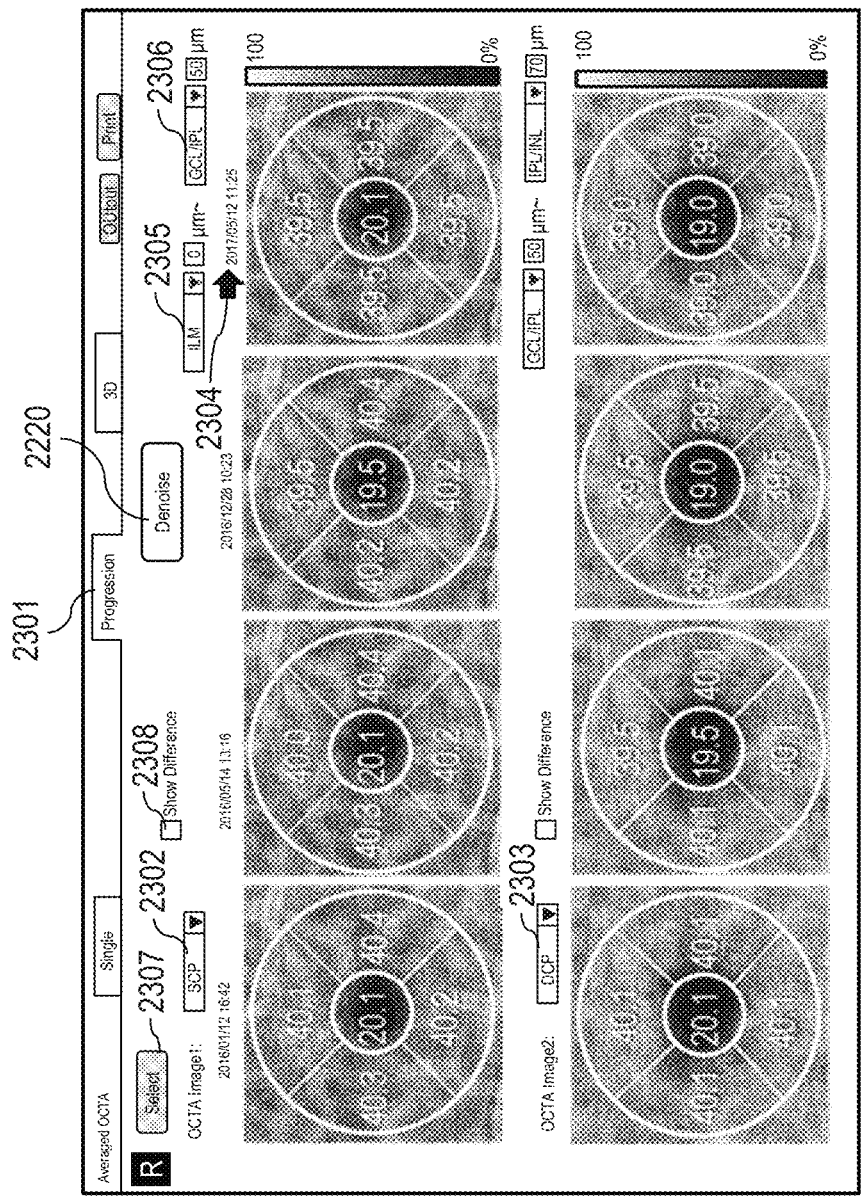
FIG. 23 illustrates an example of a user interface according to Example 7.

Note that an example of the display screen for follow-up observation is illustrated in FIG. 23. When a tab 2301 is selected in response to an instruction from the examiner, the display screen for follow-up observation is displayed as shown in FIG. 23. At this time, the depth ranges of OCTA front images can be changed by selecting a set desired by the examiner from a predetermined depth range set displayed in list boxes 2302, 2303. For example, the retina surface layer is selected in the list box 2302, and the retina deep layer is selected in the list box 2303. Analysis results of OCTA front images of the retina surface layer are displayed in an upper display region, and analysis results of OCTA front images of the retina deep layer are displayed in a lower display region. When a depth range is selected, the plurality of images at different dates and times are collectively changed to parallel display of analysis results of the plurality of OCTA front images of the selected depth range.

At this time, collective change to parallel display of the plurality of OCTA front images at different dates and times may be performed when the display of the analysis results is turned into a non-selected state. Then, when the button 2220 is specified in response to an instruction from the examiner, the display of the plurality of OCTA front images is collectively changed to the display of a plurality of high quality images.

Additionally, in a case where the display of analysis results is in a selected state, when the button 2220 is specified in response to an instruction from the examiner, the display of the analysis results of the plurality of OCTA front images is collectively changed to the display of analysis results of a plurality of high quality images. Here, in the display of the analysis results, the analysis result may be displayed superimposed on the images with arbitrary transparency. At this time, the change to the display of the analysis results from the display of the images may be, for example, the change to a state in which the analysis results are superimposed on the displayed images with arbitrary transparency. Additionally, the change to the display of the analysis results from the display of the images may be, for example, the change to the display of images (for example, two-dimensional maps) obtained by performing blending processing on the analysis results and the images with arbitrary transparency.

In addition, the kind and offset position of a layer boundary used for specification of the depth range can be collectively changed from user interfaces 2305, 2306, respectively. Note that the user interfaces 2305, 2306 for changing the kind and offset position of the layer boundary is an example, and any other form of interface may be used. Note that the depth ranges of a plurality of OCTA front images of different dates and times may be collectively changed by also displaying a tomographic image, and moving the layer boundary data superimposed on the tomographic image according to an instruction from the examiner. At this time, a plurality of tomographic images of different dates and times may be arranged and displayed side by side, and when the above-described movement is performed on one tomographic image, the layer boundary data may be similarly moved on the other tomographic images.

Additionally, the presence or absence of an image projection method and projection artifact suppression processing may be changed by, for example, selecting it from a user interface such as a context menu.

Additionally, a selection screen, which is not illustrated, may be displayed by selecting a select button 2307, and an image selected from an image list displayed on the selection screen may be displayed. Note that an arrow 2304 displayed in an upper part of FIG. 23 is a mark indicating a currently selected examination, and the baseline examination (Baseline) is the examination (the leftmost image in FIG. 23) selected at the time of Follow-up imaging. Of course, a mark indicating the baseline examination may be displayed in the display unit.

Additionally, when a "Show Difference" check box 2308 is specified, a measurement value distribution (a map or a sector map) for a reference image is displayed on the reference image. Further, in this case, in regions corresponding to the other examination days, the difference measurement value maps between the measurement value distribution calculated for the reference image and the measurement value distributions calculated for an image displayed in the regions are displayed. As a measurement result, a trend graph (a graph of measurement values for an image of each examination day obtained by measurement of change over time) may be displayed on the report screen. In other words, time series data (for example, a time series graph) of a plurality of analysis results corresponding to a plurality of images of different dates and times may be displayed. At this time, analysis results for dates and times other than the plurality of dates and times corresponding to the plurality of displayed images may also be displayed as time series data in a state that can be distinguished from the plurality of analysis results corresponding to the plurality of displayed images (for example, the color of each point on a time series graph is different depending on whether or not an image is displayed). Additionally, the regression line (curved line) and corresponding equation of the trend graph may be displayed on the report screen.

In the present example, although the OCTA front images have been described, images on which the processing according to the present example is applied are not limited to these. Images related to the processing such as displaying, image quality improving, and image analysis according to the present example may be intensity En-Face images. Further, the images may be not only En-Face images, but may be different images, such as a tomographic image by the B-scan, an SLO image, a fundus image, or a fluorescence fundus image. In that case, a user interface for performing the image quality improving processing may be one for instructing the performing of the image quality improving processing on a plurality of images of different kinds, and one for selecting an arbitrary image from the plurality of images of different kinds to instruct the performing of the image quality improving processing.

For example, when displaying tomographic images by the B-scan by improving the image quality, the tomographic images Im2211, Im2212 illustrated in FIG. 22A may be displayed by improving the image quality. Additionally, tomographic images whose image quality has been improved may be displayed in the regions where the OCTA front images Im2207, Im2208 are displayed. Note that, for the tomographic images displayed by improving the image quality, only one may be displayed, or a plurality may be displayed. When a plurality of tomographic images are displayed, tomographic images obtained at respective different positions in the sub-scanning direction may be displayed, or when a plurality of tomographic images obtained by, for example, cross scan are displayed by improving the image quality, images in respective different scanning directions may be displayed. Additionally, when a plurality of tomographic images obtained by, for example, radial scan are displayed by improving the image quality, a plurality of partially selected tomographic images (for example, two tomographic images at mutually symmetrical positions with respect to a reference line) may be respectively displayed. Further, a plurality of tomographic images may be displayed on the display screen for follow-up observation as illustrated in FIG. 23, and the display of instructions for image quality improving and analysis results (for example, the thickness of a specific layer) may be performed by a technique similar to the above-described method. Additionally, the image quality improving processing may be performed on tomographic images based on information saved in the database in a technique similar to the above-described method.

Similarly, when displaying an SLO image by improving the image quality, for example, the SLO image Im2205 may be displayed by improving the image quality. Further, when displaying an intensity En-Face image by improving the image quality, for example, the intensity En-Face image 2209 may be displayed by improving the image quality. Further, a plurality of SLO images and intensity En-Face images may be displayed on the display screen for follow-up observation as illustrated in FIG. 23, and the display of instructions for image quality improving and analysis results (for example, the thickness of a specific layer) may be performed by a technique similar to the above-described method. Additionally, the image quality improving processing may be performed on SLO images and intensity En-Face images based on information saved in the database in a technique similar to the above-described method. Note that the display of tomographic images. SLO images, and the intensity En-Face images is exemplification, and these images may be displayed in arbitrary forms according to a desired configuration. Additionally, at least two or more of OCTA front images, tomographic images, SLO images, and intensity En-Face images may be displayed by improving the image quality with a single instruction.

With such a configuration, the display controlling unit 25 can display, on the display unit 50, images on which the first processing unit 822 according to the present example performed the image quality improving processing. At this time, as described above, when in a state in which at least one of a plurality of conditions related to the display of a high quality image, the display of an analysis result, and the depth range of a displayed front image, etc., is selected, even when the display screen is transitioned, the selected state may be maintained.

Additionally, as described above, when in a state in which at least one of a plurality of conditions is selected, even when the state is changed into a state in which the other condition is selected, the state in which the at least one is selected may be maintained. For example, when the display of the analysis result is in the selected state, the display controlling unit 25 may change the display of the analysis result of a low quality image to the display of the analysis result of a high quality image, according to an instruction from the examiner (for example, when the button 2220 is specified). Additionally, when in a state in which the display of an analysis result is selected, the display controlling unit 25 may change the display of the analysis result of a high quality image to the display of the analysis result of a low quality image, according to an instruction from the examiner (for example, when the specification of the button 2220 is canceled).

Additionally, when the display of a high quality image is in the non-selected state, the display controlling unit 25 may change the display of the analysis result of a low quality image to the display of the low quality image, according to an instruction from the examiner (for example, when the specification of the display of the analysis result is canceled). In addition, when the display of a high quality image is in the non-selected state, the display controlling unit 25 may change the display of a low quality image to the display of the analysis result of the low quality image, according to an instruction from the examiner (for example, when the display of the analysis result is specified). Additionally, when the display of a high quality image is in the selected state, the display controlling unit 25 may change the display of the analysis result of a high quality image to the display of the high quality image, according to an instruction from the examiner (for example, when the specification of the display of the analysis result is canceled). In addition, when the display of a high quality image is in the selected state, the display controlling unit 25 may change the display of a high quality image to the display of the analysis result of the high quality image, according to an instruction from the examiner (for example, when the display of the analysis result is specified).

Additionally, a case is considered where the display of a high quality image is in the non-selected state, and the display of the analysis result of a first kind is in the selected state. In this case, the display controlling unit 25 may change the display of the analysis result of the first kind of a low quality image to the display of the analysis result of a second kind of the low quality image, according to an instruction from the examiner (for example, when the display of the analysis result of the second kind is specified). Additionally, a case is considered where the display of a high quality image is in the selected state, and the display of the analysis result of the first kind is in the selected state. In this case, the display controlling unit 25 may change the display of the analysis result of the first kind of a high quality image to the display of the analysis result of the second kind of the high quality image, according to an instruction from the examiner (for example, when the display of the analysis result of the second kind is specified).

Note that the display screen for follow-up observation may be configured such that these changes to the display may be collectively reflected to a plurality of images obtained at different dates and times as described above. Here, in the display of the analysis results, the analysis results may be displayed superimposed on the images with arbitrary transparency. At this time, the change to the display of the analysis results may be, for example, the change to a state in which the analysis results are superimposed on the displayed images with arbitrary transparency. Additionally, the change to the display of the analysis results may be, for example, the change to the display of images (for example, two-dimensional maps) obtained by performing blending processing on the analysis results and the images with arbitrary transparency.

Note that, in the present example, the first processing unit 822 generates the high quality image obtained by improving the image quality of the tomographic image by using the learned model (image quality improving model) related to the image quality improving processing. However, the component that generates a high quality image by using the image quality improving model is not limited to the first processing unit 822. For example, a third processing unit (image quality improving unit) different from the first processing unit 822 may be provided, and the third processing unit may generate a high quality image by using the image quality improving model. In this case, the third processing unit and the image quality improving model may include a software module executed by a processor, such as a CPU, an MPU, a GPU, and an FPGA, or may include a circuit that achieves specific functions, such as an ASIC.

Modifications of Examples 6 and 7

In Examples 6 and 7, the display controlling unit 25 can cause the display unit 50 to display an image selected according to an instruction from the examiner among the high quality images generated by the first processing unit 822 and the input images. Additionally, the display controlling unit 25 may switch the display on the display unit 50 from an imaged image (input image) to a high quality image, according to an instruction from the examiner. In other words, the display controlling unit 25 may change the display of a low quality image to the display of a high quality image, according to an instruction from the examiner. Additionally, the display controlling unit 25 may change the display of a high quality image to the display of a low quality image, according to an instruction from the examiner.

Further, the first processing unit 822 may perform the start of the image quality improving processing by an image quality improving engine (image quality improving model) (the input of an image to the image quality improving engine) according to an instruction from the examiner, and the display controlling unit 25 may display the generated high quality image on the display unit 50. In contrast, when an input image is imaged by the imaging apparatus (OCT apparatus 10), the first processing unit 822 may automatically generate a high quality image based on the input image by using the image quality improving engine, and the display controlling unit 25 may cause the display unit 50 to display the high quality image according to an instruction from the examiner. Here, the image quality improving engine includes a learned model that performs the above-described processing for improving image quality (image quality improving processing).

Note that these pieces of processing can also be similarly performed on the output of an analysis result. In other words, the display controlling unit 25 may change the display of the analysis result of a low quality image to the display of the analysis result of a high quality image, according to an instruction from the examiner. Additionally, the display controlling unit 25 may change the display of the analysis result of a high quality image to the display of the analysis result of a low quality image, according to an instruction from the examiner. Further, the display controlling unit 25 may change the display of the analysis result of a low quality image to the display of the low quality image, according to an instruction from the examiner. Additionally, the display controlling unit 25 may change the display of a low quality image to the display of the analysis result of the low quality image, according to an instruction from the examiner. Further, the display controlling unit 25 may change the display of the analysis result of a high quality image to the display of the high quality image, according to an instruction from the examiner. In addition, the display controlling unit 25 may change the display of a high quality image to the display of the analysis result of the high quality image, according to an instruction from the examiner.

Further, the display controlling unit 25 may change the display of the analysis result of a low quality image to the display of other kind of analysis result of the low quality image, according to an instruction from the examiner. Additionally, the display controlling unit 25 may change the display of the analysis result of a high quality image to the display of other kind of analysis result of the high quality image, according to an instruction from the examiner.

Here, in the display of the analysis result of a high quality image, the analysis result of the high quality image may be displayed superimposed on the high quality image with arbitrary transparency. Additionally, in the display of the analysis result of a low quality image, the analysis result of the low quality image may be displayed superimposed on the low quality image with arbitrary transparency. At this time, the change to the display of the analysis result may be, for example, the change to a state in which the analysis result is superimposed on the displayed images with arbitrary transparency. Additionally, the change to the display of the analysis result may be, for example, the change to the display of an image (for example, a two-dimensional map) obtained by performing blending processing on the analysis result and the image with arbitrary transparency.

Note that, in the present modification, the first processing unit 822 generates the high quality image obtained by improving the image quality of the tomographic image by using the learned model (image quality improving model) related to the image quality improving processing. However, the component that generates a high quality image by using the image quality improving model is not limited to the first processing unit 822. For example, a third processing unit different from the first processing unit 822 may be provided, and the third processing unit may generate a high quality image by using the image quality improving model. In this case, the third processing unit and the image quality improving model may include a software module executed by a processor, such as a CPU, an MPU, a GPU, and an FPGA, or may include a circuit that achieves specific functions, such as an ASIC.

Additionally, in Example 7, the image is displayed on which the image quality improving processing has been performed by using the image quality improving model, according to the active state of the button 2220 in the display screen. In contrast, the system may be configured such that, according to the active state of the button 2220, an analysis value using the result of the image segmentation processing using the learned model is displayed. In this case, for example, when the button 2220 is in a non-active state (the image segmentation processing using the learned model is in a non-selected state), the display controlling unit 25 causes the display unit 50 to display the analysis result using the result of the image segmentation processing performed by the second processing unit 823. In contrast, when the button 2220 is turned into the active state, the display controlling unit 25 causes the display unit 50 to display the analysis result using the result of the image segmentation processing performed by the first processing unit 822 alone, or by the first processing unit 822 and the second processing unit 823.

In such a configuration, the analysis result using the result of the image segmentation processing that does not use the learned model, and the analysis result using the result of the image segmentation processing that uses the learned model are switched and displayed according to the active state of the button. Since these analysis results are respectively based on the results of the processing by the learned model and the image processing by a rule base, there may be a difference in both the results. Therefore, by switching and displaying these analysis results, the examiner can compare the both, and can use a more convincing analysis result for diagnosis.

Note that, when the image segmentation processing is switched, for example, in a case where a displayed image is a tomographic image, the numerical value of the layer thickness analyzed for each layer may be switched and displayed. Additionally, for example, when a tomographic image divided into layers by colors, hatching patterns, etc., is displayed, a tomographic image in which the shapes of the layers are changed according to the result of the image segmentation processing may be switched and displayed. Further, when a thickness map is displayed as an analysis result, the thickness map in which the color indicating the thickness is changed according to the result of the image segmentation processing may be displayed. Additionally, a button for specifying the image quality improving processing and a button for specifying the image segmentation processing using the learned model may be separately provided, only either one may be provided, or both the buttons may be provided as one button.

Additionally, similar to the switching of the above-described image quality improving processing, the switching of the image segmentation processing may be performed based on information saved (recorded) in the database. Note that, also for the processing at the time of screen transition, the switching of the image segmentation processing may be performed similarly to the above-described image quality improving processing.

In Examples 1 to 7, the obtaining unit 21 obtains the interference signal obtained by the OCT apparatus 10 and the three-dimensional tomographic data generated by the tomographic image generating unit 221. However, the configuration in which the obtaining unit 21 obtains these signals and data is not limited to this. For example, the obtaining unit 21 may obtain these signals from a server and an imaging apparatus connected to the image processing apparatus 20 via a LAN, a WAN, or the Internet. In this case, the processing related to imaging can be omitted, and three-dimensional tomographic data that has been imaged can be obtained. Then, the boundary detection processing can be performed in step S304, step S904, etc. Therefore, the series of processing time from the obtaining of tomographic information to the display of a front image, a thickness map, etc., can be shortened.

Note that the learned model for image segmentation used by the processing unit 222 and the first processing unit 822, and the learned model for improving image quality can be provided in the image processing apparatuses 20, 80, 152. The learned models may include, for example, a software module executed by a processor, such as a CPU, an MPU, a GPU, and an FPGA, or may include a circuit that achieves specific functions, such as an ASIC. Additionally, these learned models may be provided in another server apparatus, etc., connected to the image processing apparatuses 20, 80, 152. In this case, the image processing apparatuses 20, 80, 152 can use the learned models by being connected to the server, etc., including the learned models via an arbitrary network, such as the Internet. Here, the server including the learned models may be, for example, a cloud server, a fog server, and an edge server.

Additionally, in Examples 2 to 7, although a label image in which labeling is performed for each pixel has been described as the label image, a label image in which labeling is performed for each region may be used as the label image.

Note that the configuration of the OCT apparatus 10 is not limited to the above-described configuration, and a part of the configuration included in the OCT apparatus 10 may be configured as a different body from the OCT apparatus 10. Additionally, the user interface such as the button, and the layout of display are not limited to those illustrated above.

According to above-described Examples 1 to 7 and their modifications, the boundary detection of the retina layers can be performed regardless of diseases, sites, etc.

Example 8

In the medical field, in order to specify the disease of a subject, or to observe the degree of the disease, the image diagnosis utilizing images obtained by various imaging apparatuses is performed. As the kinds of imaging apparatuses, there are, for example, an X-ray imaging apparatus, an X-ray computerized tomography imaging apparatus (CT), a magnetic resonance imaging system (MRI), and a positron emission tomography imaging apparatus (PET) in the radiology field. Additionally, in the ophthalmology field, there are, for example, a fundus camera, a scanning laser ophthalmoscope (SLO), an optical coherence tomography (OCT) apparatus, and an OCT angiography (OCTA) apparatus.

Although the image diagnosis is basically performed by a medical worker by observing the pathological change, etc., depicted in an image, in recent years, various kinds of information useful for diagnosis can be obtained with improvements in the image analysis technology. For example, by performing image analysis, a small pathological change that may be overlooked can be detected to assist the medical worker, quantitative measurement can be performed for the shape and volume of the pathological change, and further, a disease can be specified without the observation by the medical worker.

Note that, although there are various techniques for image analysis, the processing for specifying a region such as an organ or a pathological change depicted in an image, which is called the image segmentation processing, is the processing required for performing many techniques for image analysis. Hereinafter, for simplification, the image segmentation processing is also referred to as segmentation processing.

The conventional image segmentation processing is performed by an image processing algorithm based on the medical knowledge and image characteristics related to a target organ or a pathological change as in Japanese Patent Application Laid-Open No. 2008-73099. However, an image obtained from an imaging apparatus at an actual medical setting may not be finely imaged due to various factors, such as the clinical condition of a subject, the imaging environment of the imaging apparatus, and lack of skill of a person who performs imaging. Therefore, in the conventional image segmentation processing, the target organ or pathological change are not depicted as expected, and in some cases, a specific region cannot be extracted with high accuracy.

Specifically, in an image obtained by imaging a diseased eye with, for example, disappearance of a retina layer, bleeding, vitiligo, and occurrence of new blood vessels by an OCT apparatus, the depiction of the shape of the retina layers can be irregular. In such a case, erroneous detection may occur in the region detection processing of the retina layers, which is a kind of the image segmentation processing.

One of the objects of the following Examples 8 to 19 is providing a medical image processing apparatus, a medical image processing method, and a program that can perform the image segmentation processing with higher accuracy than the conventional image segmentation processing.

Description of Terms

Here, the terms used in the present disclosure will be described.

In a network in the present specification, each apparatus may be connected with a wired or wireless line. Here, the line connecting each apparatus in the network includes, for example, a dedicated line, a local area network (hereinafter written as a LAN) line, a wireless LAN line, an Internet line, Wi-Fi (registered trademark), and Bluetooth (registered trademark).

A medical image processing apparatus may include two or more apparatuses that can communicate with each other, or may include a single apparatus. Additionally, each component of the medical image processing apparatus may include a software module performed by a processor, such as a CPU, an MPU, a GPU, and an FPGA. In addition, the each component may include a circuit that achieves specific functions, such as an ASIC. Further, it may include a combination of other arbitrary hardware and arbitrary software.

Additionally, a medical image processed by the medical image processing apparatus or the medical image processing method is a tomographic image of the subject obtained by using the OCT apparatus. Here, the OCT apparatus may include a time domain OCT (TD-OCT) apparatus and a Fourier domain OCT (FD-OCT) apparatus. Additionally, the Fourier domain OCT apparatus may include a spectral domain OCT (SD-OCT) apparatus and a wavelength sweep type OCT (SS-OCT) apparatus. In addition, the OCT apparatus may include a wavefront compensation OCT (AO-OCT) apparatus using a wavefront compensation optical system, a line OCT apparatus that forms measurement light irradiated on a subject in a line form, a full-field OCT apparatus that forms measurement light in a surface shape.

The medical image includes a tomographic image of an eye of the subject (an eye to be examined). The tomographic image of the eye to be examined is not limited to a tomographic image of the retina, etc., in the posterior ocular segment of the eye to be examined, and includes tomographic images of the anterior ocular segment and the eye chamber of the eye to be examined. Additionally, when using the OCT apparatus for an endoscope, etc., a tomographic image of the skin or an organ of the subject may be used as a medical image to be processed by the medical image processing apparatus or the medical image processing method according to the following examples.

An image management system is an apparatus and a system that receive and save images imaged by an imaging apparatus such as the OCT apparatus, and images on which image processing has been performed. Additionally, the image management system can transmit an image according to a request from a connected apparatus, can perform image processing on the saved images, and can request a request for image processing to other apparatus. The image management system can include, for example, a picture archiving and communication system (PACS). Especially, an image management system according to the following examples includes a database that can also save various kinds of information associated with the received image, such as information on the subject and imaging time. Additionally, the image management system is connected to a network, and can transmit and receive images according to a request from other apparatus, can convert images, and can transmit and receive various kinds of information associated with the saved images.

Imaging conditions are various kinds of information at the time of imaging of an image obtained by an imaging apparatus. The imaging conditions include, for example, the information related to the imaging apparatus, the information related to a facility where imaging is performed, the information on examination related to imaging, the information related to a person who performs imaging, and the information on the subject. Additionally, the imaging conditions include, for example, information related to the date and time of imaging, an imaged site name, an imaged region, an imaging angle of view, an imaging system, the resolution and gradation of an image, the image size, an applied image filter, and the data format of the image. Note that the imaged region can include a surrounding region shifted from a specific imaged site, and a region including a plurality of imaged sites. Additionally, the imaging system may include an arbitrary imaging system for OCT, such as a spectral domain system, and a wavelength sweep system.

The imaging conditions can be saved in the data structure constituting an image, can be saved as imaging condition data different from the image, or can be saved in a database relevant to the imaging apparatus and the image management system. Therefore, the imaging conditions can be obtained in a procedure corresponding to a saving unit of the imaging conditions of the imaging apparatus. Specifically, the imaging conditions are obtained by, for example, analyzing the data structure of an image output by the imaging apparatus, obtaining the imaging condition data corresponding to the image, or accessing an interface for obtaining the imaging conditions from the database relevant to the imaging apparatus.

Note that, depending on the imaging apparatus, there is also an imaging condition that cannot be obtained due to reasons such as not being saved. For example, there is a case where there is no function for obtaining and saving a specific imaging condition in the imaging apparatus, or where such a function is disabled. Additionally, for example, there is also a case where an imaging condition is not saved since the imaging condition is not relevant to the imaging apparatus or imaging. Further, for example, there is a case where an imaging condition is hidden, is encrypted, or cannot be obtained without a right. However, there is a case where even an imaging condition that is not saved can be obtained. For example, the imaged site name and the imaged region can be specified by performing image analysis.

Figure 24:
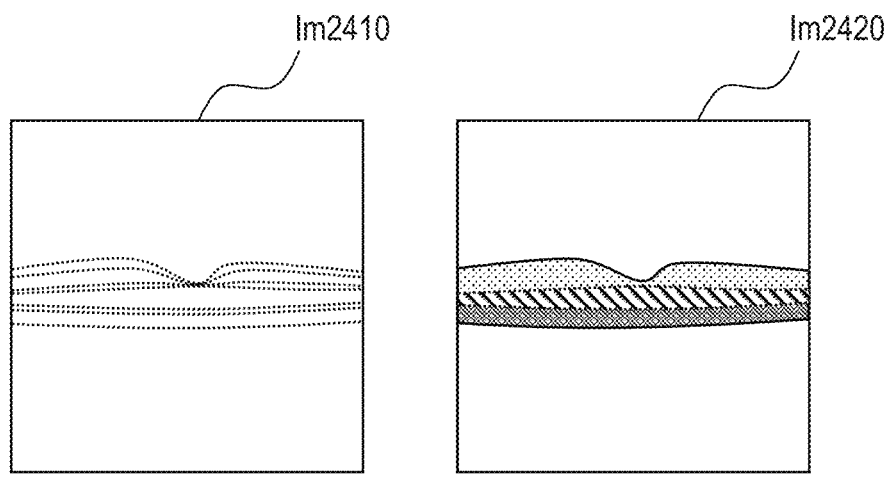
FIG. 24 illustrates an example of a region label image pertaining to a description of terms.

A region label image refers to a label image in which a label for a region is given for each pixel. Specifically, as illustrated in FIG. 24, it is an image Im2420 divided by pixel values (hereinafter, region label values) that can specify an arbitrary region among the regions depicted in an image Im2410 obtained by the imaging apparatus. Here, the specified arbitrary region includes a region of interest (ROI: Region Of Interest), and a volume of interest (VOI: Volume Of Interest).

When the coordinates of pixels with an arbitrary region label value are specified from the image Im2420, the coordinates of pixels depicting a corresponding region such as the retina layers in the image Im2410 can be specified. Specifically, for example, when a region label value indicating the ganglion cell layer constituting the retina is 1, the coordinates whose pixel value is 1 among the pixels of the image Im2420 are specified, and the pixels corresponding to the coordinates are extracted from the image Im2410. Accordingly, the region of the ganglion cell layer in the image Im2410 can be specified.

Note that, in some examples, the processing of performing reduction or enlargement processing on a region label image is included. At this time, as an image completion processing technique used for the reduction or enlargement of a region label image uses a nearest neighbor method, etc., that does not erroneously generate an undefined region label value and a region label value not supposed to exist in corresponding coordinates.

The image segmentation processing is the processing that specifies a region called a ROI or VOI, such as an organ or a pathological change depicted in an image, for utilizing the region for image diagnosis or image analysis. For example, according to the image segmentation processing, the regions of the layers constituting the retina can be specified from an image obtained by the imaging of the OCT that uses the posterior segment of eyeball as an imaging target. Note that the number of specified regions is 0 when the region to be specified is not depicted in an image. Additionally, when a plurality of regions to be specified are depicted in an image, the number of specified regions may be plural, or may be one region surrounding the regions so as to include the regions.

The specified regions are output as information that can be utilized in the other processing. Specifically, for example, the coordinates of pixels constituting each of the specified regions can be output as a numerical data group. Additionally, for example, the coordinates indicating a square region, an elliptic region, a parallelepiped region, an ellipsoid region, etc., including each of the specified regions can also be output as the numerical data group. Further, for example, the coordinates indicating a straight line, a curved line, a flat surface, or a curved surface, etc., corresponding to a boundary of the specified regions can also be output as the numerical data group. Additionally, for example, a region label image indicating the specified regions can also be output.

Note that, hereinafter, when the accuracy of the image segmentation processing is expressed as high, or when a region label image is expressed as highly accurate, the fact is indicated that the percentage of correctly specifying a region is high. Additionally, conversely, when the accuracy of the image segmentation processing is expressed as low, the fact is indicated that the percentage of erroneously specifying a region is high.

A region-label-less image is a kind of a region label image, and is a region label image in which the information corresponding to a ROI or VOI to be utilized for image diagnosis or image analysis is not included. Specifically, as an example, a case will be described where the region of the ganglion cell layer constituting the retina depicted in a medical image is desired to be found in order to be utilized for image analysis.

Here, it is assumed that the region label value indicating the region of the ganglion cell layer is 1, and the region label value indicating the rest of the region is 0. When a region label image corresponding to a certain medical image is generated by the image segmentation processing, etc., in a case where the ganglion cell layer is not depicted in the medical image, all the pixel values of a region label image are 0. In this case, the region label image is a region-label-less image, since a region that corresponds to the ROI of the ganglion cell layer to be utilized for image analysis, and that has a region label value of 1 does not exist in the region label image. Note that, depending on the setting or implementation, the region-label-less image may not be an image, and may be a numerical data group, etc., indicating the coordinates with information similar to an image.

Here, a machine learning model refers to a learning model with machine learning algorithms. As specific algorithms for machine learning, a nearest neighbor method, the Naive Bayesian method, a decision tree, a support vector machine, etc., can be listed. Additionally, depths learning (deep learning) that generates by itself a characteristic amount for learning, and a combined weighting factor by utilizing a neural network can also be listed. Appropriately, the algorithm that can be utilized among the above-described algorithms may be used to be applied to the learning models according to examples. The learned model is a model for which training (learning) has been performed in advance on a machine learning model according to arbitrary machine learning algorithms by using appropriate training data. However, it is assumed that the learned model is not one that does not perform further learning, but can also perform incremental learning. The training data includes one or more pairs of input data and ground truth. Note that the format and combination of input data and ground truth of the pairs constituting the training data may be those suitable for a desired configuration, such as one is an image and the other is a numerical value, one includes a plurality of images and the other is a character string, or the both are images.

Specifically, for example, the training data including the pairs of an image obtained by the OCT and the imaged site label corresponding to the image (hereinafter, first training data) can be listed. Note that the imaged site label is a unique numerical value or a character string representing a site. Additionally, as an example of the other training data, the training data including the pairs of an image obtained by the imaging of the OCT that uses the posterior ocular segment as the imaging target, and a region label image of the retina layers corresponding to the image (hereinafter, second training data) can be listed. Further, as an example of the other training data, training data including the pairs of a low quality image with a lot of noise obtained by the usual imaging of the OCT, and a high quality image on which the image quality improving processing has been performed by imaging by the OCT a plurality of times (hereinafter, third training data) can be listed.

When input data is input to a learned model, output data according to the design of the learned model is output. The learned model outputs, for example, output data that is highly likely to correspond to the input data according to a tendency trained by using the training data. Additionally, the learned model can perform, for example, outputting the probability corresponding to the input data as a numerical value for each of the kinds of output data, according to the tendency trained by using the training data.

Specifically, for example, when an image obtained by the OCT is input to the learned model trained with the first training data, the learned model outputs the imaged site label of an imaged site imaged in the image, and outputs the probability for each imaged site label. Additionally, for example, when an image depicting the retina layers obtained by the imaging of the OCT that uses the posterior ocular segment as the imaging target is input to the learned model trained with the second training data, the learned model outputs the region label image for the retina layers depicted in the image. Further, for example, when a low quality image with a lot of noise obtained by the usual imaging of the OCT is input to the learned model trained with the third training data, the learned model outputs a high quality image corresponding to an image on which the image quality improving processing has been performed by imaging by the OCT a plurality of times.

The machine learning algorithm includes a technique related to deep learning, such as a convolutional neural network (CNN). In the technique related to deep learning, when the settings of parameters for the layers and nodes constituting a neural network are different, the degree to which the tendency trained by using the training data can be reproduced in the output data may vary.

For example, in the learned model of deep learning using the first training data, when a more appropriate parameter is set, the probability of outputting a correct imaged site label may become higher. Additionally, for example, in the learned model using the second training data, when a more appropriate parameter is set, a more accurate region label image may be able to be output. Further, for example, in the learned model of deep learning using the third training data, when a more appropriate parameter is set, an image with a higher image quality may be able to be output.

Specifically, the parameter in the CNN can include, for example, the kernel size of a filter, the number of filters, the value of a stride, and the value of dilation that are set to the convolutional layer, and the number of nodes output by a fully connected layer. Note that the parameters and the number of epochs of training can be set to values preferable for the utilization form of the learned model based on the training data. For example, based on the training data, the parameters and the number of epochs can be set that can output a correct imaged site label with a higher probability, that can output a more accurate region label image, or that can output an image with a higher image quality.

One of determination methods of such parameters and the number of epochs will be illustrated. First, 70 percent of the pairs constituting the training data are used for training, and the remaining 30 percent is randomly set for evaluation. Next, the training of a learned model is performed by using the pairs for training, and a training evaluation value is calculated by using the pairs for evaluation at the time of the end of each epoch of training. The training evaluation value is, for example, an average value of the values obtained by evaluating the output at the time when the input data constituting each pair is input to the learned model during training, and the ground truth corresponding to the input data by a loss function. Lastly, the parameters and the number of epochs at the time when the training evaluation value becomes the smallest are determined as the parameters and the number of epochs for the learned model. Note that, by performing the determination of the number of epochs by dividing the pairs constituting the training data into the training data for training and the training data for evaluation, the learned model can be prevented from performing over-learning of the pairs for training.

The image segmentation engine is a module that performs the image segmentation processing, and outputs the region label image corresponding to an input image that is input. As examples of the input image, there are a B scan image, a three-dimensional tomographic image (three-dimensional OCT volume image), etc., of the OCT. Additionally, as examples of the region label image, there are a region label image indicating each layer of the retina layers in a case where the input image is a B scan image of the OCT, and a region label image indicating a three-dimensional region that indicates each layer of the retina layers in a case where the input image is a three-dimensional tomographic image of the OCT.

In the image processing technique constituting the image segmentation processing technique in the following examples, the processing using the learned model according to various machine learning algorithms, such as deep learning, is performed. Note that the image processing technique may perform not only machine Teaming algorithms, but also other existing arbitrary processing. The image processing includes processing, such as various image filtering processing, the matching processing using a database of region label images corresponding to similar images, the image registration processing of a reference region label image, and the knowledge-based image processing.

Figure 25:
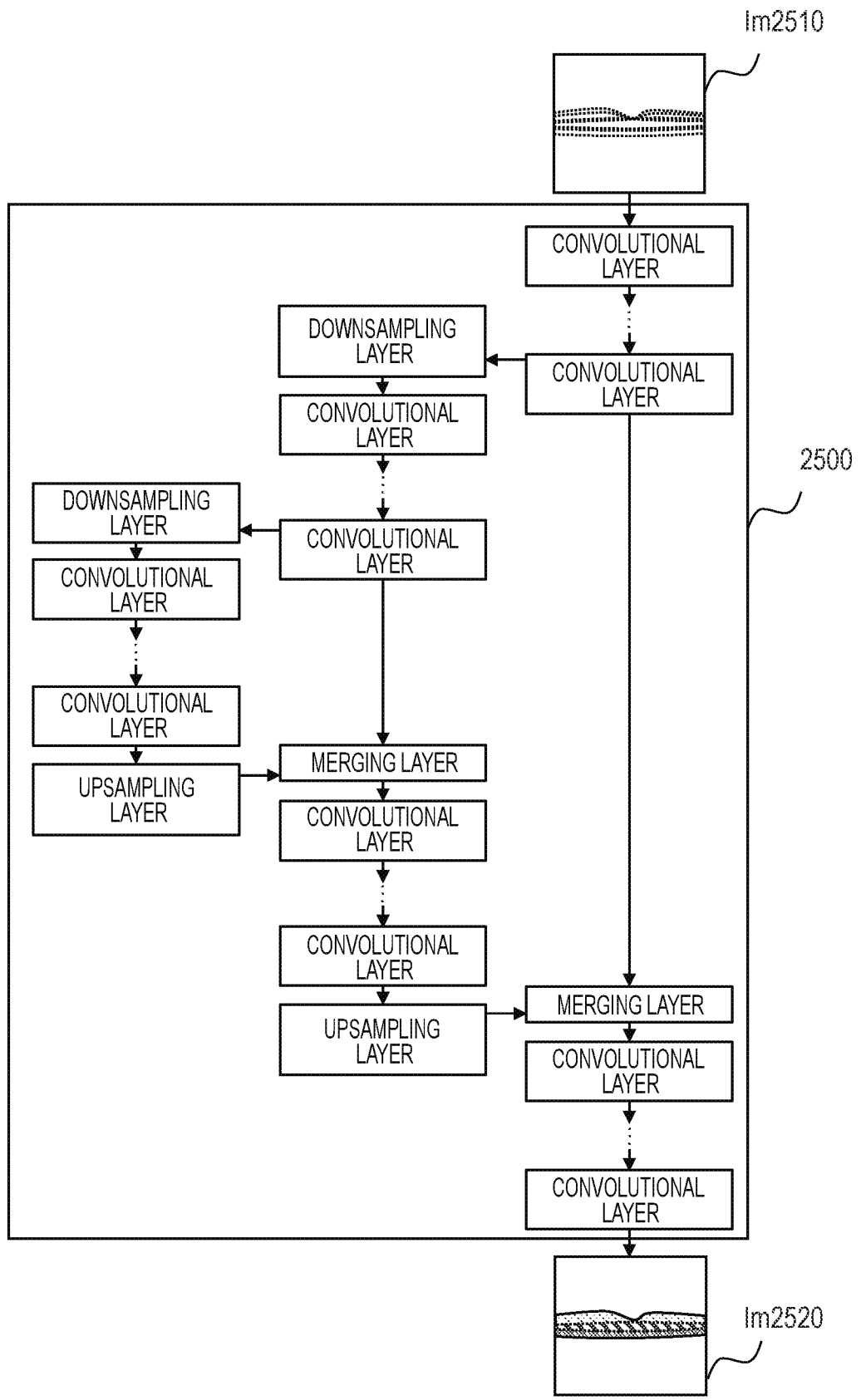
FIG. 25 illustrates an example of the configuration of a neural network pertaining to the description of terms.

Especially, there is a configuration 2500 illustrated in FIG. 25 as an example of the convolutional neural network (CNN) that performs the image segmentation processing on a two-dimensional image Im2510 that is input as the input image to generate a region label image Im2520. The configuration 2500 of the CNN includes a plurality of layers that are responsible for the processing of processing and outputting input values. Note that, as the types of layers included in the configuration 2500, as illustrated in FIG. 25, there are a convolutional (Convolution) layer, a downsampling (Downsampling) layer, an upsampling (Upsampling) layer, and a merging (Merger) layer. Note that, similar to the configuration 601 of the CNN described in Example 1, the configuration 2500 of the CNN used in the present example is a U-net type machine learning model.

The convolutional layer is a layer that performs the convolutional processing on input values according to parameters, such as the kernel size of a filter, the number of filters, the value of a stride, and the value of dilation that are set. The downsampling layer is a layer that performs the processing that reduces the number of output values to be less than the number of input values by thinning out or combining the input values. As the processing performed in the downsampling layer, specifically, there is Max Pooling processing, for example.

The upsampling layer is a layer that performs the processing of increasing the number of output values to be greater than the number of input values by duplicating the input values, or adding a value interpolated from the input values. As the processing performed in the upsampling layer, specifically, there is linear interpolation processing, for example. The merging layer is a layer that performs the processing of inputting values, such as the output values of a certain layer or the pixel values constituting an image, from a plurality of sources, and combining them by connecting or adding them.

Note that the image segmentation processing with a constant accuracy is enabled by, for example, setting the kernel size of a filter to 3 pixels in width, and 3 pixels in height, and setting the number of filters to 64 as the parameters that are set to the convolutional layers included in the configuration of the CNN. However, caution is required, since when the setting of the parameters to the layers and nodes constituting a neural network is different, the degree of tendency trained from the training data that can be reproduced in the output data may be different. In other words, in many cases, since appropriate parameters for each of the layers and each of the nodes are different depending on examples, the parameters may be changed according to the needs.

Additionally, depending on examples, the CNN may be able to obtain better characteristics not only by changing the parameters as described above, but by changing the configuration of the CNN. The better characteristics are, for example, highly accurate image segmentation processing, a short time of the image segmentation processing, and a short time for training of a learned model. Examples of change to the configuration of the CNN includes, for example, incorporating a batch normalization (Batch Normalization) layer and an activation layer using a normalized linear function (Rectifier Linear Unit) after the convolutional layer.

Note that, as the machine learning model used by the image segmentation engine, for example, an FCN or SegNet can also be used as in Example 1. Additionally, a machine learning model that performs object recognition in the units of region as described in Example 1 may be used according to a desired configuration.

Note that, when a one-dimensional image, a three-dimensional image, and a four-dimensional image need to be processed, the kernel size of a filter may correspond to one dimension, three dimensions, and four dimensions. Here, the four-dimensional image includes, for example, a three-dimensional video, and an image in which the parameter at each pixel position in a three-dimensional image is indicated by a different hue.

Additionally, the image segmentation processing may be performed only with one image processing technique, or may be performed by combining two or more image processing techniques. Further, a plurality of image segmentation processing techniques can be performed to generate a plurality of region label images.

Additionally, depending on examples, there is a method of generating a region label image by diving an input image into small regions, performing the image segmentation processing on each to obtain the region label images of small regions, and combining the region label images of the small regions. Note that, when the input image is a three-dimensional image, the small region may be a three-dimensional image smaller than the input image, may be a two-dimensional image, or may be a one-dimensional image. Additionally, when the input image is a two-dimensional image, the small region may be a two-dimensional image smaller than the input image, or may be a one-dimensional image. In addition, depending on examples, a plurality of region label images may be output.

Additionally, parameters may be input to the image segmentation engine along with the input image. The parameters that are input in this case can include, for example, a parameter specifying the degree of the range for which the image segmentation processing is performed, such as the upper limit of the size of a pathological change, and a parameter specifying the image filter size used for the image processing technique. Note that, depending on examples, the image segmentation engine may output the other images and coordinate data group by which regions can be specified, instead of region label images.

Note that, when performing a plurality of image segmentation processing techniques, and when performing the image segmentation processing on a plurality of small regions, the processing time can be reduced by performing the image segmentation processing in parallel.

Note that caution is required for the image size in a case where some image processing techniques are utilized, such as the image processing using the CNN. Specifically, it should be noted that, for countermeasures against problems such as the segmentation processing is not performed with a sufficient accuracy on the surrounding portion of a region label image, different image sizes may be required for an image that is input and a region label image that is output.

For a clear description, although not clearly mentioned in examples described later, when the image segmentation engine that requires different image sizes for the image that is input to the image segmentation engine and the image that is output, it is assumed that the image size is appropriately adjusted. Specifically, the image size is adjusted by performing padding on an image used for the training data for training a learned model, and an input image such as an image that is input to the image segmentation engine, and by combining the surrounding imaged regions of the input image. Note that the region on which padding is performed is filled with a constant pixel value, filled with a neighboring pixel value, or subjected to mirror padding, according to the characteristics of the image segmentation processing technique, so that the image segmentation processing can be effectively performed.

The term "imaging location estimation engine" refers to a module that estimates an imaged site or imaged region of an input image. The imaging location estimation engine can output the location of an imaged site or imaged region that is depicted in an input image, or for each imaged site label or imaged region label of a required detail level, can output a probability of being the relevant imaged site or imaged region.

In some cases, the imaged site or imaged region is not stored as an imaging condition by the imaging apparatus, or the imaging apparatus could not acquire and store the imaged site or imaged region. There are also cases where even though an imaged site or imaged region is stored, an imaged site or imaged region of a required detail level is not stored. For example, if only "posterior segment of eyeball" is stored as an imaged site, it may not be known if the detailed location of the imaged site is the "macular area", the "optic nerve head", or is the "macular area and optic nerve head", or is an "other area". Further, as another example, if only "breast" is stored as the imaged site, it may not be known whether, in more detail, this means "right breast", "left breast" or "both". Therefore, by using the imaging location estimation engine, the imaged site or imaged region of an input image in such cases can be estimated.

In the image and data processing techniques constituting the estimating method of the imaging location estimation engine, processing that uses learned models in accordance with various kinds of machine learning algorithms such as deep learning is performed. Note that, in the image and data processing techniques in question, in addition to or instead of processing using machine learning algorithms, any known estimation processing such as natural language processing, matching processing using a database of similar images and similar data, and knowledge-based processing may be performed. Note that, images to which a label of an imaged site or imaged region is attached can be adopted as training data for training a learned model that was built using a machine learning algorithm. In this case, in relation to the training data, an image for which an imaged site or an imaged region is to be estimated is used as input data, and a label of the imaged site or imaged region is used as ground truth.

Figure 26:
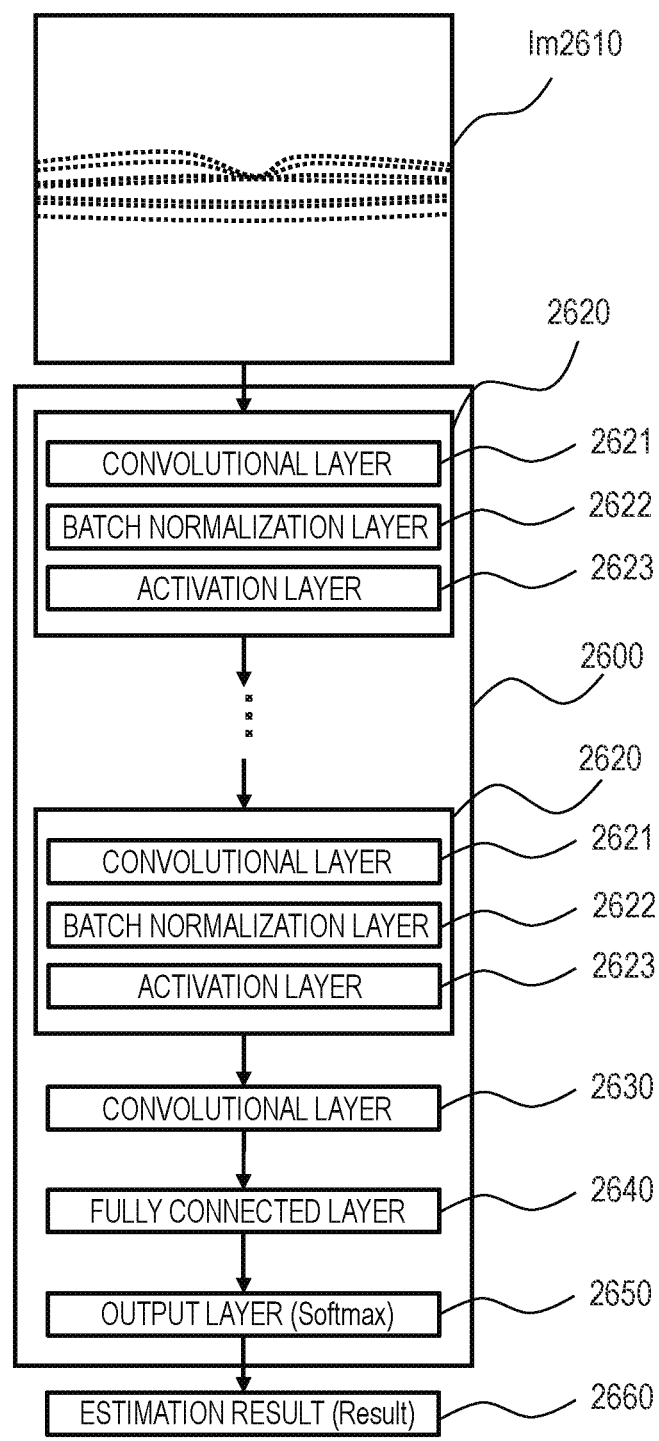
FIG. 26 illustrates an example of the configuration of the neural network pertaining to the description of terms.

In particular, a configuration 2600 illustrated in FIG. 26 is available as an example of the configuration of a CNN that estimates the imaging location of a two-dimensional input image Im2610. The configuration 2600 of the CNN includes a group of a plurality of convolutional processing blocks 2620 which are each constituted by a convolutional layer 2621, a batch normalization layer 2622, and an activation layer 2623 that uses a rectifier linear unit. The configuration 2600 of the CNN also includes a final convolutional layer 2630, a fully connected layer 2640, and an output layer 2650. The fully connected layer 2640 fully connects output value groups of the convolutional processing blocks 2620. Further, the output layer 2650 utilizes the softmax function to output the probability for each assumed imaged site label with respect to the input image Im2610 as an estimation result (Result) 2660. In this kind of configuration 2600, for example, if the input image Im2610 is an image obtained by imaging a "macular area", the highest probability is output for an imaged site label corresponding to "macular area".

Note that, for example, by setting the number of convolutional processing blocks 2620 to 16, and, as the parameters of the groups of convolutional layers 2621 and 2630, setting the kernel size of the filters to a width of three pixels and a height of three pixels, and the number of filters to 64, an imaged site can be estimated with a certain accuracy. However, in practice, as mentioned in the description of the aforementioned learned model, a better parameter group can be set by using training data corresponding to the utilization form of the learned model. Note that, in a case where it is necessary to process a one-dimensional image, a three-dimensional image or a four-dimensional image, the kernel size of the filters may be extended to one dimension, three dimensions or four dimensions. Note that, the estimating method is sometimes carried out using only one image and data processing technique, and is sometimes carried out using a combination of two or more image and data processing techniques.

The term "region label image evaluating engine" refers to a module that evaluates whether or not a region label image that is input underwent likely image segmentation processing. Specifically, as an image evaluation index, the region label image evaluating engine outputs a True value if the input region label image is likely, and outputs a False value if the input region label image is not likely. Examples of techniques for performing the evaluation include processing using learned models in accordance with various kinds of machine learning algorithms such as deep learning, and knowledge-based processing. One available method of knowledge-based processing is, for example, a method that utilizes anatomical knowledge, for example, a method that performs an evaluation of a region label image utilizing known anatomical knowledge such as the regularity of the retinal shape.

Specifically, as one example, a case of using knowledge-based processing to evaluate a region label image corresponding to an OCT tomographic image for which the posterior segment of the eyeball is taken as an imaging target will be described. In the posterior segment of the eyeball, there are anatomically fixed positions for tissue groups. Therefore, a method is available which checks the coordinates of a pixel value group in a region label image, that is, the coordinates of a region label value group, and evaluates whether or not positions are correctly output. According to the evaluation method in question, for example, in a certain range, if there is a region label value corresponding to the crystalline lens at coordinates that are close to the anterior ocular segment, and there is a region label value corresponding to a retina layer group at coordinates that are distant from the anterior ocular segment, it is evaluated that the region label image underwent likely image segmentation processing. On the other hand, if these region label values are not present at such assumed positions, it is evaluated that the region label image did not appropriately undergo image segmentation processing.

Figure 27:
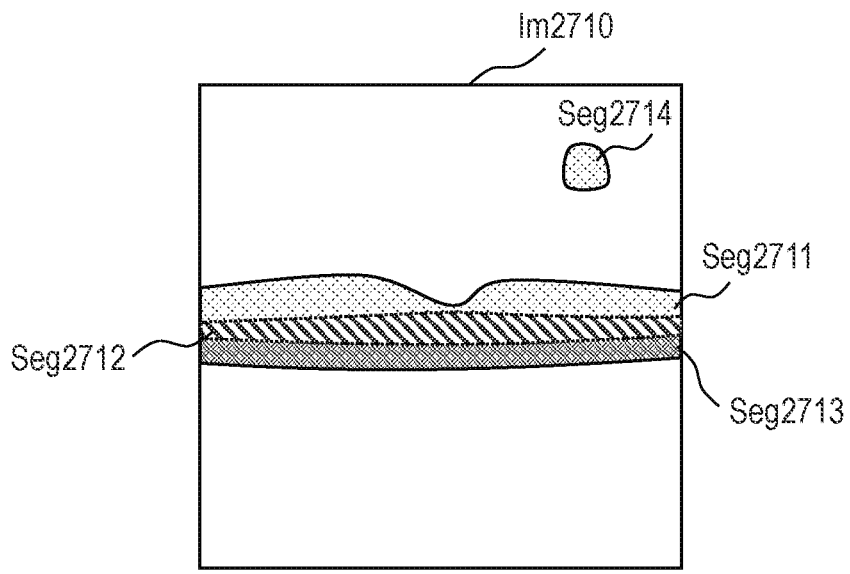
FIG. 27 illustrates an example of a region label image pertaining to the description of terms.

The knowledge-based evaluation method in question will be described more specifically using a region label image Im2710 of a layer group constituting retina layers, which corresponds to an OCT tomographic image for which the posterior segment of the eyeball was taken as an imaging target, that is illustrated in FIG. 27. Because there are anatomically fixed positions for tissue groups in the posterior segment of the eyeball, whether or not a region label image is a likely image can be determined by checking the coordinates of a pixel value group in the region label image, that is, the coordinates of a region label value group.

A region Seg2711, a region Seg2712, a region Seg2713, and a region Seg2714 which are respectively constituted by a group of pixels having the same region label value in succession are included in the region label image Im2710. Although the region label value is the same for the region Seg2711 and the region Seg2714, because a group of layers that anatomically constitute retina layers form a layered structure, based on the shape and the positional relationship with respect to other layers it is evaluated that the region Seg2714 was incorrectly subjected to image segmentation processing. In this case, the region label image evaluating engine outputs a False value as the image evaluation index.

Furthermore, methods of knowledge-based evaluation processing also include a method that evaluates whether or not a pixel having a region label value corresponding to a region that should definitely be present in the imaging target is included in the region label image. Other available methods include, for example, a method that evaluates whether or not a certain number or more of pixels having a region label value corresponding to a region that should definitely be present in the imaging target is included in the region label image.

Further, in a case where the image segmentation engine performs a plurality of image segmentation processing techniques and generates a plurality of region label images, the region label image evaluating engine can also select and output one region label image that is the most likely among the plurality of region label images.

Note that, in a case where each of a group of a plurality of region label images is a likely region label image, it may not be possible to select a single region label image to be output. In such a case where it is not possible to select a single region label image, the region label image evaluating engine can, for example, select a single region label image according to a predetermined priority. Further, the region label image evaluating engine, for example, can assign weights to the plurality of region label images and merge the plurality of region label images into a single region label image. In addition, for example, the region label image evaluating engine may display a group of a plurality of region label images on a user interface equipped with any display unit or the like so that selection of one of the region label images can be performed according to an instruction from the examiner (user). Note that, the region label image evaluating engine may output all of the likely plurality of region label images.

The term "region label image modifying engine" refers to a module that modifies a region that was incorrectly subjected to image segmentation processing in an input region label image. Examples of techniques for performing the relevant modification include knowledge-based processing. One method of knowledge-based processing that is available utilizes, for example, anatomical knowledge.

The region label image Im2710 of the group of layers constituting retina layers which corresponds to an OCT tomographic image for which the posterior segment of the eyeball was taken as an imaging target that is illustrated in FIG. 27 will now be used again to more specifically describe a knowledge-based modifying method relating to modification of the region label image in question. As mentioned above, in the region label image Im2710, because a group of layers that anatomically constitute retina layers form a layered structure, based on the shape and the positional relationship with respect to other layers it is found that the region Seg2714 is a region which was incorrectly subjected to image segmentation processing. The region label image modifying engine detects the region which was incorrectly subjected to image segmentation processing, and overwrites the detected region with a different region label value. For example, in the case illustrated in FIG. 27, the region label image modifying engine overwrites the region Seg2714 with a region label value that indicates that the region Seg2714 is not any of the retina layers.

Note that, the region label image modifying engine may perform detection or identification of an incorrectly segmented region by using an evaluation result obtained by the region label evaluating engine. Further, the region label image modifying engine may overwrite a label value of an incorrectly segmented region that was detected, with label information that is estimated based on label information of a region at the periphery of the relevant region. In the example illustrated in FIG. 27, in a case where label information has been assigned to a region surrounding the region Seg2714, the label information of the region Seg2714 can be overwritten with the label information of the region in question. Note that, with regard to the label information of a peripheral region, the label information is not limited to the label information of a region that completely surrounds the region to be modified, and may be the label information which is present in the greatest number among the label information of regions that are contiguous to the region to be modified.

Figure 28:
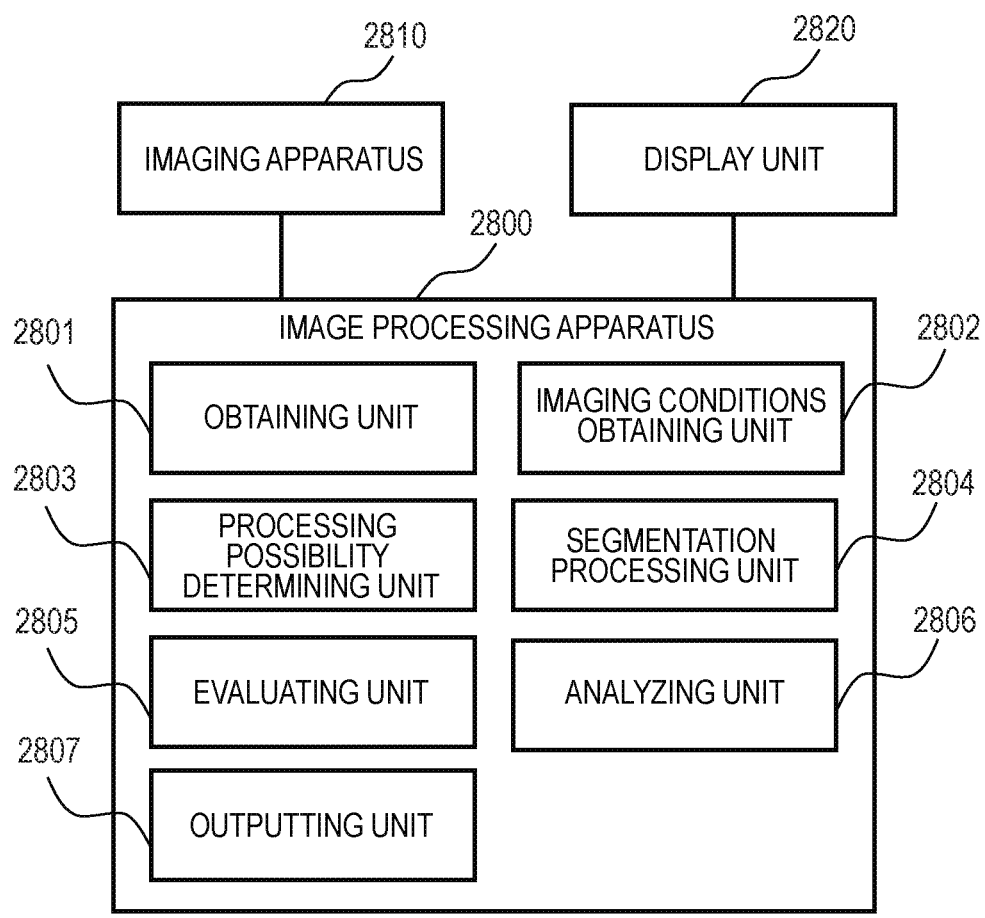
FIG. 28 illustrates an example of the configuration of an image processing apparatus according to Example 8.

(Configuration of image processing apparatus according to Example 8) Hereunder, a medical image processing apparatus according to Example 8 is described while referring to FIG. 28 to FIG. 32. Note that, hereinafter, to simplify the description, the medical image processing apparatus is referred to simply as "image processing apparatus". FIG. 28 is a view illustrating an example of a schematic configuration of the image processing apparatus according to the present example.

An image processing apparatus 2800 is connected through a circuit or a network to an imaging apparatus 2810 and a display unit 2820. The imaging apparatus 2810 and the display unit 2820 may also be directly connected. Note that, although in the present example these apparatuses are assumed to be separate apparatuses to each other, some or all of these apparatuses may be constituted integrally with each other. Further, these apparatuses may be connected through a circuit or network to any other apparatuses, and may be constituted integrally with any other apparatus.

An obtaining unit 2801, an imaging conditions obtaining unit 2802, a processing possibility determining unit 2803, a segmentation processing unit 2804, an evaluating unit 2805, an analyzing unit 2806 and an outputting unit 2807 (display controlling unit) are provided in the image processing apparatus 2800. Note that, the image processing apparatus 2800 may be constituted by a plurality of apparatuses which are each provided with one or more of these components.

The obtaining unit 2801 can obtain various kinds of data and images from the imaging apparatus 2810 or another apparatus, and can obtain an input by an examiner through an input apparatus (not illustrated). A mouse, a keyboard, a touch panel and any other input apparatuses may be adopted as an input apparatus. In addition, the display unit 2820 may be configured as a touch panel display.

The imaging conditions obtaining unit 2802 obtains imaging conditions of a medical image (input image) that the obtaining unit 2801 obtained. Specifically, in accordance with the data format of the medical image, an imaging conditions group that is stored in the data structure constituting the medical image is obtained. Note that, in a case where imaging conditions are not stored in the medical image, an imaging information group can be obtained from the imaging apparatus 2810 or the image management system through the obtaining unit 2801.

The processing possibility determining unit (determining unit) 2803 determines whether the relevant medical image can be handled by the segmentation processing unit 2804, using the imaging conditions group obtained by the imaging conditions obtaining unit 2802. The segmentation processing unit 2804 performs image segmentation processing on a medical image which can be handled, using an image segmentation engine (segmentation engine) that includes a learned model, to thereby generate a region label image (region information).

The evaluating unit 2805 evaluates a region label image generated by the segmentation processing unit 2804, using a region label image evaluating engine (evaluating engine), and determines whether or not to output the region label image based on the evaluation result. As an image evaluation index, the region label image evaluating engine outputs a True value if the input region label image is likely, and outputs a False value if the input region label image is not likely. In a case where the image evaluation index determined as the result of evaluating the region label image is the True value, the evaluating unit 2805 determines that the region label image is to be output.

The analyzing unit 2806 performs image analysis processing of an input image, using a region label image which the evaluating unit 2805 determined should be output and the input image. The analyzing unit 2806 can, for example, calculate changes in the shape of tissue included in the retina layers or a layer thickness or the like by the image analysis processing. Note that, any image analysis processing that is known may be used as the image analysis processing. The outputting unit 2807 causes the display unit 2820 to display a region label image or an analysis result obtained by the analyzing unit 2806. The outputting unit 2807 may also store a region label image or an analysis result in a storage apparatus or an external apparatus or the like connected to the image processing apparatus 2800.

Next, the segmentation processing unit 2804 will be described in detail. The segmentation processing unit 2804 generates a region label image corresponding to an input image (input) using an image segmentation engine. According to an image segmentation processing technique of the image segmentation engine according to the present example, processing that uses a learned model is performed.

In the present example, training data that is constituted by pair groups composed of pairs of input data which is an image obtained under specific imaging conditions which are assumed as a processing object, and ground truth which is a region label image corresponding to the input data is used for training a machine learning model. Note that, the specific imaging conditions include, specifically, an imaged site, imaging system, imaging angle of view, image size and the like which are determined in advance.

In the present example, the input data of the training data is an image obtained by the same model of equipment as the imaging apparatus 2810 and using the same settings as the imaging apparatus 2810. Note that, the input data of the training data may be an image obtained from an imaging apparatus having the same image quality tendency as the imaging apparatus 2810.

Further, the ground truth of the training data is a region label image that corresponds to the input data. For example, referring to the example illustrated in FIG. 24, the input data is a tomographic image Im2410 of retina layers that was imaged by OCT. Further, the ground truth is a region label image Im2420 in which, in accordance with the kinds of retina layers visualized in the tomographic image Im2410, region label values representing the kinds of the corresponding retina layers, respectively, are assigned to separate the respective regions. The region label image can be prepared by the medical specialist referring to the tomographic image to create the region label image, or by creating the region label image by performing arbitrary image segmentation processing, or by the medical specialist creating the region label image by modifying a region label image that was created by the image segmentation processing.

Note that, input images having various conditions that are assumed as processing objects are comprehensively included in the input data group of the pair groups of the training data. The term "various conditions" refers to, specifically, conditions of images that arise due to differences with regard to combinations of variations such as the disease state of the subject, the imaging environment of the imaging apparatus, the skill level of the person performing the imaging and the like. As a result of the conditions of the images included in the input data group being comprehensive, the machine learning model is trained so that highly accurate image segmentation processing can also be executed with respect to images for which conditions are poor, that are images for which the accuracy in the case of performing conventional image segmentation processing would be low. Therefore, by using an image segmentation engine including a learned model which was trained in this manner, the segmentation processing unit 2804 can consistently generate a highly accurate region label image with respect to images of various conditions.

Note that, among the pair groups constituting the training data, pairs that do not contribute to image segmentation processing can be removed from the training data. For example, in a case where a region label value of a region label image as ground truth constituting a pair of the training data is incorrect, there is a high probability that the region label value of a region label image obtained using a learned model that learned using the relevant training data will also be incorrect. That is, the accuracy of the image segmentation processing will be low. Therefore, there is a probability that the accuracy of a learned model included in an image segmentation engine can be improved by removing a pair that has a region label image having an incorrect region label value as ground truth from the training data.

By using an image segmentation engine that includes such a learned model, in a case where a medical image obtained by imaging is input, the segmentation processing unit 2804 can output a region label image in which an organ or a lesion that is visualized in the medical image can be identified.

Figure 29:
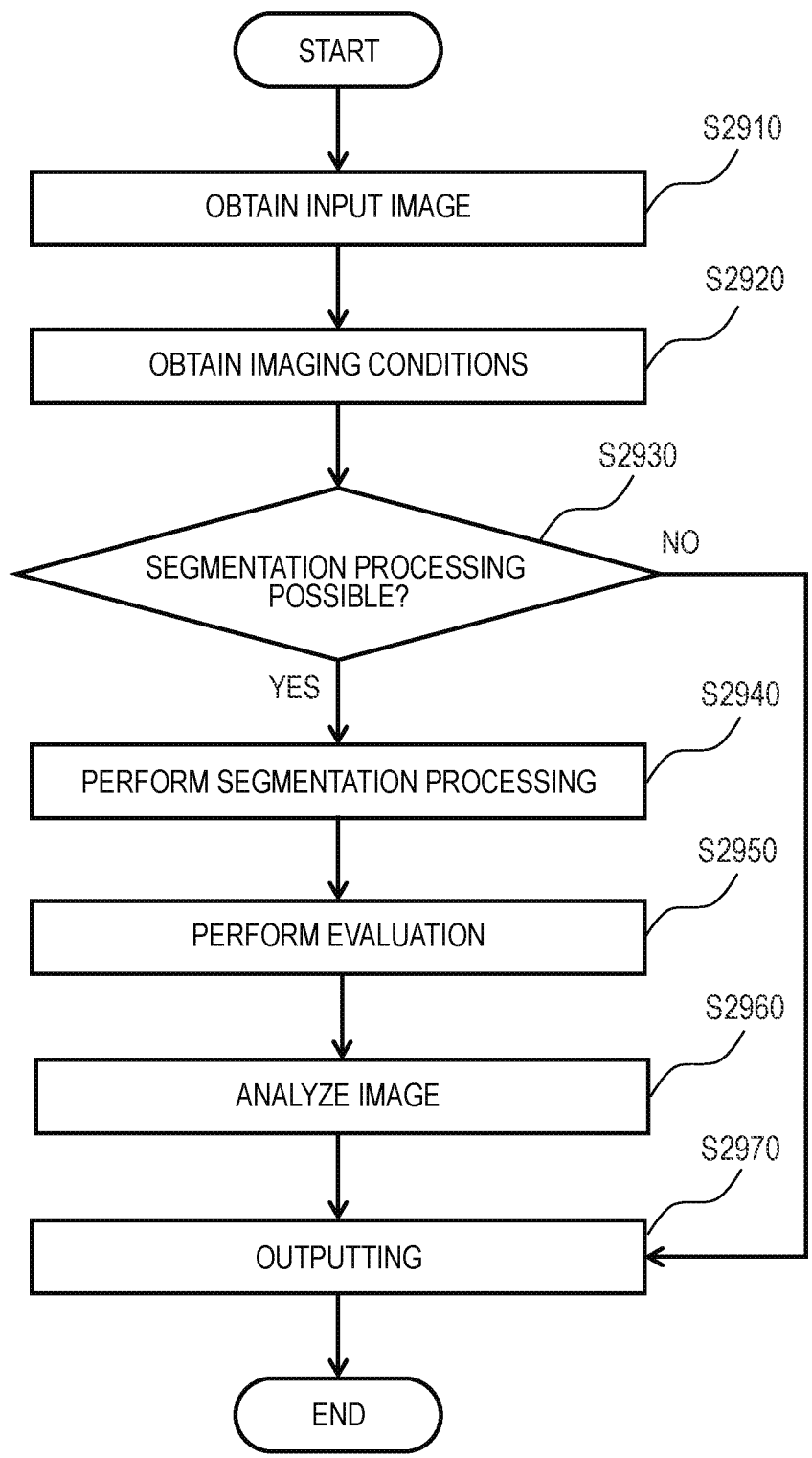
FIG. 29 is a flowchart illustrating an example of the processing flow of an image processing apparatus according to Example 8.

Next, a series of image processing operations according to the present example will be described referring to the flowchart in FIG. 29. FIG. 29 is a flowchart illustrating the series of image processing operations according to the present example. First, when the series of image processing operations according to the present example is started, the processing shifts to step S2910.

In step S2910, an image that was imaged by the imaging apparatus 2810 is obtained as an input image by the obtaining unit 2801 from the imaging apparatus 2810 connected to the obtaining unit 2801 through a circuit or a network. Note that, the obtaining unit 2801 may obtain an input image in response to a request from the imaging apparatus 2810. Such a request may be issued, for example, when the imaging apparatus 2810 generated an image, or when displaying an image which the imaging apparatus 2810 generated on the display unit 2820 before storing the image in a recording apparatus of the imaging apparatus 2810 or displaying the stored image on the display unit 2820 after storing the image in the recording apparatus, or when utilizing a region label image for image analysis processing.

Note that, the obtaining unit 2801 may obtain data for generating an image from the imaging apparatus 2810, and the image processing apparatus 2800 may obtain an image generated based on the relevant data as an input image. In this case, the image processing apparatus 2800 may employ any existing image generating method as an image generating method for generating various kinds of images.

In step S2920, the imaging conditions obtaining unit 2802 obtains an imaging conditions group of the input image. Specifically, in accordance with the data format of the input image, the imaging conditions obtaining unit 2802 obtains an imaging conditions group stored in the data structure constituting the input image. Note that, as mentioned above, in a case where imaging conditions are not stored in the input image, the imaging conditions obtaining unit 2802 can obtain an imaging information group from the imaging apparatus 2810 or the image management system which is not illustrated in the drawings.

In step S2930, the processing possibility determining unit 2803 uses the obtained imaging conditions group to determine whether it is possible for the input image to be subjected to image segmentation processing by the image segmentation engine that the segmentation processing unit 2804 uses. Specifically, the processing possibility determining unit 2803 determines whether the imaged site, imaging system, imaging angle of view and image size of the input image match conditions which can be handled using the learned model of the image segmentation engine.

The processing possibility determining unit 2803 makes a determination regarding all of the imaging conditions, and if the processing possibility determining unit 2803 determines that the imaging conditions can be handled, the processing shifts to step S2940. On the other hand, if the processing possibility determining unit 2803 determines based on these imaging conditions that the image segmentation engine is not capable of handling the input image, the processing shifts to step S2970.

Note that, depending on the settings or implementation form of the image processing apparatus 2800, even if it is determined that the input image cannot be processed based on some conditions among the imaged site, imaging system, imaging angle of view and image size, the processing in step S2940 may be performed. For example, such processing may be performed in a case where it is assumed that the image segmentation engine is capable of comprehensively handling any imaged site of the subject, and is implemented so as to be capable of handling input data even if an unknown imaged site is included in the input data. In addition, the processing possibility determining unit 2803 may determine whether or not at least one condition among the imaged site, imaging system, imaging angle of view and image size of an input image matches a condition which the image segmentation engine is capable of handling according to a desired configuration.

In step S2940, the segmentation processing unit 2804 uses the image segmentation engine to perform image segmentation processing with respect to the input image and generate a region label image from the input image. Specifically, the segmentation processing unit 2804 inputs the input image to the image segmentation engine. The image segmentation engine generates the region label image as region information that can identify an organ or a lesion visualized in the input image, based on a learned model that performed machine learning using training data.

Note that, depending on the settings or implementation form of the image processing apparatus 2800, the segmentation processing unit 2804 may input parameters together with the input image into the image segmentation engine in accordance with the imaging conditions group, to adjust the extent of the range of the image segmentation processing or the like. Further, the segmentation processing unit 2804 may also input parameters in accordance with an input by the examiner together with the input image into the image segmentation engine to adjust the extent of the range of the image segmentation processing or the like.

In step S2950, the evaluating unit 2805 uses a region label image evaluating engine to evaluate whether the region label image generated by the segmentation processing unit 2804 is a likely image. In the present example, the evaluating unit 2805 evaluates whether the region label image is a likely image using a region label evaluating engine that uses a knowledge-based evaluation method.

Specifically, the region label evaluating engine checks a pixel value group in the region label image, that is, checks the coordinates of a region label value group, and evaluates whether positions are output at anatomically correct positions. In this case, for example, in a certain range, if there is a region label value corresponding to the crystalline lens at coordinates that are close to the anterior ocular segment, and there is a region label value corresponding to a retina layer group at coordinates that are distant from the anterior ocular segment, it is evaluated that the region label image underwent likely image segmentation processing. On the other hand, if these region label values are not present at such assumed positions, it is evaluated that the region label image did not appropriately undergo image segmentation processing. With respect to a region label, the region label evaluating engine outputs a True value as an image evaluation index in a case where it was evaluated that the region label underwent likely image segmentation processing, and outputs a False value in a case where it was evaluated that the region label did not undergo likely image segmentation processing.

The evaluating unit 2805 determines whether to output the region label image based on the image evaluation index that is output from the region label evaluating engine. Specifically, the evaluating unit 2805 makes a determination to output the region label image in a case where the image evaluation index is the True value. On the other hand, if the image evaluation index is the False value, the evaluating unit 2805 makes a determination not to output the region label image generated by the segmentation processing unit 2804. Note that, in a case where the evaluating unit 2805 makes a determination not to output the region label image generated by the segmentation processing unit 2804, an image without region labels can be generated.

In step S2960, if the evaluating unit 2805 made a determination to output the region label image, the analyzing unit 2806 performs image analysis processing of the input image using the region label image and the input image. The analyzing unit 2806, for example, calculates changes in the layer thickness or tissue shape or the like that are visualized in the input image by image analysis processing. Note that, any known processing may be adopted as the method of image analysis processing. Further, in a case where the evaluating unit 2805 made a determination not to output the region label image, or a case where an image without region labels was generated, the processing proceeds without performing image analysis.

In step S2970, when the evaluating unit 2805 determined that the region label image is to be output, the outputting unit 2807 outputs the region label image and the image analysis result and causes the region label image and the image analysis to be displayed on the display unit 2820. Note that, instead of causing the region label image and the image analysis result to be displayed on the display unit 2820, the outputting unit 2807 may cause the region label image and the image analysis result to be displayed on the imaging apparatus 2810 or another apparatus or may store the region label image and the image analysis result. Further, depending on the settings or implementation form of the image processing apparatus 2800, the outputting unit 2807 may process the region label image and the image analysis result so that they can be utilized by the imaging apparatus 2810 or another apparatus, or may convert the data format of the region label image and the image analysis result so that they can be transmitted to the image management system or the like. In addition, the outputting unit 2807 is not limited to a configuration that outputs both the region label image and the image analysis result, and may be configured to output only either one of the region label image and the image analysis result.

On the other hand, if it is determined in step S2930 that image segmentation processing is not possible, the outputting unit 2807 outputs an image without region labels that is one kind of region label image, to cause the image without region labels to be displayed on the display unit 2820. Note that, instead of outputting an image without region labels, the outputting unit 2807 may transmit a signal indicating that image segmentation processing was not possible to the imaging apparatus 2810.

Further, in a case where it is determined in step S2950 that image segmentation processing could not be properly performed, the outputting unit 2807 outputs an image without region labels to cause the image without region labels to be displayed on the display unit 2820. In this case also, instead of outputting an image without region labels, the outputting unit 2807 may transmit a signal indicating that image segmentation processing could not be properly performed to the imaging apparatus 2810. When the output processing in step S2970 ends, the series of image processing operations ends.

As described above, the image processing apparatus 2800 according to the present example includes the obtaining unit 2801 and the segmentation processing unit 2804. The obtaining unit 2801 obtains an input image that is a tomographic image of a predetermined site of a subject. The segmentation processing unit 2804 uses an image segmentation engine that includes a learned model to generate a region label image which is region information that can distinguish an anatomical region from the input image. The image segmentation engine includes a learned model for which tomographic images obtained under various conditions and region label images were adopted as training data. A tomographic image is adopted as input of the image segmentation engine, and a region label image is adopted as the output.

The image processing apparatus 2800 also includes the evaluating unit 2805. The evaluating unit 2805 evaluates a region label image using a knowledge-based evaluating engine that uses anatomical features, and determines whether or not to output the region label image according to the result of the evaluation.

By this configuration, the image processing apparatus 2800 according to the present example can use a segmentation engine that includes a learned model to generate a region label image as region information to be used for image diagnosis or for identifying an ROI or a VOI which can be utilized in image analysis. Therefore, with respect to an input image whose conditions are unfavorable with respect to the conventional segmentation processing also, a highly accurate region label image can be output and can be provided for image diagnosis or can provide an ROI or a VOI which can be utilized in image analysis.

In addition, by using the evaluating unit 2805 to evaluate whether a region label image is a likely image, the image processing apparatus 2800 can prevent an unsuitable region label image being used for image diagnosis or image analysis.

Further, the image processing apparatus 2800 also includes the imaging conditions obtaining unit 2802 and the processing possibility determining unit 2803. The imaging conditions obtaining unit 2802 obtains imaging conditions that include at least one of the imaged site, imaging system, imaging angle of view and image size of the input image. The processing possibility determining unit 2803 determines whether it is possible to generate a region label image from the input image using the image segmentation engine. The processing possibility determining unit 2803 performs the determination in question based on the imaging conditions of the input image.

By this configuration, the image processing apparatus 2800 according to the present example can omit an input image which the segmentation processing unit 2804 cannot process from the image segmentation processing, and thus the processing load of the image processing apparatus 2800 and the occurrence of errors can be decreased.

In addition, the image processing apparatus 2800 also includes the analyzing unit 2806 that performs image analysis of an input image using a region label image that is region information. By this configuration, the image processing apparatus 2800 can perform image analysis using a highly accurate region label image that was generated by the segmentation processing unit 2804, and can obtain a highly accurate analysis result.

Figure 30:
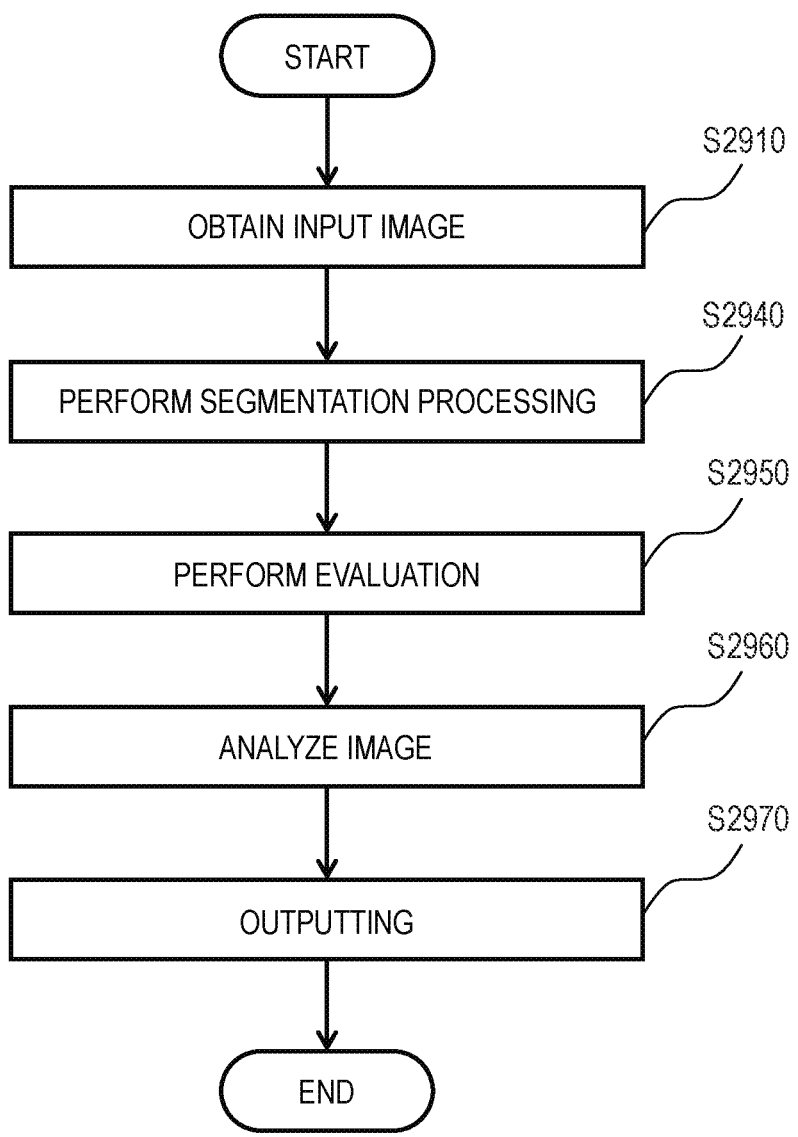
FIG. 30 is a flowchart illustrating an example of the processing flow of the image processing apparatus according to Example 8.
Figure 32:
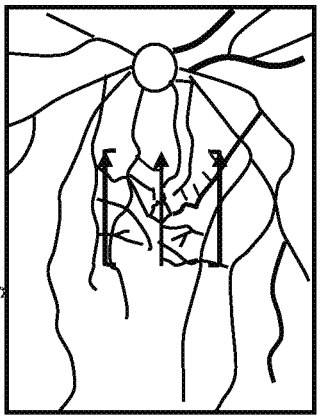
FIG. 32 is a diagram illustrating an example of a user interface included in the imaging apparatus according to Example 8.

In the present example, the processing possibility determining unit 2803 determines whether it is possible to subject an input image to image segmentation processing by the image segmentation engine. Thereafter, if the processing possibility determining unit 2803 determined that the input image is an image that can be processed by the segmentation processing unit 2804, the segmentation processing unit 2804 performs image segmentation processing. In this regard, in a case where only imaging under imaging conditions which enable image segmentation processing is performed by the imaging apparatus 2810 or the like, image segmentation processing may be performed unconditionally on an image obtained from the imaging apparatus 2810. In this case, as illustrated in FIG. 30, the processing in step S2920 and step S2930 can be omitted, and step S2940 can be executed after step S2910.

Note that, although in the present example the outputting unit 2807 (display controlling unit) is configured to cause a generated region label image or analysis result to be displayed on the display unit 2820, the operations of the outputting unit 2807 are not limited thereto. For example, the outputting unit 2807 can also output a region label image or analysis result to the imaging apparatus 2810 or to another apparatus connected to the image processing apparatus 2800. Therefore, a region label image or analysis result can be displayed on a user interface of these apparatuses, can be stored in any recording apparatus, can be utilized for any image analysis, or can be transmitted to the image management system.

Figure 31:
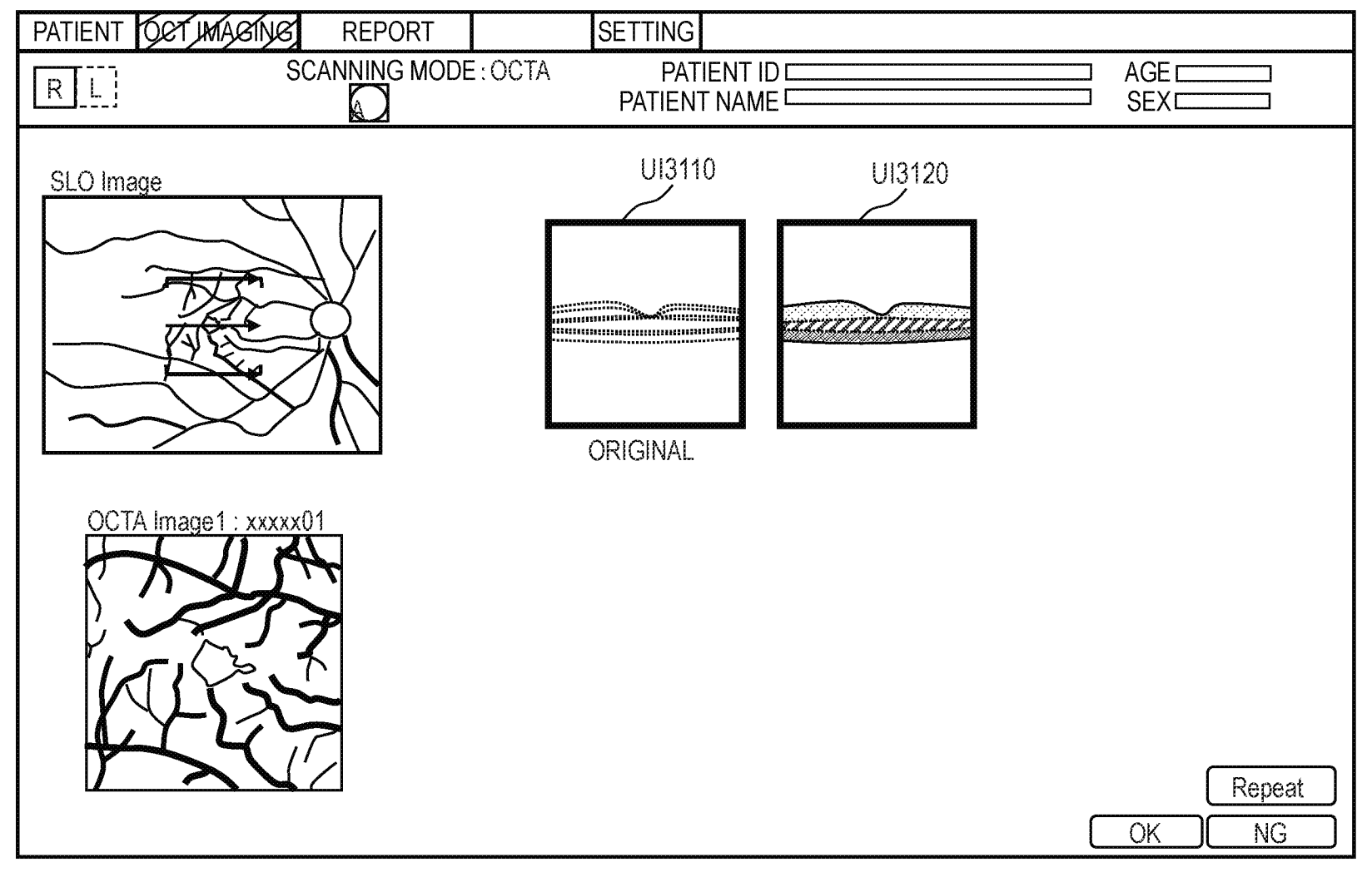

Further, in the present example, the outputting unit 2807 is configured to cause a region label image or an image analysis result to be displayed on the display unit 2820. However, the outputting unit 2807 may cause a region label image or an image analysis result to be displayed on the display unit 2820 in response to an instruction from the examiner. For example, the outputting unit 2807 may display a region label image or an image analysis result on the display unit 2820 in response to the examiner pressing an arbitrary button on a user interface of the display unit 2820. In this case, the outputting unit 2807 may switch from displaying the input image to display the region label image. Further, the outputting unit 2807 may display a region label image UI3120 side by side with an input image UI3110 as illustrated in FIG. 31, or may display a region label image which was made semi-transparent in a superimposed manner on an input image as illustrated in any of UI3210 to UI3240 in FIG. 32. Note that, any known method may be used as a method for making a region label image semi-transparent, and for example, the region label image can be made semi-transparent by setting the degree of transparency of the region label image to a desired value.

Further, the outputting unit 2807 may cause information to the effect that the region label image is an image that was generated using a learned model or information to the effect that the image analysis result is a result obtained by image analysis performed based on a region label image generated using a learned model to be displayed on the display unit 2820. In addition, the outputting unit 2807 may cause a display indicating what kind of training data the learned model used to perform learning to be displayed on the display unit 2820. The display in question may include a description of the kinds of input data and ground truth of the training data, or any display relating to the training data such as an imaged site included in the input data and ground truth.

In the present example, if the processing possibility determining unit 2803 determines that the input image can be handled by the image segmentation engine, the processing shifts to step S2940, and image segmentation processing by the segmentation processing unit 2804 is started. In this regard, a configuration may also be adopted in which the outputting unit 2807 causes the result of determination by the processing possibility determining unit 2803 to be displayed on the display unit 2820, and the segmentation processing unit 2804 starts image segmentation processing in response to an instruction from the examiner. At such time, together with the result of the determination, the outputting unit 2807 can also cause the input image or imaging conditions such as the imaged site obtained with respect to the input image to be displayed on the display unit 2820. In this case, since image segmentation processing is performed after the examiner has determined whether or not the result of the determination is correct, image segmentation processing based on an erroneous determination can be reduced.

Further, in this regard, a configuration may also be adopted in which determination is not performed by the processing possibility determining unit 2803, and the outputting unit 2807 causes the input image or imaging conditions such as the imaged site obtained with respect to the input image to be displayed on the display unit 2820. In this case, the segmentation processing unit 2804 can start image segmentation processing in response to an instruction from the examiner.

In addition, according to the present example, the evaluating unit 2805 evaluated a region label image generated by the segmentation processing unit 2804, using a region label image evaluating engine that adopts a knowledge-based evaluation method. In this regard, the evaluating unit 2805 may evaluate whether or not a region label image is a likely image, using a region label image evaluating engine that includes a learned model which performed training using region label images and image evaluation indexes obtained by a predetermined evaluation technique as training data.

In this case, training data of a machine learning model included in the region label image evaluating engine adopts region label images as well as false images that seem like region label images as input data, and adopts image evaluation indexes with respect to the respective images as ground truth. As the image evaluation indexes, a True value is used in a case where the input data is an appropriate region label image, and a False value is used in a case where the input data is a false image. Note that, the method adopted for generating a false image may be a method that uses an arbitrary generator of region label images for which conditions that are not appropriate were set, or a method that generates a false image by intentionally overwriting an inappropriate region label onto an appropriate region label image or the like.

In a case where the evaluating unit 2805 evaluates whether or not a region label image is a likely image using a region label image evaluating engine including a learned model that performed such kind of learning also, the use of an inappropriate region label image for image diagnosis or image analysis can be prevented.

Note that, in a case where it is determined by the processing possibility determining unit 2803 that image segmentation processing is not possible, an image without region labels may be generated by the outputting unit 2807 or may be generated by the processing possibility determining unit 2803. Further, in a case where it is determined by the evaluating unit 2805 that image segmentation was not appropriately performed, in step S2970 the outputting unit 2807 may cause information to the effect that image segmentation could not be properly performed to be displayed on the display unit 2820.

Example 9

Next, an image processing apparatus according to Example 9 will be described referring to FIG. 28 and FIG. 33. In Example 8, the segmentation processing unit 2804 is equipped with one image segmentation engine. In contrast, in the present example, a segmentation processing unit generates a plurality of region label images with respect to an input image, using a plurality of image segmentation engines that include learned models that performed machine learning using different training data to each other.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8. Note that, since the configuration of the image processing apparatus according to the present example is the same as the configuration of the image processing apparatus according to Example 8, components illustrated in FIG. 28 are denoted by the same reference numerals as in Example 8, and a description of the components is omitted hereunder.

The segmentation processing unit 2804 according to the present example performs image segmentation processing with respect to an input image using two or more image segmentation engines which include learned models that were subjected to machine learning using different training data to each other.

A method for creating a training data group according to the present example will now be described. Specifically, first, imaging of various imaged sites is performed, and pair groups composed of pairs of an image as input data and a region label image as ground truth are prepared. Next, pair groups are grouped for each imaged site to create a training data group. For example, a training data group is created by creating first training data composed of pair groups obtained by imaging a first imaged site, and creating second training data composed of pair groups obtained by imaging a second imaged site.

Thereafter, machine learning models included in the respective image segmentation engines are caused to perform machine learning using the respective training data. For example, a first image segmentation engine that includes a learned model that was trained using the first training data is prepared. In addition, a second image segmentation engine that includes a learned model that was trained using the second training data is prepared. In this way, an image segmentation engine group is prepared.

The training data used for training the learned model included in each image segmentation engine differs for each of the image segmentation engines. Consequently, the degree of accuracy to which each of these image segmentation engines can perform image segmentation processing of an input image input to the image segmentation engines will differ according to the imaging conditions of the input image. Specifically, in the case of the first image segmentation engine, the accuracy of image segmentation processing with respect to an input image obtained by imaging the first imaged site is high, and the accuracy of image segmentation processing with respect to an input image obtained by imaging the second imaged site is low. Similarly, in the case of the second image segmentation engine, the accuracy of image segmentation processing with respect to an input image obtained by imaging the second imaged site is high, and the accuracy of image segmentation processing with respect to an image obtained by imaging the first imaged site is low.

Since each set of training data is composed of pair groups which are grouped according to the imaged site, there will be a similar image quality tendency among the images of an image group constituting the relevant pair groups. Therefore, if the imaged site corresponds to the relevant image segmentation engine, the image segmentation engine can perform image segmentation processing more accurately than the image segmentation engine according to Example 8. Note that, an imaging condition for grouping pairs of the training data is not limited to the imaged site, and may be the imaging angle of view or the resolution of the image, or a combination of two or more of these conditions.

Figure 33:
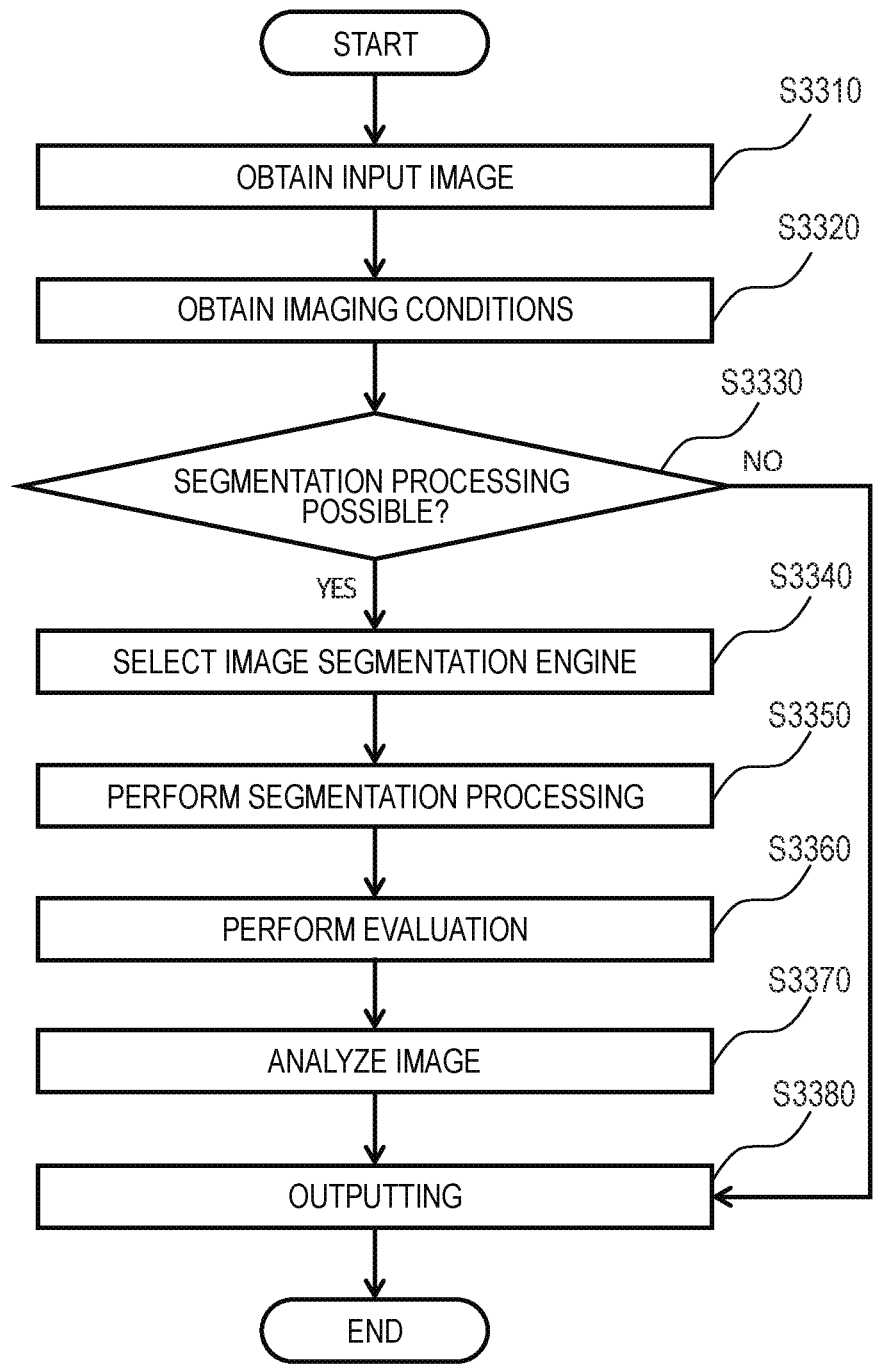
FIG. 33 is a flowchart illustrating an example of the processing flow of an image processing apparatus according to Example 9.

Hereunder, a series of image processing operations according to the present example is described referring to FIG. 33. FIG. 33 is a flowchart of the series of image processing operations according to the present example. Note that, the processing in step S3310 and step S3320 is the same as the processing in step S2910 and step S2920 according to Example 8, and hence a description of the processing is omitted here. Note that, in a case where an input image is to be unconditionally subjected to image segmentation processing, after performing the processing in step S3320, the processing in step S3330 can be omitted and the processing can shift to step S3340.

Upon the imaging conditions of the input image being obtained in step S3320, the processing shifts to step S3330. In step S3330, the processing possibility determining unit 2803 uses the imaging conditions group obtained in step S3320 to determine whether or not any of the aforementioned group of image segmentation engines can handle the input image.

If the processing possibility determining unit 2803 determines that none of the group of image segmentation engines is capable of handling the input image, the processing shifts to step S3380. On the other hand, if the processing possibility determining unit 2803 determines that any of the group of image segmentation engines is capable of handling the input image, the processing shifts to step S3340. Note that, depending on the settings or implementation form of the image processing apparatus 2800, similarly to Example 8, even if it is determined that the image segmentation engines are not capable of handling some of the imaging conditions, the processing in step S3340 may be executed.

In step S3340, the segmentation processing unit 2804 selects the image segmentation engine to perform processing, based on the imaging conditions of the input image obtained in step S3320 and information pertaining to the training data of the image segmentation engine group. Specifically, for example, the segmentation processing unit 2804 selects an image segmentation engine which, with respect to the imaged site in the imaging conditions group obtained in step S3320, has information of training data relating to the same imaged site or a peripheral imaged site and can perform highly accurate image segmentation processing. In the aforementioned example, if the imaged site is the first imaged site, the segmentation processing unit 2804 selects the first image segmentation engine.

In step S3350, the segmentation processing unit 2804 generates a region label image by using the image segmentation engine selected in step S3340 to subject the input image to image segmentation processing. Steps S3360 and S3370 are the same as step S2950 and S2960 in Example 8, and hence a description of these steps is omitted here.

After image analysis is performed in step S3370, the processing shifts to step S3380. In step S3380, if the evaluating unit 2805 determined that the region label image is to be output, the outputting unit 2807 outputs the region label image and analysis result to cause the region label image and analysis result to be displayed on the display unit 2820. Note that, when causing the region label image to be displayed on the display unit 2820, the outputting unit 2807 may also cause information to the effect that the region label image is a region label image which was generated using an image segmentation engine selected by the segmentation processing unit 2804 to be displayed. Note that, the outputting unit 2807 may also output only either one of the region label image and the analysis result.

On the other hand, if it was determined in step S3330 that image segmentation processing is not possible, the outputting unit 2807 outputs an image without region labels that is one kind of region label image, and causes the image without region labels to be displayed on the display unit 2820. Note that, instead of generating an image without region labels, the outputting unit 2807 may transmit a signal indicating that image segmentation processing was not possible to the imaging apparatus 2810.

Further, in a case where it was determined in step S3360 that image segmentation processing could not be properly performed also, the outputting unit 2807 outputs an image without region labels that is one kind of region label image, and causes the image without region labels to be displayed on the display unit 2820. In this case also, instead of generating an image without region labels, the outputting unit 2807 may transmit a signal indicating that image segmentation processing could not be properly performed to the imaging apparatus 2810. When the output processing in step S3380 ends, the series of image processing operations ends.

As described above, the segmentation processing unit 2804 according to the present example generates a region label image using at least one of a plurality of image segmentation engines which each includes a learned model that performed learning using different training data from the training data used by the learned models of the other image segmentation engines. In the present example, each of the plurality of image segmentation engines includes a learned model that performed learning using training data that is different from the training data used by the other learned models with respect to at least one of the imaged site, the imaging angle of view, and the image resolution. The segmentation processing unit 2804 generates a region label image using an image segmentation engine in accordance with at least one imaging condition among the imaged site, the imaging angle of view, and the image resolution of the input image.

According to this configuration, the image processing apparatus 2800 according to the present example can perform more accurate image segmentation processing in accordance with the imaging conditions.

Although in the present example the segmentation processing unit 2804 selects an image segmentation engine to be used for image segmentation processing based on an imaging condition of the input image, processing for selecting an image segmentation engine is not limited thereto. For example, the outputting unit 2807 may cause the imaging conditions of the obtained input image and an image segmentation engine group to be displayed on a user interface of the display unit 2820. In addition, the segmentation processing unit 2804 may select the image segmentation engine to be used for image segmentation processing according to an instruction from the examiner.

Note that, the outputting unit 2807 may cause information pertaining to the training data used for learning by the respective image segmentation engines to be displayed on the display unit 2820 together with the image segmentation engine group. Note that, information pertaining to training data used for learning by an image segmentation engine may be displayed in any form, and for example the image segmentation engine group may be displayed using names associated with the training data used for learning.

Further, the outputting unit 2807 may cause an image segmentation engine that was selected by the segmentation processing unit 2804 to be displayed on the user interface of the display unit 2820, and may accept an instruction from the examiner. In this case, the segmentation processing unit 2804 may determine whether or not to ultimately select the relevant image segmentation engine as the image segmentation engine to be used for image segmentation processing in accordance with the instruction from the examiner.

Note that, similarly to Example 8, the outputting unit 2807 may output a generated region label image and an evaluation result to the imaging apparatus 2810 or to another apparatus connected to the image processing apparatus 2800. Further, depending on the settings or implementation form of the image processing apparatus 2800, the outputting unit 2807 may process the region label image and the evaluation result so that they can be utilized by the imaging apparatus 2810 or another apparatus, or may convert the data format of the region label image and the evaluation result so that they can be transmitted to the image management system or the like.

Example 10

Next, an image processing apparatus according to Example 10 will be described referring to FIG. 28 and FIG. 33. In Examples 8 and 9, the imaging conditions obtaining unit 2802 obtains an imaging conditions group from the data structure or the like of the input image. In contrast, in the present example, an imaging conditions obtaining unit uses an imaging location estimation engine to estimate an imaged site or imaged region of an input image, based on the input image.

Unless explicitly stated otherwise, the configuration and processing of the image processing apparatus according to the present example are the same as the image processing apparatus 2800 according to Example 9. Therefore, hereunder, the image processing apparatus according to the present example is described centering on differences from the image processing apparatus according to Example 9. Note that, since the configuration of the image processing apparatus according to the present example is the same as the configuration of the image processing apparatus according to Examples 8 and 9, components illustrated in FIG. 28 are denoted by the same reference numerals as in Examples 8 and 9, and a description of the components is omitted hereunder.

The imaging conditions obtaining unit 2802 according to the present example uses an imaging location estimation engine (estimation engine) to estimate and obtain an imaged site or imaged region that is depicted in an input image which the obtaining unit 2801 obtained. According to a technique for estimating an imaging location of the imaging location estimation engine according to the present example, estimation processing is performed using a machine learning algorithm.

In the present example, training data constituted by a pair group composed of input data that is an image and ground truth that is an imaged site label corresponding to the input data is used for training a learned model pertaining to an imaged location estimating technique that uses a machine learning algorithm. Here, the term "input data" refers to an image which has specific imaging conditions assumed for a processing object (input image). An image obtained from an imaging apparatus having the same image quality tendency as the imaging apparatus 2810 can be used as the input data, and it is better if the imaging apparatus is the same model of equipment as the imaging apparatus 2810 and was set with the same settings as the imaging apparatus 2810. The kinds of imaged site labels serving as the ground truth may be the relevant imaged site which is at least partially included in the input data. The kinds of imaged site labels serving as the ground truth may be, for example, "macular area", "optic nerve head", "macular area and optic nerve head" and "other".

By including a learned model that performed learning using such kind of training data, the imaging location estimation engine according to the present example can output information indicating the location of an imaged site or imaged region that is visualized in an input image. Further, for each imaged site label or imaged region label of a required level of detail, the imaging location estimation engine can also output the probability of being the relevant imaged site or imaged region.

By using the imaging location estimation engine, based on an input image, the imaging conditions obtaining unit 2802 can estimate an imaged site or imaged region of the input image and thereby obtain the imaged site or imaged region as an imaging condition with respect to the input image. Note that, in a case where, for each imaged site label or imaged region label, the imaging location estimation engine outputs the probability of being the relevant imaged site or imaged region, the imaging conditions obtaining unit 2802 obtains the imaged site or imaged region with the highest probability as an imaging condition of the input image.

Next, similarly to Example 9, a series of image processing operations according to the present example is described referring to a flowchart in FIG. 33. Note that, since the processing in step S3310 and step S3330 to step S3380 according to the present example is the same as the processing in these steps in Example 9, a description of the processing is omitted here. Note that, in a case where the input image is to be unconditionally subjected to image segmentation processing, after the processing in step S3320, the processing in step S3330 can be omitted and the processing can shift to step S3340.

Upon an input image being obtained in step S3310, the processing shifts to step S3320. In step S3320, the imaging conditions obtaining unit 2802 obtains an imaging conditions group of the input image obtained in step S3310.

Specifically, an imaging conditions group stored in the data structure constituting the input image is obtained according to the data format of the input image. Further, if information relating to the imaged site or imaged region is not included in the imaging conditions group, the imaging conditions obtaining unit 2802 inputs the input image to the imaging location estimation engine to estimate which imaged site or imaged region was imaged to obtain the input image. Specifically, the imaging conditions obtaining unit 2802 inputs the input image to the imaging location estimation engine, evaluates the probabilities that are output with respect to each imaged site or imaged region of an imaged site label group or imaged region label group, and sets and obtains the imaged site or imaged region with the highest probability as an imaging condition of the input image.

Note that, in a case where imaging conditions other than the imaged site or imaged region are not stored in the input image, the imaging conditions obtaining unit 2802 can obtain an imaging information group from the imaging apparatus 2810 or the image management system (not illustrated). The subsequent processing is the same as in the series of image processing operations according to Example 9, and hence a description thereof is omitted here.

As described above, the imaging conditions obtaining unit 2802 according to the present example functions as an estimating unit that estimates at least one of an imaged site and an imaged region of an input image using an imaging location estimation engine that includes a learned model. The imaging conditions obtaining unit 2802 estimates an imaged site or an imaged region of an input image by inputting the input image to an imaging location estimation engine that includes a learned model for which learning was performed using images to each of which was attached a label of an imaged site or an imaged region as training data.

Thus, the image processing apparatus 2800 according to the present example can obtain an imaging condition regarding the imaged site or imaged region of an input image, based on the input image.

Note that, in the present example, in a case where information pertaining to an imaged site or imaged region is not included in the imaging conditions group, the imaging conditions obtaining unit 2802 performs an estimation regarding the imaged site or imaged region of the input image using the imaging location estimation engine. However, a situation in which an estimation regarding an imaged site or imaged region is performed using the imaging location estimation engine is not limited to this situation. The imaging conditions obtaining unit 2802 may also perform an estimation regarding an imaged site or imaged region using the imaging location estimation engine in a case where information regarding the imaged site or imaged region included in the data structure of the input image is insufficient as information of a required detail level.

Further, irrespective of whether or not information regarding the imaged site or imaged region is included in the data structure of an input image, the imaging conditions obtaining unit 2802 may estimate the imaged site or imaged region of the input image using the imaging location estimation engine. In this case, the outputting unit 2807 may cause the display unit 2820 to display an estimation result output from the imaging location estimation engine and information regarding the imaged site or imaged region included in the data structure of the input image, and the imaging conditions obtaining unit 2802 may make a determination regarding these imaging conditions according to an instruction from the examiner.

Example 11

Next, an image processing apparatus according to Example 11 is described referring to FIG. 28, FIG. 29, FIG. 34 and FIG. 35. In the present example, a segmentation processing unit enlarges or reduces an input image so that the size of the input image becomes an image size that the image segmentation engine is capable of handling. Further, the segmentation processing unit generates a region label image by reducing or enlarging an output image from the image segmentation engine so that the image size of the output image becomes the image size of the input image.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8. Note that, since the configuration of the image processing apparatus according to the present example is the same as the configuration of the image processing apparatus according to Example 8, components illustrated in FIG. 28 are denoted by the same reference numerals as in Example 8, and a description of the components is omitted hereunder.

The segmentation processing unit 2804 according to the present example includes an image segmentation engine that is similar to the image segmentation engine according to Example 8. However, in the present example, the training data that is used for learning by the machine learning model that the image segmentation engine includes is different from the training data in Example 8. Specifically, in the present example, pair groups of input data and ground truth constituted by an image group in which each image of the input data and each image of the ground truth is enlarged or reduced so as to be a certain image size is used as training data.

Figure 34:
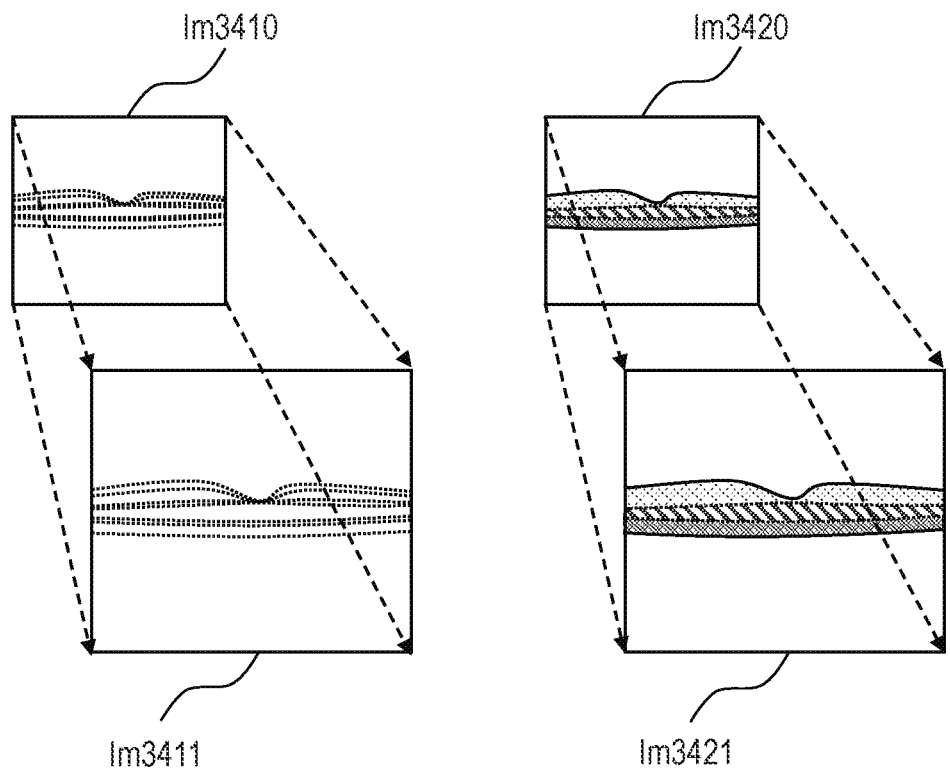
FIG. 34 illustrates image processing according to Example 11.

The training data of the learned model which the image segmentation engine according to the present example includes will now be described referring to FIG. 34. As illustrated in FIG. 34, for example, let us consider a case in which there are an input image Im3410 and a region label image Im3420 which are smaller than a certain image size set with respect to the training data. In this case, the input image Im3410 and the region label image Im3420 are each enlarged so as to become the certain image size set for the training data. The enlarged image Im3411 and the enlarged region label image Im3421 are then taken as a pair, and the relevant pair is used as one piece of training data.

Note that, similarly to Example 8, an image having specific imaging conditions assumed as a processing object (input image) is used for the input data of the training data, and the relevant specific imaging conditions are an imaged site, an imaging system and an imaging angle of view determined in advance. In other words, unlike Example 8, the image size is not included in the specific imaging conditions according to the present example.

The segmentation processing unit 2804 according to the present example generates a region label image by subjecting the input image to image segmentation processing using the image segmentation engine for which learning was performed using such training data. At such time, the segmentation processing unit 2804 generates a modified image by enlarging or reducing the input image so as to become a certain image size set with respect to the training data, and inputs the modified image to the image segmentation engine.

Further, the segmentation processing unit 2804 generates a region label image by reducing or enlarging an output image from the image segmentation engine so as to become the image size of the input image. Hence, even in the case of an input image having an image size that cannot be handled according to Example 8, the segmentation processing unit 2804 according to the present example can generate a region label image by image segmentation processing using the image segmentation engine.

Figure 35:
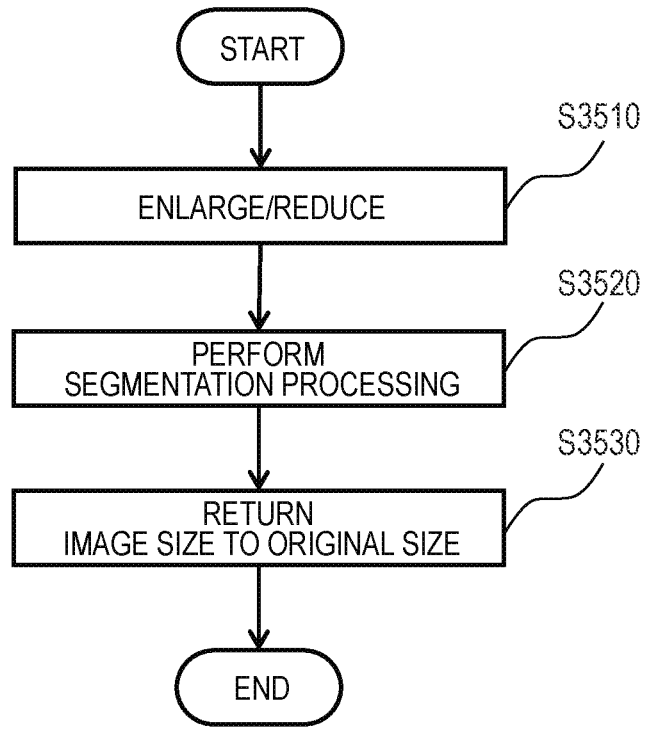
FIG. 35 is a flowchart illustrating an example of the processing flow of an image processing apparatus according to Example 11.

Next, a series of image processing operations according to the present example will be described referring to FIG. 29 and FIG. 35. FIG. 35 is a flowchart illustrating segmentation processing according to the present example. Note that, the processing in step S2910, step S2920 and step S2950 to step S2970 according to the present example is the same as the processing in these steps in Example 8, and hence a description of the processing is omitted here. Note that, in a case where an input image is to be subjected to image segmentation processing unconditionally with regard to imaging conditions other than the image size, after performing the processing in step S2920, the processing in step S2930 can be omitted and the processing can shift to step S2940.

In step S2920, similarly to Example 8, upon the imaging conditions obtaining unit 2802 obtaining the imaging conditions group of the input image, the processing shifts to step S2930. In step S2930, the processing possibility determining unit 2803 uses the obtained imaging conditions group to determine whether or not the input image can be handled by the image segmentation engine. Specifically, with respect to the imaging conditions of the input image, the processing possibility determining unit 2803 determines whether or not the imaged site, imaging system and imaging angle of view can be handled by the image segmentation engine. Unlike Example 8, the processing possibility determining unit 2803 does not make a determination regarding the image size.

The processing possibility determining unit 2803 makes determination regarding the imaged site, imaging system and imaging angle of view, and if it is determined that the input image can be handled, the processing shifts to step S2940. On the other hand, in a case where, based on these imaging conditions, the processing possibility determining unit 2803 determines that the image segmentation engine is not capable of handling the input image, the processing shifts to step S2970. Note that, depending on the settings or implementation form of the image processing apparatus 2800, even if it is determined that the input image cannot be processed based on one or more conditions among the imaged site, imaging system and imaging angle of view, the image segmentation processing in step S2940 may be performed.

Upon the processing shifting to step S2940, image segmentation processing according to the present example illustrated in FIG. 35 is started. In the image segmentation processing according to the present example, first, in step S3510, the segmentation processing unit 2804 enlarges or reduces the input image to a certain image size set with respect to the training data, to thereby generate a modified image.

Next, in step S3520, the segmentation processing unit 2804 inputs the generated modified image to the image segmentation engine to obtain a first region label image subjected to image segmentation processing.

Thereafter, in step S3530, the segmentation processing unit 2804 reduces or enlarges the first region label image to the image size of the input image to generate a final region label image. Upon the segmentation processing unit 2804 generating the final region label image in step S3530, the image segmentation processing according to the present example ends, and the processing shifts to step S2950. Since the processing from step S2950 onward is the same as the processing from step S2950 onward in Example 8, a description of the processing is omitted here.

As described above, the segmentation processing unit 2804 according to the present example adjusts the image size of an input image to an image size which the image segmentation engine is capable of handling, and inputs the resultant image whose size was adjusted into the image segmentation engine. Further, the segmentation processing unit 2804 generates a region label image by adjusting the image size of the output image from the image segmentation engine to the original image size of the input image. Thus, the image processing apparatus 2800 of the present example can also perform image segmentation processing with respect to an input image having an image size that cannot be handled according to Example 8, and can generate a region label image including information pertaining to an ROI or VOI which can be utilized for image diagnosis or image analysis.

Example 12

Next, an image processing apparatus according to Example 12 is described referring to FIG. 28, FIG. 29, FIG. 36 and FIG. 37. In the present example, a segmentation processing unit generates a region label image by image segmentation processing based on a certain resolution which is performed by an image segmentation engine.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8. Note that, since the configuration of the image processing apparatus according to the present example is the same as the configuration of the image processing apparatus according to Example 8, components illustrated in FIG. 28 are denoted by the same reference numerals as in Example 8, and a description of the components is omitted hereunder.

The segmentation processing unit 2804 according to the present example includes an image segmentation engine that is similar to Example 8. However, in the present example, the training data used for learning by the machine learning model that the image segmentation engine includes differs from the training data in Example 8. Specifically, after an image group composed of pair groups of input data and ground truth of the training data is enlarged or reduced to an image size such that the resolution of the image group becomes a certain resolution, padding is performed so that the image size of each image of the image group becomes a sufficiently large certain image size. Here, the phrase "resolution of the image group" refers to, for example, the spatial resolution of the imaging apparatus or the resolution with respect to an imaged region.

Figure 36:
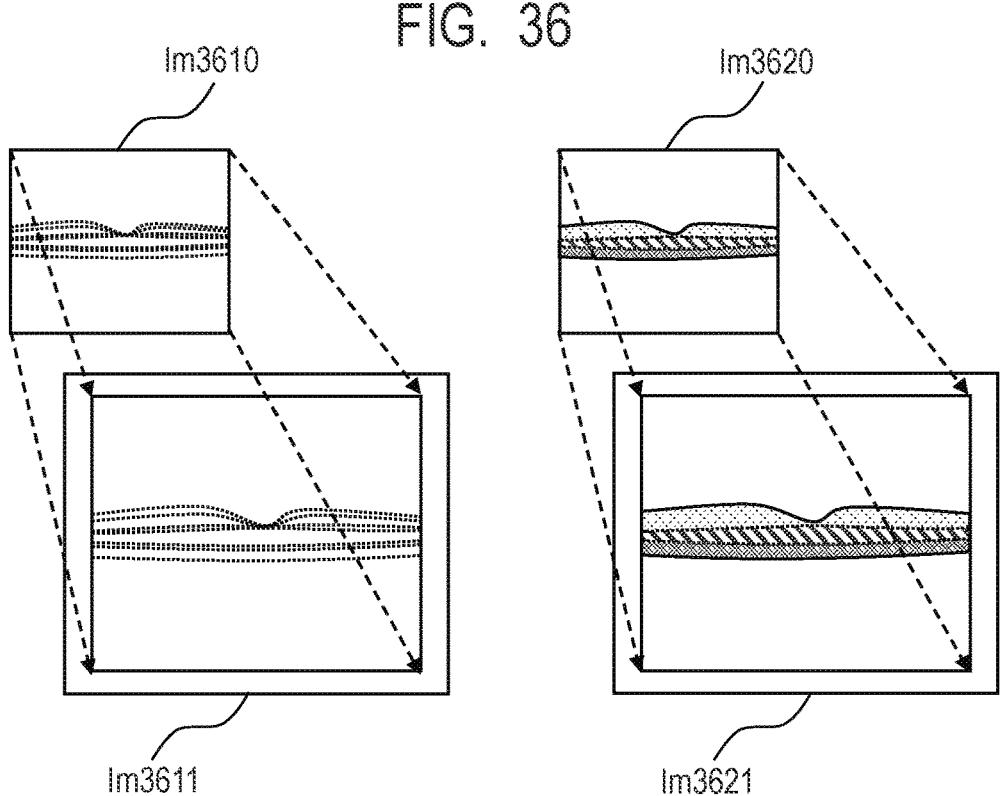
FIG. 36 illustrates image processing according to Example 12.

The training data of the image segmentation engine according to the present example will now be described referring to FIG. 36. As illustrated in FIG. 36, for example, let us consider a case where there are an image Im3610 and a region label image Im3620 which have a lower resolution than a certain resolution set for the training data. In this case, the image Im3610 and the region label image Im3620 are each enlarged so that the resolution becomes the certain resolution set for the training data. In addition, the enlarged image Im3610 and region label image Im3620 are each padded so as to become a certain image size set for the training data. The image Im3611 and region label image Im3621 subjected to enlargement and padding are then taken as a pair, and the pair is used as one piece of training data.

Note that, the phrase "certain image size set for the training data" refers to the largest image size that an image assumed as a processing object (input image) can become when enlarged or reduced so that the resolution of the image becomes a certain resolution. In a case where the certain image size is not sufficiently large, there is a probability that when an image input to the image segmentation engine is enlarged, the image will be an image size that the learned model is not capable of handling.

Further, a region subjected to padding is filled using a fixed pixel value, is filled using a neighboring pixel value, or is mirror-padded, in accordance with the characteristics of the learned model so that image segmentation processing can be effectively performed. Note that, similarly to Example 8, an image having specific imaging conditions assumed as a processing object is used for the input data, and the specific imaging conditions in question are an imaged site, an imaging system and an imaging angle of view determined in advance. In other words, unlike Example 8, the image size is not included in the specific imaging conditions according to the present example.

The segmentation processing unit 2804 according to the present example generates a region label image by subjecting the input image to image segmentation processing using the image segmentation engine that includes the learned model for which learning was performed using such training data. At such time, the segmentation processing unit 2804 generates a modified image by enlarging or reducing the input image so as to become a certain resolution set with respect to the training data. Further, the segmentation processing unit 2804 performs padding with respect to the modified image so that the modified image becomes a certain image size set for the training data to thereby generate a padded image, and inputs the padded image to the image segmentation engine.

Further, with respect to a first region label image output from the image segmentation engine, the segmentation processing unit 2804 trims only a region corresponding to a region at which padding was performed, to thereby generate a second region label image. Thereafter, the segmentation processing unit 2804 reduces or enlarges the generated second region label image so as to be the image size of the input image, thereby generating a final region label image.

Therefore, even in the case of an input image having an image size that cannot be handled according to Example 8, the segmentation processing unit 2804 according to the present example can generate a region label image by image segmentation processing by the image segmentation engine.

Figure 37:
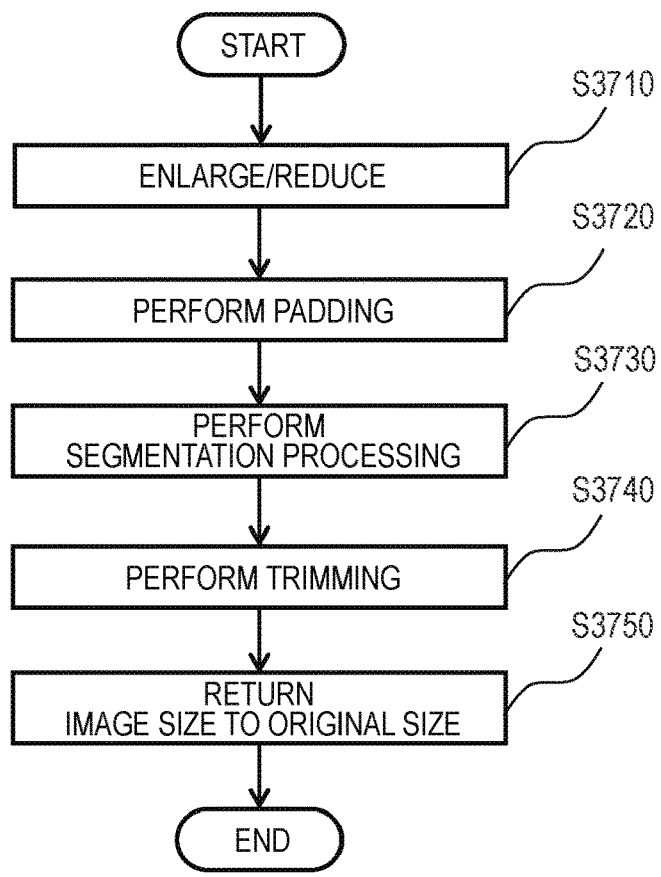
FIG. 37 is a flowchart illustrating an example of the processing flow of an image processing apparatus according to Example 13.

Next, a series of image processing operations according to the present example will be described referring to FIG. 29 and FIG. 37. FIG. 37 is a flowchart illustrating image segmentation processing according to the present example. Note that, the processing in step S2910, step S2920 and step S2950 to step S2970 according to the present example is the same as the processing in these steps in Example 8, and hence a description of the processing is omitted here. Note that, in a case where an input image is to be subjected to image segmentation processing unconditionally with regard to the imaging conditions other than the image size, after performing the processing in step S2920, the processing in step S2930 can be omitted and the processing can shift to step S2940.

In step S2920, similarly to Example 8, upon the imaging conditions obtaining unit 2802 obtaining the imaging conditions group of the input image, the processing shifts to step S2930. In step S2930, the processing possibility determining unit 2803 uses the obtained imaging conditions group to determine whether or not the input image can be handled by the image segmentation engine. Specifically, with respect to the imaging conditions of the input image, the processing possibility determining unit 2803 determines whether or not the imaged site, imaging system and imaging angle of view can be handled by the image segmentation engine. Unlike Example 8, the processing possibility determining unit 2803 does not make a determination regarding the image size.

The processing possibility determining unit 2803 makes determination regarding the imaged site, imaging system and imaging angle of view, and if it is determined that the input image can be handled, the processing shifts to step S2940. On the other hand, in a case where, based on these imaging conditions, the processing possibility determining unit 2803 determines that the image segmentation engine is not capable of handling the input image, the processing shifts to step S2970. Note that, depending on the settings or implementation form of the image processing apparatus 2800, even if it is determined that the input image cannot be processed based on one or more conditions among the imaged site, imaging system and imaging angle of view, the image segmentation processing in step S2940 may be performed.

Upon the processing shifting to step S2940, image segmentation processing according to the present example illustrated in FIG. 37 is started. In the image segmentation processing according to the present example, first, in step S3710, the segmentation processing unit 2804 enlarges or reduces the input image so as to become a certain resolution set with respect to the training data, to thereby generate a modified image.

Next, in step S3720, the segmentation processing unit 2804 performs padding with respect to the generated modified image so that the modified image becomes an image size set for the training data, to thereby generate a padded image.

At such time, with regard to a region in which padding is performed, the segmentation processing unit 2804 performs padding by filling the region using a fixed pixel value or using a neighboring pixel value or by mirror-padding in accordance with the characteristics of the learned model so that image segmentation processing can be effectively performed.

In step S3730, the segmentation processing unit 2804 inputs the padded image to the image segmentation engine to thereby obtain a first region label image subjected to image segmentation processing.

Next, in step S3740, with respect to the first region label image, the segmentation processing unit 2804 trims only a region corresponding to a region at which padding was performed in step S3720, to thereby generate a second region label image.

Thereafter, in step S3750, the segmentation processing unit 2804 reduces or enlarges the second region label image to the image size of the input image to generate a final region label image. Upon the segmentation processing unit 2804 generating the final region label image in step S3750, the image segmentation processing according to the present example ends, and the processing shifts to step S2950. Since the processing from step S2950 onward is the same as the processing from step S2950 onward in Example 8, a description of the processing is omitted here.

As described above, the segmentation processing unit 2804 according to the present example adjusts the image size of an input image so that the resolution of the input image becomes a predetermined resolution. Further, with respect to the input image whose image size was adjusted, the segmentation processing unit 2804 generates a padded image subjected to padding so that the adjusted image size becomes an image size which the image segmentation engine is capable of handling, and then inputs the padded image to the image segmentation engine. Thereafter, the segmentation processing unit 2804 subjects an output image from the image segmentation engine to trimming so as to trim only a region corresponding to a region in which padding was performed. The segmentation processing unit 2804 then adjusts the image size of the image on which trimming was performed to the original image size of the input image, to thereby generate a region label image.

Thus, even in the case of an input image having an image size that cannot be handled according to Example 8, the segmentation processing unit 2804 of the present example can subject the input image to image segmentation processing by the image segmentation engine to thereby generate a region label image. Further, by using an image segmentation engine which learned with training data based on the resolution, in some cases image segmentation processing of an input image can be performed more efficiently than in the case of the image segmentation engine according to Example 10 that processes images of the same image size.

Example 13

Next, an image processing apparatus according to Example 13 is described referring to FIG. 28, FIG. 29, and FIG. 38 to FIG. 40. In the present example, a segmentation processing unit generates a region label image by performing image segmentation processing of each region of a certain image size of an input image.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8. Note that, since the configuration of the image processing apparatus according to the present example is the same as the configuration of the image processing apparatus according to Example 8, components illustrated in FIG. 28 are denoted by the same reference numerals as in Example 8, and a description of the components is omitted hereunder.

The segmentation processing unit 2804 according to the present example includes a similar image segmentation engine to Example 8. However, in the present example, the training data used for learning by a machine learning model that the image segmentation engine includes differs from the training data in Example 8. Specifically, pair groups composed of input data that is an input image and ground truth that is a region label image corresponding to the input image that constitutes the training data are constituted by rectangular region images of a certain image size which have a corresponding positional relationship in the input image and the region label image.

Figure 38:
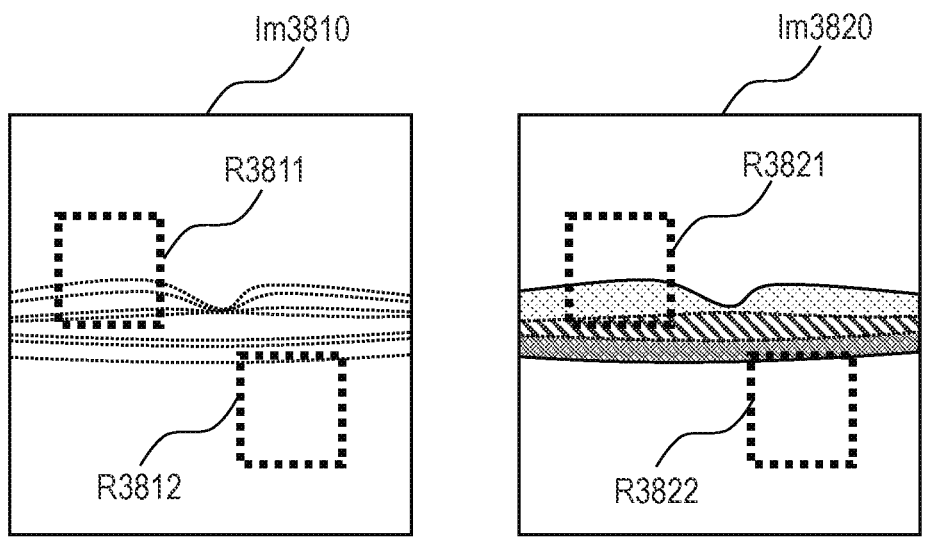
FIG. 38 illustrates image processing according to Example 13.

The training data of the image segmentation engine according to the present example will now be described referring to FIG. 38. As illustrated in FIG. 38, with regard to one of the pair groups constituting the training data, a case will be considered in which it is assumed that, for example, there is an image Im3810 that is an input image, and a region label image Im3820 that is a region label image corresponding to the image Im3810. In this case, in Example 8, the image Im3810 is adopted as the input data and the region label image Im3820 is adopted as the ground truth of the training data.

In contrast, in the present example, a rectangular region image R3811 in the image Im3810 is adopted as the input data, and a rectangular region image R3821 which, in the region label image Im3820, is the same (corresponding) imaged region as the rectangular region image R3811, is adopted as the ground truth. Further, a pair (hereinafter, referred to as a "first rectangular region image pair") of the training data is constituted by the rectangular region image R3811 that is the input data and the rectangular region image R3821 that is the ground truth.

Here, it is assumed that the rectangular region image R3811 and the rectangular region image R3821 are images of a certain image size. Note that, the image Im3810 and the region label image Im3820 may be aligned by any method. Further, the positional relationship corresponding to the rectangular region image R3811 and the rectangular region image R3821 may be identified by any method such as template matching. Note that, depending on the design of the machine learning model that the image segmentation engine includes, the respective image sizes and number of dimensions of the input data and the ground truth may differ from each other. For example, a case where the input data is one part of a B-scan image (two-dimensional image) and the ground truth is one part of an A-scan image (one-dimension) is one such case.

The aforementioned certain image size can be determined based on, for example, a common divisor of a group of the numbers of pixels of each dimension which corresponds to an image size group of images assumed as the processing object (input image). In this case, the positional relationships between a group of rectangular region images which the image segmentation engine outputs can be prevented from overlapping.

Specifically, let us consider a case where, for example, the image assumed as a processing object is a two-dimensional image, a first image size in an image size group is a width of 500 pixels and a height of 500 pixels, and a second image size in the image size group is a width of 100 pixels and a height of 100 pixels. Here, the certain image size relating to the rectangular region images R3811 and R3821 is selected from the common divisors for each side. In this case, for example, the certain image size is selected from a width of 100 pixels and a height of 100 pixels, a width of 50 pixels and a height of 50 pixels, or a width of 25 pixels and a height of 25 pixels and the like. In a case where the image assumed as the processing object has three dimensions, the number of pixels relating to the width, height and depth is determined.

Note that, it is possible to set a plurality of rectangular regions for one pair of an image corresponding to input data and a region label image corresponding to ground truth. Therefore, for example, a rectangular region image R3812 in the image Im3810 is adopted as input data, and a rectangular region image R3822 that, in the region label image Im3820, is the same imaged region as the rectangular region image R3812 is adopted as ground truth. Further, a pair of the training data is composed of the rectangular region image R3812 as input data and the rectangular region image R3822 as ground truth. By this means, a rectangular region image pair that is different from the first rectangular region image pair can be created.

Note that, the content of pair groups constituting the training data can be enhanced by creating a large number of pairs of rectangular region images while changing the image of the rectangular region to images with different coordinates. It can be expected that efficient image segmentation processing will be performed by an image segmentation engine which performed training using the pair groups constituting the training data in question. However, a configuration can be adopted so that pairs which do not contribute to image segmentation processing by the learned model are not added to the training data.

Note that, as the input data and the ground truth of the training data, images depicting a region with one layer or to which one label is attached can be used as training data. Further, as the input data and the ground truth of the training data, images of a region depicting a plurality of layers, for example, two layers, and more preferably three or more layers can also be used. Similarly, images of a region depicting a plurality of regions in which labels are separated in a region label image can also be used. In these cases, in comparison to a case where images depicting a region with one layer or to which one label is attached are used as training data, it can be expected that more suitable image segmentation processing can be performed using the learned model, based on the positional relationship with respect to the learned layers or regions.

In addition, let us consider a case where, for example, between two rectangular region images forming a pair, there is a large difference with respect to the structure or position of the imaging target to be rendered between a rectangular region image created from an input image and a rectangular region image created from a region label image. In this case, there is a possibility that an image segmentation engine for which learning was performed using such kind of training data will output a region label image which has low accuracy. Therefore, such kinds of pairs can be removed from the training data.

Note that, similarly to Example 8, an image having specific imaging conditions assumed as a processing object is used for the input data of the training data, and the specific imaging conditions in question are an imaged site, an imaging system and an imaging angle of view determined in advance. In other words, unlike Example 8, the image size is not included in the specific imaging conditions according to the present example.

The segmentation processing unit 2804 according to the present example generates a region label image by subjecting an input image to image segmentation processing using an image segmentation engine for which learning was performed using such training data. At such time, the segmentation processing unit 2804 divides the input image into a group of rectangular region images having a certain image size set for the training data, continuously and without gaps. The segmentation processing unit 2804 subjects each image in the rectangular region image group into which the input image was divided to image segmentation processing using the image segmentation engine, to thereby generate a group of divided region label images. Thereafter, the segmentation processing unit 2804 arranges and combines the generated group of divided region label images in accordance with the positional relationship between the divided region label images in the input image to thereby generate a final region label image.

Thus, the segmentation processing unit 2804 of the present example subjects the input image to image segmentation processing in rectangular region units, and combines the images which underwent the image segmentation processing. By this means, the segmentation processing unit 2804 of the present example can also subject an image having an image size that cannot be handled according to Example 8 to image segmentation processing to generate a region label image.

Figure 39:
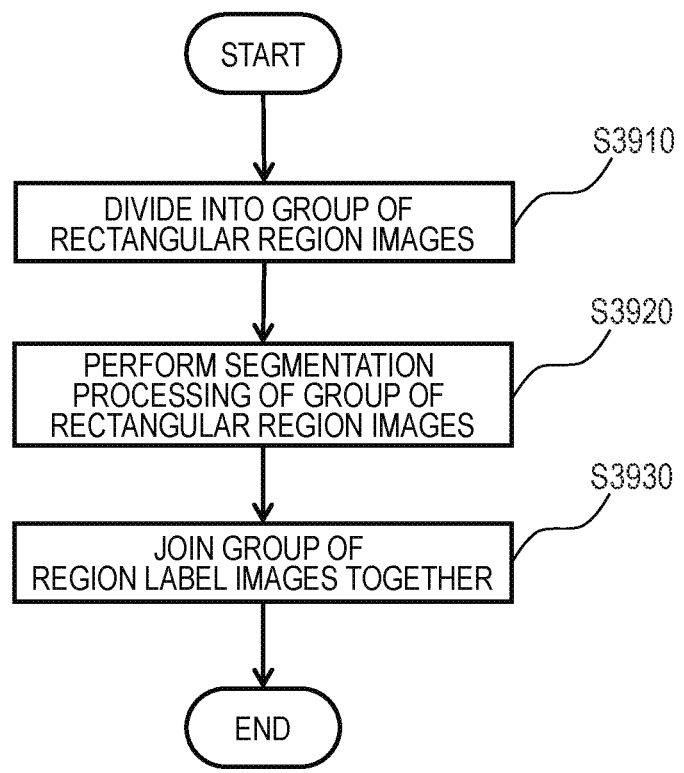
FIG. 39 is a flowchart illustrating an example of the processing flow of an image processing apparatus according to Example 13.
Figure 40:
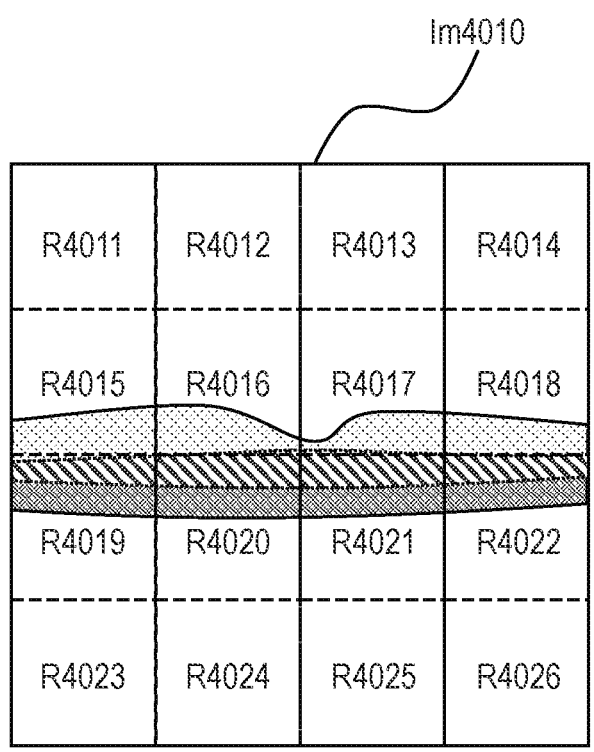
FIG. 40 illustrates image processing according to Example 13.

Next, a series of image processing operations according to the present example will be described referring to FIG. 29, FIG. 39 and FIG. 40. FIG. 39 is a flowchart illustrating image segmentation processing according to the present example. Note that, the processing in step S2910, step S2920 and step S2950 to step S2970 according to the present example is the same as the processing in these steps in Example 8, and hence a description of the processing is omitted here. Further, in a case where an input image is to be subjected to image segmentation processing unconditionally with regard to the imaging conditions other than the image size, after performing the processing in step S2920, the processing in step S2930 can be omitted and the processing can shift to step S2940.

In step S2920, similarly to Example 8, upon the imaging conditions obtaining unit 2802 obtaining the imaging conditions group of the input image, the processing shifts to step S2930. In step S2930, the processing possibility determining unit 2803 uses the obtained imaging conditions group to determine whether or not the input image can be handled by the image segmentation engine. Specifically, with respect to the imaging conditions of the input image, the processing possibility determining unit 2803 determines whether or not the imaged site, imaging system and imaging angle of view can be handled by the image segmentation engine. Unlike Example 8, the processing possibility determining unit 2803 does not make a determination regarding the image size.

The processing possibility determining unit 2803 makes determination regarding the imaged site, imaging system and imaging angle of view, and if it is determined that the input image can be handled, the processing shifts to step S2940. On the other hand, in a case where, based on these imaging conditions, the processing possibility determining unit 2803 determines that the image segmentation engine is not capable of handling the input image, the processing shifts to step S2970. Note that, depending on the settings or implementation form of the image processing apparatus 2800, even if it is determined that the input image cannot be processed based on one or more conditions among the imaged site, imaging system and imaging angle of view, the image segmentation processing in step S2940 may be performed.

Upon the processing shifting to step S2940, image segmentation processing according to the present example illustrated in FIG. 39 is started. In the image segmentation processing according to the present example, first, in step S3910, as illustrated in FIG. 40, the input image is divided continuously and without gaps into a group of rectangular region images of a certain image size set for the training data. FIG. 40 illustrates one example of an input image Im4010 divided into a group of rectangular region images R4011 to R4026 of a certain image size. Note that, depending on the design of the machine learning model that the image segmentation engine includes, the input image and the output image may differ from each other with respect to the image size or the number of dimensions. In this case, to ensure there is no loss with respect to the combined region label image generated in step S3920, the positions at which the aforementioned input image is divided are adjusted by causing the positions to overlap or by separating the positions.

Next, in step S3920, the segmentation processing unit 2804 uses the image segmentation engine to subject each of the group of rectangular region images R4011 to R4026 to image segmentation processing, and thereby generates a group of divided region label images.

Subsequently, in step S3930, the segmentation processing unit 2804 arranges and combines each of the generated group of divided region label images according to the same positional relationship as the respective images of the group of rectangular region images R4011 to R4026 obtained by dividing the input image. By this means, the segmentation processing unit 2804 can generate a region label image.

Upon the segmentation processing unit 2804 generating the region label image in step S3930, the image segmentation processing according to the present example ends, and the processing shifts to step S2950. Since the processing from step S2950 onward is the same as the processing from step S2950 onward in Example 8, a description of the processing is omitted here.

As mentioned above, the segmentation processing unit 2804 according to the present example divides an input image into a plurality of rectangular region images R4011 to R4026 of a predetermined image size. Thereafter, the segmentation processing unit 2804 inputs the divided plurality of rectangular region images R4011 to R4026 to the image segmentation engine to generate a plurality of divided region label images, and then integrates the plurality of divided region label images to generate a region label image. Note that, in a case where positional relationships among the group of rectangular regions overlap during integration, pixel value groups of the rectangular region group are integrated or overwritten.

Thus, even in the case of an input image having an image size that cannot be handled according to Example 8, the segmentation processing unit 2804 of the present example can generate a region label image by image segmentation processing using an image segmentation engine. Further, by creating training data from a plurality of images obtained by dividing images into a predetermined image size, a large amount of training data can be created from a small number of images. Hence, in this case, the number of input images and region label images used for creating training data can be reduced.

Further, the learned model which the image segmentation engine according to the present example includes is a model that was subjected to learning using tomographic images including two or more layers as input data, and using region label images corresponding to the tomographic images as ground truth. Therefore, it can be expected that in comparison to a case where images depicting regions with one layer or to which one label is attached are used as training data, more suitable image segmentation processing can be performed using the learned model, based on the positional relationships with respect to the learned layers or regions.

Example 14

Next, an image processing apparatus according to Example 14 will be described referring to FIG. 28, FIG. 41 and FIG. 42. In the present example, an evaluating unit selects a region label image that has the highest accuracy among a plurality of region label images that are output from a plurality of image segmentation engines, in accordance with an instruction from the examiner.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8. Note that, since the configuration of the image processing apparatus according to the present example is the same as the configuration of the image processing apparatus according to Example 8, components illustrated in FIG. 28 are denoted by the same reference numerals as in Example 8, and a description of the components is omitted hereunder.

The segmentation processing unit 2804 according to the present example performs image segmentation processing with respect to an input image using two or more image segmentation engines which include learned models that were subjected to machine learning using different training data to each other.

A method for creating a training data group according to the present example will now be described. Specifically, first, pair groups composed of input data that are images obtained by imaging according to various kinds of imaging conditions and ground truth that are region label images are prepared. Next, a training data group is created by grouping pair groups according to arbitrary combinations of arbitrary imaging conditions. For example, a training data group is created that includes first training data composed of pair groups obtained according to a first combination of imaging conditions, and second training data composed of pair groups obtained according to a second combination of imaging conditions.

Thereafter, the machine learning models included in the respective image segmentation engines are caused to perform machine learning using the respective training data. For example, a first image segmentation engine that includes a learned model that was trained using the first training data is prepared. In addition, a second image segmentation engine that includes a learned model that was trained using the second training data is prepared. In this way, an image segmentation engine group is prepared.

The training data used for training the learned model included in each image segmentation engine differs for each of the image segmentation engines. Consequently, the accuracy with which each of these image segmentation engines can perform image segmentation processing of an input image input to the image segmentation engines will differ according to the imaging conditions of the input image. Specifically, in the case of the first image segmentation engine, the accuracy of image segmentation processing with respect to an input image obtained by imaging according to the first combination of imaging conditions is high. On the other hand, in the case of the first image segmentation engine, the accuracy of image segmentation processing with respect to an image obtained by imaging according to the second combination of imaging conditions is low. Similarly, in the case of the second image segmentation engine, the accuracy of image segmentation processing with respect to an input image obtained by imaging according to the second combination of imaging conditions is high. On the other hand, in the case of the second image segmentation engine, the accuracy of image segmentation processing with respect to an image obtained by imaging according to the first combination of imaging conditions is low.

Since each set of training data is composed of pair groups that are grouped according to a combination of imaging conditions, there will be a similar image quality tendency among the images of an image group constituting the relevant pair groups. Therefore, if the combination of imaging conditions corresponds to the training data used for training the relevant image segmentation engine, the relevant image segmentation engine can perform image segmentation processing more accurately than the image segmentation engine according to Example 8. Note that, a combination of imaging conditions for grouping pairs of the training data may be any combination of imaging conditions, and for example may be a combination of two or more imaging conditions selected from among the imaged site, the imaging angle of view and the resolution of the image. Further, grouping of the training data may be performed based on a single imaging condition, similarly to Example 9.

In a similar manner as in Example 8, the evaluating unit 2805 performs an evaluation with respect to a plurality of region label images that the segmentation processing unit 2804 generated using a plurality of image segmentation engines. Thereafter, in a case where there are a plurality of region label images for which the evaluation result is a True value, in accordance with an instruction from the examiner, the evaluating unit 2805 selects the region label image that has the highest accuracy among the plurality of region label images, and determines the selected region label image as the region label image to be output. Note that, similarly to Example 8, the evaluating unit 2805 may perform the evaluation using a region label image evaluating engine that includes a learned model, or may perform the evaluation using a knowledge-based region label image evaluating engine.

The analyzing unit 2806 performs image analysis processing in a similar manner to Example 8 with respect to the input image, using the region label image determined as the region label image to be output by the evaluating unit 2805 and the input image. The outputting unit 2807 can cause the region label image determined as the region label image to be output and the analysis result to be displayed on the display unit 2820 or to be output to another apparatus in a similar manner to Example 8. Note that, the outputting unit 2807 can cause a plurality of region label images for which the evaluation result is a True value to be displayed on the display unit 2820, and the evaluating unit 2805 can select a region label image that has the highest accuracy in accordance with an instruction from the examiner who checked the region label images on the display unit 2820.

Thus, the image processing apparatus 2800 can output a region label image that has the highest accuracy in accordance with an instruction from the examiner from among the plurality of region label images generated using the plurality of image segmentation engines.

Figure 41:
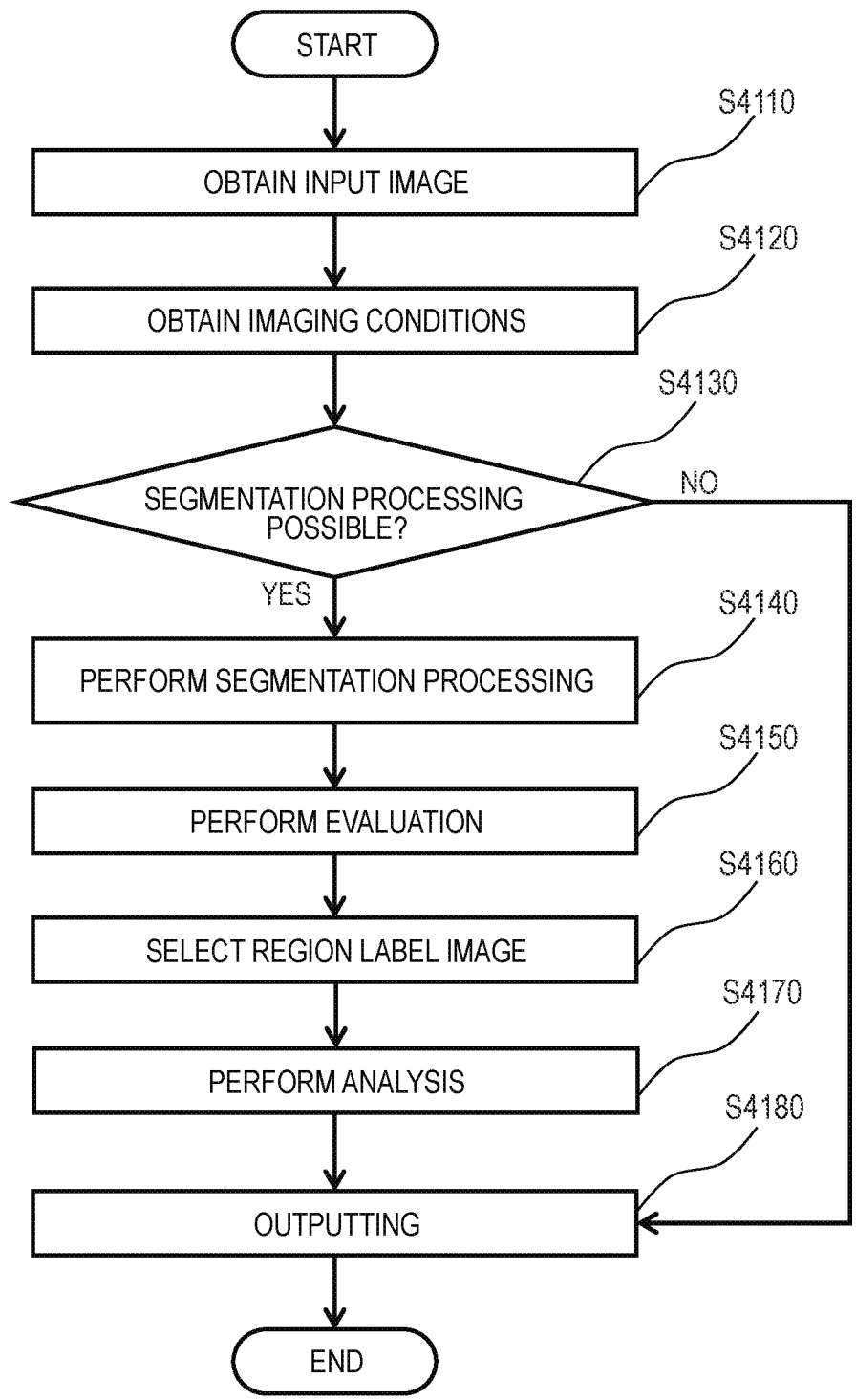
FIG. 41 is a flowchart illustrating an example of the processing flow of an image processing apparatus according to Example 14.
Figure 42:
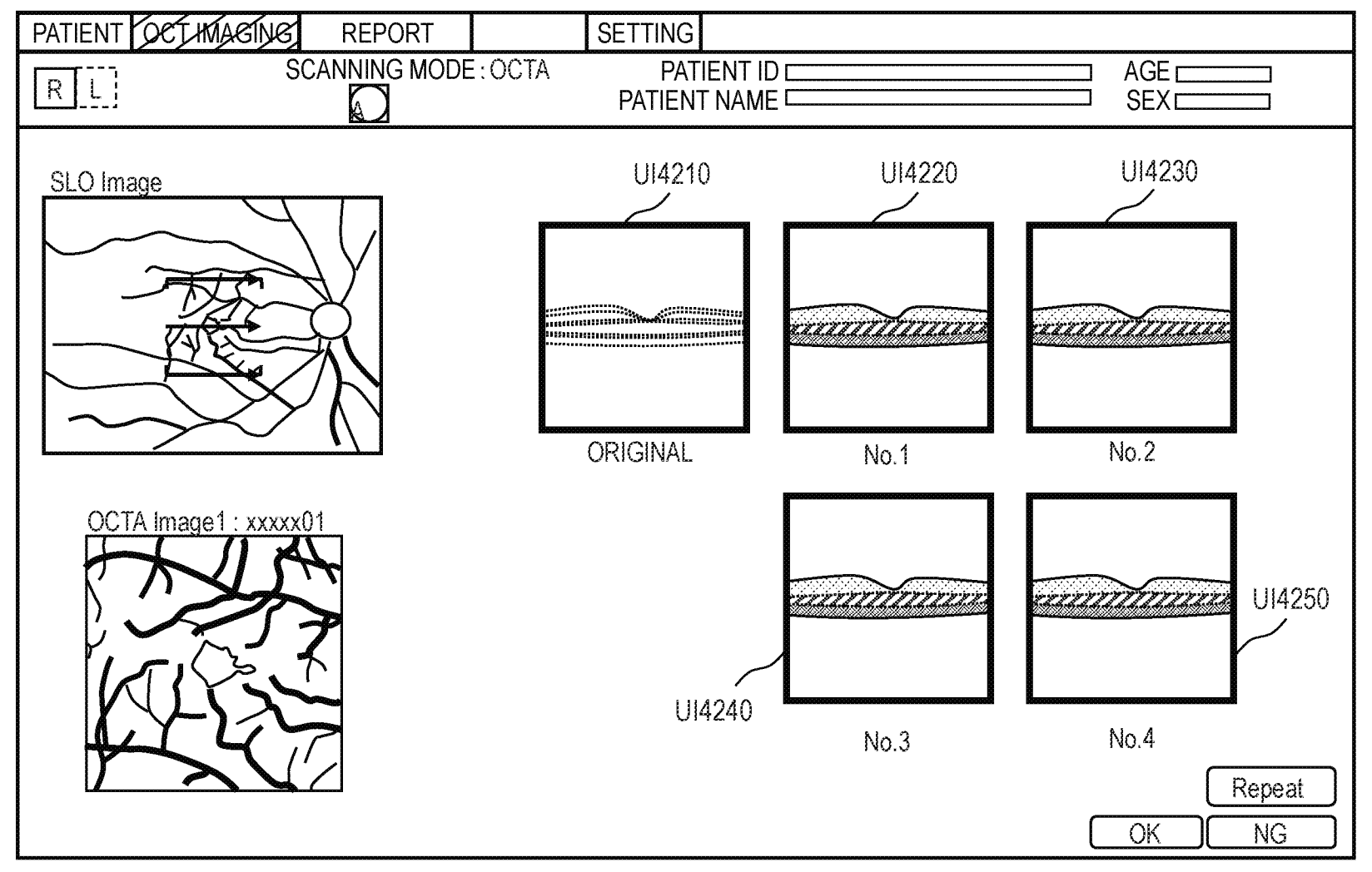

Hereunder, a series of image processing operations according to the present example is described referring to FIG. 41 and FIG. 42. FIG. 41 is a flowchart illustrating the series of image processing operations according to the present example. Note that, the processing in step S4110 and step S4120 according to the present example is the same as the processing in step S2910 and step S2920 in Example 8, and hence a description of the processing is omitted here. Note that, in a case where an input image is to be subjected to image segmentation processing unconditionally with regard to imaging conditions, after performing the processing in step S4120, the processing in step S4130 can be omitted and the processing can shift to step S4140.

In step S4120, similarly to Example 8, upon the imaging conditions obtaining unit 2802 obtaining the imaging conditions group of the input image, the processing shifts to step S4130. In step S4130, the processing possibility determining unit 2803 uses the obtained imaging conditions group to determine whether or not any of the group of image segmentation engines which the segmentation processing unit 2804 uses can handle the input image.

If the processing possibility determining unit 2803 determines that none of the group of image segmentation engines is capable of handling the input image, the processing shifts to step S4180. On the other hand, if the processing possibility determining unit 2803 determines that any of the group of image segmentation engines is capable of handling the input image, the processing shifts to step S4140. Note that, depending on the settings or implementation form of the image processing apparatus 2800, similarly to Example 8, even if it is determined that some of the imaging conditions cannot be handled by any of the image segmentation engines, the processing in step S4140 may be executed.

In step S4140, the segmentation processing unit 2804 inputs the input image obtained in step S4110 to each of the group of image segmentation engines, to thereby generate a region label image group. Note that, the segmentation processing unit 2804 may input the input image only to image segmentation engines which the processing possibility determining unit 2803 determined as being capable of handling the input image.

In step S4150, similarly to Example 8, the evaluating unit 2805 evaluates the region label image group generated in step S4140, using the region label image evaluating engine. In step S4160, in a case where there are a plurality of region label images for which the evaluation result (image evaluation index) is a True value, the evaluating unit 2805 selects/determines the region label image to be output according to an instruction from the examiner.

In this case, first, the outputting unit 2807 causes the region label image group for which the evaluation result is a True value to be displayed on a user interface of the display unit 2820. An example of the interface in this case is illustrated in FIG. 42. An input image UI4210, and region label images UI4220, UI4230, UI4240 and UI4250 for which the evaluation result is a True value are each displayed on the interface. The examiner operates an arbitrary input apparatus (not illustrated) to designate a region label image that has the highest accuracy among the image group (region label images UI4220 to UI4250). The evaluating unit 2805 selects the region label image designated by the examiner, as the region label image to be output.

Note that, in a case where there is only one region label image for which the evaluation result is a True value, the evaluating unit 2805 selects/determines the region label image as the region label image to be output. Further, in a case where there is no region label image for which the evaluation result is a True value, the evaluating unit 2805 makes a determination not to output a region label image generated by the segmentation processing unit 2804, and generates and outputs/selects an image without region labels, and advances the processing to step S4170.

In step S4170, similarly to Example 8, the analyzing unit 2806 performs image analysis processing with respect to the input image, using the region label image determined as the region label image to be output by the evaluating unit 2805 and the input image. Note that, in a case where an image without region labels is output by the evaluating unit 2805, the analyzing unit 2806 advances the processing to step S4180 without performing image analysis processing.

In step S4180, the outputting unit 2807 causes the display unit 2820 to display the region label image determined as the region label image to be output and the image analysis result. Note that, instead of causing the display unit 2820 to display the region label image and the image analysis result, the outputting unit 2807 may cause the region label image and the image analysis result to be displayed on the imaging apparatus 2810 or another apparatus or may store the region label image and the image analysis result. Further, depending on the settings or implementation form of the image processing apparatus 2800, the outputting unit 2807 may process the region label image and the image analysis result so that they can be utilized by the imaging apparatus 2810 or another apparatus, or may convert the data format of the region label image and the image analysis result so that they can be transmitted to the image management system or the like. In addition, the outputting unit 2807 is not limited to a configuration that outputs both the region label image and the image analysis result, and may be configured to output only either one of the region label image and the image analysis result.

On the other hand, in a case where it is determined in step S4130 that image segmentation processing is not possible, the outputting unit 2807 outputs an image without region labels to cause the image without region labels to be displayed on the display unit 2820. Note that, instead of outputting an image without region labels, the outputting unit 2807 may transmit a signal indicating that image segmentation processing was not possible to the imaging apparatus 2810.

Further, in a case where it is determined in step S4150 that image segmentation processing could not be properly performed (it is determined not to output a generated region label image), the outputting unit 2807 also outputs an image without region labels to cause the image without region labels to be displayed on the display unit 2820. In this case also, instead of outputting an image without region labels, the outputting unit 2807 may transmit a signal indicating that image segmentation processing could not be properly performed to the imaging apparatus 2810. When the output processing in step S4170 ends, the series of image processing operations ends.

As described above, the segmentation processing unit 2804 according to the present example generates a plurality of region label images from an input image by using a plurality of image segmentation engines which each include a learned model that is different from the learned models of the other image segmentation engines. In addition, in accordance with an instruction of an examiner (user), the evaluating unit 2805 evaluates a plurality of sets of region information, and selects at least one set of the region information from among a plurality of sets of the region information determined as region information to be output. More specifically, in a case where there are a plurality of region label images for which an image evaluation index is a True value, in accordance with an instruction from the examiner, the evaluating unit 2805 selects/determines the region label image which has the highest accuracy as the region label image to be output. Thus, from among a plurality of region label images generated using the plurality of image segmentation engines, the image processing apparatus 2800 can output a region label image which has the highest accuracy in accordance with an instruction from the examiner.

In the present example, in accordance with an instruction from the examiner, the evaluating unit 2805 selects/determines a region label image which has the highest accuracy as a region label image to be output. In this regard, in accordance with an instruction from the examiner, the evaluating unit 2805 may select/determine a plurality of region label images for which the evaluation result is a True value as region label images to be output. In this case, the analyzing unit 2806 performs image analysis processing with respect to the plurality of region label images selected as the region label images to be output. Further, the outputting unit 2807 outputs the selected plurality of region label images and the analysis results for the relevant plurality of region label images.

Further, in the present example, in accordance with an instruction from the examiner, the evaluating unit 2805 selects a region label image to be output from among a plurality of region label images for which the evaluation result is a True value. In this regard, a configuration may be adopted in which the outputting unit 2807 causes all region label images generated by the segmentation processing unit 2804 to be displayed on the display unit 2820, and the evaluating unit 2805 selects a region label image to be output from among the plurality of region label images in question in accordance with an instruction from the examiner. In this case also, in accordance with an instruction from the examiner, the evaluating unit 2805 may select/determine a plurality of the region label images as region label images to be output.

Example 15

Next, an image processing apparatus according to Example 15 is described referring to FIG. 28 and FIG. 41. In the image processing apparatus according to Example 14, with respect to a plurality of region label images for which an evaluation result obtained by the evaluating unit 2805 is a True value, the evaluating unit 2805 selects/determines an image to be output according to an instruction from the examiner. In contrast, in the present example, the evaluating unit selects/determines a region label image to be output from among a plurality of region label images for which an evaluation result is a True value, based on a predetermined selection criterion.

Unless explicitly stated otherwise, the configuration and processing of the image processing apparatus according to the present example are the same as the image processing apparatus 2800 according to Example 14. Therefore, hereunder, the image processing apparatus according to the present example is described centering on differences from the image processing apparatus according to Example 14. Note that, since the configuration of the image processing apparatus according to the present example is the same as the configuration of the image processing apparatus according to Examples 8 and 14, components illustrated in FIG. 28 are denoted by the same reference numerals as in Examples 8 and 14, and a description of the components is omitted hereunder.

The evaluating unit 2805 according to the present example evaluates a plurality of region label images generated by the segmentation processing unit 2804 using region label image evaluating engines, and selects a region label image to be output according to an image evaluation index and a predetermined selection criterion.

Hereunder, a series of image processing operations according to the present example is described referring to FIG. 41. Note that, since the processing other than step S4160 according to the present example is the same as the processing in Example 14, a description of the processing is omitted here. Note that, in a case where the input image is to be subjected to image segmentation processing unconditionally with regard to imaging conditions, after the processing in step S4120, the processing in step S4130 can be omitted and the processing can shift to step S4140.

In step S4160, in a case where there are a plurality of region label images for which the evaluation result obtained in step S4150 is a True value, the evaluating unit 2805 selects/determines a region label image to be output from among the plurality of region label images according to a predetermined selection criterion. The evaluating unit 2805, for example, selects a region label image for which a True value as an evaluation result is output first in chronological order. Note that, the selection criterion is not limited thereto, and may be set arbitrarily according to a desired configuration. The evaluating unit 2805 may, for example, from among region label images for which the evaluation result is a True value, select/determine a region label image generated by an image segmentation engine with respect to which the imaging conditions group of the input image and the combination of imaging conditions of the training data are closest (match).

Further, in a case where the evaluation result is a False value for all of the region label images, the evaluating unit 2805 determines that image segmentation processing could not be properly performed, and generates an image without region labels, and outputs/selects the image without region labels. The processing from step S4170 onward is the same as the processing from step S4170 onward in Example 14, and hence a description of the processing is omitted here.

As described above, in the image processing apparatus 2800 according to the present example, the segmentation processing unit 2804 generates a plurality of region label images from an input image by using a plurality of image segmentation engines. Based on a predetermined selection criterion, the evaluating unit 2805 selects at least one region label image among region label images evaluated as being region label images to be output or selects an image without region labels. The outputting unit 2807 outputs the region label image selected by the evaluating unit 2805.

By this means, in the image processing apparatus 2800 according to the present example, output of a region label image for which image segmentation processing failed can be prevented based on the output of the region label image evaluating engine. Further, in a case where there are a plurality of region label images for which the image evaluation index that the region label image evaluating engine outputs is a True value, a region label image can be automatically selected from among the plurality of region label images and displayed or output.

Note that, although in the present example a configuration is adopted in which at least one region label image is selected and output from among a plurality of region label images for which the image evaluation index is a True value, a configuration may also be adopted that outputs all of a plurality of region label images for which the image evaluation index is a True value. In this case, the analyzing unit 2806 performs image analysis on all of the region label images that were output from the evaluating unit 2805. Furthermore, the outputting unit 2807 may cause all the region label images output from the evaluating unit 2805 and all the corresponding analysis results to be displayed on the display unit 2820 or may output all the region label images and all the corresponding analysis results to another apparatus.

Example 16

Next, an image processing apparatus according to Example 16 will be described referring to FIG. 28 and FIG. 29. In the present example, first, a segmentation processing unit divides a three-dimensional input image into a plurality of two-dimensional images (two-dimensional image group). Next, the segmentation processing unit inputs the two-dimensional image group into an image segmentation engine, and the segmentation processing unit then combines an output image group from the image segmentation engine to generate a three-dimensional region label image.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8. Note that, since the configuration of the image processing apparatus according to the present example is the same as the configuration of the image processing apparatus according to Example 8, components illustrated in FIG. 28 are denoted by the same reference numerals as in Example 8, and a description of the components is omitted hereunder.

The obtaining unit 2801 according to the present example obtains a three-dimensional image composed of a group of two-dimensional images which are structurally continuous. Specifically, the three-dimensional image is, for example, a three-dimensional OCT volume image composed of a group of OCT B-scan images (tomographic images).

The segmentation processing unit 2804 uses the image segmentation engine according to the present example to perform segmentation processing with respect to a three-dimensional image that is an input image, and thereby generates a plurality of two-dimensional region label images. Pair groups of input data and ground truth forming the training data of the image segmentation engine according to the present example are constituted by image groups composed of two-dimensional images. The segmentation processing unit 2804 divides an obtained three-dimensional image into a plurality of two-dimensional images, and inputs each two-dimensional image into the image segmentation engine. By this means, the segmentation processing unit 2804 can generate a plurality of two-dimensional region label images. In addition, the segmentation processing unit 2804 arranges and combines the plurality of two-dimensional region label images according to the arrangement of the two-dimensional images before the obtained three-dimensional image was divided, to thereby generate a three-dimensional region label image.

The evaluating unit 2805 uses the region label image evaluating engine to determine whether or not the three-dimensional region label image is a likely region label image. In a case where the evaluation result is a True value, the evaluating unit 2805 determines that the three-dimensional region label image is a region label image to be output, and outputs the three-dimensional region label image. On the other hand, if the evaluation result is a False value, the evaluating unit 2805 generates and outputs a three-dimensional image without region labels.

Note that, in a case where the region label image evaluating engine includes a learned model, three-dimensional region label images and image evaluation indexes can be used as training data for the learned model. Further, the evaluating unit 2805 may perform an evaluation with respect to each of the two-dimensional region label images before combining the two-dimensional region label images.

The analyzing unit 2806 performs image analysis processing with respect to a three-dimensional region label image which was determined as being a likely region label image by the evaluating unit 2805. Note that, the analyzing unit 2806 may perform image analysis processing with respect to each of the two-dimensional region label images before combining the two-dimensional region label images. Further, in a case where a three-dimensional image without region labels is output by the evaluating unit 2805, the analyzing unit 2806 does not perform image analysis.

The outputting unit 2807 outputs a three-dimensional region label image and an analysis result. Note that, when the outputting unit 2807 causes a generated three-dimensional region label image to be displayed on the display unit 2820, the three-dimensional region label image may be displayed in any display form.

Next, a series of image processing operations according to the present example will be described referring to FIG. 29. Note that, the processing in step S2910 to step S2930, and step S2950 to step S2970 according to the present example is the same as the processing in these steps in Example 8, and hence a description of the processing is omitted here. However, in step S2910, the obtaining unit 2801 obtains a three-dimensional image. Note that, in a case where the input image is to be subjected to image segmentation processing unconditionally with regard to imaging conditions, after performing the processing in step S2920, the processing in step S2930 can be omitted and the processing can shift to step S2940.

In step S2930, if the processing possibility determining unit 2803 determines that the input image can be handled by the image segmentation engine, the processing shifts to step S2940. In step S2940, the segmentation processing unit 2804 divides the obtained three-dimensional image into a plurality of two-dimensional images. The segmentation processing unit 2804 inputs each of the divided plurality of two-dimensional images to the image segmentation engine, to thereby generate a plurality of two-dimensional region label images. The segmentation processing unit 2804 combines the generated plurality of two-dimensional region label images based on the obtained three-dimensional image, to thereby generate a three-dimensional region label image. The processing from step S2950 onward is the same as the processing from step S2950 onward in Example 8, and hence a description of the processing is omitted here.

As described above, the segmentation processing unit 2804 according to the present example divides an input image into a plurality of images of a lower number of dimensions than the number of dimensions of the input image, and inputs each image obtained by dividing the input image into a segmentation engine. More specifically, the segmentation processing unit 2804 divides a three-dimensional input image into a plurality of two-dimensional images, and inputs each of the two-dimensional images into an image segmentation engine. The segmentation processing unit 2804 combines a plurality of two-dimensional region label images that were output from the image segmentation engine, to thereby generate a three-dimensional region label image.

Thus, the segmentation processing unit 2804 according to the present example can perform image segmentation processing of a three-dimensional image by using an image segmentation engine including a learned model for which learning was performed using training data composed of two-dimensional images.

Note that, the segmentation processing unit 2804 according to the present example divides a three-dimensional input image into a plurality of two-dimensional images, and performs image segmentation processing. However, an object on which processing pertaining to the dividing in question may be performed is not limited to a three-dimensional input image. For example, the segmentation processing unit 2804 may divide a two-dimensional input image into a plurality of one-dimensional images and perform image segmentation processing. Further, the segmentation processing unit 2804 may divide a four-dimensional input image into a plurality of three-dimensional images or a plurality of two-dimensional images and perform image segmentation processing.

Example 17

Next, an image processing apparatus according to Example 17 is described referring to FIG. 28 and FIG. 29. In the present example, a segmentation processing unit divides a three-dimensional input image into a plurality of two-dimensional images, and subjects the plurality of two-dimensional images to image segmentation processing in parallel using a plurality of image segmentation engines. Thereafter, the segmentation processing unit combines output images from the respective image segmentation engines to generate a three-dimensional region label image.

Unless explicitly stated otherwise, the configuration and processing of the image processing apparatus according to the present example are the same as the image processing apparatus 2800 according to Example 16. Therefore, hereunder, the image processing apparatus according to the present example is described centering on differences from the image processing apparatus according to Example 16. Note that, since the configuration of the image processing apparatus according to the present example is the same as the configuration of the image processing apparatus according to Examples 8 and 16, components illustrated in FIG. 28 are denoted by the same reference numerals as in Examples 8 and 16, and a description of the components is omitted hereunder.

The segmentation processing unit 2804 according to the present example generates a three-dimensional region label image by performing image segmentation processing with respect to a three-dimensional image that is an input image using a plurality of image segmentation engines that are similar to the image segmentation engines in Example 16. Note that, a group of a plurality of image segmentation engines that the segmentation processing unit 2804 uses may be implemented in a manner that enables distributed processing in a group of two or more apparatuses through a circuit or a network, or may be implemented in a single apparatus.

Similarly to Example 16, the segmentation processing unit 2804 divides an obtained three-dimensional image into a plurality of two-dimensional images. The segmentation processing unit 2804 performs image segmentation processing with respect to the plurality of two-dimensional images using the plurality of image segmentation engines by sharing the processing therebetween (parallelly), to thereby generate a plurality of two-dimensional region label images. Based on the three-dimensional image that is the processing object, the segmentation processing unit 2804 combines the plurality of two-dimensional region label images output from the plurality of image segmentation engines, to thereby generate a three-dimensional region label image. More specifically, the segmentation processing unit 2804 arranges and combines the plurality of two-dimensional region label images according to the arrangement of the two-dimensional images before the obtained three-dimensional image was divided, to thereby generate a three-dimensional region label image.

Next, a series of image processing operations according to the present example will be described referring to FIG. 29. Note that, the processing in step S2910 to step S2930, and step S2950 to step S2970 according to the present example is the same as the processing in these steps in Example 16, and hence a description of the processing is omitted here. Note that, in a case where the input image is to be subjected to image segmentation processing unconditionally with regard to imaging conditions, after performing the processing in step S2920, the processing in step S2930 can be omitted and the processing can shift to step S2940.

In step S2930, if the processing possibility determining unit 2803 determines that the input image can be handled by the image segmentation engines, the processing shifts to step S2940. In step S2940, the segmentation processing unit 2804 divides the obtained three-dimensional image into a plurality of two-dimensional images. The segmentation processing unit 2804 inputs each of the divided plurality of two-dimensional images to the plurality of image segmentation engines to perform image segmentation processing of the two-dimensional images in parallel and thereby generate a plurality of two-dimensional region label images. The segmentation processing unit 2804 combines the generated plurality of two-dimensional region label images based on the obtained three-dimensional image to thereby generate a three-dimensional region label image.

As described above, the segmentation processing unit 2804 according to the present example includes a plurality of image segmentation engines. The segmentation processing unit 2804 divides a three-dimensional input image into a plurality of two-dimensional images, and generates a plurality of two-dimensional region label images with respect to the divided plurality of two-dimensional images by using the plurality of image segmentation engines in parallel. The segmentation processing unit 2804 integrates the plurality of two-dimensional region label images to generate a three-dimensional region label image.

Thus, the segmentation processing unit 2804 according to the present example can subject a three-dimensional image to image segmentation processing by using image segmentation engines including learned models for which learning was performed using training data composed of two-dimensional images. Further, the three-dimensional image can be subjected to image segmentation processing more efficiently in comparison to Example 16.

Note that, similarly to Example 16, an object on which processing pertaining to the dividing by the segmentation processing unit 2804 may be performed is not limited to a three-dimensional input image. For example, the segmentation processing unit 2804 may divide a two-dimensional input image into a plurality of one-dimensional images and perform image segmentation processing. Further, the segmentation processing unit 2804 may divide a four-dimensional input image into a plurality of three-dimensional images or a plurality of two-dimensional images and perform image segmentation processing.

Furthermore, the training data of the plurality of image segmentation engines may be training data that differs according to a processing object on which processing is to be performed by the respective image segmentation engines. For example, a first image segmentation engine may perform learning using training data for a first imaged region, and a second image segmentation engine may perform learning using training data for a second imaged region. In this case, the respective image segmentation engines can perform image segmentation processing with respect to a two-dimensional image with higher accuracy.

In addition, similarly to the segmentation processing unit 2804, the evaluating unit 2805 can also evaluate a three-dimensional region label image in a parallel manner using a plurality of region label image evaluating engines which each includes a learned model. In this case, the evaluating unit 2805 uses the plurality of region label image evaluating engines in parallel manner to perform an evaluation with respect to a plurality of two-dimensional region label images generated by the segmentation processing unit 2804.

Thereafter, in a case where the image evaluation index for each two-dimensional region label image is a True value, the evaluating unit 2805 can determine that the three-dimensional region label image is a likely region label image and can output the three-dimensional region label image. In this case, the training data for the learned models which the region label image evaluating engines include can be constituted by two-dimensional region label images and image evaluation indexes. Note that, in a case where the image evaluation index is a True value for some of the respective two-dimensional region label images, the evaluating unit 2805 can also determine that the three-dimensional region label image is a likely region label image and can output the three-dimensional region label image.

Example 18

Figure 43:
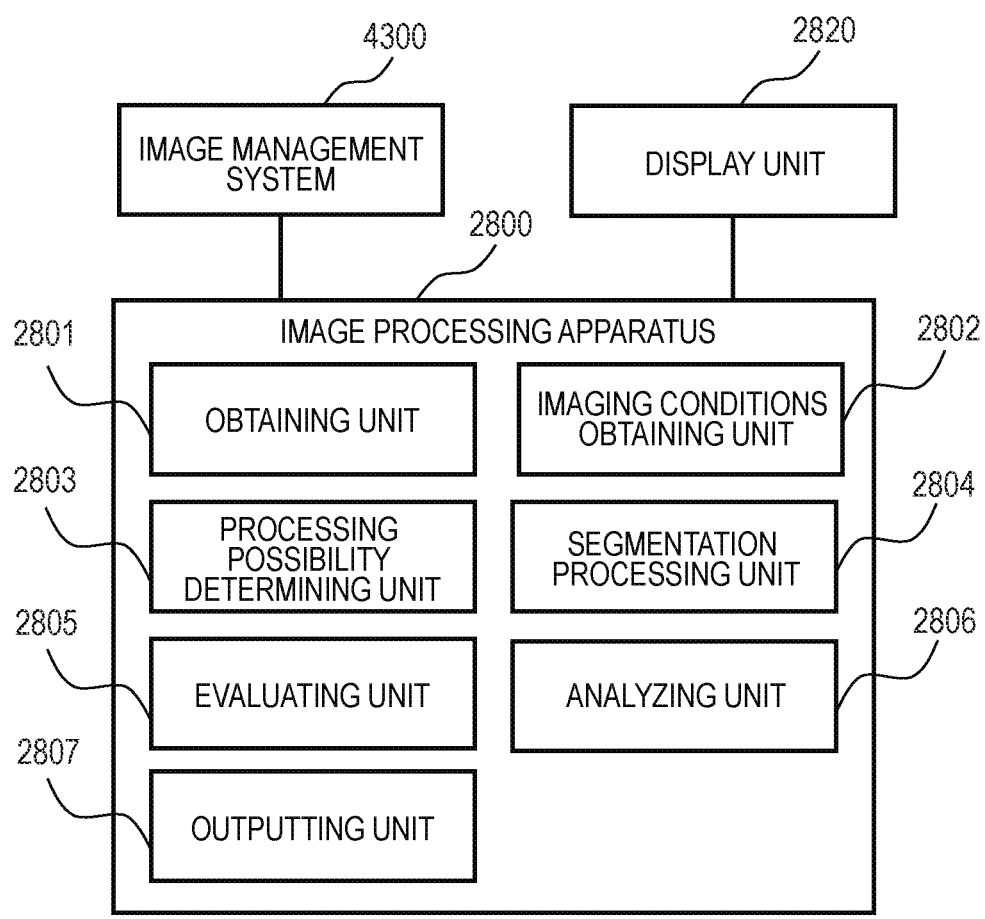
FIG. 43 illustrates an example of the configuration of an image processing apparatus according to Example 18.

Next, an image processing apparatus according to Example 18 is described referring to FIG. 29 and FIG. 43. In the present example, an obtaining unit obtains an input image from an image management system and not from an imaging apparatus.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8. Note that, since the configuration of the image processing apparatus according to the present example is the same as the configuration of the image processing apparatus 2800 according to Example 8, components illustrated in FIG. 28 are denoted by the same reference numerals as in Example 8, and a description of the components is omitted hereunder.

FIG. 43 is a view illustrating a schematic configuration of the image processing apparatus 2800 according to the present example. The image processing apparatus 2800 according to the present example is connected to an image management system 4300 and the display unit 2820 through any circuit or network. The image management system 4300 is an apparatus and system configured to receive and store images imaged by any imaging apparatus or images subjected to image processing. Further, the image management system 4300 can transmit an image in response to a request from a connected apparatus, perform image processing on a stored image, and request another apparatus to carry out a request for image processing. A picture archiving and communication system (PACS) can be included as an example of the image management system 4300.

The obtaining unit 2801 according to the present example can obtain an input image from the image management system 4300 connected to the image processing apparatus 2800. Further, the outputting unit 2807 can output a region label image generated by the segmentation processing unit 2804 to the image management system 4300. Note that, similarly to Example 8, the outputting unit 2807 can also cause a region label image to be displayed on the display unit 2820.

Next, a series of image processing operations according to the present example will be described referring to FIG. 29. Note that, the processing in step S2920 to step S2960 according to the present example is the same as the processing in these steps in Example 8, and hence a description of the processing is omitted here. Note that, in a case where the input image is to be subjected to image segmentation processing unconditionally with regard to imaging conditions, after performing the processing in step S2920, the processing in step S2930 can be omitted and the processing can shift to step S2940.

In step S2910, an image stored in the image management system 4300 is obtained as an input image by the obtaining unit 2801 from the image management system 4300 that is connected to the image processing apparatus 2800 through a circuit or network. Note that, the obtaining unit 2801 may obtain the input image in response to a request from the image management system 4300. Such a request may be issued, for example, when the image management system 4300 stores an image, or before transmitting a stored image to another apparatus, or when displaying a stored image on the display unit 2820. Further, the relevant request may be issued, for example, when a user operates the image management system 4300 to make a request for image segmentation processing, or when an image analysis function that the image management system 4300 includes utilizes a region label image.

The processing in step S2920 to step S2960 is the same as the processing in these steps in Example 8. In step S2970, if it is determined by the evaluating unit 2805 in step S2950 that the region label image is to be output, the outputting unit 2807 outputs the region label image as an output image to the image management system 4300. Note that, depending on the settings or implementation of the image processing apparatus 2800, the outputting unit 2807 may process the output image so that the output image can be utilized by the image management system 4300, or may convert the data format of the output image. Further, the outputting unit 2807 can also output an analysis result obtained by the analyzing unit 2806 to the image management system 4300.

On the other hand, if the evaluating unit 2805 determined in step S2950 that image segmentation processing could not be properly performed, the outputting unit 2807 outputs an image without region labels as an output image to the image management system 4300. Further, in a case where the processing possibility determining unit 2803 determined in step S2930 that image segmentation processing of the input image is not possible, the outputting unit 2807 outputs an image without region labels to the image management system 4300.

As described above, the obtaining unit 2801 according to the present example obtains an input image from the image management system 4300. Therefore, based on an image that the image management system 4300 stores, the image processing apparatus 2800 of the present example can output a region label image that is suitable for image diagnosis without increasing the invasiveness with respect to the subject or the labor of the person performing the imaging. Further, an output region label image or image analysis result can be stored in the image management system 4300, or can be displayed on a user interface which the image management system 4300 includes. Furthermore, an output region label image can be utilized by an image analysis function that the image management system 4300 includes, or can be transmitted through the image management system 4300 to another apparatus connected to the image management system 4300.

Note that, the image processing apparatus 2800, the image management system 4300 and the display unit 2820 may be connected through a circuit or network to other apparatuses (not illustrated). Further, although in the present example these apparatuses are assumed to be separate apparatuses to each other, some or all of these apparatuses may be constituted integrally with each other.

Example 19

Figure 44:
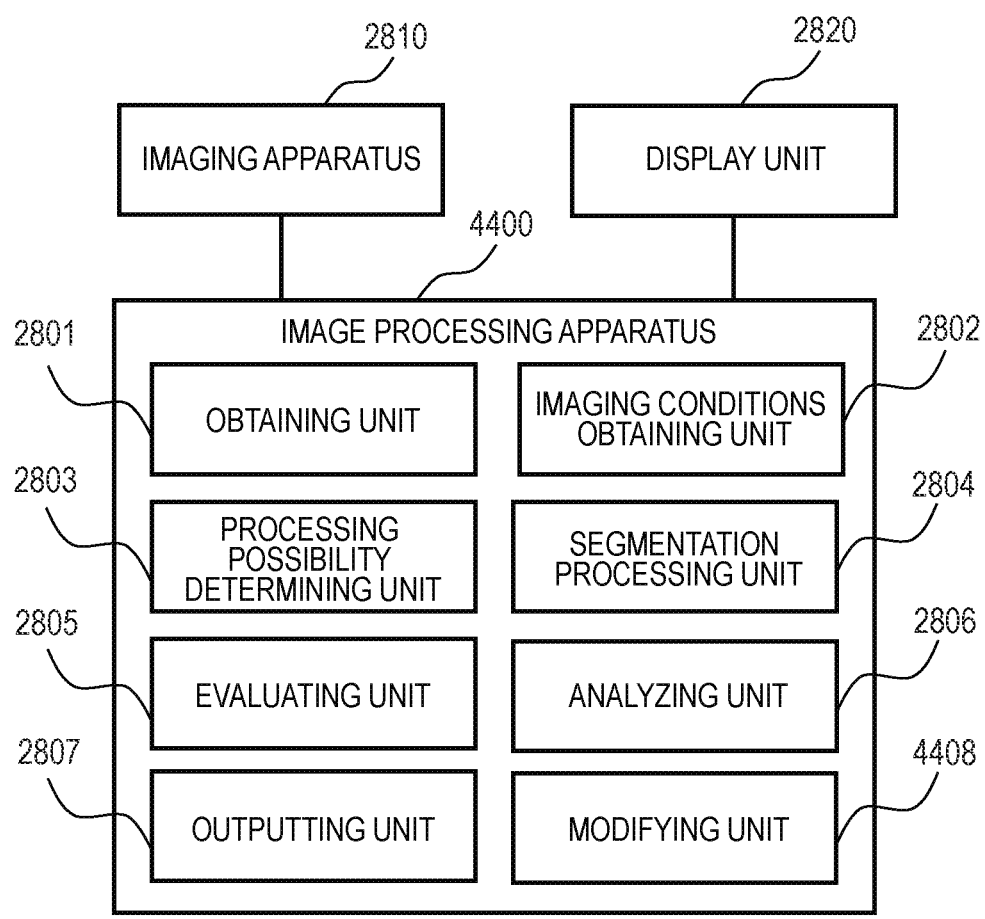
FIG. 44 illustrates an example of the configuration of an image processing apparatus according to Example 19.

Next, an image processing apparatus according to Example 19 is described referring to FIG. 44 and FIG. 45. In the present example, if an incorrect region label value is set for a region label image that was output from an image segmentation engine, a modifying unit modifies the incorrect region label value using a region label image modifying engine.

Unless explicitly stated otherwise, the configuration and processing of the image processing apparatus according to the present example are the same as the image processing apparatus 2800 according to Example 8. Therefore, hereunder, the image processing apparatus according to the present example is described centering on differences from the image processing apparatus according to Example 8.

FIG. 44 is a view illustrating a schematic configuration of an image processing apparatus 4400 according to the present example. The image processing apparatus 4400 according to the present example is provided with a modifying unit 4408 in addition to the obtaining unit 2801, the imaging conditions obtaining unit 2802, the processing possibility determining unit 2803, the segmentation processing unit 2804, the evaluating unit 2805, the analyzing unit 2806 and the outputting unit 2807. Note that, the image processing apparatus 4400 may be constituted by a plurality of apparatuses which are each provided with one or more of these components. Since the configuration other than the modifying unit 4408 of the image processing apparatus 4400 according to the present example is the same as the configuration of the image processing apparatus according to Example 8, components that are the same as in the configuration illustrated in FIG. 28 are denoted by the same reference numerals as in Example 8, and a description of the components is omitted hereunder.

Further, similarly to the image processing apparatus 2800 according to Example 8, the image processing apparatus 4400 may be connected through any circuit or network to the imaging apparatus 2810, the display unit 2820 and another apparatus (not illustrated). Further, these apparatuses may be connected through a circuit or network to any other apparatuses, and may be constituted integrally with any other apparatus. Note that, although in the present example these apparatuses are assumed to be separate apparatuses to each other, some or all of these apparatuses may be constituted integrally with each other.

A region label image modifying engine that modifies an input region label image is provided in the modifying unit 4408 according to the present example. As mentioned above in the explanation of terms, the region label image modifying engine performs modification of a region label value by anatomical knowledge-based processing. Note that, for example, with respect to a region label value that is used to overwrite a continuous region of region label values that are a modification object, it is assumed that overwriting is performed with a region label value for which a number of pixels abutting the continuous region in question is largest.

Next, a series of image processing operations according to the present example will be described referring to FIG. 45. Note that, the processing in step S4510 to step S4540 according to the present example is the same as the processing in step S2910 to step S2940, respectively, in Example 8, and hence a description of the processing is omitted here. Note that, in a case where the input image is to be subjected to image segmentation processing unconditionally with regard to imaging conditions, after performing the processing in step S4520, the processing in step S4530 can be omitted and the processing can shift to step S4540.

In step S4540, upon the segmentation processing unit 2804 generating a region label image, the processing shifts to step S4550. In step S4550, the evaluating unit 2805 uses the region label image evaluating engine to evaluate the generated region label image in a similar manner to Example 8. If the evaluation result is a True value, the evaluating unit 2805 determines the relevant region label image as a region label image to be output. On the other hand, if the evaluation result is a False value, the evaluating unit 2805 according to the present example determines that the relevant region label image is a region label image that requires modification.

In step S4560, the modifying unit 4408 subjects the region label image that was determined as a region label image that requires modification in step S4540 to region label value modification using the region label image modifying engine. Specifically, the modifying unit 4408 inputs the region label image that was determined as a region label image that requires modification in step S4540 to the region label image modifying engine. The region label image modifying engine modifies the region label value that was incorrectly set of the input region label image, in accordance with anatomical knowledge-based processing, and outputs the modified region label image.

Note that, in step S4550, in a case where it is determined that the generated region label image is a region label image to be output, the modifying unit 4408 advances the processing without performing modification of the region label image.

In step S4570, the analyzing unit 2806 performs image analysis processing of the input image using the region label image determined as a region label image to be output in step S4540, or the region label image for which modification of a region label was performed in step S4550. Since the content of the image analysis processing is the same as in Example 8, a description thereof is omitted here.

In step S4580, the outputting unit 2807 causes the region label image determined as a region label image to be output or the region label image for which a region label was modified and the image analysis result to be displayed on the display unit 2820. Note that, instead of causing the region label image and the image analysis result to be displayed on the display unit 2820, the outputting unit 2807 may cause the region label image and the image analysis result to be displayed on the imaging apparatus 2810 or another apparatus or may store the region label image and the image analysis result. Further, depending on the settings or implementation form of the image processing apparatus 4400, the outputting unit 2807 may process the region label image and the image analysis result so that they can be utilized by the imaging apparatus 2810 or another apparatus, or may convert the data format of the region label image and the image analysis result so that they can be transmitted to the image management system or the like. In addition, the outputting unit 2807 is not limited to a configuration that outputs both the region label image and the image analysis result, and may be configured to output only either one of the region label image and the image analysis result.

On the other hand, in a case where it is determined in step S4530 that image segmentation processing is not possible, the outputting unit 2807 outputs an image without region labels to cause the image without region labels to be displayed on the display unit 2820. Note that, instead of outputting an image without region labels, the outputting unit 2807 may transmit a signal indicating that image segmentation processing was not possible to the imaging apparatus 2810. When the output processing in step S4580 ends, the series of image processing operations ends.

As described above, the image processing apparatus 4400 according to the present example further includes the modifying unit 4408. The modifying unit 4408 modifies a region label image generated by the segmentation processing unit 2804, using a region label image modifying engine that performs knowledge-based processing by a predetermined modifying technique. The outputting unit 2807 outputs the region label image that was modified by the modifying unit 4408.

In particular, the modifying unit 4408 according to the present example performs modification of a region label with respect to a region label image for which the evaluating unit 2805 determined that image segmentation processing could not be properly performed. Further, the analyzing unit 2806 performs image analysis processing with respect to the region label image for which a region label was modified.

By this means, in the image processing apparatus 2800 according to the present example, an error in a region label image for which image segmentation processing failed can be corrected by the region label image modifying engine, and the modified region label image can be output.

Note that, in the present example, the modifying unit 4408 modifies a region label with respect to a region label image for which an evaluation result obtained by the evaluating unit 2805 is a False value. However, the configuration of the modifying unit 4408 is not limited to this configuration. The modifying unit 4408 may modify a region label with respect to a region label image for which an evaluation result obtained by the evaluating unit 2805 is a True value. In this case, the analyzing unit 2806 performs image analysis processing of the input image using the modified region label. Further, the outputting unit 2807 outputs the modified region label image and the analysis result.

In addition, in this case, the evaluating unit 2805 can also be configured to generate an image without region labels if an evaluation result for a region label image is a False value, so as not to cause modification of a region label by the modifying unit 4408 to be performed with respect to the region label image for which the evaluation result is a False value. When an image without region labels is generated by the evaluating unit 2805, the modifying unit 4408 can advance the processing to the next step without performing modification.

In a case where a region label image is modified by the modifying unit 4408 when the evaluation result obtained by the evaluating unit 2805 is a True value, the image processing apparatus 2800 can output a region label image and an analysis result that have higher accuracy.

Although in the foregoing Examples 8 to 19, configurations are described in which the segmentation processing unit 2804 generates a region label image as region information that can distinguish an anatomical region, region information which the segmentation processing unit 2804 generates is not limited thereto. The segmentation processing unit may generate a numerical value data group such as the coordinate values of pixels having respective region labels, as region information that is generated from an input image using an image segmentation engine.

Note that, the respective learned models included in the image segmentation engine, the region label image evaluating engine and the imaging location estimation engine can be provided in the image processing apparatuses 2800 and 4400. A learned model, for example, may be constituted by a software module that is executed by a processor such as a CPU, an MPU, a GPU or an FPGA, or may be constituted by a circuit or the like that serves a specific function such as an ASIC. Further, a learned model may be provided in an apparatus of a different server that is connected to the image processing apparatus 2800 or 4400. In this case, the image processing apparatus 2800 or 4400 can use the learned model by connecting to the server or the like that includes the learned model through any network such as the Internet. The server that includes the learned model may be, for example, a cloud server, a FOG server, or an edge server.

According to Examples 8 to 19, image segmentation processing of higher accuracy than the conventional image segmentation processing can be performed.

Modification 1

In Examples 1 to 7 and the modifications of Examples 1 to 7, the processing unit 222 or the first processing unit 822 detects retina layers from a tomographic image using a learned model, and generates a boundary image. Further, in Examples 9 to 19 the segmentation processing unit 2804 generates a region label image corresponding to an input image using an image segmentation engine that includes a learned model.

In this respect, information pertaining to retina layers detected using a learned model, or a generated boundary image or region label image may be manually modified according to an instruction from an operator. For example, an operator can specify at least one part of a detection result with respect to retina layers or a boundary image or a region label image which is displayed on the display unit 50 or 2820, and change the position of a retina layer or a label. In this case, modification of the detection result or modification of the boundary image or region label image may be performed according to an instruction of the operator by the processing unit 222, the first processing unit 822 or the segmentation processing unit 2804, or may be performed by a component such as a modifying unit that is separate from these units. Therefore, the processing unit 222, the first processing unit 822, the segmentation processing unit 2804 or the relevant modifying unit functions as one example of a modifying unit that modifies the structure of a retina layer detected by the first processing unit, according to an instruction by an operator. Note that, the modifying unit or the like may be constituted by a software module or the like that is executed by a processor such as a CPU, an MPU, a GPU or an FPGA, or may be constituted by a circuit or the like that serves a specific function such as an ASIC.

Modification 2

Data that was modified manually according to Modification 1 may be used for incremental learning with respect to a learned model which the processing unit 222 or the first processing unit 822 uses and a learned model included in an image segmentation engine that the segmentation processing unit 2804 uses. Specifically, with respect to a learned model which the processing unit 222 or the first processing unit 822 uses, incremental learning is performed by adopting an input tomographic image as input data of the training data, and adopting information pertaining to retina layers (layer boundaries) whose positions were modified according to an instruction from the operator as ground truth (correct answer data). Note that, a boundary image in which a label was modified according to an instruction from the operator may also be adopted as ground truth. Further, with respect to a learned model included in an image segmentation engine, incremental learning is performed by adopting an input image as input data of the training data, and adopting a region label image in which a position of a label was changed according to an instruction from the operator as ground truth.

By performing such kind of incremental learning with respect to a learned model, it can be expected that the accuracy of detection processing or segmentation processing using the learned model will be improved. Further, by performing such kind of processing, labeling processing (annotation processing) relating to training data can be easily performed, and training data of higher accuracy can be easily created.

Modification 3

The incremental learning described in Modification 2 may be performed according to an instruction by an operator. For example, in a case where a modification was performed according to an instruction by an operator according to Modification 1, the display controlling unit 25 or the outputting unit 2807 can cause a display for selecting whether to use a modified detection result for a retina layer or a modified region label image or the like as training data to be displayed on the display unit 50 or 2820. By selecting one of the choices displayed on the display unit 50 or 2820, the operator can specify whether or not incremental learning is necessary. By this means, the image processing apparatus 20, 80, 2800 or 4400 can determine whether or not incremental learning is necessary according to an instruction by the operator.

Note that, as mentioned above, a learned model can also be provided in an apparatus such as a server. In such a case, the image processing apparatus 20, 80, 2800 or 4400 can, according to an instruction by an operator to perform incremental learning, transmit and store an input image and the aforementioned detection result or region label image or the like on which a modification was performed as a pair of training data to the relevant server or the like. In other words, the image processing apparatus 20, 80, 2800 or 4400 can determine whether to transmit training data for incremental learning to an apparatus such as a server which is equipped with a learned model, according to an instruction by an operator.

Modification 4

In the various examples and modifications described above, configurations have been described that perform processing for detecting retina layers or processing for generating a region label image or the like with respect to a still image. In this regard, with respect to a moving image, the processing for detecting retina layers or processing for generating a region label image or the like according to the aforementioned examples and modifications may be repeatedly executed. In general, in an ophthalmic apparatus, a preview image (moving image) for aligning the apparatus and the like is generated and displayed before performing the main imaging. Therefore, for example, the processing for detecting retina layers or processing for generating a region label image or the like according to the aforementioned examples and modifications may be repeatedly executed for every at least one frame of a moving image of a tomographic image that is the preview image in question.

In this case, the display controlling unit 25 or the outputting unit 2807 can cause a retina layer or a region label image or the like detected with respect to the preview image to be displayed on the display unit 50 or 2820. Further, the image processing apparatus 20, 80, 2800 or 4400 can control an OCT apparatus so that a retina layer that was detected with respect to the preview image, or a region at which labeling of a retina layer was performed is located at a predetermined position in a tomographic image display region. More specifically, the image processing apparatus 20, 80, 2800 or 4400 changes a coherence gate position so that a retina layer that was detected with respect to the preview image, or a region at which labeling of a retina layer was performed is located at a predetermined position in a tomographic image display region. Note that, adjustment of the coherence gate position may be performed, for example, by driving of the coherence gate stage 14 by the drive controlling unit 23.

Note that, the adjustment of the coherence gate position may be performed manually according to an instruction by the operator. In this case, the operator can input an adjustment amount for the coherence gate position into the image processing apparatus 20, 80, 2800 or 4400 based on a retina layer or a region label image detected with respect to a preview image which is displayed on the display unit 50 or 2820.

According to such processing, alignment of the OCT apparatus with respect to the eye to be examined can be appropriately performed based on a retina layer that was detected or a region label image that was generated using a learned model.

Note that, a moving image to which processing for detecting retina layers or processing for generating a region label image or the like according to the aforementioned examples and modifications can be applied is not limited to a live moving image, and for example the moving image may be a moving image stored (saved) in the storage. Further, during various kinds of adjustment such as adjustment of the coherence gate position, there is a probability that the imaging target such as the retina of the eye to be examined cannot yet be successfully imaged. Thus, since there is a large difference between the medical image input to the learned model and the medical image used as training data, there is a probability that a detection result with respect to the retina layers or a region label image will not be accurately obtained. Therefore, a configuration may be adopted so that when an evaluation value such as a value obtained when the image quality of a tomographic image (B scan) is evaluated exceeds a threshold value, processing for detecting retina layers or processing for generating a region label image or the like that uses a learned model automatically starts. Further, a configuration may be adopted so that when an evaluation value such as a value obtained when the image quality of a tomographic image (B scan) is evaluated exceeds a threshold value, a button used for instructing image segmentation processing using a learned model is changed to a state (active state) in which the button can be designated by the examiner.

Modification 5

In the case of a diseased eye, the image features will differ according to the kind of disease. Therefore, learned models used in the various examples and modifications described above may be generated and prepared for each kind of disease or each abnormal site. In this case, for example, the image processing apparatus 20, 80, 2800 or 4400 can select a learned model to be used for processing, according to an input (instruction) such as the kind disease or the abnormal site of the eye to be examined from the operator. Note that, a learned model that is prepared for each kind of disease or each abnormal site is not limited to a learned model that is to be used for detecting retina layers or for generating a region label image or the like, and for example may be a learned model that is to be used in an engine for evaluating an image or in an engine for analysis or the like.

Further, the image processing apparatus 20, 80, 2800 or 4400 may identify the kind of disease or an abnormal site of an eye to be examined from an image using a separately prepared learned model. In this case, the image processing apparatus 20, 80, 2800 or 4400 can automatically select a learned model to be used in the aforementioned processing based on the kind of disease or the abnormal site that was identified using the separately prepared learned model. Note that, a learned model for identifying the kind of disease or an abnormal site of the eye to be examined can perform learning using pairs of training data for which a tomographic image or a fundus image or the like is adopted as input data, and kinds of diseases or abnormal sites in these images are adopted as ground truth. In this case, with respect to the input data of the training data, a tomographic image or a fundus image or the like may be independently adopted as input data, or a combination of these images may be adopted as input data.

Further, in the case of detecting an abnormal site, a generative adversarial network (GAN) or a variational autoencoder (VAE) may be used. For example, a DCGAN (Deep Convolutional GAN) that is composed of a generator that is obtained by learning to generate a tomographic image, and a discriminator that is obtained by Teaming to distinguish between a new tomographic image which the generator generated and a real front image of the ocular fundus can be used as a machine learning model.

In the case of using a DCGAN, for example, the discriminator subjects an input tomographic image to encoding to convert the tomographic image into a latent variable, and the generator generates a new tomographic image based on the latent variable. Thereafter, a difference between the input tomographic image and the new tomographic image that was generated can be extracted as an abnormal site. Further, in the case of using a VAE, for example, an input tomographic image is converted into a latent variable by encoding the tomographic image using an encoder, and a new tomographic image is generated by decoding the latent variable using a decoder. Thereafter, a difference between the input tomographic image and the new tomographic image that was generated can be extracted as an abnormal site. Note that, although an example of input data has been described taking a tomographic image as one example, a fundus image or a front image of the anterior ocular segment or the like may also be used as the input data.

Modification 6

In the various examples and modifications described above, in a case of detecting a region of an eye to be examined using a learned model by means of the processing unit 222, the first processing unit 822 or the segmentation processing unit 2804, predetermined image processing can also be performed for each detected region. For example, let us consider a case of detecting at least two regions among a vitreous region, a retina region and a choroid region. In this case, when performing image processing such as contrast adjustment with respect to the at least two regions that were detected, adjustment that is suited to the respective regions can be performed by using respectively different image processing parameters. By displaying an image on which adjustment that is suited to the respective regions was performed, the operator can more appropriately diagnose a disease or the like in each region. Note that, with regard to a configuration that uses image processing parameters that differ for each detected region, for example, such a configuration may also be similarly applied with respect to regions of an eye to be examined which were detected by the second processing unit 823 that detects regions of an eye to be examined without using a learned model.

Modification 7

The display controlling unit 25 or the outputting unit 2807 in the various embodiments and modifications described above may cause analysis results such as the thickness of a desired layer or various blood vessel densities to be displayed on the report screen of the display screen. Further, a parameter value (distribution) relating to a site of interest including at least one of the optic nerve head, the macular area, a vascular zone, a nerve fascicle, a vitreous region, a macular region, a choroid region, a sclera region, a lamina cribrosa region, a retinal layer boundary, a retinal layer boundary edge, a photoreceptor cell, a blood cell, a blood vessel wall, a blood vessel inner wall boundary, a blood vessel external boundary, a ganglion cell, a corneal region, a corner region, and Schlemm's canal and the like may be displayed as an analysis result. At such time, for example, an accurate analysis result can be displayed by analyzing a medical image subjected to various kinds of artifact removal processing. Note that, an artifact may be, for example, a false image region caused by light absorption by a vascular zone or the like, a projection artifact, or a band-like artifact in a front image that arises in the main scanning direction of the measurement light due to the state of the eye to be examined (movement or blinking or the like). Further, an artifact may be of any kind as long as the artifact is an imaging failure region that, for example, randomly arises at each imaging on a medical image of a predetermined site of the subject. Further, the display controlling unit 25 or the outputting unit 2807 may cause the value (distribution) of a parameter relating to a region including at least one of the various kinds of artifacts (imaging failure regions) described above to be displayed as an analysis result on the display unit 50 or 2820. Furthermore, the value (distribution) of a parameter relating to a region including at least one abnormal site such as drusen, a neovascular site, leucoma (hard exudates), pseudodrusen or the like may be displayed as an analysis result.

An analysis result may be displayed using an analysis map, or using sectors which indicate statistical values corresponding to respective divided regions or the like. Note that, an analysis result may be generated using a learned model (analysis result generating engine, or a learned model for generating analysis results) obtained by learning the analysis results of a medical image as training data. At such time, the learned model may be a model obtained by learning using training data including a medical image and an analysis result for the medical image, or training data including a medical image and an analysis result for a medical image of a different kind from the relevant medical image or the like.

Further, the training data may include a detection result with respect to retina layers obtained by the processing unit 222 or the first processing unit 822 and/or the second processing unit 823, a region label image generated by the segmentation processing unit 2804, and a result of analyzing a medical image using the aforementioned detection result and region label image. In this case, the image processing apparatus, for example, can function as one example of an analysis result generating unit that generates an analysis result with respect to a tomographic image from a result obtained by executing first detection processing using a learned model for generating analysis results.

In addition, a learned model may be a model obtained by learning using training data including input data in which a plurality of medical images of different kinds of a predetermined site, such as an intensity front image and a motion contrast front image, are taken as a set. Here, an intensity front image corresponds to an intensity En-face image, and a motion contrast front image corresponds to an OCTA En-face image.

Further, a configuration may be adopted so as to display an analysis result obtained using a high quality image generated using a learned model for improving image quality. In this case, input data included in the training data may be a high quality image generated using a learned model for improving image quality, or may be a set composed of a low quality image and a high quality image. Note that, the training data may be an image obtained by manually or automatically modifying at least one part of an image that was subjected to image quality improving using a learned model.

Further, the training data may be, for example, data obtained by labeling input data for which information including at least one kind of information among an analysis value (for example, an average value or a median value) obtained by analyzing an analysis region, a table including analysis values, an analysis map, and a position of an analysis region such as a sector in an image or the like, is adopted as correct answer data (of supervised learning). Note that, a configuration may be adopted so that an analysis result obtained using a learned model for generating analysis results is displayed according to an instruction from the examiner.

The display controlling unit 25 and the outputting unit 2807 in the embodiments and modifications described above may cause various kinds of diagnosis results such as results relating to glaucoma or age-related macular degeneration to be displayed on the report screen of the display screen. At such time, for example, an accurate diagnosis result can be displayed by analyzing a medical image subjected to various kinds of artifact removal processing as described above. Further, in the diagnosis result, the position of a specified abnormal site may be displayed on the image, and the state of an abnormal site or the like may be displayed using characters or the like. Further, a classification result (for example, Curtin's classification) for an abnormal site may be displayed as a diagnosis result.

Note that, a diagnosis result may be a result generated using a learned model (diagnosis result generating engine, or a learned model for diagnosis result generation) obtained by learning using diagnosis results for medical images as training data. Further, the learned model may be a model obtained by learning using training data including a medical image and a diagnosis result for the medical image, or training data including a medical image and a diagnosis result for a medical image of a different kind from the relevant medical image or the like.

Furthermore, the training data may include a detection result with respect to retina layers obtained by the processing unit 222 or the first processing unit 822 and/or the second processing unit 823, a region label image generated by the segmentation processing unit 2804, and a result of diagnosing a medical image using the aforementioned detection result and region label image. In this case, the image processing apparatus, for example, can function as one example of a diagnosis result generating unit that generates a diagnosis result with respect to a tomographic image from a result obtained by executing first detection processing using a learned model for diagnosis result generation.

In addition, a configuration may be adopted so as to display a diagnosis result obtained using a high quality image generated using a learned model for improving image quality. In this case, input data included in the training data may be a high quality image generated using a learned model for improving image quality, or may be a set composed of a low quality image and a high quality image. Note that, the training data may be an image obtained by manually or automatically modifying at least one part of an image that was subjected to image quality improving using a learned model.

Further, the training data may be, for example, data obtained by labeling input data for which information including at least one kind of information among the diagnosis, a kind or state (extent) of a lesion (abnormal site), the position of a lesion in the image, the position of a lesion relative to a region of interest, the findings (interpretation findings or the like), grounds for the diagnosis (affirmative medical support information or the like), and grounds for negating the diagnosis (negative medical support information) and the like is adopted as correct answer data (of supervised learning). Note that, a configuration may be adopted so that a diagnosis result obtained using a learned model for diagnosis result generation is displayed according to an instruction from the examiner.

Further, the display controlling unit 25 and the outputting unit 2807 according to the various examples and modifications described above may cause an object recognition result (object detection result) or a segmentation result with respect to a site of interest, an artifact, an abnormal site or the like as described above to be displayed on the report screen of the display screen. At such time, for example, a rectangular frame or the like may be superimposed around an object on the image and displayed. Further, for example, a color or the like may be superimposed on an object in the image and displayed. Note that, an object recognition result or a segmentation result may be a result generated using a learned model obtained by learning using training data in which information that indicates object recognition or segmentation is labeled on a medical image as correct answer data. Note that, the aforementioned analysis result generation or diagnosis result generation may be realized by utilizing the aforementioned object recognition result or segmentation result. For example, processing for generating an analysis result or for generating a diagnosis result may be performed with respect to a site of interest obtained by object recognition processing or segmentation processing.

Furthermore, particularly a learned model for diagnosis result generation may be a learned model obtained by learning using training data including input data in which a plurality of medical images of different kinds that are images of a predetermined site of a subject are taken as a set. At such time, for example, data in which a motion contrast front image of the fundus and an intensity front image (or intensity tomographic image) are taken as a set is conceivable as input data included in the training data. Further, for example, input data in which a tomographic image (B-scan image) of the fundus and a color fundus image (or fluorescence fundus image) are taken as a set is conceivable as input data included in the training data. In addition, the plurality of medical images of different kinds may be of any kind as long as the medical images were obtained by different modalities, different optical systems, or different principles or the like.

Further, particularly a learned model for diagnosis result generation may be a learned model obtained by learning using training data including input data in which a plurality of medical images of different sites of a subject are taken as a set. At such time, for example, input data in which a tomographic image (B-scan image) of the fundus and a tomographic image (B-scan image) of the anterior ocular segment are taken as a set is conceivable as input data included in the training data. Further, for example, input data in which a three-dimensional OCT image (three-dimensional tomographic image) of the macula of the fundus and a tomographic image obtained by circular scanning (or raster scanning) of the optic nerve head of the fundus are taken as a set is also conceivable as input data included in the training data.

Note that, the input data included in the training data may be a plurality of medical images of different sites of the subject and of different kinds. At such time, for example, input data in which a tomographic image of the anterior ocular segment and a color fundus image are taken as a set is conceivable as input data included in the training data. Further, the learned model described above may be a learned model obtained by learning using training data including input data in which a plurality of medical images of different imaging angles of view that are images of a predetermined site of the subject are taken as a set. Further, input data included in the training data may be data obtained by joining together a plurality of medical images obtained by time-dividing a predetermined site into multiple regions, such as in the case of a panorama image. At such time, by using a wide-angle image such as a panorama image as training data, the result of processing can be enhanced since there is a probability that a feature value of the image can be acquired with good accuracy for reasons such as the fact that the amount of information is greater than in the case of a narrow-angle image. Further, input data included in the training data may be input data in which a plurality of medical images obtained at different dates and times of a predetermined site of the subject are taken as a set.

Further, a display screen on which at least one result among an analysis result, a diagnosis result, an object recognition result and a segmentation result described above is to be displayed is not limited to the report screen. Such a display screen may be, for example, at least one display screen among an imaging confirmation screen, a display screen for follow-up observation, and a preview screen for performing various kinds of adjustments before imaging (a display screen on which various kinds of live moving images are displayed) and the like. For example, by causing the aforementioned at least one result obtained using a learned model described above to be displayed on the imaging confirmation screen, the examiner can check an accurate result even immediately after imaging. Further, changing the display between a low quality image and a high quality image as described in Example 7 and the like may be, for example, changing the display between an analysis result for a low quality image and an analysis result for a high quality image.

The various kinds of learned models described above can be obtained by machine learning which uses training data. For example, deep learning which is composed of a multi-level neural network is one kind of machine learning. Further, for example, a convolutional neural network (CNN) can be used for at least a part of a multi level neural network. In addition, technology pertaining to auto-encoders may be used for at least a part of a multi-level neural network. Furthermore, technology pertaining to back-propagation (error back-propagation method) may be used for learning. However, the machine learning is not limited to deep learning, and any learning may be employed as long as the learning uses a model that is capable of, by itself, extracting (representing) a feature value of training data such as an image by learning. The machine learning model may be, for example, a capsule network (CapsNet). In this case, in a common neural network, by configuring each unit (each neuron) so as to output a scalar value, the neural network is configured so that, for example, spatial information relating to spatial positional relationships (relative positions) between features in an image is reduced. By this means, for example, learning can be performed in which the influence of local distortion or parallel displacement in an image is reduced. On the other hand, in a capsule network, each unit (each capsule) is configured so as to output spatial information as a vector, and for example, is configured so that spatial information is held. By this means, for example, learning can be performed in which spatial positional relationships (relative positions) between features in an image is taken into consideration.

Furthermore, the image quality improving engine (learned model for improving image quality) may be a learned model obtained by incremental learning using training data including at least one high quality image generated by an image quality improving engine. At such time, a configuration may be adopted that enables a selection as to whether a high quality image is to be used as training data for incremental learning to be made by an instruction from the examiner.

Modification 8

A configuration may be adopted so that, on a preview screen in the various examples and modifications described above, a learned model for improving image quality described above is used for every at least one frame of a live moving image. At such time, a configuration may be adopted so that, in a case where a plurality of live moving images of different sites or different kinds are displayed on the preview screen, learned models that correspond to the respective live moving images are used. By this means, for example, since the processing time can be shortened even for a live moving image, the examiner can obtain highly accuracy information prior to the start of imaging. Therefore, for example, since failures of re-imaging and the like can be reduced, the accuracy and efficiency of diagnosis can be improved. Note that, the plurality of live moving images may include, for example, a moving image of the anterior ocular segment for alignment in the XYZ-directions, and a front moving image of the fundus for OCT focus adjustment or focus adjustment of a fundus observation optical system. Further, the plurality of live moving images may also include, for example, a tomographic moving image of the fundus for coherence gate adjustment in OCT (adjustment of the optical path length difference between the measurement optical path length and the reference optical path length) and the like.

Furthermore, a moving image to which a learned model described above can be applied is not limited to a live moving image, and for example the moving image may be a moving image stored (saved) in the storage. At such time, for example, a moving image obtained by performing alignment with respect to every at least one frame of a tomographic moving image of the fundus stored (saved) in the storage may be displayed on the display screen. For example, in a case where it is desired to suitably observe the vitreous body, first, a reference frame based on conditions such as that the vitreous body is present as much as possible in the frame may be selected. At such time, each frame is a tomographic image (B-scan image) in the X-Z direction. Subsequently, a moving image in which other frames have been aligned in the X-Z direction with respect to the selected reference frame may be displayed on the display screen. At such time, for example, a configuration may be adopted so as to cause high quality images (high image quality frames) sequentially generated using a learned model for improving image quality for even at least one frame of the moving image to be consecutively displayed.

Note that, as methods for performing alignment among frames described above, the same method may be applied with respect to the method for performing alignment in the X-direction and the method for performing alignment in the Z-direction (depth direction), or the methods that are applied may all be different. In addition, alignment in the same direction may be performed a plurality of times by different methods. For example, a rough alignment may be performed, and thereafter a fine alignment may be performed. Further, as a method for alignment, for example, a method is available that performs (rough Z-direction) alignment using a retinal layer boundary obtained by subjecting a tomographic image (B-scan image) to segmentation processing. In addition, as a method for alignment, for example, a method is also available that performs (fine X-direction or Z-direction) alignment using correlation information (similarity) between a plurality of regions obtained by dividing a tomographic image and a reference image. As further methods for alignment, for example, a method is available that performs (X-direction) alignment using a one-dimensional projection image generated for each tomographic image (B scan image), and a method is available that performs (X-direction) alignment using a two-dimensional front image generated for each tomographic image (B scan image) and the like. Further, a configuration may be adopted so as to perform fine alignment in sub-pixel units after rough alignment was performed in pixel units.

In this case there is a probability that, during various kinds of adjustment, the imaging target such as the retina of the eye to be examined could not yet be successfully imaged. Thus, since there is a large difference between the medical image input to the learned model and the medical image used as training data, there is a probability that a high quality image was not accurately obtained. Therefore, a configuration may be adopted so that when an evaluation value such as a value obtained when the image quality of a tomographic image (B scan) is evaluated exceeds a threshold value, display of a high-quality moving image (consecutive display of high image quality frames) is automatically started. Further, a configuration may be adopted so that when an evaluation value such as a value obtained when the image quality of a tomographic image (B scan) is evaluated exceeds a threshold value, the image quality improving button is changed to a state (active state) in which the button can be designated by the examiner.

Further, a configuration may be adopted in which different learned model for improving image quality are prepared for each imaging mode for which scanning patterns or the like are different, and learned model for improving image quality that corresponds to a selected imaging mode is selected. Further, one learned model for improving image quality obtained by learning using training data including various medical images obtained in different imaging modes may be used.

Modification 9

In the various examples and modifications described above, in a case where various kinds of learned model are undergoing incremental learning, there is a probability that it will be difficult to output (infer/predict) using a learned model which is undergoing incremental learning itself. Therefore, input of a medical image to a learned model which is undergoing incremental learning may be prohibited. Further, a learned model that is the same as a learned model which is undergoing incremental learning may be prepared as another auxiliary learned model. At such time, a configuration may be adopted so that input of a medical image to the auxiliary learned model can be executed while incremental learning is being performed. Subsequently, after the incremental learning is completed, the learned model which underwent the incremental learning is evaluated, and if there is no problem, it suffices to switch from the auxiliary learned model to the learned model which underwent the incremental learning. Further, a configuration may be adopted so that the auxiliary learned model is used if there is a problem.

Further, a configuration may be adopted so that learned models obtained by learning for respective imaged sites can be selectively utilized. Specifically, a plurality of learned models can be prepared that include a first learned model obtained using training data including a first imaged site (lung, eye to be examined, or the like), and a second learned model obtained using training data including a second imaged site that is different from the first imaged site. Further, a controlling unit 200 may have a selecting unit for selecting any one of this plurality of learned models. At such time, the controlling unit 200 may have a control unit for executing incremental learning with respect to a selected learned model. The control unit can, in accordance with an instruction from the examiner, retrieve data in which an imaged site corresponding to a selected learned model and an image obtained by imaging the relevant imaged site form a pair, and execute learning in which the retrieved and obtained data is adopted as training data, as incremental learning with respect to the selected learned model. Note that, an imaged site corresponding to a selected learned model may be a site obtained based on header information of data, or a site that is manually input by the examiner. Further, retrieval of data may be performed, for example, through a network from a server or the like of an external facility such as a hospital or a laboratory. By this means, incremental learning can be efficiently performed for each imaged site by using an image obtained by imaging an imaged site that corresponds to the learned model.

Note that, the selecting unit and the control unit may be constituted by a software module that is executed by a processor such as an MPU or a CPU of the controlling unit 200. Further, the selecting unit and the control unit may be constituted by a circuit that serves a specific function such as an ASIC or by an independent apparatus or the like.

Further, when obtaining training data for incremental learning through a network from a server or the like of an external facility such as a hospital or a laboratory, it is useful to reduce a decrease in reliability due to falsification or system trouble during incremental learning or the like. Therefore, the correctness of the training data for incremental learning may be detected by confirming the consistency by a digital signature or hashing. By this means the training data for incremental learning can be protected. At such time, in a case where the correctness of the training data for incremental learning could not be detected as the result of confirming the consistency by a digital signature or hashing, a warning to that effect is given and incremental learning is not performed using the training data in question. Note that, the server may be any form of server, such as a cloud server, a FOG server, or an edge server, regardless of the installation location thereof.

Modification 10

In the various examples and modifications described above, an instruction from the examiner may be a voice instruction or the like in addition to a manual instruction (for example, an instruction using a user interface or the like). At such time, for example, a machine learning model including a speech recognition model (a speech recognition engine or a learned model for speech recognition) obtained by machine learning may be used. In addition, a manual instruction may be an instruction by character input using a keyboard, a touch panel, or the like. At such time, for example, a machine learning model including a character recognition model (a character recognition engine or a learned model for character recognition) obtained by machine learning may be used. Further, an instruction from the examiner may be an instruction by a gesture or the like. At such time, a machine learning model including a gesture recognition model (a gesture recognition engine or a learned model for gesture recognition) obtained by machine learning may be used.

Further, an instruction from the examiner may be a result of detection of the line of sight of the examiner on the display unit 50 or 2820. The line-of-sight detection result may be, for example, a pupil detection result using a moving image of the examiner obtained by imaging from around the display unit 50 or 2820. At such time, the pupil detection from the moving image may use an object recognition engine as described above. Further, an instruction from the examiner may be an instruction by brain waves, or a faint electric signal flowing through the body or the like.

In such a case, for example, the training data may be training data in which character data or voice data (waveform data) or the like indicating an instruction to display a result obtained by processing of various learned models as described above is adopted as input data, and an execution command for causing a result obtained by processing of various learned models to be actually displayed on a display unit is adopted as correct answer data. Further, the training data may be training data in which, for example, character data or voice data or the like indicating an instruction to display a high quality image obtained with a learned model for improving image quality is adopted as input data, and an execution command for displaying a high quality image and an execution command for changing the button 2220 as illustrated in FIG. 22A and FIG. 22B to an active state are adopted as correct answer data. Note that, any kind of training data may be used as long as, for example, the instruction content indicated by the character data or voice data or the like and the execution command content correspond with each other. Further, voice data may be converted to character data using an acoustic model or a language model or the like. Further, processing that reduces noise data superimposed on voice data may be performed using waveform data obtained with a plurality of microphones. Further, a configuration may be adopted so that a selection between an instruction issued by characters or voice or the like and an instruction input using a mouse or a touch panel or the like can be made according to an instruction from the examiner. In addition, a configuration may be adopted so that a selection can be made to turn instruction by characters or voice or the like on or off according to an instruction from the examiner.

In this case, the machine learning includes deep learning as described above, and for example, a recurrent neural network (RNN) can be used as at least a part of the multi-layer neural network. Here, as an example of the machine learning model according to the present modification, an RNN that is a neural network that handles time-series information will be described with reference to FIG. 46A and FIG. 46B. Further, a long short-term memory (hereinafter referred to as an "LSTM"), which is a kind of RNN, will be described with reference to FIG. 47A and FIG. 47B.

Figure 46A:
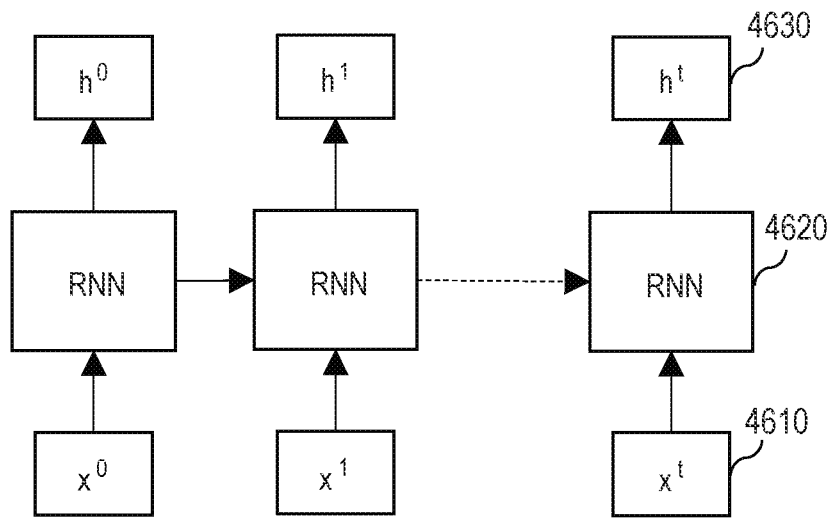
FIG. 46A illustrates an example of the configuration of a neural network used as a machine learning model according to Modification 9.
Figure 46B:
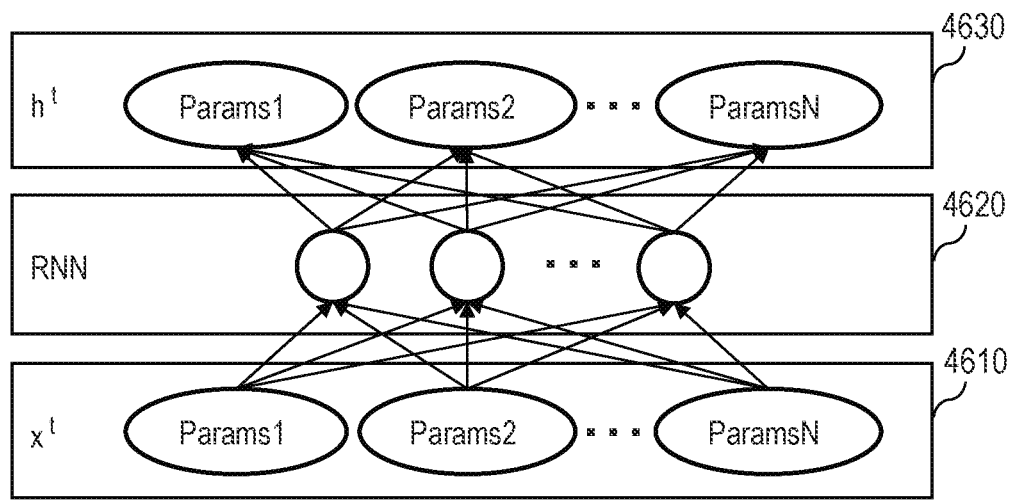
FIG. 46B illustrates an example of the configuration of the neural network used as the machine learning model according to Modification 9.

FIG. 46A illustrates a structure of an RNN that is a machine learning model. An RNN 4620 has a loop structure in the network, and data $x^t$ 4610 is input to the RNN 4620 at time t, and the RNN 4620 outputs data $h^t$ 4630. Since the RNN 4620 has a loop function in the network, the state at the current time can be taken over to the next state, and hence time-series information can be handled. FIG. 46B illustrates an example of the input/output of parameter vectors at time t. The data $x^t$ 4610 includes N pieces of data (Params 1 to Params N). Further, the data $h^t$ 4630 output by the RNN 4620 includes N pieces of data (Params 1 to Params N) corresponding to the input data.

Figure 47A:
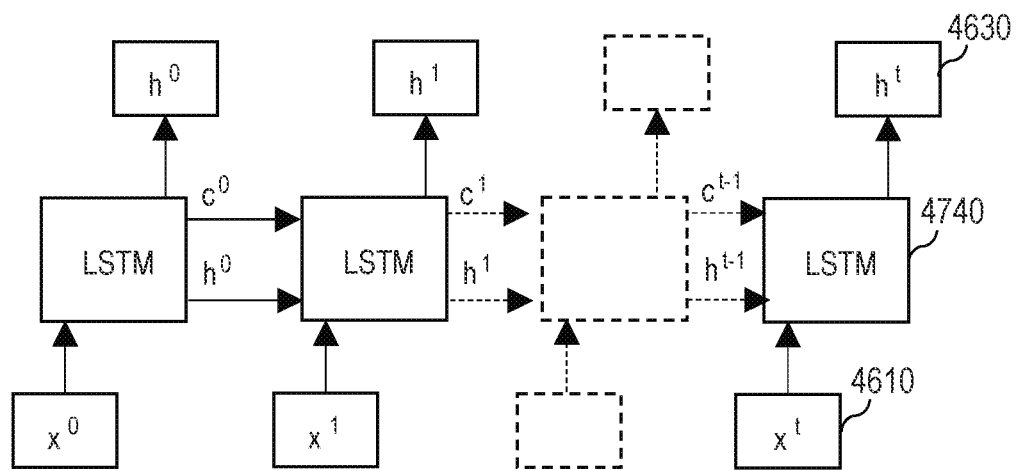
FIG. 47A illustrates an example of the configuration of the neural network used as the machine learning model according to Modification 9.

However, since the RNN cannot handle long-term information during back propagation, the LSTM may be used. The LSTM can learn long-term information by providing a forget gate, an input gate, and an output gate. FIG. 47A illustrates a structure of the LSTM. In an LSTM 4740, information that the network takes over at the next time t is an internal state $c^{t-1}$ of the network called a cell and output data $h^{t-1}$. Note that lowercase letters (c, h, x) in the figure represent vectors.

Figure 47B:
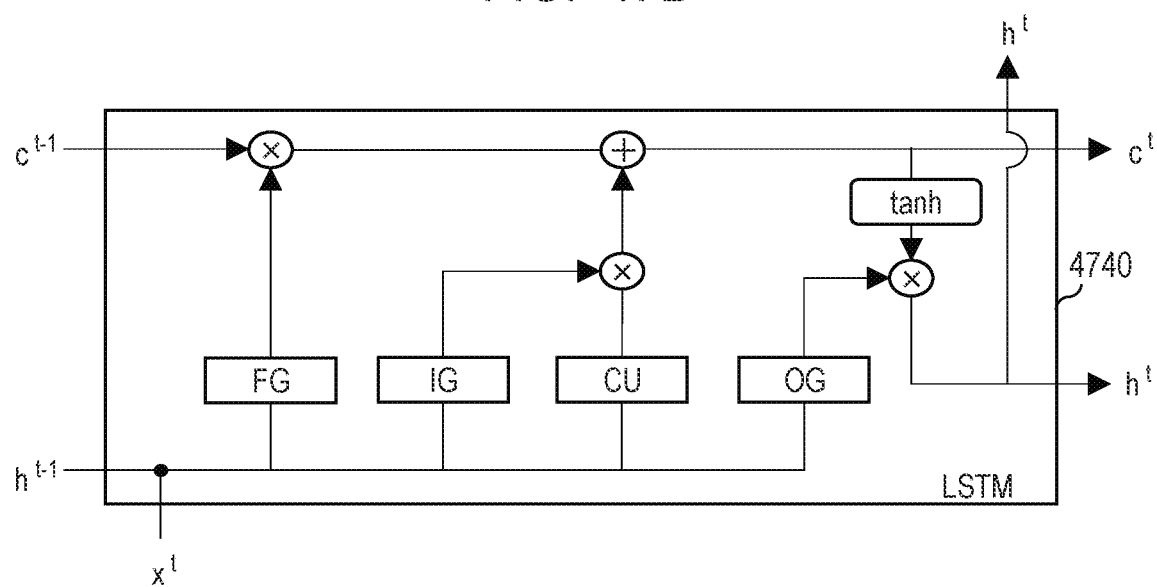
FIG. 47B illustrates an example of the configuration of the neural network used as the machine learning model according to Modification 9.

Next, the LSTM 4740 is illustrated in detail in FIG. 47B. A forget gate network FG, an input gate network IG and an output gate network OG are illustrated in FIG. 47B, and each of these networks is a sigmoid layer. Therefore, a vector in which each element has a value from 0 to 1 is output. The forget gate network FG determines how much past information is held, and the input gate network IG determines which value is to be updated. A cell update candidate network CU is also illustrated in FIG. 47B, and the cell update candidate network CU is an activation function tanh layer. This creates a vector of new candidate values to be added to the cell. The output gate network OG selects an element of a cell candidate and selects how much information is to be transmitted at the next time.

Note that, the LSTM model described above is a basic form, and the present invention is not limited to the network illustrated here. The coupling between networks may be changed. A QRNN (quasi-recurrent neural network) may be used instead of an LSTM. In addition, the machine learning model is not limited to a neural network, and Boosting or Support Vector Machine or the like may be used. Further, in a case where an instruction from the examiner is input by characters or voice or the like, a technique relating to natural language processing (for example, Sequence to Sequence) may be applied. Further, a dialogue engine (a dialogue model or a learned model for dialogue) that responds to the examiner with an output such as text or voice may be applied.

Modification 11

In the various examples and modifications described above, a boundary image, a region label image or a high quality image or the like may be stored in the storage in accordance with an instruction from the operator. At such time, for example, after an instruction from the operator to save a high quality image, when registering a file name, a file name that includes information (for example, characters) indicating that the image is an image generated by processing using a learned model for improving image quality (image quality improving processing) at any part of the file name (for example, the first part or the last part) may be displayed as a recommended file name in a state in which the file name can be edited according to an instruction from the operator. Note that, with respect to a boundary image or a region label image or the like also, a file name including information indicating that the image is an image generated by processing using a learned model may be displayed in a similar manner.

Further, when causing the display unit 50 or 2820 to display a high quality image on various display screens such as the report screen, a display indicating that the image being displayed is a high quality image generated by processing using a learned model for improving image quality may be displayed together with the high quality image. In this case, since the operator can easily discern by the relevant display that the displayed high quality image is not the actual image obtained by imaging, misdiagnosis can be reduced and the diagnosis efficiency can be improved. Note that, a display indicating that a high quality image was generated by processing that used a learned model for improving image quality may be of any form as long as it is a display which makes it possible to distinguish between the input image and the high quality image generated by the relevant processing. Further, with regard to processing using various learned models as described above also, and not just processing using a learned model for improving image quality, a display indicating that the result being displayed was generated by processing using the relevant kind of learned model may be displayed together with the relevant result. Further, when displaying an analysis result with respect to segmentation results obtained using a learned model for image segmentation processing also, a display indicating that the analysis result is based on results obtained using a learned model for image segmentation may be displayed together with the analysis result.

At such time, the display screen such as a report screen may be stored in the storage in accordance with an instruction from the operator. For example, a report screen may be stored in the storage as a single image in which high quality images or the like and a display indicating that these images are images generated by processing using a learned model are displayed side by side.

Further, with respect to the display indicating that a high quality image was generated by processing that used a learned model for improving image quality, a display indicating what kind of training data the learned model for improving image quality used when performing learning may be displayed on the display unit. The display in question may include a display of a description of the kinds of input data and correct answer data of the training data, or any display relating to the input data and the correct answer data such as an imaged site included in the correct answer data. Note that, with regard to processing using the various kinds of learned models as described above such as image segmentation processing also, a display indicating what kind of training data the relevant kind of learned model used when performing learning may be displayed on the display unit.

A configuration may also be adopted so that information (for example, characters) indicating that an image was generated by processing using a learned model is displayed or stored in a state in which the information is superimposed on the image or the like. At such time, a place at which the information is superimposed on the image may be any place as long as the place is in a region (for example, at an edge of the image) which does not overlap with a region in which the site of interest or the like that is the imaging target is displayed. Further, a non-overlapping region may be determined, and the information may be superimposed in the determined region. Note that, processing may be performed in a similar manner with respect to, for example, an image obtained by processing that used the various kinds of learned models described above such as image segmentation processing, and not just processing that used a learned model for improving image quality.

Figure 22B:
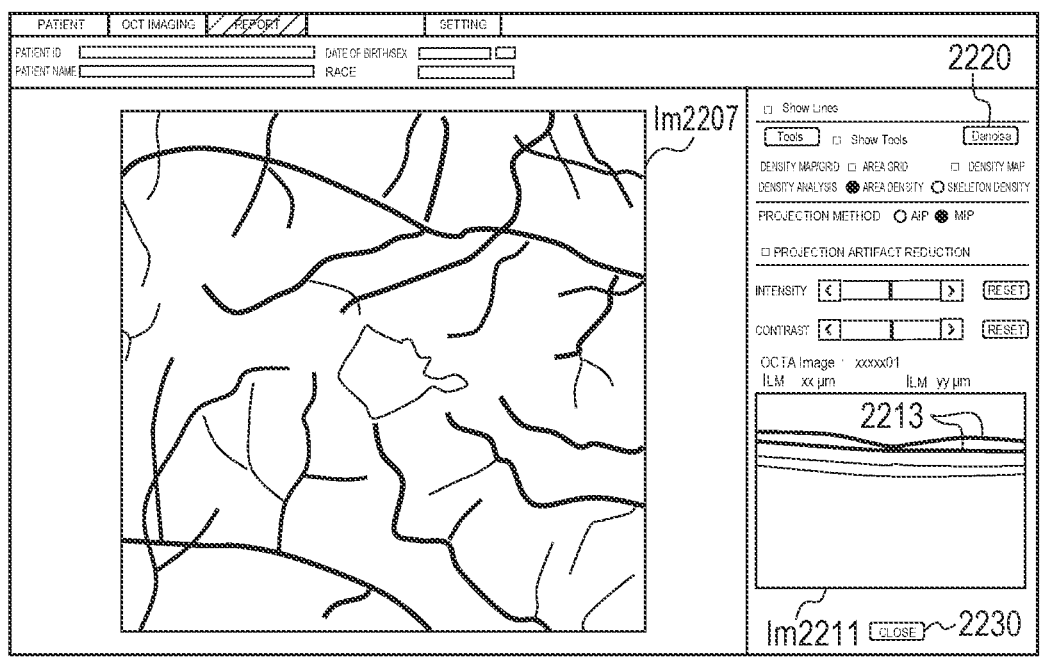
FIG. 22B illustrates an example of a user interface according to Example 7.

Further, a configuration may be adopted so that in a case where, as an initial display screen of the report screen, the default setting is set so that the button 2220 as illustrated in FIG. 22A and FIG. 22B enters an active state (image quality improving processing is set to "on"), a report image corresponding to the report screen that includes a high quality image or the like is transmitted to a server in accordance with an instruction from the examiner. Further, a configuration may be adopted so that in a case where the default setting is set so that the button 2220 enters an active state, when an examination ends (for example, in a case where the imaging confirmation screen or the preview screen is changed to the report screen in accordance with an instruction from the examiner), a report image corresponding to the report screen that includes a high quality image or the like is (automatically) transmitted to a server. At such time, a configuration may be adopted so that a report image generated based on various kinds of settings of the default settings (for example, settings relating to at least one of the depth range for generating an en-face image on the initial display screen of the report screen, whether or not to superimpose an analysis map, whether or not the image is a high quality image, and whether or not to show a display screen for follow-up observation and the like) is transmitted to a server. Note that, similar processing may be performed in relation to a case where the button 2220 represents switching of image segmentation processing also.

Modification 12

In the various examples and modifications described above, among the aforementioned various kinds of learned models, an image obtained with a first kind of learned model (for example, a high quality image, an image showing an analysis result such as an analysis map, an image showing an object recognition result, an image showing retina layers or an image showing a segmentation result) may be input to a second kind of learned model that is different from the first kind. At such time, a configuration may be adopted so that a result (for example, an analysis result, a diagnosis result, an object recognition result, a retina layer detection result or a segmentation result) is generated by processing of the second kind of learned model.

Further, among the various kinds of learned models described above, an image to be input to a second kind of learned model that is different from a first kind of learned model may be generated from an image input to the first kind of learned model by using a result (for example, an analysis result, a diagnosis result, an object recognition result, a retina layer detection result or a segmentation result) obtained by processing of the first kind of learned model. At such time, there is a high probability that the generated image is an image that is suitable as an image for processing using the second kind of learned model. Therefore, the accuracy of an image (for example, a high quality image, an image showing an analysis result such as an analysis map, an image showing an object recognition result, an image showing retina layers or an image showing a segmentation result) obtained when the generated image is input to the second kind of learned model can be enhanced.

Further, retrieval of similar images utilizing an external database that is stored in a server or the like may be performed using, as a search key, an analysis result or a diagnosis result or the like obtained by processing of a learned model that is described above. Note that, in a case where a plurality of images stored in the database are already being managed in a state in which respective feature values of the plurality of images have been attached as supplementary information by machine learning or the like, a similar image search engine (a similar image search model, or a learned model for similar image searching) that utilizes an image itself as a search key may be used.

Modification 13

Note that, processing for generating motion contrast data in the aforementioned examples and modifications is not limited to a configuration in which processing is performed based on intensity values of a tomographic image. The various kinds of processing described above may be applied with respect to an interference signal obtained with the OCT apparatus 10 or the imaging apparatus 2810, a signal obtained by subjecting an interference signal to Fourier transformation, a signal obtained by subjecting the relevant signal to any processing, and tomographic data including a tomographic image or the like based on these signals. In these cases also, similar effects as the effects of the aforementioned configurations can be obtained.

Although a fiber optical system that uses a coupler as a splitting unit is used, a spatial optical system that uses a collimator and a beam splitter may also be used. Further, the configuration of the OCT apparatus 10 or the imaging apparatus 2810 is not limited to the above-described configuration, and some of the components included in the OCT apparatus 10 or the imaging apparatus 2810 may be provided as separate components from the OCT apparatus 10 or the imaging apparatus 2810.

Further, although in the foregoing examples and modifications the configuration of a Mach-Zehnder interferometer is used as the configuration of the interference optical system of the OCT apparatus 10 or the imaging apparatus 2810, the configuration of the interference optical system is not limited thereto. For example, the interference optical system of the OCT apparatus 10 or the imaging apparatus 2810 may have the configuration of a Michelson interferometer.

In addition, while a spectral domain OCT (SD-OCT) apparatus which uses the SLD as a light source is described as the OCT apparatus in the foregoing examples and modifications, the configuration of the OCT apparatus according to the present invention is not limited thereto. For example, the present invention can also be applied to a swept source OCT (SS-OCT) apparatus which uses a wavelength swept light source capable of sweeping a wavelength of emitted light, or any other kind of OCT apparatus. Further, the present invention can also be applied to a Line-OCT apparatus that uses line light.

Further, in the aforementioned examples and modifications, the obtaining unit 21 or 2801 obtains an interference signal that was obtained by the OCT apparatus 10 or the imaging apparatus 2810, or a three-dimensional tomographic image generated by an image processing apparatus or the like. However, a configuration with which the obtaining unit 21 or 2801 obtains these signals or images is not limited to the above-described configuration. For example, the obtaining unit 21 or 2801 may obtain these signals from a server or imaging apparatus connected to the control unit through a LAN, a WAN, or the Internet or the like.

Note that, a learned model can be provided in the image processing apparatuses 20, 80, 152, 172 and 2800. A learned model may be constituted, for example, by a software module that is executed by a processor such as a CPU. Further, a learned model may be provided in a separate server that is connected to the image processing apparatus 20, 80, 152, 172 or 2800. In this case, the image processing apparatus 20, 80, 152, 172 or 2800 can perform image quality improving processing using the learned model by connecting to the server that includes the learned model through any network such as the Internet.

Modification 14

Further, images to be processed by an image processing apparatus or image processing method according to the various examples and modifications described above include medical images obtained using an arbitrary modality (imaging apparatus or imaging method). The medical images to be processed can include a medical image obtained by any imaging apparatus or the like, and images created by an image processing apparatus or an image processing method in accordance with the examples and modifications described above.

In addition, a medical image to be processed is an image of a predetermined site of a subject (examinee), and the image of the predetermined site includes at least one part of the predetermined site of the subject. The medical image may also include another site of the subject. The medical image may be a still image or a moving image, and may be a black and white image or a color image. In addition, the medical image may be an image representing the structure (form) of the predetermined site or may be an image representing a function of the predetermined site. Images that represent a function include, for example, an image representing hemodynamics (blood flow volume, blood flow velocity or the like) such as an OCTA image, a Doppler OCT image, an fMRI image, and an ultrasound Doppler image. Note that, the predetermined site of the subject may be determined according to the imaging target, and the predetermined site includes any site such as an organ such as the human eye (eye to be examined), brain, lung, intestine, heart, pancreas, kidney, and liver, and the head, chest, legs and arms.

Further, the medical image may be a tomographic image of the subject, or may be a front image. Examples of a front image include a front image of the ocular fundus, a front image of the anterior ocular segment, a fundus image obtained by fluorescence imaging, and an en-face image generated using at least a partial range of data in the depth direction of the imaging target with respect to data obtained by OCT (three-dimensional OCT data). Note that, an en-face image may be an OCTA en-face image (motion contrast front image) generated using at least a partial range of data in the depth direction of the imaging target with respect to three-dimensional OCTA data (three-dimensional motion contrast data). Further, three-dimensional OCT data or three-dimensional motion contrast data is an example of three-dimensional medical image data.

In addition, the term "imaging apparatus" refers to an apparatus for performing imaging to obtain an image to be used for diagnosis. Examples of an imaging apparatus include an apparatus that obtains an image of a predetermined site of the subject by irradiating the predetermined site with light, radioactive rays such as X-rays, electromagnetic waves, or ultrasonic waves or the like, and an apparatus that obtains an image of a predetermined site by detecting radioactive rays emitted from the subject. More specifically, examples of an imaging apparatus according to the various examples and modifications described above include at least an X-ray imaging apparatus, a CT apparatus, an MRI apparatus, a PET apparatus, a SPECT apparatus, an SLO apparatus, an OCT apparatus, an OCTA apparatus, a fundus camera and an endoscope.

Note that, a time domain OCT (TD-OCT) apparatus and a Fourier domain OCT (FD-OCT) apparatus may be included as examples of an OCT apparatus. Further, examples of a Fourier domain OCT apparatus may include a spectral domain OCT (SD-OCT) apparatus and a swept source OCT (SS-OCT) apparatus. Further, an adaptive optics SLO (AO-SLO) apparatus and an adaptive optics OCT (AO-OCT) apparatus that use an adaptive optics system and the like may be included as examples of an SLO apparatus or an OCT apparatus, respectively. Furthermore, a polarization-sensitive SLO (PS-OCT) apparatus and a polarization-sensitive OCT (PS-OCT) apparatus and the like for visualizing information relating to polarization phase differences or depolarization may be included as examples of an SLO apparatus or an OCT apparatus, respectively.

Further, in the learned models for retina layer detection and for image segmentation processing according to the various examples and modifications described above, it is conceivable for the magnitude of intensity values of a tomographic image, and the order and slope, positions, distribution, and continuity of bright sections and dark sections and the like of a tomographic image to be extracted as a part of the feature values and used for estimation processing. Similarly, in the case of the learned models for evaluating or for improving image quality of a region label image, for image analysis, and for generating diagnosis results also, it is conceivable for the magnitude of intensity values of a tomographic image, and the order and slope, positions, distribution, and continuity of bright sections and dark sections and the like of a tomographic image to be extracted as a part of the feature values and used for estimation processing. On the other hand, in the case of the learned models for speech recognition, for character recognition, for gesture recognition and the like, since learning that uses time-series data is performed, it is conceivable to extract a slope between consecutive time-series data values that are input, as a part of the feature values, and to use the slope for estimation processing. Therefore, it is expected that such learned models can be utilized to perform estimation with excellent accuracy by using influences caused by changes over time in specific numerical values in estimation processing.

VARIOUS EMBODIMENTS

Embodiment 1 of the present disclosure relates to a medical image processing apparatus. The medical image processing apparatus includes: an obtaining unit configured to obtain a tomographic image of an eye to be examined; and a first processing unit configured to perform first detection processing for detecting at least one retina layer of a plurality of retina layers in the obtained tomographic image, by using a learned model obtained by training data indicating at least one retina layer of plurality of retina layers in a tomographic image of an eye to be examined.

Embodiment 2 includes the medical image processing apparatus according to Embodiment 1, and further includes a second processing unit configured to perform second detection processing for detecting at least one retina layer of the plurality of retina layers in the obtained tomographic image, without using a learned model obtained by machine learning.

Embodiment 3 includes the medical image processing apparatus according to Embodiment 2, in which the second detection processing is processing that detects at least one retina layer other than at least one retina layer detected by performing the first detection processing.

Embodiment 4 includes the medical image processing apparatus according to Embodiment 2 or 3, in which the first detection processing is processing that detects a retina region in the obtained tomographic image as the at least one retina layer, and the second detection processing is processing that detects at least one retina layer in the retina region detected by performing the first detection processing.

Embodiment 5 includes the medical image processing apparatus according to any one of Embodiments 2 to 4, in which the first detection processing is processing that detects layers from a boundary between an inner limiting membrane and a nerve fiber layer of the eye to be examined to one of a photoreceptor inner segment-outer segment junction, a retinal pigment epithelium, and a Bruch's membrane, and the second detection processing is processing that detects at least one retina layer between the layers detected by the first detection processing.

Embodiment 6 includes the medical image processing apparatus according to any one of Embodiments 2 to 5, in which the second processing unit performs the second detection processing after the first detection processing by the first processing unit.

Embodiment 7 includes the medical image processing apparatus according to Embodiment 2, and further includes a display controlling unit configured to control a display unit, in which the first detection processing and the second detection processing are processings that detect the same retina layer, and the display controlling unit displays processing results of the first detection processing and the second detection processing on the display unit.

Embodiment 8 includes the medical image processing apparatus according to Embodiment 7, in which the display controlling unit displays a mismatched portion between the processing results of the first detection processing and the second detection processing on the display unit.

Embodiment 9 includes the medical image processing apparatus according to Embodiment 7 or 8, in which the first detection processing and the second detection processing are processings that detect layers from a boundary between an inner limiting membrane and a nerve fiber layer of the eye to be examined to one of a photoreceptor inner segment-outer segment junction, a retinal pigment epithelium, and a Bruch's membrane, and the second processing unit further performs third detection processing that detects at least one retina layer between the layers detected by either one of the first detection processing and the second detection processing according to an instruction by an operator.

Embodiment 10 includes the medical image processing apparatus according to any one of Embodiments 2 to 9, and further includes a selecting unit configured to perform selection of at least one of the first detection processing and the second detection processing based on an imaging condition related to the obtained tomographic image.

Embodiment 11 includes the medical image processing apparatus according to any one of Embodiments 2 to 10, in which, among a plurality of learned models for which machine learning has been performed by using different training data, the first processing unit performs the first detection processing by using a learned model for which machine learning has been performed by using training data corresponding to an imaging condition related to the obtained tomographic image.

Embodiment 12 includes the medical image processing apparatus according to Embodiment 10 or 11, in which the imaging condition includes at least one of an imaged site, an imaging system, an imaged region, an imaging angle of view, and an image resolution.

Embodiment 13 includes the medical image processing apparatus according to any one of Embodiments 2 to 12, in which a shape characteristic of the eye to be examined is measured based on results of the first detection processing and the second detection processing.

Embodiment 14 includes the medical image processing apparatus according to any one of Embodiments 1 to 13, and further includes a correcting unit configured to correct a structure of the retina layer detected by the first processing unit, based on a medical characteristic in the retina layer.

Embodiment 15 includes the medical image processing apparatus according to any one of Embodiments 1 to 14, in which the first processing unit detects a boundary defined in advance for each imaged site for an input image, by using the learned model.

Embodiment 16 includes the medical image processing apparatus according to any one of Embodiments 1 to 15, and further includes a generating unit configured to generate a front image corresponding to a depth range of at least a part of a three-dimensional tomographic image of the eye to be examined, the depth range determined based on the detected at least one retina layer.

Embodiment 17 includes the medical image processing apparatus according to Embodiment 16, in which the generating unit generates a motion contrast front image corresponding to the determined depth range, by using three-dimensional motion contrast data corresponding to the three-dimensional tomographic image.

Embodiment 18 includes the medical image processing apparatus according to any one of Embodiments 1 to 15, and further includes a generating unit configured to generate, from the obtained tomographic image, a tomographic image whose image quality is improved compared with the obtained tomographic image, by using a learned model for improving image quality, in which the first processing unit performs the first detection processing on the generated tomographic image.

Embodiment 19 includes the medical image processing apparatus according to any one of Embodiments 1 to 18, and further includes a modifying unit configured to modify information on the retina layer detected by the first processing unit, according to an instruction by an operator, in which the modified information on the retina layer is used for incremental learning about the learned model used by the first processing unit.

Embodiment 20 includes the medical image processing apparatus according to any one of Embodiments 1 to 18, and further includes a diagnosis result generating unit configured to generate a diagnosis result of the obtained tomographic image from a result obtained by performing the first detection processing, by using a learned model for diagnosis result generation.

Embodiment 21 relates to a medical image processing method. The medical image processing method includes: obtaining a tomographic image of an eye to be examined; and performing first detection processing for detecting at least one retina layer of a plurality of retina layers of the eye to be examined in the tomographic image, by using a learned model.

Embodiment 22 relates to a program. When executed by a processor, the program causes the processor to perform each step of the medical image processing method according to Embodiment 21.

Additional Embodiment 1 of the present disclosure relates to a medical image processing apparatus. The medical image processing apparatus includes: a segmentation processing unit configured to generate region information, in which an anatomical region is distinguishable, from an input image that is a tomographic image of a predetermined site of a subject by using a segmentation engine including a learned model; and an evaluating unit configured to evaluate the region information by using an evaluating engine including a learned model or an evaluating engine that performs knowledge-based processing using anatomical knowledge.

Additional Embodiment 2 includes the medical image processing apparatus according to Additional Embodiment 1, and further includes an imaging condition obtaining unit configured to obtain an imaging condition of the input image, in which the segmentation processing unit switches and uses a plurality of segmentation engines including respective different learned models, based on the imaging condition.

Additional Embodiment 3 includes the medical image processing apparatus according to Additional Embodiment 2, in which the imaging condition obtaining unit estimates at least one of an imaged site and an imaged region from the input image, by using an imaging location estimation engine including a learned model.

Additional Embodiment 4 includes the medical image processing apparatus according to any one of Additional Embodiments 1 to 3, in which the segmentation processing unit adjusts an image size of the input image to an image size being handleable by the segmentation engine to input the input image to the segmentation engine.

Additional Embodiment 5 includes the medical image processing apparatus according to any one of Additional Embodiments 1 to 3, in which the segmentation processing unit inputs, to the segmentation engine, an image obtained by performing padding to the input image so that the image size of the input image becomes an image size being handleable by the segmentation engine.

Additional Embodiment 6 includes the medical image processing apparatus according to any one of Additional Embodiments 1 to 3, in which the segmentation processing unit divides the input image into images of a plurality of regions, and inputs each of the images of the divided regions to the segmentation engine.

Additional Embodiment 7 includes the medical image processing apparatus according to any one of Additional Embodiments 1 to 6, in which the evaluating unit determines whether or not to output the region information according to a result of the evaluation.

Additional Embodiment 8 includes the medical image processing apparatus according to any one of Additional Embodiments 1 to 7, in which the segmentation processing unit generates a plurality of sets of the region information from the input image by using a plurality of segmentation engines including respective different learned models, and the evaluating unit evaluates the plurality of sets of the region information, and selects at least one of the plurality of sets of the region information determined to be output, according to an instruction by a user.

Additional Embodiment 9 includes the medical image processing apparatus according to any one of Additional Embodiments 1 to 7, in which the segmentation processing unit generates a plurality of sets of the region information from the input image by using a plurality of segmentation engines including respective different learned models, and the evaluating unit evaluates the plurality of sets of the region information, and selects at least one of the plurality of sets of the region information determined to be output, based on a predetermined selection criterion.

Additional Embodiment 10 includes the medical image processing apparatus according to any one of Additional Embodiments 1 to 9, and further includes a determining unit configured to determine whether or not the region information is capable of being generated from the input image by using the segmentation engine.

Additional Embodiment 11 includes the medical image processing apparatus according to any one of Additional Embodiments 1 to 10, in which the segmentation processing unit divides the input image into a plurality of images having a lower number of dimensions than a number of dimensions of the input image, and inputs each of the divided images to the segmentation engine.

Additional Embodiment 12 includes the medical image processing apparatus according to Additional Embodiment 11, in which the segmentation processing unit processes the plurality of images in parallel by using a plurality of segmentation engines.

Additional Embodiment 13 includes the medical image processing apparatus according to any one of Additional Embodiments 1 to 12, in which the region information is a label image in which a label of a region is given to each pixel.

Additional Embodiment 14 includes the medical image processing apparatus according to Additional Embodiment 13, in which a tomographic image is input to the segmentation engine, and the label image is output by the segmentation engine.

Additional Embodiment 15 includes the medical image processing apparatus according to Additional Embodiment 14, in which a learned model of the segmentation engine is a model in which learning has been performed by using a tomographic image including two or more layers as input data, and using a label image corresponding to the tomographic image as ground truth.

Additional Embodiment 16 includes the medical image processing apparatus according to any one of Additional Embodiments 1 to 15, in which the medical image processing apparatus obtains the input image from an imaging apparatus, or obtains data of the predetermined site of the subject from the imaging apparatus and obtains the input image based on the data.

Additional Embodiment 17 includes the medical image processing apparatus according to any one of Additional Embodiments 1 to 15, in which the medical image processing apparatus obtains the input image from an image management system, outputs the region information to the image management system, or obtains the input image from the image management system and outputs the region information to the image management system.

Additional Embodiment 18 includes the medical image processing apparatus according to any one of Additional Embodiments 1 to 17, and further includes a modifying unit configured to modify the region information by anatomical knowledge-based processing.

Additional Embodiment 19 includes the medical image processing apparatus according to any one of Additional Embodiments 1 to 18, and further includes an analyzing unit configured to perform image analysis of the input image by using the region information output from the evaluating unit.

Additional Embodiment 20 includes the medical image processing apparatus according to any one of Additional Embodiments 1 to 19, in which the medical image processing apparatus outputs that the region information is information generated by using a learned model.

Additional Embodiment 21 relates to a medical image processing method. The medical image processing method includes: generating region information, in which an anatomical region is distinguishable, from an input image that is a tomographic image of a predetermined site of a subject by using a segmentation engine including a learned model; and evaluating the region information by using an evaluating engine including a learned model or a knowledge-based evaluating engine using anatomical knowledge.

Additional Embodiment 22 relates to a program. When executed by a processor, the program causes the processor to perform each step of the medical image processing method according to Additional Embodiment 21.

Other Examples

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Examples of the processor or circuit may include a central processing unit (CPU), a micro processing unit (MPU), a graphics processing unit (GPU), an application specific integrated circuit (ASIC), or a field programmable gateway (FPGA). Further, examples of the processor or circuit may include a digital signal processor (DSP), a data flow processor (DFP) or a neural processing unit (NPU).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical image processing apparatus comprising at least one of (a) one or more processors connected to one or more memories storing a program including instructions executed by the one or more processors and (b) circuitry configured to function as:
    an obtaining unit configured to obtain a two-dimensional tomographic image in a depth direction of an eye to be examined;
    a first processing unit configured to perform first detection processing for outputting, as output data of a learned model, a detection result relating to at least one layer of a plurality of layers in the obtained two-dimensional tomographic image, by using the obtained two-dimensional tomographic image as an input data of the learned model, wherein the learned model has been obtained by using training data including data indicating information on at least one layer of a plurality of layers in a two-dimensional tomographic image in a depth direction of an eye to be examined; and
    a second processing unit configured to perform, after the first detection processing is performed, second detection processing for detecting information on at least one layer of the plurality of layers in the obtained two-dimensional tomographic image, without using a learned model obtained by machine learning, wherein the second detection processing is processing that detects the information on the at least one layer which is not obtained in the detection result output by performing the first detection processing.

2. The medical image processing apparatus according to claim 1, wherein the first detection processing is processing that detects a retina region in the obtained two-dimensional tomographic image as the at least one layer, and
the second detection processing is processing that detects at least one layer in the detected retina region.

3. The medical image processing apparatus according to claim 1, wherein the first detection processing is processing that detects layers from a boundary between an inner limiting membrane and a nerve fiber layer of an eye to be examined to one of a photoreceptor inner segment-outer segment junction, a retinal pigment epithelium, and a Bruch's membrane, and
the second detection processing is processing that detects at least one layer between the detected layers.

4. The medical image processing apparatus according to claim 1, wherein the at least one of (a) and (b) is further configured to function as a display controlling unit configured to cause at least one of (c) processing results of the first detection processing and the second detection processing and (d) a measurement result of a shape characteristic of an eye to be examined obtained based on the processing results of the first detection processing and the second detection processing to be displayed on a display unit.

5. The medical image processing apparatus according to claim 1, wherein the at least one of (a) and (b) is further configured to function as:
a display controlling unit configured to cause a processing result of the first detection processing to be displayed on a display unit; and
a modifying unit configured to modify the information on the at least one layer detected by the first detection processing, according to an instruction by an operator, wherein the corrected information is used for incremental learning of the learned model.

6. The medical image processing apparatus according to claim 4, wherein the display controlling unit causes information indicating that the processing result of the first detection processing is a processing result detected by using a learned model to be displayed on the display unit.

7. The medical image processing apparatus according to claim 1, wherein, among a plurality of learned models for which machine learning has been performed by using different kinds of training data corresponding to a plurality of imaging conditions, the first processing unit performs the first detection processing by using a learned model selected based on an imaging condition related to the obtained two-dimensional tomographic image.

8. The medical image processing apparatus according to claim 1, wherein the at least one of (a) and (b) is further configured to function as a generating unit configured to generate an En-Face image corresponding to a depth range of at least a part of a three-dimensional tomographic image of an eye to be examined, the depth range determined based on the detected at least one layer.

9. The medical image processing apparatus according to claim 8, wherein the generating unit generates a motion contrast En-Face image corresponding to the determined depth range, by using three-dimensional motion contrast data corresponding to the three-dimensional tomographic image.

10. The medical image processing apparatus according to claim 1, wherein the at least one of (a) and (b) is further configured to function as an image quality improving unit configured to generate, from the obtained two-dimensional tomographic image, a two-dimensional tomographic image whose image quality is improved compared with the obtained two-dimensional tomographic image, by using a learned model for improving image quality,
wherein the first processing unit performs the first detection processing on the generated two-dimensional tomographic image.

11. The medical image processing apparatus according to claim 1, wherein the at least one of (a) and (b) is further configured to function as a diagnosis result generating unit configured to generate a diagnosis result of the obtained two-dimensional tomographic image from a processing result of the first detection processing, by using a learned model for diagnosis result generation.

12. The medical image processing apparatus according to claim 1, wherein the first processing unit inputs, to the learned model, an image obtained by adjusting the obtained two-dimensional tomographic image into a state being handleable by the learned model, by using images of a plurality of regions obtained by dividing the obtained two-dimensional tomographic image.

13. The medical image processing apparatus according to claim 1, wherein the first processing unit inputs, to the learned model, an image obtained by performing padding to the obtained two-dimensional tomographic image so that the image size of the obtained two-dimensional tomographic image becomes an image size being handleable by the learned model.

14. The medical image processing apparatus according to claim 1, wherein the at least one of (a) and (b) is further configured to function as an evaluating unit configured to evaluate the detected at least one layer as region information by using an evaluating engine that performs knowledge-based processing using anatomical knowledge or learned model for evaluation.

15. The medical image processing apparatus according to claim 14, wherein the at least one of (a) and (b) is further configured to function as a modifying unit configured to modify the region information by anatomical knowledge-based processing.

16. A medical image processing method comprising:
obtaining a two-dimensional tomographic image in a depth direction of an eye to be examined;
performing first detection processing for outputting, as output data of a learned model, a detection result relating to at least one layer of a plurality of layers in the obtained two-dimensional tomographic image, by using the obtained two-dimensional tomographic image as an input data of the learned model, wherein the learned model has been obtained by using training data including data indicating information on at least one layer of a plurality of layers in a two-dimensional tomographic image in a depth direction of an eye to be examined; and
performing, after the first detection processing is performed, second detection processing for detecting information on at least one layer of the plurality of layers in the obtained two-dimensional tomographic image, without using a learned model obtained by machine learning, wherein the second detection processing is processing that detects the information on the at least one layer which is not obtained in the detection result output by performing the first detection processing.

17. A non-transitory computer-readable medium having stored thereon a program that, when executed by a processor, causes the processor to perform each step of the medical image processing method according to claim 16.

18. A medical image processing apparatus comprising at least one of (a) one or more processors connected to one or more memories storing a program including instructions executed by the one or more processors and (b) circuitry configured to function as:

an obtaining unit configured to obtain a two-dimensional tomographic image in a depth direction of an eye to be examined;

a processing unit configured to detect, by using the obtained two-dimensional tomographic image as input data of a learned model, information on at least one layer in the obtained two-dimensional tomographic image, the learned model being obtained by using training data including (c) a two-dimensional tomographic image in a depth direction of an eye to be examined and (d) information on at least one layer in the two-dimensional tomographic image; and a generating unit configured to generate an En-Face image corresponding to a depth range of at least a part of a three-dimensional tomographic image of an eye to be examined, the depth range determined using the detected information on at least one layer.

19. A medical image processing method comprising:

obtaining a two-dimensional tomographic image in a depth direction of an eye to be examined;

detecting, by using the obtained two-dimensional tomographic image as input data of a learned model, information on at least one layer in the obtained two-dimensional tomographic image, the learned model being obtained by using training data including (a) a two-dimensional tomographic image in a depth direction of an eye to be examined and (b) information on at least one layer in the two-dimensional tomographic image; and generating an En-Face image corresponding to a depth range of at least a part of a three-dimensional tomographic image of an eye to be examined, the depth range determined using on the detected information on at least one layer.

20. A non-transitory computer-readable medium having stored thereon a program that, when executed by a processor, causes the processor to perform each step of the medical image processing method according to claim 19.

21. The medical image processing apparatus according to claim 18, wherein the at least one of (a) and (b) is further configured to function as a display controlling unit configured to cause at least one of the En-Face image and a high quality En-Face image with higher image quality than the En-Face image to be displayed on a display unit, and wherein the generating unit generates the high quality En-Face image by using the En-Face image as input data of a learned model which is different from the learned model.

22. The medical image processing apparatus according to claim 18, wherein the at least one of (a) and (b) is further configured to function as a display controlling unit configured to cause a two-dimensional tomographic image corresponding to a position determined according to an instruction by an operator to be displayed on a display unit in a state where the detected information on at least one layer is superimposed on the two-dimensional tomographic image.

* * * * *